(12) United States Patent
Lebwohl et al.

(10) Patent No.: US 11,344,620 B2
(45) Date of Patent: May 31, 2022

(54) COMBINATION THERAPIES

(71) Applicant: Novartis AG, Basel (CH)

(72) Inventors: David Lebwohl, East Hanover, NJ (US); Malte Peters, Munich (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/510,355

(22) PCT Filed: Sep. 11, 2015

(86) PCT No.: PCT/US2015/049826
§ 371 (c)(1),
(2) Date: Mar. 10, 2017

(87) PCT Pub. No.: WO2016/040892
PCT Pub. Date: Mar. 17, 2016

(65) Prior Publication Data
US 2017/0296659 A1    Oct. 19, 2017

Related U.S. Application Data

(60) Provisional application No. 62/199,030, filed on Jul. 30, 2015, provisional application No. 62/119,060, filed on Feb. 20, 2015, provisional application No. 62/059,788, filed on Oct. 3, 2014, provisional application No. 62/050,116, filed on Sep. 13, 2014.

(51) Int. Cl.
| | |
|---|---|
| *A61K 39/395* | (2006.01) |
| *C07K 16/28* | (2006.01) |
| *A61K 31/506* | (2006.01) |
| *A61K 9/00* | (2006.01) |
| *C07K 16/30* | (2006.01) |
| *A61K 31/55* | (2006.01) |
| *A61K 39/00* | (2006.01) |

(52) U.S. Cl.
CPC ...... *A61K 39/39558* (2013.01); *A61K 9/0053* (2013.01); *A61K 31/506* (2013.01); *A61K 31/55* (2013.01); *C07K 16/28* (2013.01); *C07K 16/2803* (2013.01); *C07K 16/2818* (2013.01); *C07K 16/2827* (2013.01); *C07K 16/3023* (2013.01); *A61K 2039/505* (2013.01); *A61K 2039/54* (2013.01); *A61K 2039/542* (2013.01); *A61K 2039/545* (2013.01); *C07K 2317/21* (2013.01); *C07K 2317/76* (2013.01)

(58) Field of Classification Search
CPC ................ A61K 31/53; A61K 2300/00; A61K 2039/505; C07K 16/28
See application file for complete search history.

(56) References Cited

U.S. PATENT DOCUMENTS

| | | |
|---|---|---|
| 5,324,514 A | 6/1994 | Sipos |
| 5,434,131 A | 7/1995 | Linsley et al. |
| 5,629,204 A | 5/1997 | Honjo et al. |
| 5,698,520 A | 12/1997 | Honjo et al. |
| 5,811,097 A | 9/1998 | Allison et al. |
| 5,897,862 A | 4/1999 | Hardy et al. |
| 5,968,511 A | 10/1999 | Akita et al. |
| 6,051,227 A | 4/2000 | Allison et al. |
| 6,084,083 A | 7/2000 | Levinson |
| 6,204,371 B1 | 3/2001 | Levinson |
| 6,288,218 B1 | 9/2001 | Levinson |
| 6,414,117 B1 | 7/2002 | Levinson |
| 6,562,343 B1 | 5/2003 | Levinson |
| 6,632,927 B2 | 10/2003 | Adair et al. |
| 6,632,976 B1 | 10/2003 | Tomizuka et al. |
| 6,803,192 B1 | 10/2004 | Chen |
| 6,808,710 B1 | 10/2004 | Wood et al. |
| 6,936,704 B1 | 8/2005 | Freeman et al. |
| 7,029,674 B2 | 4/2006 | Carreno et al. |
| 7,038,013 B2 | 5/2006 | Freeman et al. |
| 7,041,474 B2 | 5/2006 | Kingsbury |
| 7,101,550 B2 | 9/2006 | Wood et al. |
| 7,105,328 B2 | 9/2006 | Wood et al. |
| 7,122,372 B2 | 10/2006 | Hardy et al. |
| 7,169,791 B2 | 1/2007 | Breitenstein et al. |
| 7,172,750 B2 | 2/2007 | Levinson |
| 7,329,639 B2 | 2/2008 | Hardy et al. |
| 7,332,582 B2 | 2/2008 | Hardy et al. |
| 7,414,171 B2 | 8/2008 | Honjo et al. |
| 7,423,128 B2 | 9/2008 | Gazit-Bornstein et al. |
| 7,449,300 B2 | 11/2008 | Chen et al. |
| 7,470,428 B2 | 12/2008 | Kuchroo et al. |

(Continued)

FOREIGN PATENT DOCUMENTS

| | | |
|---|---|---|
| AU | 774391 B2 | 6/2004 |
| CN | 102492038 A | 6/2012 |
| CN | 103079644 A | 5/2013 |
| CN | 103242448 A | 8/2013 |
| EP | 0670369 A2 | 9/1995 |

(Continued)

OTHER PUBLICATIONS

NCT01454102 (ClinicalTrials.gov archive, Oct. 17, 2011 version) (Year: 2011).*
Christensen etal (Cancer Letters, 2005, vol. 225, pp. 1-26) (Year: 2005).*
[No Author Listed] Press Release: "Bristol-Myers Squibb Announces Collaboration to Evaludate Opdivo (nivolumab) in Combination with Targeted Therapies from Novartis to Treat Non-Small Cell Lung Cancer (NSCLC)," dated Oct. 6, 2014.

(Continued)

*Primary Examiner* — Karen A. Canella
(74) *Attorney, Agent, or Firm* — K&L Gates LLP

(57) ABSTRACT

Disclosed is a combination comprising an immunomodulator and a second therapeutic agent for use in treating cancer, wherein the immunomodulator is an inhibitor of an immune checkpoint molecule or an activator of a costimulatory molecule, or a combination thereof; and the second therapeutic agent is chosen from one or more of: 1) a c-MET inhibitor; 2) a CDK4/6 inhibitor; 3) a PI3K inhibitor; 4) a BRAF inhibitor; 5) an FGFR inhibitor; 6) a MEK inhibitor, or 7) a BCR-ABL inhibitor. The combination therapies can be used to treat or prevent cancerous conditions and/or disorders.

36 Claims, 6 Drawing Sheets

Specification includes a Sequence Listing.

(56) References Cited

U.S. PATENT DOCUMENTS

| | | |
|---|---|---|
| 7,488,802 B2 | 2/2009 | Collins et al. |
| 7,521,051 B2 | 4/2009 | Collins et al. |
| 7,524,498 B2 | 4/2009 | Hardy et al. |
| 7,553,939 B2 | 6/2009 | McIntire et al. |
| 7,563,869 B2 | 7/2009 | Honjo et al. |
| 7,595,048 B2 | 9/2009 | Honjo et al. |
| 7,598,257 B2 | 10/2009 | Rodgers et al. |
| 7,635,757 B2 | 12/2009 | Freeman et al. |
| 7,695,715 B2 | 4/2010 | Hardy et al. |
| 7,722,868 B2 | 5/2010 | Freeman et al. |
| 7,767,675 B2 | 8/2010 | Zhuo et al. |
| 7,794,710 B2 | 9/2010 | Chen et al. |
| 7,838,220 B2 | 11/2010 | McIntire et al. |
| 7,858,746 B2 | 12/2010 | Honjo et al. |
| 7,943,743 B2 | 5/2011 | Korman et al. |
| 8,008,449 B2 | 8/2011 | Korman et al. |
| 8,039,273 B2 | 10/2011 | Jeffrey |
| 8,039,479 B2 | 10/2011 | Michellys et al. |
| 8,088,905 B2 | 1/2012 | Collins et al. |
| 8,101,176 B2 | 1/2012 | Kuchroo et al. |
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,287,856 B2 | 10/2012 | Li et al. |
| 8,329,660 B2 | 12/2012 | Kuchroo et al. |
| 8,354,509 B2 | 1/2013 | Carven et al. |
| 8,361,736 B2 | 1/2013 | Majeti et al. |
| 8,415,355 B2 | 4/2013 | Brain et al. |
| 8,460,886 B2 | 6/2013 | Shibayama et al. |
| 8,460,927 B2 | 6/2013 | Chen |
| 8,461,330 B2 | 6/2013 | Zhuo et al. |
| 8,501,758 B2 | 8/2013 | Huang et al. |
| 8,546,336 B2 | 10/2013 | Chen et al. |
| 8,546,396 B2 | 10/2013 | Cheng et al. |
| 8,552,002 B2 | 10/2013 | Ding et al. |
| 8,552,154 B2 | 10/2013 | Freeman et al. |
| 8,552,156 B2 | 10/2013 | Takayanagi et al. |
| 8,568,728 B2 | 10/2013 | Jeffrey |
| 8,580,247 B2 | 11/2013 | Li et al. |
| 8,609,089 B2 | 12/2013 | Langermann et al. |
| 8,617,546 B2 | 12/2013 | Kang et al. |
| 8,647,623 B2 | 2/2014 | Takayanagi et al. |
| 8,685,980 B2 | 4/2014 | Besong et al. |
| 8,697,069 B2 | 4/2014 | Kuchroo et al. |
| 8,709,412 B2 | 4/2014 | Jones et al. |
| 8,709,416 B2 | 4/2014 | Langermann et al. |
| 8,709,429 B2 | 4/2014 | Majeti et al. |
| 8,715,619 B2 | 5/2014 | Karsunky |
| 8,728,474 B2 | 5/2014 | Honjo et al. |
| 8,735,551 B2 | 5/2014 | Garner et al. |
| 8,735,553 B1 | 5/2014 | Li et al. |
| 8,779,105 B2 | 7/2014 | Korman et al. |
| 8,779,108 B2 | 7/2014 | Queva et al. |
| 8,841,418 B2 | 9/2014 | Karsunky et al. |
| 8,900,587 B2 | 12/2014 | Carven et al. |
| 8,927,697 B2 | 1/2015 | Davis et al. |
| 8,952,136 B2 | 2/2015 | Carven et al. |
| 9,045,545 B1 | 6/2015 | Clube |
| 9,067,999 B1 | 6/2015 | Honjo et al. |
| 9,073,994 B2 | 7/2015 | Honjo et al. |
| 9,084,776 B2 | 7/2015 | Korman et al. |
| 9,102,727 B2 | 8/2015 | Freeman et al. |
| 9,103,832 B2 | 8/2015 | Takayanagi et al. |
| 9,109,034 B1 | 8/2015 | Clube |
| 9,132,281 B2 | 9/2015 | Zeng et al. |
| 9,175,082 B2 | 11/2015 | Zhou et al. |
| 9,238,646 B2 | 1/2016 | Cheng et al. |
| 9,333,256 B2 | 5/2016 | Kuchroo et al. |
| 9,358,289 B2 | 6/2016 | Korman et al. |
| 9,387,247 B2 | 7/2016 | Korman et al. |
| 9,409,970 B2 | 8/2016 | Mikesell et al. |
| 9,457,080 B2 | 10/2016 | Freeman et al. |
| 9,492,539 B2 | 11/2016 | Korman et al. |
| 9,492,540 B2 | 11/2016 | Korman et al. |
| 9,505,839 B2 | 11/2016 | Lonberg et al. |
| 9,605,070 B2 | 3/2017 | Sabatos-Peyton et al. |
| 9,683,048 B2 | 6/2017 | Freeman et al. |
| 9,815,898 B2 | 11/2017 | Freeman et al. |
| 9,815,901 B2 | 11/2017 | Brogdon et al. |
| 9,834,605 B2 | 12/2017 | Carven et al. |
| 9,884,913 B2 | 2/2018 | Sabatos-Peyton et al. |
| 9,908,936 B2 | 3/2018 | Triebel et al. |
| 9,944,645 B2 | 4/2018 | Zhuo et al. |
| 9,988,452 B2 | 6/2018 | Freeman et al. |
| 10,005,832 B2 | 6/2018 | Koshida et al. |
| 10,251,893 B2 | 4/2019 | Cheng et al. |
| 10,472,419 B2 | 11/2019 | Sabatos-Peyton et al. |
| 10,513,558 B2 | 12/2019 | Tipton et al. |
| 10,561,653 B2 | 2/2020 | Bilic et al. |
| 10,570,204 B2 | 2/2020 | Johnson et al. |
| 10,711,060 B2 | 7/2020 | Triebel et al. |
| 10,851,165 B2 | 12/2020 | Freeman et al. |
| 10,981,990 B2 | 4/2021 | Sabatos-Peyton et al. |
| 11,155,620 B2 | 10/2021 | Sabatos-Peyton et al. |
| 2002/0164660 A1 | 11/2002 | Spaulding et al. |
| 2003/0039653 A1 | 2/2003 | Chen et al. |
| 2003/0232323 A1 | 12/2003 | Freeman et al. |
| 2004/0073957 A1 | 4/2004 | Tomizuka et al. |
| 2004/0241745 A1 | 12/2004 | Honjo et al. |
| 2005/0191721 A1 | 9/2005 | Kuchroo et al. |
| 2005/0276756 A1 | 12/2005 | Hoo et al. |
| 2006/0110383 A1 | 5/2006 | Honjo et al. |
| 2006/0210567 A1 | 9/2006 | Collins et al. |
| 2007/0041982 A1 | 2/2007 | Ponath et al. |
| 2007/0065427 A1 | 3/2007 | Freeman et al. |
| 2007/0071675 A1 | 3/2007 | Wu et al. |
| 2007/0122378 A1 | 5/2007 | Freeman et al. |
| 2007/0202100 A1 | 8/2007 | Wood et al. |
| 2008/0025979 A1 | 1/2008 | Honjo et al. |
| 2008/0167287 A1 | 7/2008 | Zhuo et al. |
| 2008/0311117 A1 | 12/2008 | Collins et al. |
| 2009/0055944 A1 | 2/2009 | Korman et al. |
| 2009/0076250 A1 | 3/2009 | Honjo et al. |
| 2009/0155275 A1 | 6/2009 | Wu et al. |
| 2009/0304693 A1 | 12/2009 | Ghayur et al. |
| 2009/0311253 A1 | 12/2009 | Ghayur et al. |
| 2010/0028330 A1 | 2/2010 | Collins et al. |
| 2010/0056576 A1 | 3/2010 | Burger et al. |
| 2010/0061992 A1 | 3/2010 | Anderson et al. |
| 2010/0074900 A1 | 3/2010 | Ghayur et al. |
| 2010/0076178 A1 | 3/2010 | Ghayur et al. |
| 2010/0105667 A1 | 4/2010 | Furet et al. |
| 2010/0136009 A1 | 6/2010 | Papkoff et al. |
| 2010/0203056 A1 | 8/2010 | Irving et al. |
| 2010/0233079 A1 | 9/2010 | Jakob et al. |
| 2010/0233183 A1 | 9/2010 | Triebel et al. |
| 2010/0260668 A1 | 10/2010 | Ghayur et al. |
| 2010/0266531 A1 | 10/2010 | Hsieh et al. |
| 2010/0266617 A1 | 10/2010 | Carven et al. |
| 2011/0008766 A1 | 1/2011 | Ghayur et al. |
| 2011/0044894 A1 | 2/2011 | Karsunky |
| 2011/0044980 A1 | 2/2011 | Ghayur et al. |
| 2011/0054151 A1 | 3/2011 | Lazar et al. |
| 2011/0059106 A1 | 3/2011 | Kuchroo et al. |
| 2011/0081341 A1 | 4/2011 | Honjo et al. |
| 2011/0091372 A1 | 4/2011 | Ghayur et al. |
| 2011/0091463 A1 | 4/2011 | Ghayur et al. |
| 2011/0110852 A1 | 5/2011 | Miller et al. |
| 2011/0123550 A1 | 5/2011 | Shibayama et al. |
| 2011/0136781 A1 | 6/2011 | Zhuo et al. |
| 2011/0150892 A1 | 6/2011 | Thudium et al. |
| 2011/0171220 A1 | 7/2011 | Davis |
| 2011/0177088 A1 | 7/2011 | Olive et al. |
| 2011/0195068 A1 | 8/2011 | Langermann et al. |
| 2011/0209230 A1 | 8/2011 | Korman et al. |
| 2011/0212094 A1 | 9/2011 | Ghayur et al. |
| 2011/0229461 A1 | 9/2011 | Tyson |
| 2011/0236375 A1 | 9/2011 | Lazar et al. |
| 2011/0237573 A1 | 9/2011 | Cheng et al. |
| 2011/0263827 A1 | 10/2011 | Ghayur et al. |
| 2011/0271358 A1 | 11/2011 | Freeman et al. |
| 2011/0280800 A1 | 11/2011 | Wu et al. |
| 2011/0280877 A1 | 11/2011 | Tamada |
| 2011/0287009 A1 | 11/2011 | Scheer et al. |

(56) References Cited

U.S. PATENT DOCUMENTS

| | | |
|---|---|---|
| 2012/0014957 A1 | 1/2012 | Ghayur et al. |
| 2012/0034160 A1 | 2/2012 | Ghayur et al. |
| 2012/0039870 A9 | 2/2012 | Dolk et al. |
| 2012/0039906 A1 | 2/2012 | Olive |
| 2012/0070450 A1 | 3/2012 | Ishikawa et al. |
| 2012/0076805 A1 | 3/2012 | Sharpe et al. |
| 2012/0087858 A1 | 4/2012 | Ghayur et al. |
| 2012/0100131 A1 | 4/2012 | Takayanagi et al. |
| 2012/0107234 A1 | 5/2012 | Pedersen et al. |
| 2012/0114649 A1 | 5/2012 | Langermann et al. |
| 2012/0141501 A1 | 6/2012 | Koshida et al. |
| 2012/0195900 A1 | 8/2012 | Ghayur et al. |
| 2012/0201746 A1 | 8/2012 | Liu et al. |
| 2012/0201824 A1 | 8/2012 | Wasik |
| 2012/0258108 A1 | 10/2012 | Ghayur et al. |
| 2012/0263722 A1 | 10/2012 | Ghayur et al. |
| 2013/0005216 A1 | 1/2013 | Rittberger |
| 2013/0017199 A1 | 1/2013 | Langermann |
| 2013/0022623 A1 | 1/2013 | Karsunky et al. |
| 2013/0095098 A1 | 4/2013 | Tyson |
| 2013/0109843 A1 | 5/2013 | Carven et al. |
| 2013/0133091 A1 | 5/2013 | Korman et al. |
| 2013/0156774 A1 | 6/2013 | Kuchroo et al. |
| 2013/0183688 A1 | 7/2013 | Kuchroo et al. |
| 2013/0202623 A1 | 8/2013 | Chomont et al. |
| 2013/0230514 A1 | 9/2013 | Langermann et al. |
| 2013/0310375 A1 | 11/2013 | Cheng et al. |
| 2013/0324515 A1 | 12/2013 | Zhuo et al. |
| 2014/0044728 A1 | 2/2014 | Takayanagi et al. |
| 2014/0044738 A1 | 2/2014 | Langermann et al. |
| 2014/0065142 A1 | 3/2014 | Roschke et al. |
| 2014/0155678 A1 | 6/2014 | Zeng et al. |
| 2014/0178370 A1 | 6/2014 | Freeman et al. |
| 2014/0212422 A1 | 7/2014 | Korman et al. |
| 2014/0234320 A1 | 8/2014 | Croft et al. |
| 2014/0242094 A1 | 8/2014 | Kuchroo et al. |
| 2014/0274788 A1 | 9/2014 | Ishikawa et al. |
| 2014/0294852 A1 | 10/2014 | Korman et al. |
| 2014/0314714 A1 | 10/2014 | Honjo et al. |
| 2014/0328833 A1 | 11/2014 | Korman et al. |
| 2014/0341902 A1 | 11/2014 | Maecker et al. |
| 2014/0341978 A1 | 11/2014 | Kim et al. |
| 2014/0348743 A1 | 11/2014 | Korman et al. |
| 2015/0017185 A1 | 1/2015 | Akbar et al. |
| 2015/0023986 A1 | 1/2015 | Jones et al. |
| 2015/0079109 A1 | 3/2015 | Li et al. |
| 2015/0086574 A1 | 3/2015 | Karsunky et al. |
| 2015/0093380 A1 | 4/2015 | Honjo et al. |
| 2015/0125386 A1 | 5/2015 | Hansen et al. |
| 2015/0210769 A1 | 7/2015 | Freeman et al. |
| 2015/0218274 A1 | 8/2015 | Sabatos-Peyton et al. |
| 2015/0232555 A1 | 8/2015 | Carven et al. |
| 2015/0259420 A1 | 9/2015 | Triebel et al. |
| 2015/0290316 A1 | 10/2015 | Graziano et al. |
| 2015/0307609 A1 | 10/2015 | Lonberg et al. |
| 2016/0002334 A1 | 1/2016 | Kuchroo et al. |
| 2016/0068601 A1 | 3/2016 | Brogdon et al. |
| 2016/0082014 A1 | 3/2016 | Cheng et al. |
| 2016/0108123 A1 | 4/2016 | Freeman et al. |
| 2016/0159905 A1 | 6/2016 | Abdiche et al. |
| 2016/0222121 A1 | 8/2016 | Johnson et al. |
| 2016/0326178 A1 | 11/2016 | Zhuo et al. |
| 2017/0044259 A1 | 2/2017 | Tipton et al. |
| 2017/0088615 A1 | 3/2017 | Korman et al. |
| 2017/0137514 A1 | 5/2017 | Lonberg et al. |
| 2017/0190777 A1 | 7/2017 | Sabatos-Peyton et al. |
| 2017/0198041 A1 | 7/2017 | Sabatos-Peyton et al. |
| 2017/0209574 A1 | 7/2017 | Cao et al. |
| 2017/0210804 A1 | 7/2017 | Triebel et al. |
| 2017/0247456 A1 | 8/2017 | Freeman et al. |
| 2017/0281624 A1 | 10/2017 | Peters et al. |
| 2017/0304443 A1 | 10/2017 | Lebwohl et al. |
| 2017/0340733 A1 | 11/2017 | Cao |
| 2018/0000832 A1 | 1/2018 | Cheng et al. |
| 2018/0066054 A1 | 3/2018 | Thudium et al. |
| 2018/0086830 A1 | 3/2018 | Triebel et al. |
| 2018/0155427 A1 | 6/2018 | Freeman et al. |
| 2018/0186882 A1 | 7/2018 | Freeman et al. |
| 2018/0207273 A1 | 7/2018 | Dranoff et al. |
| 2018/0222982 A1 | 8/2018 | Dranoff et al. |
| 2018/0282340 A1 | 10/2018 | Zhuo et al. |
| 2018/0340025 A1 | 11/2018 | Dranoff et al. |
| 2018/0371093 A1 | 12/2018 | Bilic et al. |
| 2019/0365746 A1 | 12/2019 | Dobson et al. |
| 2020/0030442 A1 | 1/2020 | Cao |
| 2020/0172617 A1 | 6/2020 | Stein et al. |
| 2020/0223917 A1 | 7/2020 | Sabatos-Peyton et al. |
| 2020/0223924 A1 | 7/2020 | Stein et al. |
| 2020/0277378 A1 | 9/2020 | Sabatos-Peyton et al. |
| 2020/0308277 A1 | 10/2020 | Sabatos-Peyton et al. |
| 2020/0339689 A1 | 10/2020 | Freeman et al. |
| 2020/0377600 A1 | 12/2020 | Johnson et al. |
| 2021/0000951 A1 | 1/2021 | Cao et al. |

FOREIGN PATENT DOCUMENTS

| | | |
|---|---|---|
| EP | 0742795 A1 | 11/1996 |
| EP | 1165616 A1 | 1/2002 |
| EP | 1210424 A1 | 6/2002 |
| EP | 1334659 A1 | 8/2003 |
| EP | 1385533 A1 | 2/2004 |
| EP | 1445264 A1 | 8/2004 |
| EP | 1537878 A1 | 6/2005 |
| EP | 1576014 A1 | 9/2005 |
| EP | 1591527 A1 | 11/2005 |
| EP | 1870399 A1 | 12/2007 |
| EP | 1896582 A1 | 3/2008 |
| EP | 2161336 A1 | 3/2010 |
| EP | 2195347 A1 | 6/2010 |
| EP | 2206517 A1 | 7/2010 |
| EP | 2243493 A1 | 10/2010 |
| EP | 2270051 A2 | 1/2011 |
| EP | 2307050 A1 | 4/2011 |
| EP | 2328920 A2 | 6/2011 |
| EP | 2342228 A1 | 7/2011 |
| EP | 2342229 A1 | 7/2011 |
| EP | 2360254 A1 | 8/2011 |
| EP | 2370593 A2 | 10/2011 |
| EP | 2397155 A1 | 12/2011 |
| EP | 2397156 A1 | 12/2011 |
| EP | 2412825 A1 | 2/2012 |
| EP | 2417984 A1 | 2/2012 |
| EP | 2418278 A2 | 2/2012 |
| EP | 2439272 A2 | 4/2012 |
| EP | 2439273 A2 | 4/2012 |
| EP | 2482849 A2 | 8/2012 |
| EP | 2504364 A1 | 10/2012 |
| EP | 2099447 B1 | 11/2012 |
| EP | 2535354 A1 | 12/2012 |
| EP | 2545076 A1 | 1/2013 |
| EP | 2545078 A1 | 1/2013 |
| EP | 2051990 B1 | 2/2013 |
| EP | 2581113 A1 | 4/2013 |
| EP | 2170959 B1 | 10/2013 |
| EP | 2691112 A1 | 2/2014 |
| EP | 2699264 A1 | 2/2014 |
| EP | 2723381 A2 | 4/2014 |
| EP | 2320940 B1 | 3/2015 |
| EP | 2905030 A1 | 8/2015 |
| EP | 2344474 B1 | 9/2015 |
| EP | 2927240 A1 | 10/2015 |
| EP | 2474545 B1 | 11/2016 |
| EP | 3222634 A1 | 9/2017 |
| JP | H07291996 A | 11/1995 |
| JP | 2002194491 A | 7/2002 |
| JP | 2003029846 A | 1/2003 |
| JP | 2004512005 A | 4/2004 |
| JP | 2006521783 A | 9/2006 |
| JP | 2006340714 A | 12/2006 |
| JP | 2010514791 A | 5/2010 |
| JP | 2012503984 A | 2/2012 |
| RU | 2494107 C2 | 9/2013 |
| WO | 8808135 A1 | 10/1988 |
| WO | 9520605 A1 | 8/1995 |

(56) References Cited

FOREIGN PATENT DOCUMENTS

| | | |
|---|---|---|
| WO | 1996027603 A1 | 9/1996 |
| WO | 9707671 A1 | 3/1997 |
| WO | 0032231 A1 | 6/2000 |
| WO | 0058363 A1 | 10/2000 |
| WO | 0071078 A2 | 11/2000 |
| WO | 0073498 A1 | 12/2000 |
| WO | 0114424 A2 | 3/2001 |
| WO | 0114556 A1 | 3/2001 |
| WO | 0114557 A1 | 3/2001 |
| WO | 0139722 A2 | 6/2001 |
| WO | 01077342 A1 | 10/2001 |
| WO | 01083750 A2 | 11/2001 |
| WO | 200194413 A2 | 12/2001 |
| WO | 0200692 A2 | 1/2002 |
| WO | 0200730 A2 | 1/2002 |
| WO | 0224891 A2 | 3/2002 |
| WO | 2002022577 A2 | 3/2002 |
| WO | 0232378 A2 | 4/2002 |
| WO | 0234205 A2 | 5/2002 |
| WO | 0239813 A1 | 5/2002 |
| WO | 02078731 A1 | 10/2002 |
| WO | 02079499 A1 | 10/2002 |
| WO | 02086083 A2 | 10/2002 |
| WO | 03000066 A1 | 1/2003 |
| WO | 03002722 A2 | 1/2003 |
| WO | 03011911 A1 | 2/2003 |
| WO | 03033644 A2 | 4/2003 |
| WO | 03042402 A2 | 5/2003 |
| WO | 03063792 A2 | 8/2003 |
| WO | 03077914 A1 | 9/2003 |
| WO | 03099196 A2 | 12/2003 |
| WO | 2004004771 A1 | 1/2004 |
| WO | 2004005281 A1 | 1/2004 |
| WO | 2004007679 A2 | 1/2004 |
| WO | 2004056875 A1 | 7/2004 |
| WO | 2004072286 A1 | 8/2004 |
| WO | 2004078928 A2 | 9/2004 |
| WO | 2005027854 A2 | 3/2005 |
| WO | 2005033144 A2 | 4/2005 |
| WO | 2005097211 A2 | 10/2005 |
| WO | 2006004988 A2 | 1/2006 |
| WO | 2006021955 A2 | 3/2006 |
| WO | 2006042237 A2 | 4/2006 |
| WO | 2006121168 A1 | 11/2006 |
| WO | 2006124269 A2 | 11/2006 |
| WO | 2006133396 A2 | 12/2006 |
| WO | 2007005874 A2 | 1/2007 |
| WO | 2007011968 A2 | 1/2007 |
| WO | 2007024705 A2 | 3/2007 |
| WO | 2007024715 A2 | 3/2007 |
| WO | 2007070514 A1 | 6/2007 |
| WO | 2007082154 A2 | 7/2007 |
| WO | 2007084786 A1 | 7/2007 |
| WO | 2007113648 A2 | 10/2007 |
| WO | 2007146968 A2 | 12/2007 |
| WO | 2008016893 A1 | 2/2008 |
| WO | 2008060617 A2 | 5/2008 |
| WO | 2008064157 A1 | 5/2008 |
| WO | 2008071447 A2 | 6/2008 |
| WO | 2008073687 A2 | 6/2008 |
| WO | 2008083174 A2 | 7/2008 |
| WO | 2008085562 A2 | 7/2008 |
| WO | 2008156712 A1 | 12/2008 |
| WO | 2009014708 A2 | 1/2009 |
| WO | 2009024531 A1 | 2/2009 |
| WO | 2009029342 A2 | 3/2009 |
| WO | 2009091547 A1 | 7/2009 |
| WO | 2009097394 A2 | 8/2009 |
| WO | 2009101611 A1 | 8/2009 |
| WO | 2009114335 A2 | 9/2009 |
| WO | 2009120905 A2 | 10/2009 |
| WO | 2009141386 A1 | 11/2009 |
| WO | 2010001617 A1 | 1/2010 |
| WO | 2010019570 A2 | 2/2010 |
| WO | 2010026124 A1 | 3/2010 |
| WO | 2010027423 A2 | 3/2010 |
| WO | 2010027827 A2 | 3/2010 |
| WO | 2010027828 A2 | 3/2010 |
| WO | 2010029082 A1 | 3/2010 |
| WO | 2010029434 A1 | 3/2010 |
| WO | 2010029435 A1 | 3/2010 |
| WO | 2010036959 A2 | 4/2010 |
| WO | 2010051502 A2 | 5/2010 |
| WO | 2010063011 A2 | 6/2010 |
| WO | 2010077634 A1 | 7/2010 |
| WO | 2010084999 A1 | 7/2010 |
| WO | 2010089411 A2 | 8/2010 |
| WO | 2010098788 A2 | 9/2010 |
| WO | 2010101849 A1 | 9/2010 |
| WO | 2010102278 A1 | 9/2010 |
| WO | 2010110346 A1 | 9/2010 |
| WO | 2010117057 A1 | 10/2010 |
| WO | 2011005481 A1 | 1/2011 |
| WO | 2011011027 A1 | 1/2011 |
| WO | 2011025927 A1 | 3/2011 |
| WO | 2011041613 A2 | 4/2011 |
| WO | 2011066342 A2 | 6/2011 |
| WO | 2011066389 A1 | 6/2011 |
| WO | 2011069104 A2 | 6/2011 |
| WO | 2011076786 A1 | 6/2011 |
| WO | 2011100841 A1 | 8/2011 |
| WO | 2011110604 A1 | 9/2011 |
| WO | 2011110621 A1 | 9/2011 |
| WO | 2011131472 A1 | 10/2011 |
| WO | 2011155607 A1 | 12/2011 |
| WO | 2011159877 A2 | 12/2011 |
| WO | 2012018538 A2 | 2/2012 |
| WO | 2012022814 A1 | 2/2012 |
| WO | 2012064733 A2 | 5/2012 |
| WO | 2012079000 A1 | 6/2012 |
| WO | 2012106587 A1 | 8/2012 |
| WO | 2012135408 A1 | 10/2012 |
| WO | 2012145493 A1 | 10/2012 |
| WO | 2012177624 A2 | 12/2012 |
| WO | 2012177788 A1 | 12/2012 |
| WO | 2013006490 A2 | 1/2013 |
| WO | 2013006727 A1 | 1/2013 |
| WO | 2013019906 A1 | 2/2013 |
| WO | WO-2013019906 A1 * | 2/2013 ....... A61K 39/39558 |
| WO | 2013043647 A1 | 3/2013 |
| WO | 2013066761 A1 | 5/2013 |
| WO | 2013079174 A1 | 6/2013 |
| WO | 2013079945 A1 | 6/2013 |
| WO | 2013169693 A1 | 11/2013 |
| WO | 2013173223 A1 | 11/2013 |
| WO | 2013181452 A1 | 12/2013 |
| WO | 2013181634 A2 | 12/2013 |
| WO | 2013184757 A1 | 12/2013 |
| WO | 2014008218 A1 | 1/2014 |
| WO | 2014018632 A1 | 1/2014 |
| WO | 2014022138 A2 | 2/2014 |
| WO | 2014022332 A1 | 2/2014 |
| WO | 2014022758 A1 | 2/2014 |
| WO | 2014047350 A1 | 3/2014 |
| WO | 2014055648 A1 | 4/2014 |
| WO | 2014055897 A2 | 4/2014 |
| WO | 2014072493 A1 | 5/2014 |
| WO | 2014085318 A1 | 6/2014 |
| WO | 2014100079 A1 | 6/2014 |
| WO | 2014165082 A2 | 10/2014 |
| WO | 2014165422 A1 | 10/2014 |
| WO | 2014179664 A2 | 11/2014 |
| WO | 2014189805 A1 | 11/2014 |
| WO | 2014195852 A1 | 12/2014 |
| WO | WO-2014204791 A1 * | 12/2014 ............. A61K 47/38 |
| WO | 2015009856 A2 | 1/2015 |
| WO | 2015026634 A1 | 2/2015 |
| WO | 2015026684 A1 | 2/2015 |
| WO | 2015035606 A1 | 3/2015 |
| WO | 2015036394 A1 | 3/2015 |
| WO | 2015036499 A1 | 3/2015 |
| WO | 2015036511 A1 | 3/2015 |
| WO | 2015042246 A1 | 3/2015 |
| WO | 2015048312 A1 | 4/2015 |

(56) References Cited

FOREIGN PATENT DOCUMENTS

| | | |
|---|---|---|
| WO | 2015048520 A1 | 4/2015 |
| WO | 2015061668 A1 | 4/2015 |
| WO | 2015070060 A1 | 5/2015 |
| WO | 2015075725 A1 | 5/2015 |
| WO | 2015081158 A1 | 6/2015 |
| WO | 2015085847 A1 | 6/2015 |
| WO | 2015088847 A1 | 6/2015 |
| WO | 2015095423 A2 | 6/2015 |
| WO | 2015095811 A2 | 6/2015 |
| WO | 2015103602 A1 | 7/2015 |
| WO | 2015109124 A2 | 7/2015 |
| WO | 2015109391 A1 | 7/2015 |
| WO | 2015112800 A1 | 7/2015 |
| WO | 2015112805 A1 | 7/2015 |
| WO | 2015112900 A1 | 7/2015 |
| WO | 2015117002 A1 | 8/2015 |
| WO | 2015118175 A2 | 8/2015 |
| WO | 2015119944 A1 | 8/2015 |
| WO | 2015120198 A1 | 8/2015 |
| WO | 2015134605 A1 | 9/2015 |
| WO | 2015138920 A1 | 9/2015 |
| WO | 2015176033 A1 | 11/2015 |
| WO | 2015181342 A1 | 12/2015 |
| WO | 2015195163 A1 | 12/2015 |
| WO | 2016000619 A1 | 1/2016 |
| WO | 2016028672 A1 | 2/2016 |
| WO | 2016040880 A1 | 3/2016 |
| WO | 2016040882 A1 | 3/2016 |
| WO | 2016040892 A1 | 3/2016 |
| WO | 2016054555 A2 | 4/2016 |
| WO | 2016061142 A1 | 4/2016 |
| WO | 2016069727 A1 | 5/2016 |
| WO | 2016079049 A1 | 5/2016 |
| WO | 2016100882 A1 | 6/2016 |
| WO | 2016161239 A1 | 10/2016 |
| WO | 2016166656 A1 | 10/2016 |
| WO | 2016168716 A1 | 10/2016 |
| WO | 2017017623 A1 | 2/2017 |
| WO | 2017017624 A1 | 2/2017 |
| WO | 2017019894 A1 | 2/2017 |
| WO | 2017019896 A1 | 2/2017 |
| WO | 2017019897 A1 | 2/2017 |
| WO | 2017034916 A1 | 3/2017 |
| WO | 2017097407 A1 | 6/2017 |
| WO | 2017106656 A1 | 6/2017 |
| WO | 2017189433 A1 | 11/2017 |
| WO | 2018150312 A1 | 8/2018 |
| WO | 2019006007 A1 | 1/2019 |
| WO | 2019018640 A1 | 1/2019 |
| WO | 2019018730 A1 | 1/2019 |
| WO | 2019099838 A1 | 5/2019 |
| WO | 2019180576 A1 | 9/2019 |
| WO | 2019200229 A1 | 10/2019 |
| WO | 2021079188 A1 | 4/2021 |
| WO | 2021079195 A1 | 4/2021 |
| WO | 2021123902 A1 | 6/2021 |
| WO | 2021144657 A1 | 7/2021 |

OTHER PUBLICATIONS

Abbas, A.K., et al., Cellular and Molecular Immunobiology, 2nd ed., pp. 8, 47-50, W.B. Saunders Company, United States (1991).

Acquaviva et al: "FGFR3 Translocations in Bladder Cancer: Differential Sensitivity to HSP90 Inhibition Based on Drug Metabolism". Molecular Cancer Research, vol. 12. No. 7. Jul. 1, 2014 (Jul. 1, 2014). pp. 1042-1054.

Adams, G.P. and Weiner, L.M., "Monoclonal antibody therapy of cancer," Nature Biotechnology 23(9):1147-1157, Nature Publishing Group, United States (2005).

Agata, Y., et al., "Expression of the PD-1 antigen on the surface of stimulated mouse T and B lymphocytes," International Immunology 8(5):765-772, Oxford University Press, England (1996).

Allard et al. "Targeting CD73 Enhances the Antitumor Activity of Anti-FD-1 and Anti-CTLA-4 mAbs" Clinical Cancer Research (2013) vol. 19, No. 20, pp. 5626-5635.

Allison, J.P. and Krummel, M.F., "The Yin and Yang of T Cell Costimulation," Science 270(5238):932-933, American Association for the Advancement of Science, United States (1995).

Almagro et al. "Humanization of Antibodies" Frontiers in Bioscience (2008) vol. 13, pp. 1619-1633.

Amin et al: "Nivolumab (anti-PD-1; BMS-936558, ONO-4538) in combination with sunitinib or pazopanib in patients (pts) with metastatic renal cell carcinoma (mRCC)" Journal of Clinical Oncology (2014) vol. 32, No. 15 suppl, Abstract 5010.

Anderson et al. "Tim-3, a negative regulator of anti-tumor immunity" Current Opinion in Immunology (2012) vol. 24, No. 2, pp. 213-216.

Andre, E., et al., "Precise Characterization of the Epitope Recognized by a Monoclonal Antibody Against *Escherichia coli* RNA Polymerase," Hybridoma 24(1):1-5, Mary Ann Liebert, Inc., United States (Feb. 2005).

Ansari, M.J., et al., "The programmed death-1 (PD-1) pathway regulates autoimmune diabetes in nonobese diabetic (NOD) mice," The Journal of Experimental Medicine 198(1)163-69, The Rockefeller University Press, United States (2003).

Ansell, S.M., et al., "PD-1 Blockade with Nivolumab in Relapsed or Refractory Hodgkin's Lymphoma," The New England Journal of Medicine 372(4):311-319, Massachusetts Medical Society, United States (Jan. 22, 2015).

Armand, P., et al., "289 Nivolumab in Patients with relapsed or Refractory Hodgkin Lymphoma-Preliminary Safety, Efficacy and Biomarker Results of a Phase I Study," 56th ASH Annual Meeting and Exposition, Abstracts & Program, San Francisco, CA, Dec.6-9, 2014.

Aspeslagh et al. "Rationale for anti-OX40 cancer immunotherapy" European Journal of Cancer (2016) vol. 52, pp. 50-66.

Barber, Daniel L., et al.; "Restoring function in exhausted CD8 T cells during chronic viral infection"; Nature 439:682-687 (2006).

Bellucci et al: "JAK1 and JAK2 Modulate Tumor Cell Susceptibility To Natural Killer (NK) Cells Through Regulation of PDLI Expression", Blood (Nov. 15, 2013), Retrieved from the Internet: URL:http://www.bloodjournal.orgjcontent/122/21/3472.full.pdf [retrieved on Apr. 2014, 2016].

Bennett, F., et al., "Program death-1 engagement upon TCR activation has distinct effects on costimulation and cytokine-driven proliferation: attenuation of ICOS, IL-4, and IL-21, but not CD28, IL-7, and IL-15 responses," The Journal of Immunology 170(2):711-718, The American Association of Immunologists, United States (2003).

Benson et al. "The PD-1/PD-L1 axis modulates the natural killer cell versus multiple myeloma effect: a therapeutic target for CT-011, a novel monoclonal anti-PD-1 antibody" Blood (2010) vol. 116, No. 13, pp. 2286-2294.

Berg, J.M., et al., "The Immune System," in Biochemistry 5th ed., pp. 921-950, W.H. Freeman and Company, United States (2002).

Berger, R., et al., "Phase I safety and pharmacokinetic study of CT-011, a humanized antibody interacting with PD-1, in patients with advanced hematologic malignancies," Clinical Cancer Research 14(10):3044-3051, American Association for CancerResearch, United States (2008).

Blank et al "Combination of targeted therapy and immunotherapy in melanoma" Cancer Immunol Immunother (2011) vol. 60, pp. 1359-1371.

Blank, C., et al., "Interaction of PD-L1 on tumor cells with PD-1 on tumor-specific T cells as a mechanism of immune evasion: implications for tumor immunotherapy," Cancer Immunology Immunotherapy 54(4):307-314, Springer-Verlag, Germany (2005).

Blank, C., et al., "PD-L1/B7H-1 inhibits the effector phase of tumor rejection by T cell receptor (TCR) transgenic CD8+ T cells," Cancer Research 64(3): 1140-1145, American Association for Cancer Research, United States (2004).

Blank, Christian, et al.; "Contribution of the PD-L1/PD-1 pathway to T-cell exhaustion: an update on implications for chronic infections and tumor evasion"; Cancer Immunol. Immunotherapy; 56(5):739-745 (2007).

(56) References Cited

OTHER PUBLICATIONS

Blazar, B.R., et al., "Infusion of anti-B7.1 (CD80) and anti-B7.2 (CD86) monoclenal antibodies inhibits murine graft-versus-host disease lethality in part via direct effects on CD4+ and CD8+ T cells," The Journal of Immunology 157(8):3250-3259, TheAmerican Association of Immunologists, United States (1996).
Brahmer, J.R., et al., "Safety and activity of MDX-1106 (ONO-4538) anti-PD-1 monoclonal antibody in patients with selected refractory or relapsed malignancies," Journal of Clinical Oncology 26:Abstract No. 3006, American Society of ClinicalOncology, United States (2008).
Brahmer., J.R., et al., "Phase I study of single-agent anti-programmed death-1 (MDX-1106) in refractory solid tumors: Safety, clinical activity, pharmacodynamics, and immunologic correlates," Journal of Clinical Oncology 28(19):3167-3175, AmericanSociety of Clinical Oncology, United States (2005).
Brown et al., "Blockade of Programmed Death-1 Ligands on Dendritic Cells Enhances T Cell Activation and Cytokine Production", J. Immunol. (2003) vol. 170, pp. 1257-1266.
Brown et al., "Tolerance to Single, but Not Multiple, Amino Acid Replacements in Antibody VH CDR2: A Means of Minimizing B Cell Wastage from Somatic Hypermutation?" J Immunol (1996) vol. 156, pp. 3285-3291.
Brown, J.A., et al., "Expression and functional consequences PD-1 ligands on natural APCS and tumors," The FASEB Journal 15(4):A345 (abstract No. 275.23), Federation of American Societies for Experimental Biology, United States (2001).
Campbell, A.M., "Characterisation of monoclonal antibodies," in Laboratory Techniques in Biochemistry and Molecular Biology, Monoclonal Antibody Technology: The Production and Characterization of Rodent and Human Hybridomas, vol. 13, pp. 186-215,Elsevier, the Netherlands (1984).
Carreno, B,M, and Collins, M., "The B7 family of ligands and its receptors: new pathways for costimulation and inhibition of immune responses," Annual Review of Immunology 20:29-53, Annual Reviews, United States (2002).
Carreno, B.M., "BTLA: a new inhibitory receptor with a B7-like ligand," TRENDS in Immunology 24(10):524-527, Elsevier, England (2003).
Carter, L.L. and Carreno, B.M., et al., "Cytotoxic T-lymphocyte antigen-4 and programmed death-1 function as negative regulators of lymphocyte activation," Immunologic Research 28(1):49-59, Humana Press, United States (2003).
Carter, L.L., et al., "PD-1:PD-L inhibitory pathway affects both CD4(+) and CD8(+) T cells and is overcome by IL-2," European Journal of Immunology 32(3):634-643, WILEY-VCH Verlag GmbH, Germany (2002).
Chan et al. "Therapeutic antibodies for autoimmunity and inflammation" Nature Reviews Immunology (2010) vol. 10, pp. 301-316.
Chen, L., "Co-inhibitory molecules of the B7-CD28 family in the control of T-cell immunity," Nature Reviews Immunology 4(5):336-347, Nature Publishing Group, England (2004).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).
Chervontseva A M et al: "Effect of cytarabine on expression of cell adhesion molecules and on endothelium-leukocyte interaction in vitro.", Terapevticheskii Arkhiv 2006, vol. 78, No. 7, 2006, pp. 67-72.
Chesi et al., "IAP antagonists induce anti-tumor immunity in multiple myeloma," Nat Med (2016) vol. 22, No. 12, pp. 1411-1420.
Christiansen et al: "Eradication of solid tumors using histone deacetylase inhibitors combined with immune-stimulating antibodies", Proceedings of the National Academy of Sciences, vol. 108 No 10, Feb. 22, 2011 (Feb. 22, 2011), pp. 4141-4146.
Christiansson Lisa et al: "The tyrosine kinase inhibitors imatinib and dasatinib reduce myeloid suppressor cells and release effector lymphocyte responses.", Molecular Cancer Therapeutics, vol. 14, No. 5, May 2015 (May 2015), pp. 1181-1191.

ClincalTrials.gov Identifier: NCT01988896 "A Phase 1 b Study of MPDL3280A (an Engineered Anti-PDL1 Antibody) in Combination With Cobimetinib in Patients With Locally Advanced or Metastatic Solid Tumors" Clinicaltrials.gov, last updated Dec. 1, 2014.
ClincalTrials.gov Identifier: NCT02323126 "Study of Efficacy and Safety of Nivolumab in Combination With EGF816 and of Nivolumab in Combination With INC280 in Patients With Previously Treated Non-small Cell Lung Cancer (EGF816)," Clinicaltrials.gov, last updated Jun. 6, 2018.
ClinicalTrials.gov Identifier: NCT02040064 "Tolerability and Efficacy of Tremelimumab in Combination With Gefitinib in NSCLC Patients", ClinicalTrials.gov; last updated Jan. 17, 2014.
ClinicalTrials.gov Identifier: NCT02263508 "A Phase 1 b/3, Multicenter, Open-label Trial of Tafimogene Laherparepvec in Combination With Pembrolizumab (MK-3475) for Treatment of Unresected,Stage IIIB to IVM1c Melanoma (MASTERKEY-265)", ClinicalTrials.gov; last updated Jun. 22, 2015.
ClinicalTrials.gov Identifier: NCT02339571 "Randomized Phase II/III Study of Nivolumab Plus Ipilimumab Plus Sargramostim Versus Nivolumab Plus Ipilimumab in Patients With Unresectable Stage III or Stage IV Melanoma", ClinicalTrials.gov; last updated Apr. 9, 2015.
Cloeckaert, A., et al., "O-Polysaccharide epitopic heterogeneity at the surface of Brucella spp.studied by enzyme-inked immunosorbent assay and flow cytometry," Clinical and Diagnostic Laboratory Immunology 5(6):862-870, American Society forMicrobiology, United States (1998).
Collins et al., "The B7 family of immune-regulatory ligands" Genome Biology (2005) vol. 6 No 223.
Iwai, Y., et al., "Microanatomical localization of PD-1 in human tonsils," Immunology Letters 83(3):215-220, Elsevier, Netherlands (2002).
Iwai, Y., et al., "PD-1 inhibits antiviral immunity at the effector phase in the liver," The Journal of Experimental Medicine 198(1):39-50, The Rockefeller University Press, United States (2003).
Jason-Moller, L., et al., "Overview of Biacore Systems and Their Applications," Current Protocols in Protein Science S45:19.13.1-19.13.14, John Wiley & Sons, Inc., United States (2006).
Jiang et al, "mTOR Kinase Inhibitor AZD8855 Enhances the Inmunotherapeutic Activity of an Agonist CD40 Antibody in Cancer Treatment" Cancer Research (2011) vol. 71 No 12, pp. 4074-4084.
Jiang X et al: "The activation of MAPK in melanoma cells resistant to BRAF inhibition promotes PD-L1 expression that is reversible by MEK and PI3K inhibition", Clinical Cancer Research, The American Association for Cancer Research, US, vol. 19, No. 3, Feb. 1, 2013 (Feb. 1, 2013). pp. 598-609.
Johne, B., "Protocol: Epitope Mapping by Surface Plasmon Resonance in the BIAcore," Molecular Biotechnology 9(1):65-71, Humana Press, United States (1998).
Ju et al., "T cell immunoglobulin-and mucin-domain-containing molecule-3 (Tim-3) mediates natural killer cell suppression in chronic hepatitis B" Journal of Hepatology (2010) vol. 52 No 3 pp. 322-329.
Kanai, T., et al., "Blockade of B7-H1 Suppresses the Development of Chronic Intestinal Inflammation," The Journal of Immunology 171(8):4156-4163, American Association of Immunologists, Inc., United States (2003).
Karu et al., "Recombinant Antibody Technology," ILAR Journal, vol. 37, No. 3, pp. 132-141 (1995).
Kasagi, S., et al., "Anti-programmed cell death 1 antibody reduces CD4+PD-1+ T cells and relieves the lupus-like nephritis of NZB/W FI mice," The Journal Immunology 184(5):2337-2347, The American Association of Immunologists, United States (2010).
Kaveh, S., "Epitope and idiotope mapping using monoclonal antibodies," Medthods in Molecular Biology 51:171-181, Humana Press, United States (1995).
Kearley et al., "Th-2 driven, allergen-induced airway inflammation is reduced after treatment with anti-Tim-3 antibody in vivo" The Journal of Experimental Medicine (2007) vol. 204 No 6 pp. 1289-1294.
Keytruda (pembrolizumab) Drug Label, Initial U.S. Approval: 2014, Revised Oct. 2016.

(56) References Cited

OTHER PUBLICATIONS

Kier et al., "PD-1 and its ligands in tolerance and immunity" Annu. Rev. Immunol. (2008) vol. 26 pp. 677-704.
Kikushige et al., "TIM-3 Is a Promising Target to Selectively Kill Acute Myeloid Leukemia Stem Cells" Cell Stem Cell (2010) vol. 7 pp. 708-717.
Kim et al: "Eradication of metastatic mouse cancers resistant to irrmune checkpoint blockade by suppression of myeloid-derived cells. (Includes Supporting Information)", Proceedings of the National Academy of Sciences of The United States of America, vol. 111, No. 32, Aug. 12, 2014 (Aug. 12, 2014), pp. 11774-11777.
Kirkwood et al., "Immunotherapy of cancer in 2012" CA: A Cancer Journal for Clinicians (2012) vol. 62 No. 5 pp. 309-335.
Klein Jan M et al: "The histone deacetylase inhibitor LBH589 (panobinostat) modulates the crosstalk of lymphocytes with Hodgkin lymphoma cell lines.", Plos One (2013) vol. 8, No. 11, E79582, 2813, pp. 1-6.
Knights et al., "Inhibitor of apoptosis protein (IAP) antagonists demonstrate divergent immunomodulatory properties in human immune subsets with implications for combination therapy" Cancer Immunology and Immunotherapy (2013) vol. 62 No. 2 pp. 321-335.
Koga, N., et al., "Blockade of the interaction between PD-1 and PD-L1 accelerates graft arterial disease in cardiac allografts," Arteriosclerosis, Thrombosis, and Vascular Biology 24(11):2057-2062, American Heart Association, Inc., United States(2004).
Konishi, J., et al., "B7-H1 expression on non-small cell lung cancer cells and its relationship with tumor-infillrating ymphocytes and their PD-1 expression," Clinical Cancer Research 10(15)15094-5100, American Association for Dancer Research,United States (2004).
Korman et al, "Checkpoint Blockade in Cancer Immunotherapy" Adv Immunol (2006) vol. 90 pp. 297-339.
Ladner, R.C., "Mapping the epitopes of Antibodies," Biotechnology and Genetic Engineering Reviews 24(1):1-30, Taylor & Francis, England (2007).
Laricchia,Robbio, L., et al., "Mapping of Monoclonal Antibody-and Receptor-Binding Domains on Human Granulocyte-Macrophage Colony-Stimulation Factor (rhGM-CSF) Using a Surface Plasmon Resonance-Based Biosensor," Hybridoma 15(5):343-350, Mary AnnLiebert, Inc. United States (1996).
Latchman, Y., et al., "PD-L2 is a second ligand for PD-1 and inhibits T cell activation," Nature Immunology 2(3):261-268, Nature Publishing Group, United States (2001).
Leach, D.R., et al., "Enhancement of antitumor immunity by CTLA-4 blockade," Science 271(5256):1734-1736, American Association for the Advancement of Science, United States (1996).
Lesokhin, A.M., et al., "291 Preliminary Results of a Phase I Study of Nivolumab (BMS-936558) in Patients with Relapsed of Refractory Lymphoid Malignancies," 56th ASH Annual Meeting and Exposition, Abstracts & Program, San Francisco, CA, UnitedStates, Dec. 6-9, 2014.
Lewis, D.E., et al., "Tumor Necrosis Factor-.alpha. and CD80 Modulate CD28 Expression through a Similar Mechanism of T-cell Receptor-Independent of Transcription," The Journal of Biological Chemistry 279(28):29130-29138, The American Society forBiochemistry and Molecular Biology, Inc., United States (2004).
Li et al., "Contribution of PD-L1 to oncogenesis of lymphoma and its RNAi-based targeting therapy" Leukemia & Lymphoma (2012) vol. 53, No. 10, pp. 2015-2023.
Li, L., et al., "A pathway regulated by cell cycle inhibitor p27Kip1 and checkpoint inhibitor Smad3 is involved in the induction of T cell tolerance," Nature Immunology 7(11):1157-1165, Nature Publishing, United States (2006).
Li, L., et al., "CD4+CD25+ regulatory T-cell lines from human cord blood have functional and molecular properties and T-cell anergy," Blood 106(9):3068-3073, American Society of Hematology, United States (Nov. 2005).
Li, L., et al., "IL-1beta-Mediated Signals Preferentially Drive Conversion of Regulatory T Cells but Not Coventional T Cells into IL-17-Producing Cells," The Journal of Immunology 185(7):4148-4153, American Association of Immunologists, Inc., UnitedStates (2010).
Li, L., et al., "Rap1-GTP is a Negative Regulator of Th Cell Function and Promotes the Generation of CD4+CD103+ Regulatory T Cells In Vivo," The Journal of Immunology 175(5):3133-3139, American Association of Immunologists, Inc., United States (Sep. 2005).
Li, L., et al., "The cyclin dependent kinase inhibitor (R)-roscovitine prevents alloreactive T cell clonal expansion and protects against acute GvHD," Cell Cycle 8(11):1794-1802, Landes Bioscience, United States (2009).
Lin, David Yin-Wei, et al.; "The PD-1/PD-L1 complex resembles the antigen-binding Fv domains of antibodies and T cell receptors"; Proc. Natl. Acad. Sci. USA 105(8):3011-3016 (2008).
Linsley et al., "Intracellular Trafficking of CTLA-4 and Focal Localization Towards Sites of TCR Engagement" Immunity (1996) vol. 4 pp. 535-543.
List of clinical trials identified in ClinicalTrials.gov relating to PDR001 as of Dec. 22, 2016.
Liu et al., "A Novel Kinase Inhibitor, INC28060, Blocks c-MET-Dependent Signaling, Neoplastic Activities, and Cross-Talk with EGFR and HER-3," Clin Cancer Res (2011) vol. 17, No. 22, pp. 7127-7138.
Lonberg, N., et al., "Antigen-specific human antibodies from mice comprising four distinct genetic modifications," Nature 368(6474):856-859, Nature Publishing Group, United States (1994).
Lute, K.D., et al., "Human CTLA4 knock-in mice unravel the quantitative link between tumor immunity and autoimmunity induced by anti-CTLA-4 antibodies," Blood 106(9):3127-3133, American Society of Hematology, United States (2005).
Mahoney et al. "The Next Immune-Checkpoint Inhibitors: PD-1/PDD-L1 Blockade in Melanoma" Clinical Therapeutics (2015) vol. 37, No. 4, pp. 764-782.
Marri et al., "Human Biochemistry" Mir Publishing, Moscow (1993) vol. 1, p. 34. Russian.
Masters et al., "Abstract 5016: Antitumor activity of anti-PD-1 in combination with tyrosine kinase inhibitors in a preclinical renal cell carcinoma model" AACR Annual Meeting (2014) vol. 74, No. 5016.
May, K.F., Jr., et al., "Anti-human CTLA-4 monoclonal antibody promotes T-cell expansion and immunity it a hu-PBL-SCID model: a new method for preclinical screening of costimulatory monoclonal antibodies," Blood 105(3):1114-1120, American Society ofHematology, United States (2005).
Mittendorf Elizabeth A et al: "PD-L1 expression in triple-negative breast cancer." Cancer Immunology Research, vol. 2. no. 4. Apr. 2014 (Apr. 2014). pp. 361-370.
Moreira Da Silva, "Nivolumab Anti-PD-1 monoclonal antibody cancer immunotherapy" Drugs of the Future (2014) vol. 39 No 1 pp. 15-24.
Naing et al. "A first-in-human phase I study of the anti-PD-1 antibody PDR001 in patients with advanced solid tumors" 2016 ASCO Annual Meeting, J Clin Oncol 34, 2016 (suppl; abstr 3060).
Nakae et al., "Mast cells enhance T cell activation: importance of mast cell costimulatory molecules and secreted INF" The Journal of Immunology (2006) vol. 176 No 4 pp. 2238-2248.
Nellore, A., et al., "The cyclin dependent kinase inhibitor (R)-roscovitine mediates selective suppression of alloreactive human T cells but preserves pathogen-specific and leukemia-specific effectors," Clinical Immunology 152(1-2):48-57 (May-Jun. 2014; Epub Mar. 12, 2014).
Nielsen, C., et al., "A putative regulatory polymorphism in PD-1 is associated with nephropathy in a population-based cohort of systemic lupus erythematosus patients," Lupus 13(7):510-516, SAGE, England (2004).
Verbrugge et al: "The curative outcome of radioinmunotherapy in a mouse breast cancer model relies on mTOR signaling", Radiation Research. Radiation Research Society, GB, (2014) vol. 182 No 2 pp. 219-229.

(56) References Cited

OTHER PUBLICATIONS

Vietta et al. "Considering Therapeutic Antibodies" Science (2006) vol. 313, pp. 308-309.
Waldmann, Thomas A.; "Effective cancer therapy through immunomodulation"; Annual Rev.; 57(1):65-81 (2006).
Wang et al. "In Vitro Characterization of the Anti-PD-1 Antibody Nivolumab, BMS-936558, and In Vivo Toxicology in Non-Human Primates" Cancer Immunology Research (2014) vol. 2, No. 9, pp. 846-856.
Wang et al., "The Mdm2 inhibitor, NVP-CGM097, in combination with the BRAF inhibitor NVP-LGX818 elicits synergistic antitumor effects in melanoma" Cancer Research (2014), Abstract 5466, Retrieved from the Internet: URL: http://cancerres.aacrjournals.orgjcontent/74/19 Supplement/5466 [retrieved on Apr. 14, 2016].
Wang et al., "VISTA, a novel mouse Ig superfamily ligand that negatively regulates T cell responses" The Journal of Experimental Medicine (2011) vol. 208 No. 3 pp. 577-592.
Wang et al: "Abstract 2929: The Mdm2 inhibitor NVP-CGM097 enhances the anti-tumor activity of NVP-LDK378 in ALK mutant neuroblastomamodels", Cancer Research (2014) Retrieved from the Internet: URL:http:jjcancerres.aacrjournals.orgjcontent/74/19 Supplement/2929 [retrieved on Apr. 14, 2016].
Weber, J.S., et al., "Safety, Efficacy, and Biomarkers of Nivolumab with Vaccine in Ipilimumab-Refractory or -Naive Melanoma," Journal of Clinical Oncology 31 (34):4311-4318, American Society of Clinical Oncology, United States (2013).
Weisberg et al., "Smac mimetics: implications for enhancement of targeted therapies in leukemia: Treating leukemia with Smac mimetics," Leukemia (2010) vol. 24, No. 12, pp. 2100-2109.
Wilson, I.A. and Stanfield, R.L., "Antibody-antigen interactions," Current Opinion in Sturctural Biology 3:113-118, Current Biology, United States (1993).
Winslow, R., "New Cancer Drugs Harness Power of Immune System", The Wall Street Journal, May 15, 2013, accessed at http://www.wsj.com/articles/SB10001424127887323398204578485401089823868, accessed on Jun. 1, 2016, 4 pages.
Wolchok, J.D., et al., "Nivolumab plus Ipilimumab in Advanced Melanoma," The New England Journal of Medicine 369(2):122-133, Massachusetts Medical Society, United States (2013).
Wong, R.M., et al., "Programmed death-1 blockade enhances expansion and functional capacity of human melanoma antigen-specific CTLs," International Immunology 19(10):1223-1234, Oxford University Press, England (2007).
Woods David M et al: "HDAC Inhibition Upregulates PD-1 Ligands in Melanoma and Augments Immunotherapy with PD-1 Blockade," Cancer Immunology Research, vol. 3, No. 12, Dec. 2015 (Dec. 2015), pp. 1375-1385.
Woods David M et al: "The antimelanoma activity of the histone deacetylase inhibitor panobinostat (LBH589) is mediated by direct tumor cytotoxicity and increased tumor immunogenicity", Melanoma Research, vol. 23, No. 5, Oct. 2013 (Oct. 2013), pp. 341-348.
Woods et al: "Abstract 4090: Inhibition of class I histone deacetylases promotes robust and durable enhancement of PDL1 expression in melanoma: Rationale for combination therapy", Cancer Research (2014) Retrieved from the Internet: URL:http://cancerres.aacrjournals.orgjcontent/74/19Supplement/4090.short [retrieved on Apr. 14, 2016].
Wu, K-P., et al., "Structural Basis of a Flavivirus Recognized by Its Neutralizing Antibody: Solution Structure of the Domain III of the Japanese Encephalitis Virus Envelope Protein," The Journal of Biological Chemistry 278(46):46007-46013, AmericanSociety for Biochemistry and Molecular Biology, Inc., United States (Nov. 2003).
Yamazaki, T., et al., "Expression of programmed death 1 ligands by murine T cells and APC," The Journal of Immunology 169(10):5538-5545, The American Association of Immunologists, United States (2002).
Yang et al., "Lack of TIM-3 Immunoregulation in Multiple Sclerosis" The Journal of Immunology (2008) vol. 180 No. 7 pp. 4409-4414.
Yi, J., et al., "Mapping the Epitope of an Inhibitory Monoclonal Antibody to the C-terminal DNA-binding Domain of HIV-1 Integrase," The Journal of Biological Chemistry 277(14):12164-12174, American Society for Biochemistry and Molecular Biology,Inc., United States (2002).
Youngnak, Pompan, et al.; "Differential binding properties of B7-H1 and B7-DC to programmed death-1"; Biochem. Biophys. Res. Commun.; 307:672-677 (2003).
Yuan Z et al, "Blockade of inhibitors of apoptosis (IAPs) in combination with tumor-targeted delivery of tumor necrosis factor-[alpha] leads to synergistic antitumor activity" Cancer Gene Therapy (2013) vol. 20 No. 1 pp. 46-56.
Zehavi-Willner, Tova, et al.; "The mitogenic activity of staphylococcal enterotoxin B (Seb): a monovalent T cell mitogen that stimulates cytolytic T lymphocytes but cannot mediate their lytic interaction"; J. Immunol.; 137(8):2682-2687 (1986).
Zhang, "Oral 31—PD1 Axis Inhibition," Abstract from Poster Presentation from International Association for the Study of Lung Cancer, Aug. 9, 2015, retrieved from library.iaslc.org/search-speaker?search_speaker=30076.
Zhang, Xuewu, et al.; "Structural and Functional Ana ysis of the Costimulatory Receptor Programmed Death-1"; Immunity; 20:337-347 (2004).
Zhou et al., "Coexpression of Tim-3 and PD-1 identifies a CD8+ T-cell exhaustion phenotype in mice with disseminated acute myelogenous leukemia" Blood (2011) vol. 117 No 17 pp. 4501-4510.
Zhuang J et al: "Selective IAP inhibition results in sensitization of unstimulated but not CD40-stimulated chronic lymphocytic leukaemia cells to TRAIL-induced apoptosis" Pharmacology Research & Perspectives (2014) vol. 2 Issue 6, Article E00081, 14 pages.
Zou, W. and Chen, L., "Inhibitory B7-family Molecules in the Tumour Microenvironment," Nature Reviews Immunology 8(6):467-477, Nature Publishing Group, England (2008).
Zuberek, K., "The role of in vivo PD-1/PD-L1 interactions in syngeneic and allogeneic antitumor responses in murine tumor models," Blood 98(11):42B (2001).
Zuberek, Krystyna, et al.; "In vitro and in vivo expression regulation of PD-1 and PD-L1 in murine tumor models" Blood; 98(11 Part 1):25a (2001).
Cragg, M.S. et al., "Complement-mediated lysis by anti-CD20 mAb correlated with segregation into lipid rafts," Blood 101(3):1045-1052, American Society of Hematology, United States (2003).
Creelan, B.C., "Update on Immune Checkpoint Inhibitors in Lung Cancer," Journal of the Moffitt Cancer Center 21(1):80-89, H. Lee Moffitt Cancer Center and Research Institute, United States (2014).
Druse, J.M. and Lewis, R.E., "Antigens and Immunogens," in Atlas of Immunology, 2nd ed., pp. 105-126, CRC Press, United States (Dec. 29, 2003).
Davies, D.R. and Cohen, G.H., "Interactions of protein antigens with antibodies," Proceedings of the National Academy of Sciences USA 93(1):7-12, National Academy of Sciences, United States (1996).
Davies, Julian, et al.; "Affinity improvement of single antibody VH domains: residues in all three hypervariable regions affect antigen binding"; ; 2:169-179 (1996).
Del-Rio, Maria-Luisa, et al.; "Antibody-mediated signaling through PD-1 costimulates T cells and enhances CD28-dependent proliferation"; Eur. J. Immunol.; 35(12):3545-3560 (2005).
Dey et al: "Nutl in-3 inhibits the NF[kappa]B Pathway in a p53 Dependent Manner: Implications in Lung Cancer Therapy". Cell Cycle, vol. 6, No. 17, Sep. 1, 2007 (Sep. 1, 2007), pp. 2178-2185.
Dong, H. and Chen, L., "B7-H1 pathway and its role in the evasion of tumor immunity," Journal of Molecular Medicine 81(5):281-287, Springer, Germany (2003).
Dong, H., et al., "Tumor-associated B7-H1 promotes T-cell apoptosis: a potential mechanism of immune evasion," Nature Medicine 8(8):793-800, Nature Publishing Company, United States (2002).
Dougan et al., "Regulation of innate and adaptive antitumor immunity by IAP antagonists," Immunotherapy (2018) vol. 10, No. 9, pp. 787-796.

(56) References Cited

OTHER PUBLICATIONS

Dougan, D.A., et al., "Effects of subsitutions in the binding surface of an antibody on antigen affinity," Protein Engineering 11(1):65-74, Oxford University Press, England (1998).
Finger, L.R., et al., "The human PD-1 gene: complete cDNA, genomic organization, and developmentally regulated expression in B cell progenitors," Gene 197(1-2): 177-187, Elsevier, United States (1997).
Fivash, M., et al., "BIAcore for macromolecular interaction," Current Opinion in Biotechnology 9(1):97-101, Current Biology, England (1998).
Fleischer, Bernhard, et al.; "T cell stimulation by staphylococcal enterotoxins"; J. Exp. Medicine; 167(5):1697-1707 (1988).
Franklin, M.C., et al., "Insights into ErbB signaling from the structure of the ErbB2-pertuzumab complex," Cancer Cell 5(4):317-328, Cell Press, United States (Apr. 2004).
Freeman, G.J., et al., "Engagement of PD-1 immunoinhibitory receptor by a novel B7 family member leads to negative regulation of lymphocyte activation," The Journal of Experimental Medicine 192(7):1027-1034, The Rockefeller University Press, UnitedStates (2000).
Fukushima et al.,"Antibodies to T-cell Ig and mucin domain-containing proteins (Tim)-1 and -3 suppress the induction and progression of murine allergic conjunctivitis" Biochemical and Biophysical Research Communications (2006) vol. 353 No. 1 p. 211-16.
Fulda, "Molecular Pathways: Targeting Inhibitor of Apoptosis Proteins in Cancer—From Molecular Mechanism to Therapeutic Application," Clin Cancer Res (2013) vol. 20, No. 2, pp. 289-295.
Garcia et al: "The Pan-PIM Kinase Inhibitor LGH447 Shows Activity In PIM2 Dependent Multiple Myeloma and In AML Models", Blood (2013) Retrieved from the Internet: URL:http://www.bloodjournal.orgjcontent/12 2/21/1666 [retrieved on Jun. 14, 2016].
Garrison K et al: "The small molecule TGF-[beta] signaling inhibitor SM16 synergizes with agonistic OX40 antibody to suppress established mammary tumors and reduce spontaneous metastasis" Cancer Immunology, Immunotherapy (2012) vol. 61 No. 4 pp. 511-521.
Ge, X., et al., "CD134-Allodepletion Allows Selective Elimination of Alloreactive Human T Cells without Loss of Virus-Specific and Leukemia-Specific Effectors," Biology of Blood and Marrow Transplantation 14(5):518-530, American Society for Bloodand Marrow Transplantation, United States (2008).
Gettinger et al. "Safety and Response 1-98 With Nivolumab (Anti-PD-1; BMS-936558, ONO-1538) Plus Erlotinib in Patients (Pts) With Epidermal Growth Factor Receptor Mutant (EGFR MT) Advanced Non-Small Cell Lung Cancer (NSCLC} Metastatic Non-Small Cell Lung Cancer" International Journal of Radiation: Oncology Biology Physics (2014) vol. 90, No. 5, pp. S34-S35.
Greenspan, N.S., "Epitopes, paratopes and other topes: do immunologists know what they are talking about?" Bulletin de l'Institut Pasteur 90(4):267-279, Elsevier, France (1992).
Grygielewicz Paulina et al: "Epithelial-mesenchymal transition confers resistance to selective FGFR inhibitors in SNU-16 gastric cancer cells". Gastric Cancer. Springer Japan. Tokyo, vol. 19. No. 1., Nov. 19, 2014 (Nov. 19, 2014). pp. 53-62.
Haitov, "Immunology: Structure and Functions of the Immune System," Geotar-Media Publishing Group, Moscow (2013) p. 110. Russian.
Hallett et al., "Immunosuppressive Effects of Multiple Myeloma Are Oversome by PD-L1 Blockade" Biol Blood Marrow Transplant (2011) vol. 17, No. 8, pp. 1133-1145.
Hansen, J.A., et al., "Monoclonal Antibodies Identifying a Novel T-Cell Antigen and Ia Antigens of Human Lymphocytes," Immunogenetics 10:247-260, Springer-Verlag (1980).
Harlow, E. and Lane, D., "Using Antibodies: A Laboratory Manual," Cold Spring Harbor Laboratory Press, Cold Spring Harbor, United States various pages (1999).
Hastings et al., "TIM-3 is Expressed on Activated Human CD4+ T Cells and Regulates Th1 and Th17 Cytokines" Eur J Immunol (2009) vol. 39 No 9 pp. 2492-2501.
He, Y-F., et al., "Blocking programmed death-1 ligand-PD-1 interactions by local gene therapy results in enhancement of antitumor effect of secondary lymphoid tissue chemokine," The Journal of Immunology 173(8):4919-4928, The American Association ofImmunologists, United States (2004).
Hirano, F., et al., "Blockade of B7-H1 and PD-1 by monoclonal antibodies potentiates cancer therapeutic immunity," Cancer Research 65(3):1089-1096, American Association for Cancer Research, United States (2005).
Hogenesch et al. "Challenges in pre-clinical testing of anti-cancer drugs in cell culture and in animal models" Journal of Controlled Release (2012) vol. 164, No. 2, pp. 183-186.
Hu Yi et al: "Essential role of AKT in tumor cells addicted to FGFR.", Anti-Cancer Drugs, vol. 25, No. 2, Feb. 2014 (Feb. 2014), pp. 183-188.
Huang, Z., "Structural chemistry and therapeutic intervention of protein-protein interactions in immune response, human immunodeficiency virus entry, and apoptosis," Pharmacology & Therapeutics 86(3):201-215, Pergamon Press, England (2000).
Hutloff, A., et al.,"ICOS is an inducible T-cell co-stimulator structurally and functionally related to CD28," Nature 397(6716):263-266, Nature Publishing Group, England (1999).
International Search Report and Written Opinion for International Application No. PCT/US2015/053799 dated May 17, 2016.
International Search Report and Written Opinion for International Application No. PCT/US2015/066812 dated Mar. 23, 2016.
International Search Report and Written Opinion for International Application No. PCT/US2016/044547 dated Oct. 18, 2016.
International Search Report and Written Opinion for PCT/US2014/057491 dated Jan. 7, 2015.
International Search Report and Written Opinion for PCT/US2015/012754 dated May 20, 2015.
International Search Report and Written Opinion for PCT/US2015/013913 dated May 4, 2015.
International Search Report and Written Opinion for PCT/US2015/049826 dated Dec. 16, 2015.
International Search Report and Written Opinion for PCT/US2015/053799 dated May 17, 2016.
International Search Report and Written Opinion issued in International Application No. PCT/US2016/067200, dated Apr. 10, 2017.
International Search Report and Written Opinion issued in PCT/US2007/085100, dated Apr. 28, 2008, 11 pages.
International Search Report for International Application No. PCT/US2015/066812 dated Mar. 23, 2016.
Ishida et al., "Induced expression of PD-1, a novel member of the immunoglobulin gene superfamily, upon programmed cell death," The EMBO Journal (1992) vol. 11, No. 11, pp. 3887-3895.
Ishima, R. and Torchia, D.A., "Protein Dynamics from NMR," Nature Structural Biology 7(9):740-743, Nature Publishing Company, United States (2000).
Iwai et al., "Involvement of PD-L1 on tumor cells in the escape from host immune system and tumor immunotherapy by PD-L1 blockade" PNAS (2002) vol. 99, pp. 12293-12297.
Iwai et al., "PD-1 blockade inhibits hematogenous spread of poorly immunogenic tumor cells by enhanced recruitment of effector T cells", International Immunology (2005) vol. 17, No. 2, pp. 133-144.
Nishimura, H., et al., "Autoimmune dilated cardiomyopathy Science in PD-1 receptor-deficient mice," Science 291(5502):319-322, American Association for the Advancement of Science, United States (2001).
Nishimura, H., et al., "Development of lupus-like autoimmune diseases by disruption of the PD-1gene encoding an ITIM motif-carrying immunoreceptor," Immunity 11 (2):141-151, Cell Press, United States (1999).
Nishimura, H., et al., "Immunological studies on PD-1 deficient mice: implication of PD-1 as a negative regulator for B cell responses," International Immunology 10(10):1563-1572, Oxford University Press, England (1998).

(56) References Cited

OTHER PUBLICATIONS

Nomi, T., et al., "Clinical significance and therapeutic potential of the programmed death-1 ligand/programmed death-1 pathway in human pancreatic cancer," Clinical Cancer Research 13(7):2151-2157, The Association, United States (2007).

Okazaki, T., et al., "New regulatory co-receptors: inducible co-stimulator and PD-1," Current Opinion in Immunology 14(6):779-782, Elsevier, England (2002).

Okazaki, T., et al., "PD-1 immunoreceptor inhibits B cell receptor-mediated signaling by recruiting src homology 2-domain-containing tyrosine phosphatase 2 to phophotyrosine," Proceeding of the National Academy of Sciences 98(24):13866-13871,National Academy of Sciences, United States (2001).

Oki Y et al: "Immune regulatory effects of panobinostat in patients with Hodgkin lymphoma through modulation of serum cytokine levels and T-cell PD1 expression," Blood Cancer Journal, vol. 4, E236, 2014, pp. 1-4.

Opdivo (nivolumab) Drug Label, Initial U.S. Approval: 2014, Revised Nov. 2016.

Ozaki, S., et al., "Immunotherapy of Multiple Myeloma with a Monoclonal Antibody Directed Against a Plasma Cell-specific Antigen, HM1.24," Blood 90(8):3179-3186, American Society of Hematology, United States (1997).

Ozkaynak, E., et al., "Programmed death-1 targeting can promote allograft survival," The Journal of Immunology 169(11):6546-6553, The American Association of Immunologists, United States (2002).

Pal et al., "Programmed Death-1 Inhibition in Renal Cell Carcinoma: Clinical Insights and Future Directions," Clinical Adv Hem Onc (2014) vol. 12, Issue 2, pp. 90-99.

Panka, et al.; "Variable region framework differences result in decreased or increased affinity of variant anti-digoxin antibodies"; Proc Natl Acad. Sci USA; 85:3080-3084 (1988).

Pardoll, D.M., "The blockade of immune checkpoints in cancer immunotherapy," Nature Reviews Cancer 12(4):252-264, Nature Publishing Group, England (2012).

Park, J.W. and Smolen, J., "Monoclonal antibody therapy," Advances in Protein Chemistry 56:369-421, Academic Press, United States (2001).

Parry, Richard V., et al.; "CTLA-4 and PD-1 Receptors Inhibit T-Cell Activation by Distinct Mechanisms"; Molecular and Cellular Biology; 25(21):9543-9553 (2005).

Patel et al., "Taming dendritic cells with TIM-3: another immunosuppressive strategy used by tumors" Immunotherapy (2012) vol. 4 No. 12 pp. 1795-1798.

Patsoukis, N., et al., "PD-1 Increases PTEN Phosphatase Activity While Decreasing PTEN Protein Stability by Inhibiting Casein Kinase 2," Molecular and Cellular Biology 33(16):3091-3098, American Society for Microbiology, United States (Aug. 2013).

Patsoukis, N., et al., "PD-1 inhibits T cell proliferation by upregulating p. 27 and p. 15 and suppressing Cdc25A," Cell Cycle 11(23):1-5, Landes Bioscience, United States (Dec. 2012).

Patsoukis, N., et al., "Selective Effects of PD-1 on Akt and Ras Pathways Regulate Molecular Components of the Cell Cycle and Inhibit T Cell Proliferation," Science Signaling 5(230): ra46, pp. 1-14, American Association for the Advancement ofScience, United States (Jun. 2012).

Perez-Gracia et al., "Orchestrating immune check-point blockade for cancer inmunotherapy in combinations", Current Opinion in Immunology (2014) vol. 27 pp. 89-97.

Pinzon-Ortiz et al: "S710: The combination of JAK inhibitor, ruxolitinib, pan-PIM inhibitor, LGH447, and CDK4/6 inhibitor, LEE011, in a preclinical mouse model of myeloproliferative neoplasia", Haematologica, The Hematology Journal: Official Organ of the European Hematology Association, vol. 99. No. Supp 1 (2014) p. 252.

Polyak, M.J. and Deans, J.P., "Alanine-170 and proline-172 are critical determinants for extracellular CD20 epitopes heterogeneity in the fine specificity of CD20 monoclonal antibodies is defined by additional requirements imposed by both aminoacid sequence and quaternary structure," Blood 99(9):3256-3262, American Society of Hematology, United States (2002).

Postel-Vinay et al. "Challenges of phase 1 clinical trials evaluating immune checkpoint-targeted antibodies" Annals of Oncology (2016) vol. 27, pp. 214-224.

Prokunina, L. and Alarcon-Riquelme, M., "The genetic basis of systemic lupus erythematosus-knowledge of today and thoughts for tomorrow," Human Molecular Genetics 13(1):R143-R148, Oxford University Press, England (2004).

Quintarelli et al: "Selective strong synergism of Ruxolitinib and second generation tyrosine kinase inhibitors to overcome bone marrow stroma related drug resistance in chronic myelogenous leukemia", Leukemia Research, New York,NY, US, vol. 38, No. 2, Nov. 15, 2013 (Nov. 15, 2013), pp. 236-242.

Riley, J.L. and June, C.H., "The CD28 family: a T-cell rheostat for therapeutic control of T-cell activation," Blood 105(1):13-21, American Society of Hematology, United States (Jan. 2005).

Rudikoff, et al.; "Single Amino Acid Substitution Altering Antigen-binding Specificity"; Proc. Natl. Acad. Sci. USA 79:1979-1983 (1982).

Salama, A.D., et al., "Critical role of the programmed death-I (PD-1) pathway in regulation of experimental autoimmune encephalomyelitis," The Journal of Experimental Medicine 198(1):71-78, The Rockefeller University Press, United States (2003).

Sanmamed et al. "Agonists of Co-stimulation in Cancer Immunotherapy Directed Against CD137, OX40, GITR, CD27, CD28, and ICOS" Seminars in Oncology (2015) vol. 42, No. 4, pp. 640-655.

Shinohara, T., et al., "Structure and chromosomal localization of the human PD-1 gene (PDCD1)," Genomics 23(3):704-706, Academic Press, United States (1994).

Sho, M., et al., "Possibility of Clinical Applications for Novel Cancer Immunotherapy via Inhibition of T-cell Negative Pathway," Magazine of the Japan Society of Clinical Oncology 40(2):590 (PS22-5) (2005).

Soh, E.Y., et al., "Neutralizing vascular endothelial growth factor activity inhibits thyroid cancer growth in vivo," Surgery 128(6):1059-1066, Mosby, United States (2000).

Song et al.: "3681 Phenotypic and Functional Effects of Novel HDAC Inhibitor LBH589 on Human Lymphocyte Populations", 51st ASH Annual Meeting and Exposition (2009) Retrieved from the Internet: URL:https:jjash.confex.comjash/2889/webpro gramjPaper22684.html [retrieved on Apr. 14, 2016].

Song W et al: "HDAC inhibition by LBH589 affects the phenotype and function of human myeloid dendritic cells.", Leukemia Jan. 2811, vol. 25, No. 1, Jan. 2011 (Jan. 2011), pp. 161-168.

Supplementary Partial European Search Report for European Application No. EP 1484888, dated Mar. 1, 2017. 10 pages.

Tamura, H., et al., "B7-H1 costimulation preferentially enhances CD28-independent T-helper cell function," Blood 97(6):1809-1816, The American Society of Hematology, United States (2001).

Tang et al. "Immunotherapy and tumor microenvironment" Cancer Letters (2016) vol. 370, pp. 85-90.

Teeling, J.L., et al., "Characterization of new human CD20 monoclonal antibodies with potent cytolytic activity against non-Hodgkin Lymphomas," Blood 104(6):1793-1800, American Society of Hematology, United States (2004).

Thomas, M.L., "Of ITAMs and ITIMs: turning on and off the B cell antigen receptor," The Journal of Experimental Medicine 181(6):1953-1956, The Rockefeller University Press, United States (1995).

Thompson, R. Houston, et al.; "PD-1 is expressed by tumor-infiltrating immune cells and is associated with poor butcome for patients with renal cell carcinoma"; Clin. Cancer Res. 13(6):1757-1761 (2007).

Tomlinson, I.M., et al., "The repertoire of human germline VH sequences reveals about fifty groups of VH segments with different hypervariable loops," Journal of Molecular Biology 227(3):776-798, Elsevier, Netherlands (1992).

(56) References Cited

OTHER PUBLICATIONS

Topalian, S., "Q&A: Suzanne Topalian on Immune Therapies", Cancer Discovery 3(7):712, American Association for Dancer Research, United States, published online Jun. 27, 2013.
Topalian, S., et al., "Nivolumab (anti-PD-1; BMS-936558; ONO-4538) in patients with advanced solid tumors: Survival and long-term safety in a phase I trial," accessed at http://meetinglibrary.asco.org/content/113543-132, accessed on Jun. 1, 2016, 2pages.
Topalian, S.L., et al., "Safety, Activity, and Immune Correlates of Anti-PD-1 Antibody in Cancer," The New England Journal of Medicine 366(26):2443-2454, Massachusetts Medical Society, United States (2012).
Trautmann, Lydie, et al.; "Upregulation of PD-1 expression on HIV-specific CD8+ T cells leads to reversible immune dysfunction"; Nat. Med.; 12(10):1198-1202 (2006).
Tsai, C-J., et al., "Protein Allostery, signal transmission and dynamics: a classification scheme of allosteric mechanisms," Molecular BioSystems 5(3):207-216, Royal Society of Chemistry, England (2009).
Tsushima, Fumihiko, et al.; "Predominant expression of B7-H1 and its immunoregulatory roles in oral squamous cell carcinoma"; Oral Oncology; 42:268-274 (2006).
UniProtKB/Swiss-Prot Database entry, PDCD1.sub.-HUMAN, accessed at http://www.uniprot.org/uniprot/Q15116.txt, accessed on Jun. 1, 2016, 5 pages.
Van Regenmortel, M.H.V., "The recognition of Proteins and Peptides by Antibodies," Journal of Immunoassay 21(2-3):85-108, Taylor & Francis, England (2000).
Vanneman et al: "Combining immunotherapy and targeted therapies in cancer treatment" Nature Reviews Cancer (2012) vol. 12 No. 4 pp. 237-251.
Ashworth et al. "Management of a Patient With Advanced BRAF-Mutant Melanoma" Journal of the National Comprehensive Cancer Network (2014) vol. 12, No. 3, pp. 315-319.
Batus et al. "Optimal Management of Metastatic Melanoma: Current Strategies and Future Directions" Am. J. Clin. Dermatol. (2013) vol. 14, No. 3, pp. 179-194.
Hamid et al., "Safety and Tumor Responses with Lambrolizumab (Anti-PD-1) in Melanoma," New England Journal of Medicine(2013) 369(2): pp. 134-144.
International Search Report and Written Opinion for International Application No. PCT/US2015/049826 dated Dec. 16, 2015.
Knight et al. " Host immunity contributes to the antimelanoma activity of BRAE inhibitors" The Journal of Clinical Investigation (2013) vol. 123, No. 3, pp. 1371-1381.
Menzies et al. "Recent advances in melanoma systemic therapy. BRAF inhibitors, CTLA4 antibodies and beyond" European Journal of Cancer (2013) vol. 49, pp. 3229-3241.
Menzies et al. "Systemic treatment for BRAF-mutant melanoma: where do we go next?" The Lancet (2014) vol. 15, pp. e371-e381.
[No Author Listed] "Crean un ADN sintético capaz de evolucionar," retrieved from www.nationalgeographic.es/ciencia/crean-un-adn-sintetico-capaz-de-evolucionar, Apr. 25, 2012, last accessed Oct. 18, 2019.
Brand et al., "Prospect for Anti-HER2 Receptor Therapy in Breast Cancer," Anticancer Research (2006) vol. 26, pp. 463-470.
ClinicalTrials.gov "History of Changes for Study NCT01454102," ClinicalTrials.Gov, latest version submitted on Nov. 3, 2017.
Highfill et al., "Disruption of CXCR2-Mediated MDSC Tumor Trafficking Enhances Anti-PD1 Efficacy," Science Translational Medicine (2014) vol. 6, Issue 237, Article 237ra67, 15 pages.
International Search Report and Written Opinion issued in PCT/US2018/061534, dated Apr. 1, 2019, 9 pages.
Koya et al., "BRAF Inhibitor Vemurafenib Improves the Antitumor Activity of Adoptive Cell Immunotherapy," Cancer Res (2012) vol. 72, No. 16, pp. 3928-3937.
Liu et al., The BRAF and MEK Inhibitors Dabrafenib and Trametinib: Effects on Immune Function and in Combination with Immunomodulatory Antibodies Targeting PD-1, PD-L1, and CTLA-4. Clinical Cancer Research, 2015, vol. 5, pp. 1639-1651.

Najjar et al., "Myeloid-Derived Suppressor Cell Subset Accumulation in Renal Cell Carcinoma Parenchyma is Associated with Intratumoral Expression of IL1beta, IL8, CXCL5, and Mip-1alpha," Clinical Cancer Research (2016) vol. 23, No. 9, pp. 2346-2355.
Neubert et al., "T cell-induced CSF1 promotes melanoma resistance to PD1 blockade," Science Translational Medicine (2018) vol. 10, No. 436, Article eaan3311, 14 pages.
Sachdev et al., "Phase 1/2a study of double immune suppression blockade by combining a CSF1R inhibitor (pexidartinib/PLX3397) with an anti-PD-1 antibody (pembrolizumab) to treat advanced melanoma and other solid tumors," Gynecologic Oncology (2016) vol. 141, pp. 147-148.
Simeone et al., "Immunomodulating antibodies in the treatment of metastatic melanoma: The experience with anti-CTLA-4, anti-CD137, and anti-PD1," Journal of Immunotoxicology (2012) vol. 9, No. 3, pp. 241-247.
Steele et al., "CXCR2 Inhibition Profoundly Suppresses Metastases and Augments Immunotherapy in Pancreatic Ductal Adenocarcinoma," Cancel Cell (2016) vol. 29, pp. 832-845.
Strome et al., "A Mechanistic Perspective of Monoclonal Antibodies in Cancer Therapy Beyond Target-Related Effects," The Oncologist (2007) vol. 12, pp. 1084-1095.
Stromnes et al., "Pancreatic Cancer: Planning Ahead for Metastatic Spread," Cancel Cell (2016) vol. 29, No. 6, pp. 774-776.
Villalobos, "Primer organismo con ADN artificial logra reproducirse," retrieved from www.fayerwayer.com/2014/05/primer-organismo-con-adn-artificial-logra-reproducirse (2014) last accessed Oct. 18, 2019.
Zhang, "P2.01-097—Phase 3 Study of Pembrolizumab vs Platinum-Based Chemotherapy for PD-L1 ," (NSCLC ID 2182) Abstract from Poster Presentation from International Association for the Study of Lung Cancer, Aug. 9, 2015, retrieved from library.iaslc.org/search-speaker?search_speaker=30076.
Zhu et al., "CSF1/CSF1R Blockade Reprograms Tumor-Infiltrating Macrophages and Improves Response to T-cell Checkpoint Immunotherapy in Pancreatic Cancer Models," Cancer Research (2014) vol. 74, No. 18, pp. 5057-5069.
Nishimura et al., "Developmentally regulated expression of the PD-1 protein on the surface of double-negative (CD4-CD8-) thymocytes," Int Immunol (1996) vol. 8, No. 5, pp. 773-780.
Ohigashi et al, "Clinical Significance of Programmed Death-1 Ligand-1 and Programmed Death-1 Ligand-2 Expression in Human Esophageal Cancer" Clin Cancer Research (2005) vol. 11, pp. 2947-2953.
Ohno et al., "Antigen-binding specificities of antibodies are primarily determined by seven residues of VH," PNAS (1985) vol. 82, pp. 2945-2949.
Okamoto et al., "T-Helper Type 1/T-Helper Type 2 Balance in Malignant Pleural Effusions Compared to Tuberculous Pleural Effusions" Chest (2005) vol. 128 pp. 4030-4035.
Okazaki et al., "PD-1 and PD-1 ligands: from discovery to clinical application" Intern. Immun. (2007) vol. 19, pp. 313-824.
Okudaira et al., "A modified version of galectin-9 suppresses cell growth and induces apoptosis of human T-cell leukemia virus type 1-infected T-cell lines" Int. J. Cancer (2007) vol. 120 pp. 2251-2261.
Opdivo (nivolumab) Dmg Label, Initial U.S. Approval: 2014, Revised May 2016.
Opdivo (nivolumab) Drug Label, Initial U.S. Approval: 2014, Revised Nov. 2016, 58 pages.
Opposition filed by ASILFA AG in corresponding Chilean Application No. 2017-00888 on Oct. 24, 2017, assigned litigation file number by the National Institute of Industrial Property of Chile (INAPI) on Feb. 27, 2018, notified by INAPI to agent on Mar. 2, 2018.
Opposition filed by Laboratorios Legrand S.A. in corresponding Colombian Application No. NC2017/0003490 an Dec. 7, 2017, admitted Dec. 19, 2017, published Dec. 20, 2017.
Opposition filed in Colombian Application No. NC2016/0001001, filed Feb. 15, 2017.
Partial European Search Report issued in European Patent Application No. 19206634.8, dated Apr. 30, 2020.

(56) References Cited

OTHER PUBLICATIONS

Paterson et al., "The Programmed Death-1 Ligand 1:B7-1 Pathway Restrains Diabetogenic Effector T Cells In Vivo," J Immunol (2011) vol. 187, pp. 1097-1105.
Phong et al., "Tim-3 enhances Fc[epsilon]RI-proximal signaling to modulate mast cell activation," J Experimental Medicine (2015) vol. 212, No. 13, pp. 2289-2304.
Post Grant Opposition filed in Colombian Patent Application No. NC2016/0001001, dated Jul. 31, 2018.
Powles et al., "MPDL3280A (anti-PD-L1) treatment leads to clinical activity in metastatic bladder cancer," Nature (2014) vol. 515, pp. 558-562.
Prigent et al., "Lymphocyte activation gene-3 induces tumor regression and antitumor immune responses," Eur J Immunol (1999) vol. 29, pp. 3867-3876.
Raziorrouh et al. "The Immunoregulatory Role of CD244 in Chronic Hepatitis B Infection and its Inhibitory Potential on Virus-Specific CD8+ T-cell Function" Hepatology (2010) vol. 52 pp. 1934-1947.
Richter et al., "On the role of the inhibitory receptor LAG-3 in acute and chronic LCMV infection," Int Immunol (2009) vol. 22, No. 1, pp. 13-23.
Rothe et al. "Enhancing dendritic cell-induced T-cell responses by immunomodulating molecules" 13th CIMT Annual Meeting (2015) p. 74.
Rowe et al., "Innate IFN-gamma is essential for programmed death ligand-1-mediated T cell stimulation following Listeria monocytogenes infection," J Immunol (2012) vol. 189, No. 2, pp. 876-884.
Rudnick et al. "Affinity and Avidity in Antibody-Based Tumor Targeting" Cancer Biotherapy and Radiopharmaceuticals (2009) vol. 24, No. 2, pp. 155-160.
Sabatos et al. "Interaction of Tim-3 and Tim-3 ligand regulates T helper type 1 responses and induction of peripheral tolerance" Nature Immunology (2003) vol. 4, pp. 1102-1110.
Sabatos-Peyton et al., "Blockade of Tim-3 binding to phosphatidylserine and CEACAM1 is a shared feature of anti-Tim-3 antibodies that have functional efficacy," Oncoimmunology (2018) vol. 7, No. 2, Article e1385690, 9 pages.
Sakuishi et al., "Emerging Tim-3 functions in anti-microbial and tumor immunity" Trends Immunol (2011) vol. 32 No. 8 pp. 345-349.
Sakuishi et al., "Targeting Tim-3 and PD-1 pathways to reverse T cell exhaustion and restore anti-tumor immunity," J Experimental Medicine (2010) vol. 207, No. 10, pp. 2187-2194.
Sakuishi et al., "TIM3+FOXP3+ regulatory T cells are tissue-specific promoters of T-cell dysfunction in cancer" OncoImmunology (2013) vol. 2 No. 4 pp. e23849-1-e23849-9.
Santiago et al., "Structures of T Cell Immunoglobulin Mucin Receptors 1 and 2 Reveal Mechanisms for Regulation of Immune Responses by the TIM Receptor Family" Immunity (2007) vol. 26 pp. 299-310.
Schroll, A. et al., "Tim3 Is Upregulated and Protective in Nephrotoxic Serum Nephritis", The American Journal of Pathology, vol. 176, No. 4, pp. 1716-1742, Apr. 2010.
Search Report and Written Opinion issued in Singapore Application No. 11201605627 dated Aug. 15, 2017.
Search Report and Written Opinion issued in Singapore Application No. 11201702401R, completed Mar. 29, 2018.
Shakhov et al., "SMUCKLER/TIM4 is a distinct member of TIM family expressed by stromal cells of secondary lymphoid tissues and associated with lymphotoxin signaling" Eur. J. Immunol (2004) vol. 34 pp. 494-503.
Sher et al. "Regulation of Immunity to Parasited by T cells and T Cell-derived Cytokines" Annual Review Immunol (1992) vol. 10, pp. 385-409.
Simmons et al., "Tim-3+ T-bet+ Tumor-Specific Th1 Cells Colocalize with and Inhibit Development and Growth of Murine Neoplasms" The Journal of Immunology (2005) vol. 174 pp. 1405-1415.
Soares et al. "Recombinant Himan Tumor Antigen MUC1 Expressed in Insect Cells: Structure and Immunogenicity" Protein Expression and Purification (2001) vol. 22, pp. 92-100.
Spigel et al., "Phase 1/2 Study of the Safety and Tolerability of Nivolumab Plus Crizotinib for the First-Line Treatment of Anaplastic Lymphona Kinase Translocation—Positive Advanced Non-Small Cell Lung Cancer (CheckMate 370)," Journal of Thoracic Oncology (2018) vol. 13, No. 5, pp. 682-688.
Stewart et al., "MEDI4736: Delivering effective blockade of immunosuppression to enhance tumour rejection; Monoclonal antibody discovery and practical development," Cancer Res (2011) vol. 71, No. 8 (Supp), Abstract LB-158.
Swallow et al., "B7h, a Novel Costimulatory Homolog of B7.1 and B7.2, Is Induced by TNFa," Immunity (1999) vol. 11, pp. 423-432.
Sánchez-Fueyo et al., "Tim-3 inhibits T helper type 1-mediated auto- and alloimmune responses and promotes immunological tolerance," Nat Immunol (2003) vol. 4, No. 11, pp. 1093-1101.
Takamura et al., "Premature Terminal Exhaustion of Friend Virus-Specific Effector CD8+ T Cells by Rapid Induction of Multiple Inhibitory Receptors" J Immunol (2010) vol. 184 pp. 4696-4707.
Talmadge et al. "Murine Models to Evaluate Novel and Conventional Therapeutic Strategies for Cancer" The American Journal of Pathology (2007) vol. 170, No. 3, pp. 793-804.
Thangamathesvaran et al., "Immune checkpoint inhibitors and radiotherapy—concept and review of current literature," Ann Transl Med (2018) vol. 6, No. 8, Article 155, 11 pages.
Thomas et al "Combined Effects of RU486 and Tamoxifen on the Growth and Cell Cycle Phases of the MCF-7 Cell Line" Journal of Clinical Endocrinology and Metabolism (1992) vol. 75, Issue 3, pp. 865-870.
Thomas et al. "Effects of Gossypol on the Cell Cycle Phases in T-47D Human Breast Cancer Cells" Anticancer Research (1991) vol. 11, No. 4, pp. 1469-1476.
Thompson et al., "Tumor B7-H1 Is Associated with Poor Prognosis in Renal Cell Carcinoma Patients with Long-term Follow-up" Cancer Res. (2006) vol. 66, pp. 3381-3385.
Thurber et al. "Antibody tumor penetration: Transport opposed by systemic and antigen-mediated clearance" Advanced Drug Delivery Reviews (2008) vol. 60, pp. 1421-1434.
Topalian et al., "Safety, Activity, and Immune Correlates of Anti-PD-1 Antibody in Cancer," N Engl J Med (2012) vol. 366, No. 26, pp. 2443-2454.
Triebel et al., "LAG-3, A Novel Lymphocyte Activation Gene Closely Related to CD4," J Exp Med (1990) vol. 171, pp. 1393-1405.
Triebel, "LAG-3: a regulator of T-cell and DC responses and its use in therapeutc vaccination," Trends Immunol (2003) vol. 24, No. 12, pp. 619-622.
Tuskan et al., "Real-time PCR analysis of candidate imprinted genes on mouse chromosome 11 shows balanced expression from the maternal and paternal chromosomes and strain-specific variation in expression levels" Epigenetics (2008) vol. 3 No. 1 pp. 43-50.
Huang et al., "Role of LAG-3 in Regulatory T Cells," Immunity (2004) vol. 21, pp. 503-513.
Huard et al., "Lymphocyte-activation gene 3/major histocompatibility complex class II interaction modulates the antigenic response of CD4+ T lymphocytes," Eur J Immunol (1994) vol. 24, pp. 3216-3221.
Huard et al., "T cell major histocompatibilty complex class II molecules down-regulate CD4+ T cell clone responses following LAG-3 binding," Eur J Immunol (1996) vol. 26, pp. 1180-1186.
International Search Report and Written Opinion for International Application No. PCT/US2015/055390, dated Dec. 17, 2015.
International Search Report and Written Opinion for International Application No. PCT/US2016/044545 dated Oct. 28, 2016.
International Search Report and Written Opinion for International Application No. PCT/US2016/044549 dated Oct. 14, 2016.
International Search Report and Written Opinion issued in International Application No. PCT/US2018/039825, dated Oct. 4, 2018.

(56) References Cited

OTHER PUBLICATIONS

Iouzalen et al., "LAP, a lymphocyte activation gene-3 (LAG-3)-associated protein that binds to a repeated EP motif in the intracellular region of LAG-3, may participate in the down-regulation of the CD3/TCR activation pathway," Eur J Immunol (2001) vol. 31, pp. 2885-2891.
Jan et al., "Prospective separation of normal and leukemic stem cells based on differential expression of TIM3, a human acute myeloid leukemia stem cell marker" PNAS (2011) vol. 108 No. 12 pp. 5009-5014.
Jin et al. "Cooperation of Tim-3 and PD-1 in CD8 T-cell exhaustion during chronic viral infection" PNAS (2010) vol. 107, Issue 33, pp. 14733-14738.
Jing et al., "Combined immune checkpoint protein blockade and low dose whole body irradiation as immunotherapy for melanoma," Journal for ImmunoTherapy of Cancer (2015) vol. 3, No. 2, 15 pages.
Jones et al., "Tim-3 expression defines a novel population of dysfunctional T cells with highly elevated frequencies in progressive HIV-1 infection," J Exp Med (2008) vol. 205, No. 12, pp. 2763-2779.
Kearl et al., "PD-1/PD-L1 Blockade after Transient Lymphodepletion to Treat Myeloma," Presentation from Society for Immunotherapy of Cancer Conference, Oct. 27, 2012, North Bethesda, Maryland, 19 pages.
Kearl et al., "Programmed Death Receptor-1/Programmed Death Receptor Ligand-1 Blockage after transient Lymphodepletion To Treat Myeloma," J Immunol (2013) vol. 190, pp. 5620-5628.
Keytruda (pembrolizumab) Drug Label, Initial U.S. Approval: 2014, Revised Aug. 2016.
Khaitov, Immunologia, Moscow, (2011) "GEOTAR-Media", p. 103.
Khalil et al. "The New Era of Cancer Immunotherapy: Manipulating T-Cell Activity to Overcome Malignancy" Immunotherapy of Cancer In: Advances in Cancer Research (2015) vol. 128, pp. 1-68.
Kikushige et al. "TIM-3 as a therapeutic target for malignant stem cells in acute myelogenous leukemia" New York Academy of Sciences (2012) vol. 1266, pp. 118-123.
Klibi et al. "Blood diffusion and Th1-suppressive effects of galectin-9-containing exosomes released by Epstein-Barr virus-infected nasopharyngeal carcinoma cells" Blood (2009) vol. 113 No. 9 pp. 1957-1966.
Kuchroo et al. "The TIM Gene Family: Emerging Roles in Immunity and Disease" Nature Reviews Immunology (2003) vol. 3, pp. 454-462.
Kuchroo et al., "B7-1 and B7-2 Costimulatory Molecules Activate Differentially the Th1/Th2 Developmental Pathways: Application to Autoimmune Disease Therapy" Cell (1995) vol. 80 No. 707-18.
Kwong et al., "Molecular Analysis of Tumor-Promoting CD8+ Cells in Two-Stage Cutaneous Chemical Carcinogenesis" J Invest Dermatol (2010) vol. 130 No. 6 pp. 1726-1736.
Lack et al. "Nebulized but not parenteral IFN-gamma decreases IgE production and normalizes airways function in a murine model of allergen sensitization" Journal of Immunology (1994) vol. 152, pp. 2546-2554.
Lee et al. "The inhibition of the T-cell immunoglobulin and mucin domain 3 (Tim3) pathway enhances the efficacy of tumor vaccine" Biochemical and Biophysical Reseach Communications (2010) vol. 402, pp. 88-93.
Lehmann et al., "Identification of human triple-negative breast cancer subtypes and preclinical models for selection of targeted therapies", J Clin Invest., 121(7): 2750-2767.
Lenschow et al., "Expression and functional significance of an additional ligand for CTLA-2," PNAS (1993) vol. 90, pp. 11054-11058.
Lenschow et al., "Long-term survival of xenogeneic pancreatic islet grafts induced by CTLA4Ig," Science (1992) vol. 257, Issue 5071, pp. 789-792.
Liblau et al. "Th1 and Th2 CD4+ T cells in the pathogenesis of organ-specific autoimmune diseases" Immunology Today (1995) vol. 16, Issue 1, pp. 34-38.

Linsley et al., "CTLA-4 Is a Second Receptor for the B Cell Activation Antigen B7," J Exp Med (1991) vol. 174, pp. 561-569.
Linsley et al., "Immunosuppression in Vivo by a Soluble Form of the CTLA-4 T Cell Activation Molecule," Science (1992) vol. 257, pp. 792-795.
Liu et al., "Targeting Wnt-driven cancer through the inhibition of Porcupine by LGK974," PNAS (2013) vol. 110, No. 50, pp. 20224-20229.
Loser et al., "IL-10 Controls Ultraviolet-Induced Carcinogenesis in Mice" The Journal of Immunology (2007) vol. 179 pp. 365-371.
Lu et al., "Everolimus enhances the cytotoxicity of bendamustine in multiple myeloma cells through a network of pro-apoptotic and cell-cycle-progression regulatory proteins," Acta Biochim Biophys Sin (2013) vol. 45, pp. 683-691.
Maier et al., "PD-1: PD-L1 Interactions Contribute to the Functional Suppression of Virus-Specific CD8+ T Lymphocytes in the Liver," J Immunol (2007) vol. 178, pp. 2714-2720.
Makishi et al. "Retracted: A modified version of galectin-9 induces cell cycle arrest and apoptosis of Burkitt and Hodgkin lymphoma cells" British Journal of Hematology (2008) vol. 142 pp. 583-594.
Manning et al., "A model of multiple myeloma: culture of 5T33 murine myeloma cells and evaluation of tumorigenicity in the C57BL/KaLwRij mouse ", Br J Cancer., 66(6): 1088-1093 (1992).
Maçon-Lemaître et al., "The negative regulatory function of the lymphocyte-activation gene-3 co-receptor (CD223) on human T cells," Immunology (2005) vol. 115, pp. 170-178.
Miska et al., "Autoimmunity-mediated antitumor immunity: Tumor as an immunoprivileged self," Eur J Immunol (2012) vol. 42, pp. 2584-2596.
Mocellin et al., "CTLA-4 blockade and the renaissance of cancer immunotherapy," Biochim Biophys Acta (2013) vol. 1836, pp. 187-196.
Mokyr et al., "Realization of the Therapeutic Potential of CTLA-4 Blockade in Low-Dose Chemotherapy-treated Tumor-bearing Mice", Cancer Research, 58:5301-5304 (1998).
Monney et al. "Th1-specific cell surface protein Tim-3 regulates macrophage activation and severity of an autoimmune disease" Nature (2002) vol. 415, pp. 536-541.
Mosmann et al. "The expanding universe of T-cell subsets: Th1, Th2 and more" Immunology Today (1996) vol. 17, Issue 3, pp. 138-146.
Mossman et al. "Two Types of Murine Helper T Cell Clone" Journal of Immunology (1986) vol. 136, Issue 7, pp. 2348-2357).
Mou et al., "Association Between TIM-1 Gene Polymorphisms and Allergic Rhinitis in a Han Chinese Population" J Investig Allergol Clin Immunol (2010) vol. 20 No. 1 pp. 3-8.
Murrey et al., Biokhimiya cheloveka, Mir (1993) vol. 1, p. 34.
Nagahara et al., "Galectin-9 Increases Tim-3+ Dendritic Cells and CD+ T Cells and Enhances Antitumor Immunity via Galectin-9-Tim-3 Interactions" The Journal of Immunology (2008) vol. 181 pp. 7660-7669.
Ngiow et al. "Prospects for TIM3-Targeted Antitumor Immunotherapy" Cancer Research (2011) vol. 71, Issue 21, pp. 3567-6571.
Ngiow et al., "Anti-TIM3 Antibody Promotes T Cell IFN-y-Mediated Antitumor Immunity and Suppresses Established Tumors" Cancer Research (2011) vol. 71 No. 10 pp. 3540-3551.
Nicholson et al., "An Altered Peptide Ligand Mediates Immune Deviation and Prevents Autoimmune Encephalomyelitis" Immunity (1995) vol. 3 pp. 397-405.
Nirschl et al., "Molecular Pathways: Coexpression of Immune Checkpoint Molecules: Signaling Pathways and Implications for Cancer Immunotherapy," Cancer Res (2013) vol. 19, No. 18, pp. 4917-4924.
Abbas et al. "Functional diversity of helper T lymphocytes" Nature (1996) vol. 383, pp. 787-793.
Anderson "TIM-3 as a therapeutic target in human inflammatory diseases" Expert Opinion on Therapeutic Targets (2007) vol. 11, issue 8, pp. 1005-1009.
Anderson et al. "Lag-3, Tim-3, and TIGIT: Co-inhibitory Receptors with Specialized Functions in Immune Regulation" Immunity (2016) vol. 44, pp. 989-1004.
Anderson et al. "Promotion of Tissue Inflammation by the Immune Receptor Tim-3 Expressed on Innate Immune Cells" Science (2007) vol. 318, pp. 1141-1143.

(56) References Cited

OTHER PUBLICATIONS

Anderson, "Tim-3: An Emerging Target in the Cancer Immunotherapy Landscape" Cancer Immunology Research (2014) vol. 2 No 5 pp. 393-398.
Ascierto et al. "Future perspectives in melanoma research" meeting report from the "Melanoma Bridge", Napoli, Dec. 5-8, 2013 Journal of Translational Medicine (2014) vol. 12, No. 277, pp. 1-29.
Baixeras et al., "Characterization of the Lymphocyte Activation Gene 3-Encoded Protein. A New Ligand for Human Leukocyte Antigen Class II Antgens," J Exp Med (1992) vol. 176, pp. 327-337.
Beckman et al. "Antibody Constructs in Cancer Therapy" Cancer (2007) vol. 109, No. 2, pp. 170-179.
Berrien-Elliott et al., "Durable Adoptive Immunotherapy for Leukemia Produced by Manipulation of Multiple Regulatory Pathways of CD8+ T-Cell Tolerance," Cancer Research (2012) vol. 73, pp. 605-616.
Bigras, et al. "Spatial distribution of DNA ploidy in colorectal carcinoma" Analytic Cellular Pathology (1994) vol. 7, pp. 289-300.
Brahmer et al., "Safety and Activity of Anti-PD-L1 Antibody in Patients with Advanced Cancer," N Engl J Med (2012) vol. 366, pp. 2455-2465.
Brunet et al., "A new member of the immunoglobin superfamily CTLA-4," Nature (1987) vol. 328, pp. 267-270.
Butte et al., "Interaction of human PD-L1 and B7-1", Mol Immunol (2008) vol. 45, pp. 3567-3572.
Butte et al., "Programmed Death-1 Ligand 1 Interacts Specifically with the B7-1 Costimulatory Molecule to Inhibit T Cell Responses," Immunity (2007) vol. 27, pp. 111-122.
Cao et al. "Genetic variations and haplotypes in TIM-3 gene and the risk pf gastric cancer" Cancer Immunol Immunother (2010) vol. 59 pp. 1851-1857.
Carvalho et al., "Doxorubicin: the good, the bad and the ugly effect," Current Medicinal Chemistry (2009) vol. 16, No. 25, pp. 3267-3285.
Casati et al., "Soluble Human LAG-3 Molecule Amplifies the In vitro Generation of Type 1 Tumor-Specific Immunity," Cancer Res (2006) vol. 66, No. 8, pp. 4450-4460.
Catherine Sabatos-Peyton, MBG453: A high affinity, ligand-blocking anti-TIM-3 monoclonal Ab. American Association for Cancer Research (AACR) Annual Meeting, Apr. 17, 2016, New Orleans, Louisiana.
Ceeraz et al., "B7 family checkpoint regulators in immune regulation and disease," Trends Immunol (2013) vol. 34, No. 11, pp. 556-563.
Cespedes "Mouse models in ocogenesis and cancer therapy" Clin. Tranl. Oncol. (2006) vol. 8, No. 5, pp. 318-329.
ClinicalTrials.gov Identifier: NCT02608268, Safety and Efficacy of MBG453 as Single Agent and in Combination With PDR001 in Patients With Advanced Malignancies, Information provided by Novartis (Novartis Pharmaceuticals), last updated Oct. 13, 2016.
ClinicalTrials.gov Identifier: NCT02817633, A Phase 1 Study of TSR-022, an Anti-TIM-3 Monoclonal Antibody, in Patients With Advanced Solid Tumors, Information provided by Tesaro, Inc., last updated Aug. 26, 2016.
Cohen et al., "Image Cytometry of Estrogen Receptors in Breaast Carcinomas" Cytometry (1988) vol. 9 pp. 579-587.
Dekruyff et al., "T Cell/Transmembrane, Ig, and Mucin-3 Allelic Variants Differentially Recognize Phosphatidylserine and MEdiate Phagocytosis of Apoptotic Cells" The Journal of Immunology (2010) vol. 184 pp. 1918-1930.
Demaria et al., "Immune-mediated inhibition of Metastases after Treatment with Local Radiation and CTLA-4 Bloackade in a Mouse Model of Breast Cancer," Clinical Cancer Research (2005) vol. 11, pp. 728-734.
Dennis "Off by a whisker" Nature (2006) vol. 442, pp. 739-741.
Dong et al., "Tumor-associated B7-H1 promotes T-cell apoptosis: A potential mechanism of immune evasion", Nat Med (2002) vol. 8 pp. 793-800.

Dorfman et al., "The phosphatidylserine receptors, T cell immunoglobulin mucin proteins 3 and 4, are markers of histiocytic sarcoma and other histiocytic and decdritic cell neoplasms" Hum Pathol (2010) vol. 41 No. 10 pp. 1486-1494.
Drake et al., "Blocking the regulatory T cell molecule LAG-3 augments in vivo anti-tumor immunity in an autochthonous model of prostate cancer," J Clin Oncol (2006) vol. 24, No. 18S, Abstract 2573.
Du Manoir et al., "Ki-67 Labeling in Postmitotic Cells Defines Different Ki-67 Pathways Within the 2c Compartment" Cytometry (1991) vol. 12 pp. 455-463.
El Mir et al., "A Soluble Lymphocyte Activation Gene-3 Molecule Used as a Vaccine Adjuvant Elicits Greater Humoral and Cellular Immune Responses to Both Particulate and Soluble Antigens," J Immunol (2000) vol. 164, pp. 5583-5589.
Enizminger et al., "De novo design of antibody complementarity determining regions binding a FLAG tetrapeptide," Sci Rep (2017), retrived from www.nature.com/ articles/s41598-017-10737-9.pdf?origin=ppub, last accessed Jan. 12, 2018.
Extended European Search Report for European Application No. EP 1484888, dated May 31, 2017.
Extended European Search Report issued in European Application No. 19199437.5, dated Mar. 12, 2020, 8 pages.
Extended European Search Report issued in European Application No. 19206634.8, dated Sep. 10, 2020, 26 pages.
Extended European Search Report issued in European Patent Application No. 18211373.8, dated Jun. 25, 2019.
Felip et al., "Efficacy and safety of capmatinib plus nivolumab in pretreated patients with EGFR wild-type non-small cell lung cancer," IASLC 2020 World Conference on Lung Cancer, Abstract No. 817, downloaded from https://cpaper.ctimeetingtech.com/wclc2020/submission/preview/print?publication_id=817.
Fessas et al., "A molecular and preclinical comparison of the PD-1-targeted T-cell checkpoint inhibitors nivolumab and pembrolizumab," Seminars in Oncology (2017) vol. 44, pp. 136-140.
Fourcade et al., "Upregulation of Tim-3 and PD-1 expression is associated with tumor antigen-specific CD8+ T cell dysfunction in melanoma patients" The Journal of Experimental Medicine (2010) vol. 207 No 10 pp. 2175-2186.
Freeman et al., "Cloning of B7-2: a CTLA-4 counter-receptor that costimulates human T cell proliferation," Science (1999) vol. 262, pp. 909-911.
Freeman et al., "TIM genes: a family of cell surface phosphatidylserine receptors that regulate innate and adaptive immunity" Immunol Rev (2010) vol. 235 No. 1 pp. 172-189.
Fujimori et al. "A Modeling Analysis of Monoclonal Antibody Percolation Through Tumors: A Binding-Site Barrier" J Mucl Med (1990) vol. 31, pp. 1191-1198.
Gao et al., "TIM-3 Expression Characterizes Regulatory T Cells in Tumor Tissues and Is Associated with Lung Cancer Progression" PLoS ONE (2012) vol. 7 No. 2 e30676.
Geng et al., "Soluble Form of T Cell Ig Mucin 3 Is an Inhibitory Molecule in T Cell-Mediated Immune Response" The Journal of Immunology (2006) vol. 176 pp. 1411-1420.
Ghebeh et al., "Doxorubicin downregulates cell surface B7-H1 expression and upregulates its nuclear expression in breast cancer cells: role of B7-H1 as an anti-apoptotic molecule," Breast Cancer Research (2010) vol. 12, No. 4, Article R48, 12 pages.
Golden-Mason et al., "Negative Immune Regulator Tim-3 Is Overexpressed on T Cells in Hepatitis C Virus Infection and Its Blockade Rescues Dysfunctional CD4+ and CD8+ T Cells," J Virol (2009) vol. 83, No. 18, pp. 9122-9130.
Henry et al., "Structure and evolution of the extended B7 family," Immunol Today (1999) vol. 20, No. 6, pp. 285-288.
Herbst et al., "A study of MPDL3280A, an engineered PD-L1 antibody in patients with locally advanced or metastatic tumors," J Clin Oncol (2013) vol. 31, No. 15 (Supp), Abstract 3000.
Hofstra et al., "Prevention of Th2-like cell responses by coadministration of IL-12 and IL-18 is associated with inhibition of antigen-induced airway hyperresponsiveness, eosinophilia, and serum IgE levels." Journal of Immunology (1998) vol. 161 No. 9 pp. 5054-5060.

(56) References Cited

OTHER PUBLICATIONS

Huang et al., "Lymphoma endothelium preferentially expresses Tim-3 and facilitates the progression of lymphoma by mediating immune evasion" The Journal of Experimental Medicine (2010) vol. 207 No. 3 pp. 505-520.

U.S. Appl. No. 15/536,718, filed Jun. 16, 2017.

Van De Weyer et al. "A highly conserved tyosine of Tim-3 is phosphorylated upon stimulation by its ligand galectin-9" Biochemical and Biophysical Research Communications (2006) vol. 351, pp. 571-576.

Vivier et al., "Immunoreceptor tyrosine-based inhibition motifs," Immunol Today (1997) vol. 18, No. 6, pp. 286-291.

Voskoglou-Nomikos et al. "Clinical Predictive Value of the in Vitro Cell Line, Human Xenograft, and Mouse Allograft Preclinical Cancer Models" Clinical Cancer Research (2003) vol. 9, pp. 4227-4239.

Walunas et al., "CTLA-4 can function as a negative regulator of T cell activation," Immunity (1994) vol. 1, No. 5, pp. 405-413.

Wang, "Interaction of TIM4-TIM1 Modulates the Function of CD4+CD25+Treg in Food Allergic Mice," Master's Thesis submitted at Zhengzhou University (2010) 65 pages, Chinese with English Abstract.

Watanabe et al., "Current approaches for the treatment of multiple myeloma," Int J Hematol (2013) vol. 97, pp. 333-344.

Wiener et al., "TIM-3 Is Expressed in Melanoma Cells and Is Upregulated in TGF-Beta Stimulated Mast Cells" Journal of Investigative Dermatology (2007) vol. 127 pp. 906-914.

Wolchok et al., "Nivolumab plus Ipilimumab in Advanced Melanoma," N Engl J Med (2013) vol. 369, pp. 122-133.

Woo et al. "Immune Inhibitory Molecules LAG-3 and PD-1 Synergistically Regulate T-cell Function to Promote Tumoral Immune Escape" Cancer Research (2011) vol. 72, No. 4, pp. 917-927.

Workman et al., "Negative Regulation of T Cell Homeostasis by Lymphocyte Activation Gene-3 (CD223)," J Immuno (2005) vol. 174, pp. 688-695.

Wu et al., "Endothelial cell-expressed Tim-3 facilitates metastasis of melanoma cells by activating the NF-κB pathway" Oncology Reports (2010) vol. 24 pp. 693-699.

Wu et al., "Immunotherapies: The Blockade of Inhibitory Signals," Int J Biol Sci (2012) vol. 8, No. 10, pp. 1420-1430.

Yan et al.,"Tim-3 Expression Defines Regulatory T Cells in Human Tumors" PLoS ONE (2013) vol. 8 No. 3 e58006.

Yervoy (ipilimumab) Drug Label, Initial U.S. Approval: 2011, Revised Oct. 2015.

Zamarin et al. "Immune checkpoint modulation: Rational design of combindation strategies" Pharmacology & Therapeutics (2015) vol. 150, pp. 23-32.

Zhang et al., "Tim-3 regulates pro-and anti-inflammatory cytokine expression in human CD14+ monocytes" Journal of Leucyte Biology (2012) vol. 91 pp. 189-196.

Extended European Search Report issued in European Application No. 21166347.1 dated Nov. 9, 2021.

Janku et al. "Abstract CT034: Phase I study of WNT974 + spartalizumab in patients (pts) with advanced solid tumors" Cancer Research (2020) vol. 80, No. 16, pp. 1-4.

Office Action from Brazilian Application No. 112017006664-5 dated Sep. 21, 2021.

\* cited by examiner

COMBINATION THERAPIES

CROSS REFERENCE TO RELATED APPLICATIONS

This application is a U.S. National Stage Application under 35 U.S.C. § 371 of International Application No. PCT/US2015/049826, filed Sep. 11, 2015, which claims the benefit of U.S. Provisional Application No. 62/050,116, filed Sep. 13, 2014, U.S. Provisional Application No. 62/059,788, filed Oct. 3, 2014, U.S. Provisional Application No. 62/119,060, filed Feb. 20, 2015, and U.S. Provisional Application No. 62/199,030, filed Jul. 30, 2015, The contents of the aforesaid applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 4, 2015, is named C2160-7005WO_SL.txt and is 14,732 bytes in size.

BACKGROUND

The ability of T cells to mediate an immune response against an antigen requires two distinct signaling interactions (Viglietta, V. et al. (2007) *Neurotherapeutics* 4:666-675; Korman, A. J. et al. (2007) *Adv. Immunol.* 90:297-339). First, an antigen that has been arrayed on the surface of antigen-presenting cells (APC) is presented to an antigen-specific naive CD4$^+$ T cell. Such presentation delivers a signal via the T cell receptor (TCR) that directs the T cell to initiate an immune response specific to the presented antigen. Second, various co-stimulatory and inhibitory signals mediated through interactions between the APC and distinct T cell surface molecules trigger the activation and proliferation of the T cells and ultimately their inhibition.

The immune system is tightly controlled by a network of costimulatory and co-inhibitory ligands and receptors. These molecules provide the second signal for T cell activation and provide a balanced network of positive and negative signals to maximize immune responses against infection, while limiting immunity to self (Wang, L. et al. (Epub Mar. 7, 2011) *J. Exp. Med.* 208(3):577-92; Lepenies, B. et al. (2008) *Endocrine, Metabolic & Immune Disorders—Drug Targets* 8:279-288). Examples of costimulatory signals include the binding between the B7.1 (CD80) and B7.2 (CD86) ligands of the APC and the CD28 and CTLA-4 receptors of the CD4$^+$ T-lymphocyte (Sharpe, A. H. et al. (2002) *Nature Rev. Immunol.* 2:116-126; Lindley, P. S. et al. (2009) *Immunol. Rev.* 229:307-321). Binding of B7.1 or B7.2 to CD28 stimulates T cell activation, whereas binding of B7.1 or B7.2 to CTLA-4 inhibits such activation (Dong, C. et al. (2003) *Immunolog. Res.* 28(1):39-48; Greenwald, R. J. et al. (2005) *Ann. Rev. Immunol.* 23:515-548). CD28 is constitutively expressed on the surface of T cells (Gross, J., et al. (1992) *J. Immunol.* 149:380-388), whereas CTLA4 expression is rapidly up-regulated following T-cell activation (Linsley, P. et al. (1996) *Immunity* 4:535-543).

Other ligands of the CD28 receptor include a group of related B7 molecules, also known as the "B7 Superfamily" (Coyle, A. J. et al. (2001) *Nature Immunol.* 2(3):203-209; Sharpe, A. H. et al. (2002) *Nature Rev. Immunol.* 2:116-126; Collins, M. et al. (2005) *Genome Biol.* 6:223.1-223.7; Korman, A. J. et al. (2007) *Adv. Immunol.* 90:297-339). Several members of the B7 Superfamily are known, including B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 and B7-H6 (Collins, M. et al. (2005) *Genome Biol.* 6:223.1-223.7).

The Programmed Death 1 (PD-1) protein is an inhibitory member of the extended CD28/CTLA4 family of T cell regulators (Okazaki et al. (2002) *Curr Opin Immunol* 14: 391779-82; Bennett et al. (2003) *J. Immunol.* 170:711-8). Other members of the CD28 family include CD28, CTLA-4, ICOS and BTLA. PD-1 is suggested to exist as a monomer, lacking the unpaired cysteine residue characteristic of other CD28 family members. PD-1 is expressed on activated B cells, T cells, and monocytes.

The PD-1 gene encodes a 55 kDa type I transmembrane protein (Agata et al. (1996) *Int Immunol.* 8:765-72). Although structurally similar to CTLA-4, PD-1 lacks the MYPPY motif (SEQ ID NO: 1) that is important for B7-1 and B7-2 binding. Two ligands for PD-1 have been identified, PD-L1 (B7-H1) and PD-L2 (B7-DC), that have been shown to downregulate T cell activation upon binding to PD-1 (Freeman et al. (2000) *J. Exp. Med.* 192:1027-34; Carter et al. (2002) *Eur. J. Immunol.* 32:634-43). Both PD-L1 and PD-L2 are B7 homologs that bind to PD-1, but do not bind to other CD28 family members. PD-L1 is abundant in a variety of human cancers (Dong et al. (2002) *Nat. Med.* 8:787-9).

PD-1 is known as an immunoinhibitory protein that negatively regulates TCR signals (Ishida, Y. et al. (1992) *EMBO J.* 11:3887-3895; Blank, C. et al. (Epub 2006 Dec. 29) *Immunol. Immunother.* 56(5):739-745). The interaction between PD-1 and PD-L1 can act as an immune checkpoint, which can lead to, e.g., a decrease in tumor infiltrating lymphocytes, a decrease in T-cell receptor mediated proliferation, and/or immune evasion by cancerous cells (Dong et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) *Proc. Nat'l. Acad. Sci.* USA 99:12293-7; Brown et al. (2003) *J. Immunol.* 170:1257-66).

Given the importance of immune checkpoint pathways in regulating an immune response, the need exists for developing novel combination therapies that activate the immune system.

SUMMARY

The present invention provides, at least in part, methods and compositions comprising an immunomodulator (e.g., one or more of: an activator of a costimulatory molecule or an inhibitor of an immune checkpoint molecule) in combination with a second therapeutic agent chosen from one or more of the agents listed in Table 1. In one embodiment, an inhibitor of an immune checkpoint molecule (e.g., one or more inhibitors of PD-1, PD-L1, LAG-3, TIM-3, CEACAM (e.g., CEACAM-1, -3 and/or -5) or CTLA4) can be combined with a second therapeutic agent chosen from one or more agents listed in Table 1 (e.g., one or more of: 1) an EGF receptor inhibitor; 2) a c-MET inhibitor; 3) an ALK inhibitor; 4) a CDK4/6-inhibitor; 5) a PI3K inhibitor; 6) a BRAF inhibitor; 7) a CAR T cell (e.g., a CAR T cell targeting CD19); 8) an FGF receptor inhibitor; 9) a MEK inhibitor, or 10) a BCR-ABL inhibitor). The combinations described herein can provide a beneficial effect, e.g., in the treatment of a cancer, such as an enhanced anti-cancer effect, reduced toxicity and/or reduced side effects. For example, the immunomodulator, the second therapeutic agent, or both, can be administered at a lower dosage than would be required to achieve the same therapeutic effect compared to a monotherapy dose. Thus, compositions and methods for treating proliferative disorders, including cancer, using the aforesaid combination therapies are disclosed.

Accordingly, in one aspect, the invention features a method of treating (e.g., inhibiting, reducing, ameliorating, or preventing) a proliferative condition or disorder (e.g., a cancer) in a subject. The method includes administering to the subject an immunomodulator (e.g., one or more of: an activator of a costimulatory molecule or an inhibitor of an immune checkpoint molecule) and a second therapeutic agent, e.g., a second therapeutic agent chosen from one or more of the agents listed in Table 1, thereby treating the proliferative condition or disorder (e.g., the cancer). In certain embodiments, the immunomodulator is an inhibitor of an immune checkpoint molecule (e.g., an inhibitor of PD-1, PD-L1, LAG-3, TIM-3, CEACAM (e.g., CEACAM-1, -3 and/or -5) or CTLA4, or any combination thereof). In other embodiments, the second therapeutic agent is chosen from one or more of the agents listed in Table 1; e.g., one or more of: 1) an EGF receptor inhibitor; 2) a c-MET inhibitor; 3) an ALK inhibitor; 4) a CDK4/6-inhibitor; 5) a PI3K inhibitor; 6) a BRAF inhibitor; 7) a CAR T cell (e.g., a CAR T cell targeting CD19); 8) an FGF receptor inhibitor; 9) a MEK inhibitor, or 10) a BCR-ABL inhibitor; e.g., listed in Table 1. The combination of the immunomodulator and the second agent can be administered together in a single composition or administered separately in two or more different compositions, e.g., one or more compositions or dosage forms as described herein. The administration of the immunomodulator and the second agent can be in any order. For example, the immunomodulator can be administered concurrently with, prior to, or subsequent to, the second agent.

In another aspect, the invention features a method of reducing an activity (e.g., growth, survival, or viability, or all), of a proliferative (e.g., a cancer) cell. The method includes contacting the cell with an immunomodulator (e.g., one or more of: an activator of a costimulatory molecule or an inhibitor of an immune checkpoint molecule) and a second therapeutic agent, e.g., a second therapeutic agent chosen from one or more of the agents listed in Table 1, thereby reducing an activity in the cell. In certain embodiments, the immunomodulator is an inhibitor of an immune checkpoint molecule (e.g., an inhibitor of PD-1, PD-L1, LAG-3, TIM-3, CEACAM (e.g., CEACAM-1, -3 and/or -5) or CTLA4, or any combination thereof). In other embodiments, the second therapeutic agent is chosen from one or more of the agents listed in Table 1; e.g., one or more of: 1) an EGF receptor inhibitor; 2) a c-MET inhibitor; 3) an ALK inhibitor; 4) a CDK4/6-inhibitor; 5) a PI3K inhibitor; 6) a BRAF inhibitor; 7) a CAR T cell (e.g., a CAR T cell targeting CD19); 8) an FGF receptor inhibitor; 9) a MEK inhibitor, or 10) a BCR-ABL inhibitor; e.g., listed in Table 1. The methods described herein can be used in vitro or in vivo, e.g., in an animal subject or as part of a therapeutic protocol. The contacting of the cell with the immunomodulator and the second agent can be in any order. In certain embodiments, the cell is contacted with the immunomodulator concurrently, prior to, or subsequent to, the second agent.

In another aspect, the invention features a composition (e.g., one or more compositions, formulations or dosage formulations) or a pharmaceutical combination, comprising an immunomodulator (e.g., one or more of: an activator of a costimulatory molecule or an inhibitor of an immune checkpoint molecule) and a second therapeutic agent, e.g., a second therapeutic agent chosen from one or more of the agents listed in Table 1. In certain embodiments, the immunomodulator is an inhibitor of an immune checkpoint molecule (e.g., an inhibitor of PD-1, PD-L1, LAG-3, TIM-3, CEACAM (e.g., CEACAM-1, -3 and/or -5) or CTLA4, or any combination thereof). In other embodiments, the second therapeutic agent is chosen from one or more of the agents listed in Table 1; e.g., one or more of: 1) an EGF receptor inhibitor; 2) a c-MET inhibitor; 3) an ALK inhibitor; 4) a CDK4/6-inhibitor; 5) a PI3K inhibitor; 6) a BRAF inhibitor; 7) a CAR T cell (e.g., a CAR T cell targeting CD19); 8) an FGF receptor inhibitor; 9) a MEK inhibitor, or 10) a BCR-ABL inhibitor), e.g., listed in Table 1. In one embodiment, the composition comprises a pharmaceutically acceptable carrier. The immunomodulator and the second agent can be present in a single composition or as two or more different compositions. The immunomodulator and the second agent can be administered via the same administration route or via different administration routes. In one embodiment, the pharmaceutical combination comprises the immunomodulator and the second agent separately or together.

In one embodiment, the composition, formulation or pharmaceutical combination is for use as a medicine, e.g., for the treatment of a proliferative disease (e.g., a cancer as described herein). In some embodiments, the immunomodulator and the second agent are administered concurrently, e.g., independently at the same time or within an overlapping time interval, or separately within time intervals. In certain embodiment, the time interval allows the immunomodulator and the second agent to be jointly active. In one embodiment, the composition, formulation or pharmaceutical combination includes an amount which is jointly therapeutically effective for the treatment of a proliferative disease, e.g., a cancer as described herein.

In another aspect, the invention features a use of a composition (e.g., one or more compositions, formulations or dosage formulations) or a pharmaceutical combination, comprising an immunomodulator (e.g., one or more of: an activator of a costimulatory molecule or an inhibitor of an immune checkpoint molecule) and a second therapeutic agent, e.g., a second therapeutic agent chosen from one or more of the agents listed in Table 1, for the manufacture of a medicament for treating a proliferative disease, e.g., a cancer. In certain embodiments, the immunomodulator is an inhibitor of an immune checkpoint molecule (e.g., an inhibitor of PD-1, PD-L1, LAG-3, TIM-3, CEACAM (e.g., CEACAM-1, -3 and/or -5) or CTLA4, or any combination thereof). In other embodiments, the second therapeutic agent is chosen from one or more of the agents listed in Table 1; e.g., one or more of: 1) an EGF receptor inhibitor; 2) a c-MET inhibitor; 3) an ALK inhibitor; 4) a CDK4/6-inhibitor; 5) a PI3K inhibitor; 6) a BRAF inhibitor; 7) a CAR T cell (e.g., a CAR T cell targeting CD19); 8) an FGF receptor inhibitor; 9) a MEK inhibitor, or 10) a BCR-ABL inhibitor), e.g., listed in Table 1.

Kits, e.g., therapeutic kits, that include the immunomodulator (e.g., one or more of: an activator of a costimulatory molecule or an inhibitor of an immune checkpoint molecule as described herein) and the second therapeutic agent, e.g., a second therapeutic agent chosen from one or more of the agents listed in Table 1, and instructions for use, are also disclosed.

Additional features or embodiments of the methods, compositions, dosage formulations, combinations, and kits described herein include one or more of the following:

In certain embodiments, the immunomodulator is an activator of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand, or any combination thereof.

In certain embodiments, the immunomodulator is an inhibitor of an immune checkpoint molecule. In one embodiment, the immunomodulator is an inhibitor of PD-1, PD-L1, PD-L2, CTLA4, TIM3, LAG3, CEACAM (e.g., CEACAM-1, -3 and/or -5), VISTA, BTLA, TIGIT, LAIR1, CD160, 2B4 and/or TGFR beta. In one embodiment, the inhibitor of an immune checkpoint molecule inhibits PD-1, PD-L1, LAG-3, TIM-3, CEACAM (e.g., CEACAM-1, -3 and/or -5) or CTLA4, or any combination thereof.

Inhibition of an inhibitory molecule can be performed at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is a polypeptide e.g., a soluble ligand (e.g., PD-1-Ig or CTLA-4 Ig). In other embodiments, the inhibitor of the inhibitory signal is an antibody or antigen-binding fragment thereof, that binds to the inhibitory molecule; e.g., an antibody or fragment thereof (also referred to herein as "an antibody molecule") that binds to PD-1, PD-L1, PD-L2, CTLA4, TIM3, LAG3, CEACAM (e.g., CEACAM-1, -3 and/or -5), VISTA, BTLA, TIGIT, LAIR1, CD160, 2B4 and/or TGFR beta, or a combination thereof.

In one embodiment, the antibody molecule is a full antibody or fragment thereof (e.g., a Fab, F(ab')$_2$, Fv, or a single chain Fv fragment (scFv)). In yet other embodiments, the antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG4 (e.g., human IgG1 or IgG4). In one embodiment, the heavy chain constant region is human IgG1 or human IgG4. In one embodiment, the constant region is altered, e.g., mutated, to modify the properties of the antibody molecule (e.g., to increase or decrease one or more of: Fc receptor binding, antibody glycosylation, the number of cysteine residues, effector cell function, or complement function).

In certain embodiments, the antibody molecule is in the form of a bispecific or multispecific antibody molecule. In one embodiment, the bispecific antibody molecule has a first binding specificity to PD-1 or PD-L1 and a second binding specifity, e.g., a second binding specificity to TIM-3, LAG-3, or PD-L2. In one embodiment, the bispecific antibody molecule binds to PD-1 or PD-L1 and TIM-3. In another embodiment, the bispecific antibody molecule binds to PD-1 or PD-L1 and LAG-3. In another embodiment, the bispecific antibody molecule binds to PD-1 or PD-L1 and CEACAM (e.g., CEACAM-1, -3 and/or -5). In another embodiment, the bispecific antibody molecule binds to PD-1 or PD-L1 and CEACAM-1. In still another embodiment, the bispecific antibody molecule binds to PD-1 or PD-L1 and CEACAM-3. In yet another embodiment, the bispecific antibody molecule binds to PD-1 or PD-L1 and CEACAM-5. In another embodiment, the bispecific antibody molecule binds to PD-1 or PD-L1. In yet another embodiment, the bispecific antibody molecule binds to PD-1 and PD-L2. In another embodiment, the bispecific antibody molecule binds to TIM-3 and LAG-3. In another embodiment, the bispecific antibody molecule binds to CEACAM (e.g., CEACAM-1, -3 and/or -5) and LAG-3. In another embodiment, the bispecific antibody molecule binds to CEACAM (e.g., CEACAM-1, -3 and/or -5) and TIM-3. Any combination of the aforesaid molecules can be made in a multispecific antibody molecule, e.g., a trispecific antibody that includes a first binding specificity to PD-1 or PD-1, and a second and third binding specifities to two or more of: TIM-3, CEACAM (e.g., CEACAM-1, -3 and/or -5), LAG-3, or PD-L2.

In certain embodiments, the immunomodulator is an inhibitor of PD-1, e.g., human PD-1. In another embodiment, the immunomodulator is an inhibitor of PD-L1, e.g., human PD-L1. In one embodiment, the inhibitor of PD-1 or PD-L1 is an antibody molecule to PD-1 or PD-L1. The PD-1 or PD-L1 inhibitor can be administered alone, or in combination with other immunomodulators, e.g., in combination with an inhibitor of LAG-3, TIM-3, CEACAM (e.g., CEACAM-1, -3 and/or -5) or CTLA4. In an exemplary embodiment, the inhibitor of PD-1 or PD-L1, e.g., the anti-PD-1 or PD-L1 antibody molecule, is administered in combination with a LAG-3 inhibitor, e.g., an anti-LAG-3 antibody molecule. In another embodiment, the inhibitor of PD-1 or PD-L1, e.g., the anti-PD-1 or PD-L1 antibody molecule, is administered in combination with a TIM-3 inhibitor, e.g., an anti-TIM-3 antibody molecule. In yet other embodiments, the inhibitor of PD-1 or PD-L1, e.g., the anti-PD-1 antibody molecule, is administered in combination with a LAG-3 inhibitor, e.g., an anti-LAG-3 antibody molecule, and a TIM-3 inhibitor, e.g., an anti-TIM-3 antibody molecule. In another embodiment, the inhibitor of PD-1 or PD-L1, e.g., the anti-PD-1 or PD-L1 antibody molecule, is administered in combination with a CEACAM inhibitor (e.g., CEACAM-1, -3 and/or -5 inhibitor), e.g., an anti-CEACAM antibody molecule. In another embodiment, the inhibitor of PD-1 or PD-L1, e.g., the anti-PD-1 or PD-L1 antibody molecule, is administered in combination with a CEACAM-1 inhibitor, e.g., an anti-CEACAM-1 antibody molecule. In another embodiment, the inhibitor of PD-1 or PD-L1, e.g., the anti-PD-1 or PD-L1 antibody molecule, is administered in combination with a CEACAM-5 inhibitor, e.g., an anti-CEACAM-5 antibody molecule. Other combinations of immunomodulators with a PD-1 inhibitor (e.g., one or more of PD-L2, CTLA4, TIM3, CEACAM (e.g., CEACAM-1, -3 and/or -5) LAG3, VISTA, BTLA, TIGIT, LAIR1, CD160, 2B4 and/or TGFR) are also within the present invention. Any of the antibody molecules known in the art or disclosed herein can be used in the aforesaid combinations of inhibitors of checkpoint molecule.

Exemplary Inhibitors of Immune Checkpoint Molecules

In one embodiment, the PD-1 inhibitor is an anti-PD-1 antibody chosen from Nivolumab, Pembrolizumab or Pidilizumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168.

In other embodiments, the anti-PD-1 antibody is Pembrolizumab. Pembrolizumab (Trade name KEYTRUDA formerly Lambrolizumab, also known as Merck 3745, MK-3475 or SCH-900475) is a humanized IgG4 monoclonal antibody that binds to PD-1. Pembrolizumab is disclosed, e.g., in Hamid, O. et al. (2013) *New England Journal of Medicine* 369 (2): 134-44, WO2009/114335, and U.S. Pat. No. 8,354,509.

In some embodiments, the anti-PD-1 antibody is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in WO2009/101611. Other anti-PD1 antibodies are disclosed in U.S. Pat. No. 8,609,089, US 2010028330, and/or US 20120114649. Other anti-PD1 antibodies include AMP 514 (Amplimmune).

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 inhibitor is AMP-224.

In some embodiments, the PD-L1 inhibitor is anti-PD-L1 antibody. In some embodiments, the anti-PD-L1 inhibitor is chosen from YW243.55.S70, MPDL3280A, MEDI-4736, MSB-0010718C, or MDX-1105.

In one embodiment, the PD-L1 inhibitor is MDX-1105. MDX-1105, also known as BMS-936559, is an anti-PD-L1 antibody described in WO2007/005874.

In one embodiment, the PD-L1 inhibitor is YW243.55.S70. The YW243.55.S70 antibody is an anti-PD-L1 described in WO 2010/077634 (heavy and light chain variable region sequences shown in SEQ ID Nos. 20 and 21, respectively, of WO 2010/077634).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in WO2010/027827 and WO2011/066342).

In one embodiment, the LAG-3 inhibitor is an anti-LAG-3 antibody molecule. In one embodiment, the LAG-3 inhibitor is BMS-986016, disclosed in more detail herein below.

One or more of the aforesaid inhibitors of immune checkpoint molecules can be used in combination with one or more of the second agents disclosed in Table 1, as more specifically exemplified below.

Exemplary Combination Therapies

In one embodiment, the inhibitor of PD-1 is Nivolumab (CAS Registry No: 946414-94-4) disclosed in e.g., U.S. Pat. No. 8,008,449, and having a sequence disclosed herein, e.g., a heavy chain sequence of SEQ ID NO:2 and a light chain sequence of SEQ ID NO:3 (or a sequence substantially identical or similar thereto, e.g., a sequence at least 85%, 90%, 95% identical or higher to the sequence specified).

In another embodiment, the inhibitor of PD-1 is Pembrolizumab, disclosed in, e.g., U.S. Pat. No. 8,354,509 and WO 2009/114335, and having a sequence disclosed herein, e.g., a heavy chain sequence of SEQ ID NO:4 and a light chain sequence of SEQ ID NO:5 (or a sequence substantially identical or similar thereto, e.g., a sequence at least 85%, 90%, 95% identical or higher to the sequence specified).

In another embodiment, the inhibitor of PD-L1 is MSB0010718C (also referred to as A09-246-2) disclosed in, e.g., WO 2013/0179174, and having a sequence disclosed herein, e.g., a heavy chain sequence of SEQ ID NO:6 and a light chain sequence of SEQ ID NO:7 (or a sequence substantially identical or similar thereto, e.g., a sequence at least 85%, 90%, 95% identical or higher to the sequence specified).

In certain embodiments, the PD-1 inhibitor, e.g., the anti-PD-1 antibody (e.g., Nivolumab) is used in a method or composition described herein. For example, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C) (alone or in combination with other immunomodulators) is used in combination with one or more of the agents listed in Table 1; e.g., one or more of: 1) an EGF receptor inhibitor; 2) a c-MET inhibitor; 3) an ALK inhibitor; 4) a CDK4/6-inhibitor; 5) a PI3K inhibitor; 6) a BRAF inhibitor; 7) a CAR T cell (e.g., a CAR T cell targeting CD19); 8) an FGF receptor inhibitor; 9) a MEK inhibitor, or 10) a BCR-ABL inhibitor), e.g., listed in Table 1, or disclosed herein, e.g., in a publication listed in Table 1. In one embodiment, one or more of the aforesaid combinations is used to treat a disorder, e.g., a disorder described herein (e.g., a disorder disclosed in Table 1). In one embodiment, one or more of the aforesaid combinations is used to treat a cancer, e.g., a cancer described herein (e.g., a cancer disclosed in Table 1). Each of these combinations is discussed in more detail below.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with an EGF receptor inhibitor to treat a cancer, e.g., a cancer described herein (e.g., a cancer disclosed in Table 1). In one embodiment, the EGF receptor inhibitor is disclosed herein, e.g., in Table 1. In one embodiment, the EGF receptor inhibitor is EGF816, or as provided herein (e.g., a publication recited in Table 1). In one embodiment, the EGF receptor inhibitor, e.g., EGF816, has the structure (compound or generic structure) provided herein, e.g., in Table 1, or as disclosed in the publication recited in Table 1. In one embodiment, one of Nivolumab, Pembrolizumab or MSB0010718C is used in combination with EGF816 to treat a cancer described herein, e.g., in Table 1, e.g., a solid tumor, e.g., a lung cancer (e.g., non-small cell lung cancer (NSCLC)), a lymphoma, or a neuroblastoma.

In one embodiment, the cancer is NSCLC and is characterized by one or more of: aberrant activation, amplification, or a mutation of epidermal growth factor receptor (EGFR). In certain embodiments the cancer is NSCLC wherein the NSCLC is characterized by harbouring an EGFR exon 20 insertion, an EGFR exon 19 deletion, EGFR L858R mutation, EGFR T790M, or any combination thereof. In some embodiments, the combination is for use in the treatment of NSCLC, wherein the NSCLC is characterized by harboring an EGFR exon 20 insertion, an EGFR exon 19 deletion, EGFR L858R mutation, EGFR T790M, or any combination thereof. In some embodiments, the NSCLC is characterized by harboring L858R and T790M mutations of EGFR. In other embodiments, the NSCLC is characterized by harboring an EGFR exon 20 insertion and T790M mutations of EGFR. In yet other embodiments, the NSCLC is characterized by harboring an EGFR exon 19 deletion and T790M mutations of EGFR. In other embodiments, the NSCLC is characterized by harboring EGFR mutation selected from the group consisting of an exon 20 insertion, an exon 19 deletion, L858R mutation, T790M mutation, and any combination thereof.

In some embodiments, the lymphoma (e.g., an anaplastic large-cell lymphoma or non-Hodgkin lymphoma) has, or is identified as having, an ALK translocation, e.g., an EML4-ALK fusion.

In certain embodiments, EGF816 is administered at an oral dose of about 50 to 500 mg, e.g., about 100 mg to 400 mg, about 150 mg to 350 mg, or about 200 mg to 300 mg, e.g., about 100 mg, 150 mg or 200 mg. The dosing schedule can vary from e.g., every other day to daily, twice or three times a day. In one embodiment, EGF816 is administered at an oral dose from about 100 to 200 mg, e.g., about 150 mg, once a day. In some embodiments, EGF816 is administered at a dose of 75, 100, 150, 225, 150, 200, 225, 300 or 350 mg. These doses may be administered once daily. E.g. EGF816 may be administered at a dose of 100 or 150 mg once daily. In embodiments of the combination, Nivolumab is administered in an amount from about 1 mg/kg to 5 mg/kg, e.g., 3 mg/kg, and may be administered over a period of 60 minutes, ca. once a week to once every 2, 3 or 4 weeks.

In another embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a c-MET inhibitor to treat a cancer, e.g., a cancer described herein (e.g., a cancer disclosed in Table 1). In one embodiment, the c-MET inhibitor is disclosed herein, e.g., in Table 1. In one embodiment, the c-MET inhibitor is INC280 (formerly known as INCB28060) as disclosed herein, or in a publication recited in Table 1. In one embodiment, the c-MET inhibitor, e.g., INC280, has the structure (compound or generic structure) provided herein, e.g., in Table 1, or as disclosed in the publication recited in Table 1. In one embodiment, one of Nivolumab, Pembrolizumab or MSB0010718C is used in combination with INC280 to treat a cancer described in Table 1, e.g., a solid tumor, e.g., a lung cancer (e.g., non-small cell lung cancer (NSCLC)), glioblastoma multiforme (GBM), a renal cancer, a liver cancer (e.g., a hepatocellular carcinoma) or a gastric cancer. In some embodiments, the cancer has, or is identified as having, a c-MET mutation (e.g., a c-MET mutation or a c-MET amplification).

In certain embodiments, INC280 is administered at an oral dose of about 100 to 1000 mg, e.g., about 200 mg to 900 mg, about 300 mg to 800 mg, or about 400 mg to 700 mg, e.g., about 400 mg, 500 mg or 600 mg. The dosing schedule can vary from e.g., every other day to daily, twice or three times a day. In one embodiment, INC280 is administered at an oral dose from about 400 to 600 mg twice a day.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with an Alk inhibitor to treat a cancer, e.g., a cancer described herein (e.g., a cancer disclosed in Table 1). In one embodiment, the Alk inhibitor is disclosed herein, e.g., in Table 1. In one embodiment, the Alk inhibitor is LDK378 (also known as ceritinib (Zykadia®), e.g., as described herein or in a publication recited in Table 1. In one embodiment, the Alk inhibitor, e.g., LDK378, has the structure (compound or generic structure) provided herein, e.g., in Table 1, or as disclosed in the publication recited in Table 1.

In one embodiment, one of Nivolumab, Pembrolizumab or MSB0010718C is used in combination with LDK378 to treat a cancer described in Table 1, e.g., a solid tumor, e.g., a lung cancer (e.g., non-small cell lung cancer (NSCLC)), a lymphoma (e.g., an anaplastic large-cell lymphoma or non-Hodgkin lymphoma), an inflammatory myofibroblastic tumor (IMT), or a neuroblastoma. In some embodiments, the NSCLC is a stage IIIB or IV NSCLC, or a relapsed locally advanced or metastic NSCLC. In some embodiments, the cancer (e.g., the lung cancer, lymphoma, inflammatory myofibroblastic tumor, or neuroblastoma) has, or is identified as having, an ALK rearrangement or translocation, e.g., an ALK fusion. In one embodiment, the ALK fusion is an EML4-ALK fusion, e.g., an EML4-ALK fusion described herein. In another embodiment, the ALK fusion is an ALK-ROS1 fusion. In certain embodiments, the cancer has progressed on, or is resistant or tolerant to, a ROS1 inhibitor, or an ALK inhibitor, e.g., an ALK inhibitor other than LDK378. In some embodiments, the cancer has progressed on, or is resistant or tolerant to, crizotinib. In one embodiment, the subject is an ALK-naïve patient, e.g., a human patient. In another embodiment, the subject is a patient, e.g., a human patient, that has been pre-treated with an ALK inhibitor. In another embodiment, the subject is a patient, e.g., a human patient, that has been pretreated with LDK378.

In one embodiment, LDK378 and Nivolumab are administered to an ALK-naïve patient. In another embodiment, LDK378 and Nivolumab are administered to a patient that has been pretreated with an ALK inhibitor. In yet another embodiment, LDK378 and Nivolumab are administered to a patient that has been pretreated with LDK378.

In certain embodiments, LDK378 is administered at an oral dose of about 100 to 1000 mg, e.g., about 150 mg to 900 mg, about 200 mg to 800 mg, about 300 mg to 700 mg, or about 400 mg to 600 mg, e.g., about 150 mg, 300 mg, 450 mg, 600 mg or 750 mg. In certain embodiment, LDK378 is administered at an oral dose of about 750 mg or lower, e.g., about 600 mg or lower, e.g., about 450 mg or lower. In certain embodiments, LDK378 is administered with food. In other embodiments, the dose is under fasting condition. The dosing schedule can vary from e.g., every other day to daily, twice or three times a day. In one embodiment, LDK378 is administered daily. In one embodiment, LDK378 is administered at an oral dose from about 150 mg to 750 mg daily, either with food or in a fasting condition. In one embodiment, LDK378 is administered at an oral dose of about 750 mg daily, in a fasting condition. In one embodiment, LDK378 is administered at an oral dose of about 750 mg daily, via capsule or tablet. In another embodiment, LDK378 is administered at an oral dose of about 600 mg daily, via capsule or tablet. In one embodiment, LDK378 is administered at an oral dose of about 450 mg daily, via capsule or tablet.

In one embodiment, LDK378 is administered at a dose of about 450 mg and nivolumab is administered at a dose of about 3 mg/kg. In another embodiment, the LDK378 dose is 600 mg and the nivolumab dose is 3 mg/kg. In one embodiment, LDK378 is administered with a low fat meal.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a CDK4/6 inhibitor to treat a cancer, e.g., a cancer described herein (e.g., a cancer disclosed in Table 1). In one embodiment, the CDK4/6 inhibitor is disclosed herein, e.g., in Table 1. In one embodiment, LEE011 (also knows as Ribociclib®), e.g., as described herein or in a publication recited in Table 1. In one embodiment, the CDK4/6 inhibitor, e.g., LEE011, has the structure (compound or generic structure) provided herein, e.g., in Table 1, or as disclosed in the publication recited in Table 1. In one embodiment, one of Nivolumab, Pembrolizumab or MSB0010718C is used in combination with LEE011 to treat a cancer described in Table 1, e.g., a solid tumor, e.g., a lung cancer (e.g., non-small cell lung cancer (NSCLC)), a neurologic cancer, melanoma or a breast cancer, or a hematological malignancy, e.g., lymphoma.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a PI3K-inhibitor to treat a cancer, e.g., a cancer described herein (e.g., a cancer disclosed in Table 1). In one embodiment, the PI3K inhibitor is disclosed herein, e.g., in Table 1. In one embodiment, the PI3K inhibitor is BKM120 or BYL719, e.g., disclosed herein or in a publication recited in Table 1. In one embodiment, the PI3K-inhibitor, e.g., BKM120 or BYL719, has the structure (compound or generic structure) provided herein, e.g., in Table 1, or as disclosed in the publication recited in Table 1. In one embodiment, one of Nivolumab, Pembrolizumab or MSB0010718C is used in combination with BKM120 or BYL719 to treat a cancer or disorder described herein, e.g., in Table 1. In some embodiments, the cancer or disorder is chosen from, e.g., a solid tumor, e.g., a lung cancer (e.g., non-small cell lung cancer (NSCLC)), a prostate cancer, an endocrine cancer, an ovarian cancer, a melanoma, a bladder cancer, a female reproductive system cancer, a digestive/gastrointestinal cancer, a colorectal cancer, glioblastoma multiforme (GBM), a head and neck cancer, a gastric cancer, a pancreatic cancer or a breast cancer; or a hematological malignancy, e.g., leukemia, non-Hodgkin lymphoma; or a hematopoiesis disorder.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a BRAF inhibitor to treat a cancer, e.g., a cancer described herein (e.g., a cancer disclosed in Table 1). In one embodiment, the BRAF inhibitor is disclosed herein, e.g., in Table 1. In one embodiment, the BRAF inhibitor is LGX818, e.g., as described herein or in a publication recited in Table 1. In one embodiment, the BRAF inhibitor, e.g., LGX818, has the structure (compound or generic structure) provided herein, e.g., in Table 1, or as disclosed in the publication recited in Table 1. In one embodiment, one of Nivolumab, Pembrolizumab or MSB0010718C is used in combination with LGX818 to treat a cancer described in Table 1, e.g., a solid tumor, e.g., a lung cancer (e.g., non-small cell lung cancer (NSCLC)), a melanoma, e.g., advanced melanoma, a thyroid cancer, e.g., papillary thyroid cancer, or a colorectal cancer. In some embodiments, the cancer has, or is identified as having, a BRAF mutation (e.g., a BRAF V600E mutation), a BRAF wildtype, a KRAS wildtype or an activating KRAS mutation. The cancer may be at an early, intermediate or late stage.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a CAR T cell targeting CD19 to treat a cancer, e.g., a cancer described herein (e.g., a cancer disclosed in Table 1). In one embodiment, the CAR T cell targeting CD19 is disclosed in Table 1, e.g., CTL019, or in a publication recited in Table 1. In one embodiment, the CAR T cell targeting CD19, e.g., CTL019, has the structure (compound or generic structure) provided herein, e.g., in Table 1, or as disclosed in the publication recited in Table 1. In one embodiment, one of Nivolumab, Pembrolizumab or MSB0010718C is used in combination with CTL019 to treat a cancer described in Table 1, e.g., a solid tumor, or a hematological malignancy, e.g., a lymphocytic leukemia or a non-Hodgkin lymphoma.

In one embodiment, the CAR T cell targeting CD19 has the USAN designation TISAGENLECLEUCEL-T. CTL019 is made by a gene modification of T cells is mediated by stable insertion via transduction with a self-inactivating, replicationdeficient Lentiviral (LV) vector containing the CTL019 transgene under the control of the EF-1 alpha promoter. CTL019 is a mixture of transgene positive and negative T cells that are delivered to the subject on the basis of percent transgene positive T cells.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with an FGF receptor inhibitor to treat a cancer, e.g., a cancer described herein (e.g., a cancer disclosed in Table 1). In one embodiment, the FGF receptor inhibitor is disclosed herein, e.g., in Table 1. In one embodiment, the FGF receptor inhibitor is BGJ398, e.g., as described herein or in a publication recited in Table 1. In one embodiment, the FGF receptor inhibitor, e.g., BGJ398, has the structure (compound or generic structure) provided herein, e.g., in Table 1, or as disclosed in the publication recited in Table 1. In one embodiment, one of Nivolumab, Pembrolizumab or MSB0010718C is used in combination with BGJ398 to treat a cancer described in Table 1, e.g., a solid tumor, e.g., a digestive/gastrointestinal cancer; or a hematological cancer.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a MEK inhibitor to treat a cancer, e.g., a cancer described herein (e.g., a cancer disclosed in Table 1). In one embodiment, the MEK inhibitor is disclosed herein, e.g., in Table 1. In one embodiment, the MEK inhibitor is MEK162, e.g., disclosed herein or in a publication recited in Table 1. In one embodiment, the MEK inhibitor, e.g., MEK162, has the structure (compound or generic structure) provided herein, e.g., in Table 1, or as disclosed in the publication recited in Table 1. In one embodiment, one of Nivolumab, Pembrolizumab or MSB0010718C is used in combination with MEK162 to treat a cancer described in Table 1. In other embodiments, the cancer or disorder treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma, a multisystem genetic disorder, a digestive/gastrointestinal cancer, a gastric cancer, or a colorectal cancer; or rheumatoid arthritis. In some embodiments, the cancer has, or is identified as having, a KRAS mutation.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a BCR-ABL inhibitor to treat a cancer, e.g., a cancer described herein (e.g., a cancer disclosed in Table 1). In one embodiment, the BCR-ABL inhibitor is disclosed herein, e.g., in Table 1. In one embodiment, the BCR-ABL inhibitor is AMN-107 (also known as Nilotinib, trade name Tasigna), e.g., disclosed herein or in a publication recited in Table 1. In one embodiment, AMN-107 has the structure (compound or generic structure) provided herein, e.g., in Table 1, or as disclosed in the publication recited in Table 1. In one embodiment, one of Nivolumab, Pembrolizumab or MSB0010718C is used in combination with AMN-107 to treat a cancer or disorder described in Table 1, e.g., a solid tumor, e.g., a neurologic cancer, a melanoma, a digestive/gastrointestinal cancer, a colorectal cancer, a head and neck cancer; or a hematological malignancy, e.g., chronic myelogenous leukemia (CML), a lymphocytic leukemia, a myeloid leukemia; Parkinson's disease; or pulmonary hypertension.

Cancers and Subjects

In certain embodiments of the compositions and methods described herein, the proliferative disorder or condition, e.g., the cancer, includes but is not limited to, a solid tumor, a soft tissue tumor (e.g., a hematological cancer, leukemia, lymphoma, or myeloma), and a metastatic lesion of any of the aforesaid cancers. In one embodiment, the cancer is a solid tumor. Examples of solid tumors include malignancies, e.g., sarcomas, adenocarcinomas, and carcinomas, of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, non-small cell lung cancer, cancer of the small intestine and cancer of the esophagus. The cancer may be at an early, intermediate, late stage or metastatic cancer.

In one embodiment, the cancer is chosen from a cancer disclosed in Table 1. For example, the cancer can be chosen from a solid tumor, e.g., a lung cancer (e.g., a non-small cell lung cancer (NSCLC) (e.g., a NSCLC with squamous and/or non-squamous histology)), a colorectal cancer, a melanoma (e.g., an advanced melanoma), a head and neck cancer (e.g., head and neck squamous cell carcinoma (HNSCC), a digestive/gastrointestinal cancer, a gastric cancer, a neurologic cancer, a glioblastoma (e.g., glioblastoma multiforme), an ovarian cancer, a renal cancer, a liver cancer, a pancreatic cancer, a prostate cancer, a liver cancer; a breast cancer, an anal cancer, a gastro-esophageal cancer, a thyroid cancer, a cervical cancer, an inflammatory myofibroblastic tumor (IMT), a neuroblastoma; or a hematological cancer (e.g., chosen from a Hogdkin lymphoma, a non-Hodgkin lymphoma, an anaplastic large-cell lymphoma, a lymphocytic leukemia, or a myeloid leukemia).

In one embodiment, the cancer is a non-small cell lung cancer (NSCLC), e.g., an ALK+NSCLC. As used herein, the term "ALK+non-small cell lung cancer" or "ALK+NSCLC" refers to an NSCLC that has an activated (e.g., constitutively activated) anaplastic lymphoma kinase activity or has a rearrangement or translocation of an Anaplastic Lymphoma Kinase (ALK) gene. Typically, compared with the general NSCLC population, patients with ALK+NSCLC are generally younger, have light (e.g., <10 pack years) or no smoking history, present with lower Eastern Cooperative Oncology Group performance status, or may have more aggressive disease and, therefore, experience earlier disease progression (Shaw et al. J Clin Oncol. 2009; 27(26):4247-4253; Sasaki et al. Eur J Cancer. 2010; 46(10):1773-1780; Shaw et al. N Engl J Med. 2013; 368(25):2385-2394; Socinski et al. J Clin Oncol. 2012; 30(17):2055-2062; Yang et al. J Thorac Oncol. 2012; 7(1):90-97).

In one embodiment, the cancer, e.g., an NSCLC, has a rearrangement or translocation of an ALK gene. In one embodiment, the rearrangement or translocation of the ALK gene leads to a fusion (e.g., fusion upstream of the ALK promoter region). In certain embodiments, the fusion results in constitutive activation of the kinase activity.

In one embodiment, the fusion is an EML4-ALK fusion. Exemplary EML4-ALK fusion proteins include, but are not limited to, E13; A20 (V1), E20; A20 (V2), E6a/b; A20 (V3a/b), E14; A20 (V4), E2a/b; A20 (V5a/b), E13b; A20 (V6), E14; A20(V7), E15; A20("V4"), or E18; A20 (V5) (Choi et al. Cancer Res. 2008; 68(13):4971-6; Horn et al. J Clin Oncol. 2009; 27(26):4232-5; Koivunen et al. Clin Cancer Res. 2008; 14(13):4275-83; Soda et al. Nature. 2007; 448(7153):561-6; Takeuchi et al. Clin Cancer Res. 2008; 14(20):6618-24; Takeuchi et al. Clin Cancer Res. 2009; 15(9):3143-9; Wong et al. Cancer. 2009 Apr. 15; 115(8): 1723-33).

In certain embodiments, the ALK gene is fused to a non-EML4 partner. In one embodiment, the fusion is a KIF5B-ALK fusion. In another embodiment, the fusion is a TFG-ALK fusion. Exemplary KIF5B-ALK and TFG-ALK fusions are described, e.g., in Takeuchi et al. Clin Cancer Res. 2009; 15(9):3143-9, Rikova et al. Cell. 2007; 131(6): 1190-203.

ALK gene rearrangements or translocations, or cancer cells that has an ALK gene rearrangement or translocation, can be detected, e.g., using fluorescence in situ hybridization (FISH), e.g., with an ALK break apart probe.

Methods and compositions disclosed herein are useful for treating metastatic lesions associated with the aforementioned cancers.

In other embodiments, the subject is a mammal, e.g., a primate, preferably a higher primate, e.g., a human (e.g., a patient having, or at risk of having, a disorder described herein). In one embodiment, the subject is in need of enhancing an immune response. In one embodiment, the subject has, or is at risk of, having a disorder described herein, e.g., a cancer as described herein. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection.

In one embodiment, the subject (e.g., a subject having a lung cancer (e.g., a non-small cell lung cancer), a lymphoma (e.g., an anaplastic large-cell lymphoma or non-Hodgkin lymphoma), an inflammatory myofibroblastic tumor, or a neuroblastoma) is being treated, or has been treated, with another ALK inhibitor and/or a ROS1 inhibitor, e.g., crizotinib. For example, crizotinib can be administered at a daily oral dose of 750 mg or lower, e.g., 600 mg or lower, e.g., 450 mg or lower.

In another embodiment, the subject or cancer (e.g., a lung cancer (e.g., a non-small cell lung cancer), a lymphoma (e.g., an anaplastic large-cell lymphoma or non-Hodgkin lymphoma), an inflammatory myofibroblastic tumor, or a neuroblastoma) has progressed on, or is resistant or tolerant to, another ALK inhibitor and/or a ROS1 inhibitor, e.g., crizotinib.

In yet another embodiment, the subject or cancer (e.g., a lung cancer (e.g., a non-small cell lung cancer), a lymphoma (e.g., an anaplastic large-cell lymphoma or non-Hodgkin lymphoma), an inflammatory myofibroblastic tumor, or a neuroblastoma) is at risk of progression on, or developing resistance or tolerance to, another ALK inhibitor and/or a ROS1 inhibitor, e.g., crizotinib.

In other embodiments, the subject or cancer is resistant or tolerant, or is at risk of developing resistance or tolerance, to a tyrosine kinase inhibitor (TKI), e.g., an EGFR tyrosine kinase inhibitor.

In some embodiments, the subject or cancer has no detectable EGFR mutation, KRAS mutation, or both.

Dosages and Administration

Dosages and therapeutic regimens of the agents described herein can be determined by a skilled artisan.

In certain embodiments, the anti-PD-1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks. In one embodiment, the anti-PD-1 antibody molecule is administered at a dose from about 10 to 20 mg/kg every other week.

In one embodiment, the anti-PD-1 antibody molecule, e.g., Nivolumab, is administered intravenously at a dose from about 1 mg/kg to 3 mg/kg, e.g., about 1 mg/kg, 2 mg/kg or 3 mg/kg, every two weeks. In one embodiment, the anti-PD-1 antibody molecule, e.g., Nivolumab, is administered intravenously at a dose of about 2 mg/kg at 3-week intervals. In one embodiment, Nivolumab is administered in an amount from about 1 mg/kg to 5 mg/kg, e.g., 3 mg/kg, and may be administered over a period of 60 minutes, ca. once a week to once every 2, 3 or 4 weeks.

The combination therapies described herein can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

The methods and compositions described herein can be used in combination with further agents or therapeutic modalities. The combination therapies can be administered simultaneously or sequentially in any order. Any combination and sequence of the anti-PD-1 or PD-L1 antibody molecules and other therapeutic agents, procedures or modalities (e.g., as described herein) can be used. The combination therapies can be administered during periods of active disorder, or during a period of remission or less active disease. The combination therapies can be administered before the other treatment, concurrently with the treatment, post-treatment, or during remission of the disorder.

In certain embodiments, the methods and compositions described herein are administered in combination with one or more of other antibody molecules, chemotherapy, other anti-cancer therapy (e.g., targeted anti-cancer therapies, gene therapy, viral therapy, RNA therapy bone marrow transplantation, nanotherapy, or oncolytic drugs), cytotoxic agents, immune-based therapies (e.g., cytokines or cell-based immune therapies), surgical procedures (e.g., lumpectomy or mastectomy) or radiation procedures, or a combination of any of the foregoing. The additional therapy may be in the form of adjuvant or neoadjuvant therapy. In some embodiments, the additional therapy is an enzymatic inhibitor (e.g., a small molecule enzymatic inhibitor) or a metastatic inhibitor. Exemplary cytotoxic agents that can be administered in combination with include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation (e.g., gamma irradiation). In other embodiments, the additional therapy is surgery or radiation, or a combination thereof. In other embodiments, the additional therapy is a therapy targeting an mTOR pathway, an HSP90 inhibitor, or a tubulin inhibitor.

Alternatively, or in combination with the aforesaid combinations, the methods and compositions described herein can be administered in combination with one or more of: a vaccine, e.g., a therapeutic cancer vaccine; or other forms of cellular immunotherapy.

In another embodiment, the combination therapy is used in combination with one, two or all of oxaliplatin, leucovorin or 5-FU (e.g., a FOLFOX co-treatment). Alternatively or in combination, combination further includes a VEGF inhibitor (e.g., a VEGF inhibitor as disclosed herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. The cancer may be at an early, intermediate or late stage.

In other embodiments, the combination therapy is administered with a tyrosine kinase inhibitor (e.g., axitinib) to treat renal cell carcinoma and other solid tumors.

In other embodiments, the combination therapy is administered with a 4-1BB receptor targeting agent (e.g., an antibody that stimulates signaling through 4-1BB (CD-137), e.g., PF-2566). In one embodiment, the combination therapy is administered in combination with a tyrosine kinase inhibitor (e.g., axitinib) and a 4-1BB receptor targeting agent.

All publications, patent applications, patents, and other references mentioned herein are incorporated by reference in their entirety.

Other features, objects, and advantages of the invention will be apparent from the description and drawings, and from the claims.

BRIEF DESCRIPTION OF THE TABLE

Figure 1:
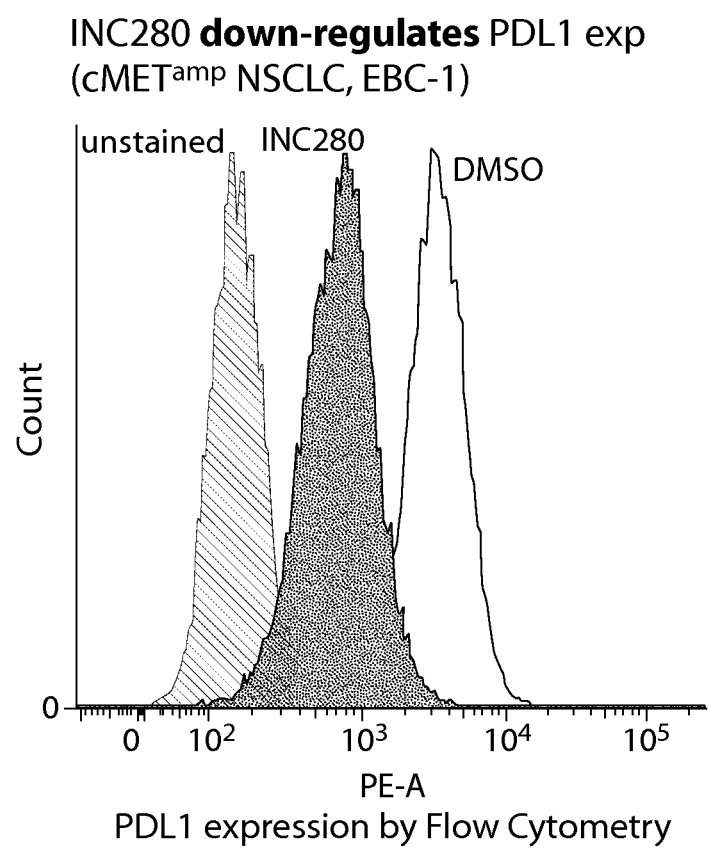
FIG. 1 shows a graphical representation of flow cytometry of PD-L1 surface expression in EBC-1 cells in vitro with or without INC280 treatment. EBC-1 cells are non-small cell lung cancer cells with a cMET amplification.

Table 1 is a summary of selected therapeutic agents that can be administered in combination with the immunomodulators (e.g., one or more of: an activator of a costimulatory molecule and/or an inhibitor of an immune checkpoint molecule) described herein. Table 1 provides from left to right the following: the Name and/or Designation of the second therapeutic agent, the Compound structure, a Patent publication disclosing the Compound, Exemplary Indications/Uses, and Generic structure.

Table 2 is a summary of the objectives and endpoints of a phase II trial relating to a combination therapy of EGF816 and Nivolumab in patients with mutated non-small cell lung cancer (NSCLC).

Table 3 is a summary of the dosage information and treatment schedule for EGF816 and Nivolumab.

DETAILED DESCRIPTION

Methods and compositions are disclosed, which comprise an immunomodulator (e.g., one or more of: an activator of a costimulatory molecule and/or an inhibitor of an immune checkpoint molecule) in combination with a second therapeutic agent chosen from one or more of the agents listed in Table 1. In one embodiment, an inhibitor of an immune checkpoint molecule (e.g., one or more of inhibitors to PD-1, PD-L1, LAG-3, TIM-3 or CTLA4) can be combined with a second therapeutic agent chosen from one or more of the agents listed in Table 1 (e.g., chosen from one or more of: 1) an EGF receptor inhibitor; 2) a c-MET inhibitor; 3) an ALK inhibitor; 4) a CDK4/6-inhibitor; 5) a PI3K inhibitor; 6) a BRAF inhibitor; 7) a CAR T cell (e.g., a CAR T cell targeting CD19); 8) an FGF receptor inhibitor; 9) a MEK inhibitor, or 10) a BCR-ABL inhibitor). The combinations described herein can provide a beneficial effect, e.g., in the treatment of a cancer, such as an enhanced anti-cancer effect, reduced toxicity and/or reduced side effects. For example, the immunomodulator, the second therapeutic agent, or both, can be administered at a lower dosage than would be required to achieve the same therapeutic effect compared to a monotherapy dose.

The term "inhibition" or "inhibitor" includes a reduction in a certain parameter, e.g., an activity, of a given molecule, e.g., an immune checkpoint inhibitor. For example, inhibition of an activity, e.g., an activity of, e.g., PD-1, PD-L1, c-MET, ALK, CDK4/6, PI3K, BRAF, FGFR, MET or BCR-ABL, of at least 5%, 10%, 20%, 30%, 40% or more is included by this term. Thus, inhibition need not be 100%.

The term "Programmed Death 1" or "PD-1" include isoforms, mammalian, e.g., human PD-1, species homologs of human PD-1, and analogs comprising at least one common epitope with PD-1. The amino acid sequence of PD-1, e.g., human PD-1, is known in the art, e.g., Shinohara T et al. (1994) *Genomics* 23(3):704-6; Finger L R, et al. *Gene* (1997) 197(1-2):177-87.

The term or "PD-Ligand 1" or "PD-L1" include isoforms, mammalian, e.g., human PD-1, species homologs of human PD-L1, and analogs comprising at least one common epitope with PD-L1. The amino acid sequence of PD-L1, e.g., human PD-L1, is known in the art The term "Lymphocyte Activation Gene-3" or "LAG-3" include all isoforms, mammalian, e.g., human LAG-3, species homologs of human LAG-3, and analogs comprising at least one common epitope with LAG-3. The amino acid and nucleotide sequences of LAG-3, e.g., human LAG-3, is known in the art, e.g., Triebel et al. (1990) *J. Exp. Med.* 171:1393-1405.

As used herein, "TIM-3" refers to a transmembrane receptor protein that is expressed on Th1 (T helper 1) cells. TIM-3 has a role in regulating immunity and tolerance in vivo (see Hastings et al., *Eur J Immunol.* 2009 September; 39(9):2492-501).

The term "Carcinoembryonic Antigen-related Cell Adhesion Molecule" or "CEACAM" includes all family members (e.g., CEACAM-1, CEACAM-3, or CEACAM-5), isoforms, mammalian, e.g., human CEACAM, species homologs of human CEACAM, and analogs comprising at least one common epitope with CEACAM. The amino acid sequence of CEACAM, e.g., human CEACAM, is known in the art, e.g., Hinoda et al. (1988) *Proc. Natl. Acad. Sci. U.S.A.* 85 (18), 6959-6963; Zimmermann W. et al. (1987) *Proc. Natl. Acad. Sci. U.S.A.* 84 (9), 2960-2964; Thompson J. et al. (1989) *Biochem. Biophys. Res. Commun.* 158 (3), 996-1004.

Additional terms are defined below and throughout the application.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The compositions and methods of the present invention encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS*, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, word-length=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a nonnatural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the invention are described in further detail below. Additional definitions are set out throughout the specification.

Antibody Molecules

In one embodiment, the antibody molecule binds to a mammalian, e.g., human, checkpoint molecule, e.g., PD-1, PD-L1, LAG-3, or TIM-3. For example, the antibody molecule binds specifically to an epitope, e.g., linear or conformational epitope, (e.g., an epitope as described herein) on PD-1, PD-L1, LAG-3, or TIM-3.

As used herein, the term "antibody molecule" refers to a protein comprising at least one immunoglobulin variable domain sequence. The term antibody molecule includes, for example, full-length, mature antibodies and antigen-binding fragments of an antibody. For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibodies of the present invention can be monoclonal or polyclonal. The antibody can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda.

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure*

*Analysis of Antibody Variable Domains*. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273, 927-948 ("Chothia" numbering scheme). As used herein, the CDRs defined according to the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an antibody molecule that comprises determinants that form an interface that binds to the PD-1 polypeptide, or an epitope thereof. With respect to proteins (or protein mimetics), the antigen-binding site typically includes one or more loops (of at least four amino acids or amino acid mimics) that form an interface that binds to the PD-1 polypeptide. Typically, the antigen-binding site of an antibody molecule includes at least one or two CDRs and/or hypervariable loops, or more typically at least three, four, five or six CDRs and/or hypervariable loops.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.*, 32:180-190 (1990)) and also because of potential allergic reactions (see, e.g., LoBuglio et al., *Hybridoma*, 5:5117-5123 (1986)).

The antibody molecule can be a polyclonal or a monoclonal antibody. In other embodiments, the antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to PD-1. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art (see e.g., Morrison, S. L., 1985, Science 229:1202-1207, by Oi et al., 1986, BioTechniques 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 Nature 321:552-525; Verhoeyan et al. 1988 Science 239:1534; Beidler et al. 1988 J. Immunol. 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) Ann N Y Acad Sci 880:263-80; and Reiter, Y. (1996) Clin Cancer Res 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

An antibody molecules may be conjugated to another molecular entity, typically a label or a therapeutic (e.g., a cytotoxic or cytostatic) agent or moiety. Radioactive isotopes can be used in diagnostic or therapeutic applications. Radioactive isotopes that can be coupled to the anti-PSMA antibodies include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At) rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99}$mTc), phosphorus ($^{32}$P), carbon ($^{14}$C), and tritium ($^{3}$H), or one or more of the therapeutic isotopes listed above.

The invention provides radiolabeled antibody molecules and methods of labeling the same. In one embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

As is discussed above, the antibody molecule can be conjugated to a therapeutic agent. Therapeutically active radioisotopes have already been mentioned. Examples of other therapeutic agents include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846, 545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclinies (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

Combination Therapies

The combination therapies (e.g., methods and compositions described herein) can include an immunomodulator (e.g., one or more of: an activator of a costimulatory molecule or an inhibitor of an immune checkpoint molecule) and a second therapeutic agent, e.g., a second therapeutic agent chosen from one or more of the agents listed in Table 1.

By "combination" or "in combination with," it is not intended to imply that the therapy or the therapeutic agents must be administered at the same time and/or formulated for delivery together (e.g., in the same composition), although these methods and compositions are within the scope described herein. The immunomodulator and the second therapeutic agent can be administered concurrently with, prior to, or subsequent to, one or more other additional therapies or therapeutic agents. The agents in the combination can be administered in any order. In general, each agent will be administered at a dose and/or on a time schedule determined for that agent. In will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

In some embodiments, a combination includes a formulation of the immunomodulator and the second therapeutic agent, with or without instructions for combined use or to combination products. The combined compounds can be manufactured and/or formulated by the same or different manufacturers. The combination partners may thus be entirely separate pharmaceutical dosage forms or pharmaceutical compositions that are also sold independently of each other. In embodiments, instructions for their combined use are provided: (i) prior to release to physicians (e.g. in the case of a "kit of part" comprising the compound of the disclosure and the other therapeutic agent); (ii) by the physicians themselves (or under the guidance of a physician) shortly before administration; (iii) the patient themselves by a physician or medical staff.

Immunomodulators

The combination therapies disclosed herein can include an inhibitor of an inhibitory molecule of an immune checkpoint molecule. The term "immune checkpoints" refers to a group of molecules on the cell surface of CD4 and CD8 T cells. These molecules can effectively serve as "brakes" to down-modulate or inhibit an anti-tumor immune response. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antigen-binding fragment thereof, that binds to the inhibitory molecule.

Immune checkpoint molecules useful in the methods and compositions of the present invention include, but are not limited to, Programmed Death 1 (PD-1), PD1, PD-L1, PD-L2, Cytotoxic T-Lymphocyte Antigen 4 (CTLA-4), TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H1, B7-H3 (CD276), B7-H4 (VTCN1), HVEM (TNFRSF14 or CD270), KIR, A2aR, MHC class I, MHC class II, GAL9, adenosine, TGFR (e.g., TGFR beta). In certain embodiments, the immunomodulator is an inhibitor of an immune checkpoint molecule (e.g., an inhibitor of PD-1, PD-L1, LAG-3, TIM-3, CEACAM (e.g., CEACAM-1, -3 and/or -5) or CTLA4, or any combination thereof).

In other embodiments, the PD-1 inhibitor is an anti-PD-1 antibody chosen from Nivolumab, Pembrolizumab or Pidilizumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. In one embodiment, the inhibitor of PD-1 is Nivolumab, and having a sequence disclosed herein (or a sequence substantially identical or similar thereto, e.g., a sequence at least 85%, 90%, 95% identical or higher to the sequence specified).

The heavy and light chain amino acid sequences of Nivolumab are as follows:

Heavy chain
(SEQ ID NO: 2)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

-continued
DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK

Light chain
(SEQ ID NO: 3)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In some embodiments, the anti-PD-1 antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335. In one embodiment, the inhibitor of PD-1 is Pembrolizumab disclosed in, e.g., U.S. Pat. No. 8,354,509 and WO 2009/114335, and having a sequence disclosed herein (or a sequence substantially identical or similar thereto, e.g., a sequence at least 85%, 90%, 95% identical or higher to the sequence specified).

The heavy and light chain amino acid sequences of Pembrolizumab are as follows:

Heavy chain
(SEQ ID NO: 4)

| QVQLVQSGVE | VKKPGASVKV | SCKASGYTFT | NYYMYWVRQA | PGQGLEWMGG | 50 |
| INPSNGGTNF | NEKFKNRVTL | TTDSSTTTAY | MELKSLQFDD | TAVYYCARRD | 100 |
| YRFDMGFDYW | GQGTTVTVSS | ASTKGPSVFP | LAPCSRSTSE | STAALGCLVK | 150 |
| DYFPEPVTVS | WNSGALTSGV | HTFPAVLQSS | GLYSLSSVVT | VPSSSLGTKT | 200 |
| YTCNVDHKPS | NTKVDKRVES | KYGPPCPPCP | APEFLGGPSV | FLFPPKPKDT | 250 |
| LMISRTPEVT | CVVVDVSQED | PEVQFNWYVD | GVEVHNAKTK | PREEQFNSTY | 300 |
| RVVSVLTVLH | QDWLNGKEYK | CKVSNKGLPS | SIEKTISKAK | GQPREPQVYT | 350 |
| LPPSQEEMTK | NQVSLTCLVK | GFYPSDIAVE | WESNGQPENN | YKTTPPVLDS | 400 |
| DGSFFLYSRL | TVDKSRWQEG | NVFSCSVMHE | ALHNHYTQKS | LSLSLGK | 447 |

Light chain
(SEQ ID NO: 5)

| EIVLTQSPAT | LSLSPGERAT | LSCRASKGVS | TSGYSYLHWY | QQKPGQAPRL | 50 |
| LIYLASYLES | GVPARFSGSG | SGTDFTLTIS | SLEPEDFAVY | YCQHSRDLPL | 100 |
| TFGGGTKVEI | KRTVAAPSVF | IFPPSDEQLK | SGTASVVCLL | NNFYPREAKV | 150 |
| QWKVDNALQS | GNSQESVTEQ | DSKDSTYSLS | STLTLSKADY | EKHKVYACEV | 200 |
| THQGLSSPVT | KSFNRGEC | | | | 218' |

In some embodiments, the anti-PD-1 antibody is Pidilizumab. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611.

Other anti-PD-1 antibodies include AMP 514 (Amplimmune), among others, e.g., anti-PD1 antibodies disclosed in U.S. Pat. No. 8,609,089, US 2010028330, and/or US 20120114649.

Exemplary PD-L1 or PD-L2 Inhibitors

In some embodiments, the PD-L1 inhibitor is an antibody molecule. In some embodiments, the anti-PD-L1 inhibitor is chosen from YW243.55.S70, MPDL3280A, MEDI-4736, MSB-0010718C, or MDX-1105.

In some embodiments, the anti-PD-L1 antibody is MSB0010718C. MSB0010718C (also referred to as A09-246-2; Merck Serono) is a monoclonal antibody that binds to PD-L1. Pembrolizumab and other humanized anti-PD-L1 antibodies are disclosed in WO2013/079174, and having a sequence disclosed herein (or a sequence substantially identical or similar thereto, e.g., a sequence at least 85%, 90%, 95% identical or higher to the sequence specified). The heavy and light chain amino acid sequences of MSB0010718C include at least the following:

Heavy chain variable region
(SEQ ID NO: 24 as disclosed in WO2013/079174)
(SEQ ID NO: 6)
EVQLLESGGGLVQPGGSLRLSCAASGFTFSSYIMMWVRQAPGKGLEWVSS

IYPSGGITFYADKGRFTISRDNSKNTLYLQMNSLRAEDTAVYYCARIKLG

TVTTVDYWGQGTLVTVSS

Light chain variable region
(SEQ ID NO: 25 as disclosed in WO2013/079174)
(SEQ ID NO: 7)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVL

In one embodiment, the PD-L1 inhibitor is YW243.55.S70. The YW243.55.S70 antibody is an anti-PD-L1 described in WO 2010/077634 (heavy and light chain variable region sequences shown in SEQ ID Nos. 20 and 21, respectively, of WO 2010/077634), and having a sequence disclosed therein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in WO2010/027827 and WO2011/066342).
Exemplary TIM-3 Inhibitors In one embodiment, a combination described herein includes a TIM-3 inhibitor. In some embodiments, the combination is used to treat a cancer, e.g., a cancer described herein, e.g., a solid tumor or a hematologic malignancy.

Exemplary anti-TIM-3 antibodies are disclosed in U.S. Pat. No. 8,552,156, WO 2011/155607, EP 2581113 and U.S Publication No.: 2014/044728.
Exemplary LAG-3 Inhibitors In one embodiment, a combination described herein includes a LAG-3 inhibitor. In some embodiments, the combination is used to treat a cancer, e.g., a cancer described herein, e.g., a solid tumor or a hematologic malignancy.

In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218.
Exemplary CTLA-4 Inhibitors In one embodiment, a combination described herein includes a CTLA-4 inhibitor. In some embodiments, the combination is used to treat a cancer, e.g., a cancer described herein, e.g., a solid tumor or a hematologic malignancy.

Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

In one embodiment, the combination includes an anti-PD-1 antibody molecule, e.g., as described herein, and an anti-CTLA-4 antibody, e.g., ipilimumab. Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg. In one embodiment, the anti-PD-1 antibody molecule is administered after treatment, e.g., after treatment of a melanoma, with an anti-CTLA4 antibody (e.g., ipilimumab) with or without a BRAF inhibitor (e.g., vemurafenib or dabrafenib).

Other exemplary anti-CTLA-4 antibodies are disclosed, e.g., in U.S. Pat. No. 5,811,097.

In one embodiment, the inhibitor is a soluble ligand (e.g., a CTLA-4-Ig), or an antibody or antibody fragment that binds to PD-L1, PD-L2 or CTLA4. For example, the anti-PD-1 antibody molecule can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer).
Additional Combinations of Inhibitors In certain embodiments, the anti-PD-1 molecules described herein are administered in combination with one or more other inhibitors of PD-1, PD-L1 and/or PD-L2, e.g., as described herein. The antagonist may be an antibody, an antigen binding fragment thereof, an immunoadhesin, a fusion protein, or oligopeptide.

In one embodiment, the anti-PD-1 or PD-L1 antibody molecule is administered in combination with an anti-LAG-3 antibody or an antigen-binding fragment thereof. In another embodiment, the anti-PD-1 or PD-L1 antibody molecule is administered in combination with an anti-TIM-3 antibody or antigen-binding fragment thereof. In yet other embodiments, the anti-PD-1 or PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In one embodiment, a bispecific antibody that includes an anti-PD-1 or PD-L1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-PD-1 and anti-LAG-3 are described, e.g., in Woo et al. (2012) *Cancer Res.* 72(4):917-27).

In another embodiment, the anti-PD-1 or PD-L1 antibody molecule is administered in combination with an inhibitor of CEACAM (e.g., CEACAM-1, -3 and/or -5). In one embodiment, the inhibitor of CEACAM (e.g., CEACAM-1, -3 and/or -5) is an anti-CEACAM antibody molecule. Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. *J Immunol.* 2002 Mar. 15; 168(6):2803-10; Markel et al. *J Immunol.* 2006 Nov. 1; 177(9):6062-71; Markel et al. *Immunology.* 2009 February; 126(2):186-200; Markel et al. *Cancer Immunol Immunother.* 2010 February;

59(2):215-30; Ortenberg et al. *Mol Cancer Ther.* 2012 June; 11(6):1300-10; Stern et al. *J Immunol.* 2005 Jun. 1; 174(11): 6692-701; Zheng et al. *PLoS One.* 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) *Nature* doi:10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

Accordingly, in some embodiments, the anti-PD-1 antibody molecule is administered in combination with a CEACAM inhibitor (e.g., CEACAM-1, CEACAM-3, and/or CEACAM-5 inhibitor). In one embodiment, the inhibitor of CEACAM is an anti-CEACAM antibody molecule. In one embodiment, the anti-PD-1 antibody molecule is administered in combination with a CEACAM-1 inhibitor, e.g., an anti-CEACAM-1 antibody molecule. In another embodiment, the anti-PD-1 antibody molecule is administered in combination with a CEACAM-3 inhibitor, e.g., an anti-CEACAM-3 antibody molecule. In another embodiment, the anti-PD-1 antibody molecule is administered in combination with a CEACAM-5 inhibitor, e.g., an anti-CEACAM-5 antibody molecule. Exemplary anti-CEACAM-1 antibodies are described in WO 2010/125571, WO 2013/082366 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. *PLoS One.* 2010 September 2; 5(9). pii: e12529 (DOI:10:1371/journal.pone.0021146), or crossreacts with CEACAM-1 and CEACAM-5 as described in, e.g., WO 2013/054331 and US 2014/0271618.

Costimulatory Modulators

In certain embodiments, the combination therapies disclosed herein include a modulator of a costimulatory molecule. In one embodiment, the costimulatory modulator, e.g., agonist, of a costimulatory molecule is chosen from an agonist (e.g., an agonistic antibody or antigen-binding fragment thereof, or soluble fusion) of an MHC class I molecule, a TNF receptor protein, an Immunoglobulin-like proteins, a cytokine receptor, an integrin, a signaling lymphocytic activation molecules (SLAM proteins), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, ITGAM, CD11b, ITGAX, CD11c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), SLAM7, BLAME (SLAMF8), SELPLG (CD162), LTBR, LAT, GADS, SLP-76, PAG/Cbp, CD19a, and a ligand that specifically binds with CD83.

In one embodiment, the combination therapies disclosed herein include a costimulatory molecule, e.g., an agonist associated with a positive signal that includes a costimulatory domain of CD28, CD27, ICOS and GITR.

Exemplary GITR Agonist

In one embodiment, a combination described herein includes a GITR agonist. In some embodiments, the combination is used to treat a cancer, e.g., a cancer described herein, e.g., a solid tumor or a hematologic malignancy.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 0920505B1, U.S Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, U.S. Pat. No. 8,709,424, PCT Publication No.:WO 2013/039954, International Publication No.: WO2013/039954, U.S. Publication No.: US2014/0072566, International Publication NO.: WO2015/026684, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, U.S. Pat. No. 6,689,607, PCT Publication No.: WO2006/083289, PCT Publication No.: WO 2005/115451, U.S. Pat. No. 7,618,632, PCT Publication No.: WO 2011/051726, International Publication No.: WO2004060319, and International Publication No.: WO2014012479.

In one embodiment, the GITR agonist is used in combination with a PD-1 inhibitor, e.g., as described in WO2015/026684.

In another embodiment, the GITR agonist is used in combination with a TLR agonist, e.g., as described in WO2004060319, and International Publication No.: WO2014012479.

Additional Combinations

In another embodiment, the combination therapies include a modified T-cell, e.g., in combination with an adoptive T-cell immunotherapy using chimeric antigen receptor (CAR) T cells (e.g., as described by John L B, et al. (2013) *Clin. Cancer Res.* 19(20): 5636-46).

In other embodiments, the combination therapies disclosed herein can also include a cytokine, e.g., interleukin-21 or interleukin-2. In certain embodiments, the combination described herein is used to treat a cancer, e.g., a cancer as described herein (e.g., a solid tumor or melanoma).

Exemplary immunomodulators that can be used in the combination therapies include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

In other embodiments, the combination therapies can be administered to a subject in conjunction with (e.g., before, simultaneously or following) one or more of: bone marrow transplantation, T cell ablative therapy using chemotherapy agents such as, fludarabine, external-beam radiation therapy (XRT), cyclophosphamide, and/or antibodies such as OKT3 or CAMPATH. In one embodiment, the anti-PD-1 or PD-L1 antibody molecules are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive the anti-PD-1 or PD-L1 antibody molecules. In an additional embodiment, the anti-PD-1 or PD-L1 antibody molecules are administered before or following surgery.

Another example of a further combination therapy includes decarbazine for the treatment of melanoma. Without being bound by theory, the combined use of PD-1 blockade and chemotherapy is believed to be facilitated by cell death, that is a consequence of the cytotoxic action of most chemotherapeutic compounds, which can result in increased levels of tumor antigen in the antigen presentation pathway. Other combination therapies that may result in synergy with PD-1 blockade through cell death are radiation, surgery, and hormone deprivation. Each of these protocols creates a source of tumor antigen in the host. Angiogenesis inhibitors may also be combined with PD-1 blockade. Inhibition of angiogenesis leads to tumor cell death which may feed tumor antigen into host antigen presentation pathways.

Combination therapies can also be used in combination with bispecific antibodies. Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of PD-1 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) J. Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). Antibodies or antigen-binding fragments thereof to each of these entities may be used in combination with anti-PD-1 to counteract the effects of the immunosuppressive agent and favor tumor immune responses by the host.

Other antibodies which may be used to activate host immune responsiveness can be used in combination with the combination therapies described herein. These include molecules on the surface of dendritic cells which activate DC function and antigen presentation. Anti-CD40 antibodies are able to substitute effectively for T cell helper activity (Ridge, J. et al. (1998) Nature 393: 474-478) and can be used in conjunction with PD-1 antibodies (Ito, N. et al. (2000) Immunobiology 201 (5) 527-40). Antibodies to T cell costimulatory molecules such as CTLA-4 (e.g., U.S. Pat. No. 5,811,097), OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) may also provide for increased levels of T cell activation.

In all of the methods described herein, PD-1 blockade can be combined with other forms of immunotherapy such as cytokine treatment (e.g., interferons, GM-CSF, G-CSF, IL-2, IL-21), or bispecific antibody therapy, which provides for enhanced presentation of tumor antigens (see e.g., Holliger (1993) Proc. Natl. Acad. Sci. USA 90:6444-6448; Poljak (1994) Structure 2:1121-1123).

The combination therapies disclosed herein can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) J. Immunol. 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

PD-1 blockade can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

PD-1 blockade can be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (ie. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269:1585-1588; Tamura, Y. et al. (1997) Science 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) Nature Medicine 4: 328-332). DCs may also be transduced by genetic means to express these tumor antigens as well. DCs have also been fused directly to tumor cells for the purposes of immunization (Kugler, A. et al. (2000) Nature Medicine 6:332-336). As a method of vaccination, DC immunization may be effectively combined with PD-1 blockade to activate more potent anti-tumor responses.

Second Therapeutic Agents

The second therapeutic agent can be chosen from one or more of: 1) an EGF receptor inhibitor; 2) a c-MET inhibitor; 3) an ALK inhibitor; 4) a CDK4/6-inhibitor; 5) a PI3K inhibitor; 6) a BRAF inhibitor; 7) a CAR T cell (e.g., a CAR T cell targeting CD19); 8) an FGF receptor inhibitor; 9) a MEK inhibitor, or 10) a BCR-ABL inhibitor); e.g., chosen from one or more of the agents listed in Table 1.

TABLE 1

| Structure Name | Name | Compound Structure | Patent Publications | Exemplary Indication/Uses | Generic structure |
|---|---|---|---|---|---|
| AMN107 | Nilotinib HCl monohydrate, Tasigna | [chemical structure of nilotinib with HCl and H₂O] | WO2004/005281 U.S. Pat. No. 7,169,791 (see e.g., Example 92 of WO2004/005281; and Formula (I), claim 1 and claim 8 of U.S. Pat. No. 7,169,791). | Lymphocytic Leukemia Therapy Antiparkinsonian Drugs Neurologic Cancer Therapy Melanoma Therapy Digestive/Gastrointestinal Cancer Therapy Colorectal Cancer Therapy Myeloid Leukemia Therapy Head and Neck Cancer Therapy Treatment of Pulmonary Hypertension | [generic structure] R1 is hydrogen R2 represents a phenyl substituted by CF₃ and [methylimidazole fragment] R4 is CH₃ |

TABLE 1-continued

| Structure Name | Name | Compound Structure | Patent Publications | Exemplary Indication/Uses | Generic structure |
|---|---|---|---|---|---|
| BGJ398 | | 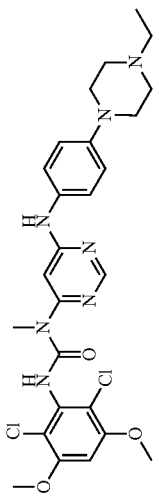 | U.S. Pat. No. 8,552,002 (see e.g., Example 145, col 171 of U.S. Pat. No. 8,552,002; e.g., encompassed by Formula (I) found in col 6. X is $CR^5$, wherein $R^5$ is H Y is N Z is N $X^1$ is O $R^1$ is a substituted organic moiety attached via a linker (L1), —L1—, wherein the organic moiety is a cyclic group (specifically phenyl) substituted by 4-ethylpiperazinyl and —L1— is $NR^a$ wherein $R^a$ is H $R^2$ is an organic moiety, specifically H $R^3$ is an organic moiety, specifically lower aliphatic, e.g., methyl n is 4 $R^4$ is specifically chloro, chloro, methoxy, or methoxy). | Digestive/Gastrointestinal Cancer Therapy Hematological Cancer Therapy Solid Tumors Therapy | 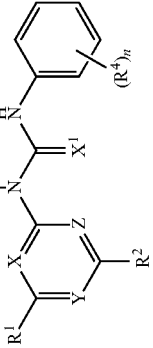 |

TABLE 1-continued

| Structure Name | Name | Compound Structure | Patent Publications | Exemplary Indication/Uses | Generic structure |
|---|---|---|---|---|---|
| BMK120 | Buparlisib | 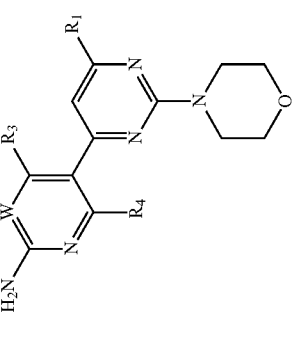 | WO2007/084786 Chemical name: 4-(trifluoromethyl)-5-(2,6-dimorpholinopyrimidin-4-yl)pyridin-2-amine (see e.g., WO2007/084786 (on pages 21-22); Compound of formula (I), wherein W is CRw and Rw is hydrogen R₁ is unsubstituted heterocyclyl R₂ is hydrogen R₃ is substituted alkyl R₄ is hydrogen Specific compound: Example 10 (in paragraph [0389] on page 140) Preparation of specific compound: Example 10). | Prostate Cancer Therapy Non-Small Cell Lung Cancer Therapy Endocrine Cancer Therapy, Leukemia Therapy, Ovarian Cancer Therapy Melanoma Therapy, Bladder Cancer Therapy Oncolytic Drugs Breast Cancer Therapy Female Reproductive System Cancer Therapy Digestive/Gastrointestinal Cancer Therapy Colorectal Cancer Therapy Glioblastoma Multiforme Therapy Solid Tumors Therapy Non-Hodgkin's Lymphoma Therapy Hematopoiesis Disorders Therapy Head and Neck Cancer Therapy | 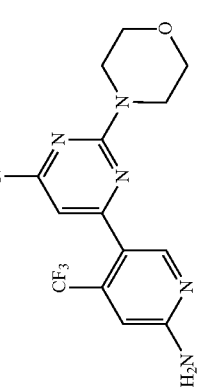 |

TABLE 1-continued

| Structure Name | Name | Compound Structure | Patent Publications | Exemplary Indication/Uses | Generic structure |
|---|---|---|---|---|---|
| | BYL719 | 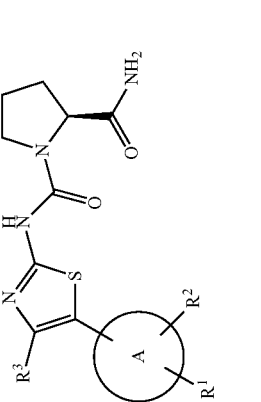 | WO2010/029082; Chemical name: (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (see e.g., in WO2010/029082: Specific compound: Example 15 on page 55 Preparation of specific compound: Example 15 on pages 55-56 Genus disclosed (see e.g., claim 1 on page 138-139); Compound of formula I, wherein A is pyridyl, pyrimidinyl, pyrazinyl, 1H-benzo[d]imidazolyl; $R^1$ is substituted $C_1$-$C_7$ alkyl, wherein said substituents are independently selected from one or more, preferably one to nine of the following deuterium, fluoro, or one or two of the following moieties $C_3$-$C_5$ cycloalkyl $R^2$ is hydrogen $R^3$ is methyl). | Gastric Cancer Therapy Breast Cancer Therapy Pancreatic Cancer Therapy Digestive/Gastrointestinal Cancer Therapy Solid Tumors Therapy Head and Neck Cancer Therapy |  |

TABLE 1-continued

| Structure Name | Name | Compound Structure | Patent Publications | Exemplary Indication/Uses | Generic structure |
|---|---|---|---|---|---|
| CTL019 | Tisagenle-cleucel-T | CART-19 | WO2012/079000 (see e.g., page 58, 65, SEQ ID NO: 12 is full CAR, and SEQ ID NO: 14 is CD19 scFv). | Lymphocytic Leukemia Therapy Non-Hodgkin's Lymphoma Therapy | |
| INC280 | | [structure image] | EP2099447; U.S. Pat. No. 7,767,675 (see e.g., for a generic in Claim 1 of EP2099447; species in claim 53 of EP2099447, and claim 4 of U.S. Pat. No. 7,767,675). | Non-Small Cell Lung Cancer Therapy Glioblastoma Multiforme Therapy Renal Cancer Therapy Solid Tumors Therapy Liver Cancer Therapy | [structure image] |
| LDK378 | Zykadia | [structure image] | WO2008/073687; U.S. Pat. No. 8,039,479 (see e.g., Example 7, compound 66 of WO2008/073687; U.S. Pat. No. 8,039,479: genus in claim 1; species in claim 5 Subgenus Formula (2) $R^1$ is halo; $R^2$ is H; $R^3$ is $SO_2R^{12}$ and $R^{12}$ is $C_{1-6}$ alkyl; $R^4$ is H (n = 1); $R^6$ is isopropoxy; and one of $R^8$ and $R^9$ is $(CR^2)_qY$ wherein q is 0, Y is piperidinyl and the other is $C_{1-6}$ alkyl). | Non-Small Cell Lung Cancer Therapy Solid Tumors Therapy | I |

TABLE 1-continued

| Structure Name | Name | Compound Structure | Patent Publications | Exemplary Indication/Uses | Generic structure |
|---|---|---|---|---|---|
| LEE011 | | 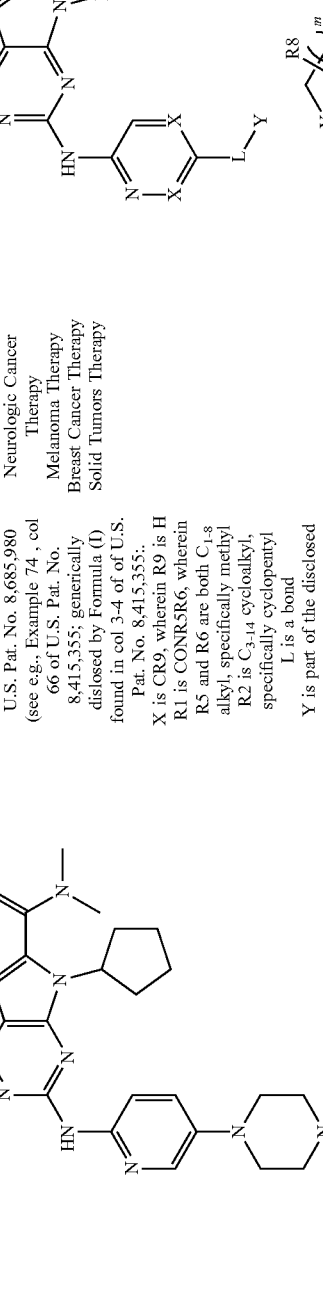 | U.S. Pat. No. 8,415,355 U.S. Pat. No. 8,685,980 (see e.g., Example 74 , col 66 of U.S. Pat. No. 8,415,355; generically dislosed by Formula (I) found in col 3-4 of of U.S. Pat. No. 8,415,355;. X is CR9, wherein R9 is H R1 is CONR5R6, wherein R5 and R6 are both methyl R2 is C$_{3-14}$ cycloalkyl, specifically cyclopentyl L is a bond Y is part of the disclosed group, wherein Y is N, zero R8 are present, W is N, m and n are both 1, and R3 is H). See also, U.S. Pat. No. 8,685,980 | Lymphoma Therapy Neurologic Cancer Therapy Melanoma Therapy Breast Cancer Therapy Solid Tumors Therapy | 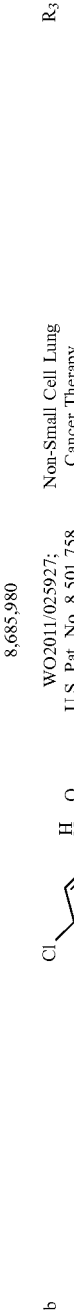 |
| LGX818 | Encorafenib | 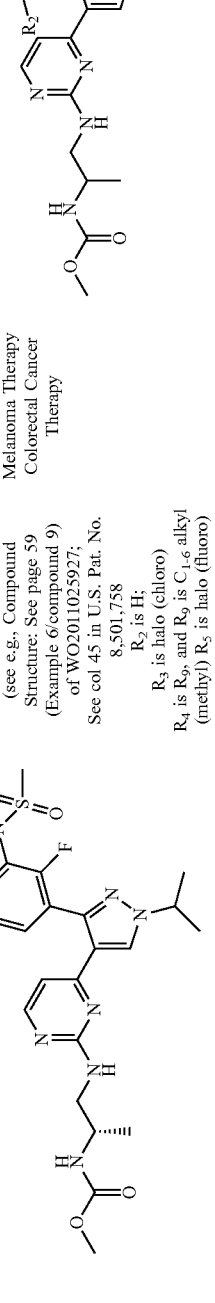 | WO2011/025927; U.S. Pat. No. 8,501,758 (see e.g., Compound Structure: See page 59 (Example 6/compound 9) of WO2011025927; See col 45 in U.S. Pat. No. 8,501,758: R$_2$ is H; R$_4$ is R$_9$, and R$_9$ is C$_{1-6}$ alkyl (methyl) R$_5$ is halo (fluoro) R$_7$ is C$_{1-4}$ alkyl (isopropyl); Y is CR$_6$ and R$_6$ is H R$_3$ is halo (chloro) WO2011/025927: generic structure on p. 6 and structure on p. 59). | Non-Small Cell Lung Cancer Therapy Melanoma Therapy Colorectal Cancer Therapy |  |

TABLE 1-continued

| Structure Name | Name | Compound Structure | Patent Publications | Exemplary Indication/Uses | Generic structure |
|---|---|---|---|---|---|
| MEK162 | Binimetinib | (structure shown) | WO03/077914 (see e.g., Generic structure: See page 8-10 of WO03/077914; specific structure: See page 70 (Example 18/compound 29III) of WO03/077914; $R^1$ is halogen; $R^2$ is hydrogen $R^3$ is $C_1$-$C_{10}$ alkyl $R^4$ is hydrogen; $R^7$ is $C_1$-$C_{10}$ alkyl substituted with OR' and R' is hydrogen $R^8$ is —Br; $R^9$ is halogen $R^{10}$ is hydrogen; W is —C(O)NR$^4$OR$^3$). | Non-Small Cell Lung Cancer Therapy Multisystem Genetic Disorders, Treatment of Melanoma Therapy Ovarian Cancer Therapy Digestive/Gastrointestinal Cancer Therapy Treatment of Rheumatoid Arthritis Colorectal Cancer Therapy | (structure shown) |
| EGF816 | | (structure shown) | WO2013/184757 (see e.g., Example 5; generically disclosed by Formula (5)—see claims 7, 10, 11 and 12. $W^1$ is $CR^1$; $W^2$ is N; $R^1$ is methyl and $R^{1'}$ is hydrogen; $R^2$ is chloro; m = 1 $R^8$ is substructure (h), q = 1 $R^{12}$, $R^{13}$, $R^{16}$ and $R^{17}$ are hydrogen $R^{14}$ and $R^{15}$ are methyl). | Cancer Therapy Solid Tumor Therapy | (structure shown) |

Exemplary Combination Therapies

In certain embodiments, the PD-1 inhibitor, e.g., the anti-PD-1 antibody (e.g., Nivolumab) is used in a method or composition described herein. For example, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C) (alone or in combination with other immunomodulators) is used in combination with one or more of the agents listed in Table 1; e.g., one or more of: 1) an EGF receptor inhibitor; 2) a c-MET inhibitor; 3) an ALK inhibitor; 4) a CDK4/6-inhibitor; 5) a PI3K inhibitor; 6) a BRAF inhibitor; 7) a CAR T cell (e.g., a CAR T cell targeting CD19); 8) an FGF receptor inhibitor; 9) a MEK inhibitor, or 10) a BCR-ABL inhibitor), e.g., listed in Table 1, or disclosed in a publication listed in Table 1. In one embodiment, one or more of the aforesaid combinations is used to treat a disorder, e.g., a disorder described herein (e.g., a disorder disclosed in Table 1). In one embodiment, one or more of the aforesaid combinations is used to treat a cancer, e.g., a cancer described herein (e.g., a cancer disclosed in Table 1). Each of these combinations is discussed in more detail below.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with an EGF receptor inhibitor to treat a cancer, e.g., a cancer described herein (e.g., a cancer disclosed in Table 1). In one embodiment, the EGF receptor inhibitor is disclosed in Table 1, e.g., EGF816, or in a publication recited in Table 1, e.g., in WO 2013/184757 (e.g., Formula (5), in claims 7, 10, 11 and 12, or in Example 5). In one embodiment, the EGF receptor inhibitor, e.g., EGF816, has the structure (compound or generic structure) provided in Table 1, or as disclosed in the publication recited in Table 1, e.g., in WO 2013/184757 (e.g., Formula (5), in claims 7, 10, 11 and 12, or in Example 5). In one embodiment, one of Nivolumab, Pembrolizumab or MSB0010718C is used in combination with EGF816 to treat a cancer described in Table 1, e.g., a solid tumor, e.g., a lung cancer (e.g., non-small cell lung cancer (NSCLC)).

In certain embodiments, EGF816 is administered at an oral dose of about 50 to 500 mg, e.g., about 100 mg to 400 mg, about 150 mg to 350 mg, or about 200 mg to 300 mg, e.g., about 100 mg, 150 mg or 200 mg. The dosing schedule can vary from e.g., every other day to daily, twice or three times a day. In one embodiment, EGF816 is administered at an oral dose from about 100 to 200 mg, e.g., about 150 mg, once a day.

In one embodiment, the EGF receptor inhibitor is of formula:

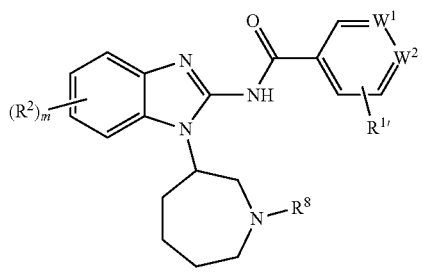

wherein $W^1$ and $W^2$ are independently $CR^1$ or N; and $R^1$, $R^{1'}$ and $R^2$ are independently hydrogen; halo; cyano; $C_{1-6}$ alkyl; $C_{1-6}$ haloalkyl; 5-6 membered heteroaryl comprising 1-4 heteroatoms selected from N, O and S; phenyl, 5-6 membered heterocyclyl comprising 1-2 heteroatoms selected from N, O, S and P, and optionally substituted by oxo; —$X^1$—C(O)O$R^3$; —$X^1$—O—C(O)$R^3$; —$X^1$—C(O)$R^3$; —$X^1$—C(O)NR$^4$R$^5$; —$X^1$—C(O)NR$^4$—$X^3$—C(O)O$R^3$; —$X^1$—C(O)NR$^4$—$X^3$—S(O)$_{0-2}$R$^6$; —$X^1$—NR$^4$R$^5$; —$X^1$NR$^4$—$X^2$—C(O)$R^3$; —$X^1$—NR$^4$—$X^2$—C(O)OR$^3$; —$X^1$—NR$^4$—$X^2$—C(O)NR$^4$R$^5$; —$X^1$—NR$^4$—$X^3$—S(O)$_{0-2}$R$^6$; —$X^1$—NR$^4$S(O)$_2$R$^6$; —$X^1$—OS(O)$_2$R$^6$; —$X^1$—OR$^3$; —$X^1$—O—$X^4$—OR$^3$; —$X^1$—O—$X^4$—S(O)$_{0-2}$R$^6$; —$X^1$—O—$X^4$—NR$^4$R$^5$; —$X^1$—S(O)$_{0-2}$R$^6$; —$X^1$—S(O)$_{0-2}$—$X^3$—NR$^4$R$^5$; —$X^1$—C(O)NR$^4$—$X^3$—P(O)R$^{6a}$R$^{6b}$; —$X^1$—NR$^4$—$X^1$—P(O)R$^{6a}$R$^{6b}$; —$X^1$—O—$X^1$—P(O)R$^{6a}$R$^{6b}$; —$X^1$—P(O)R$^{6a}$—$X^1$—NR$^4$R$^5$; —$X^1$—P(O)R$^{6a}$R$^{6b}$ or —$X^1$—S(O)$_2$NR$^4$R$^5$; wherein each phenyl, heteroaryl, or heterocyclyl in $R^1$ or $R^2$ is unsubstituted or substituted by 1-3 groups selected from OH, halo, $C_{1-6}$ alkyl, $C_{1-6}$ haloalkyl and $C_{1-6}$ haloalkoxy;

$R^3$, $R^4$ and $R^5$ are independently hydrogen, $C_{1-6}$ alkyl or $C_{1-6}$ haloalkyl; or wherein $R^4$ and $R^5$ together with N in NR$^4$R$^5$ may form a 4-7 membered ring containing 1-2 heteroatoms selected from N, O, S and P, and optionally substituted with 1-4 $R^7$;

$R^6$ is $C_{1-6}$ alkyl or $C_{1-6}$ haloalkyl;

$R^{6a}$ and $R^{6b}$ are independently hydroxy, $C_{1-6}$ alkyl, $C_{1-6}$ haloalkyl, $C_{1-6}$ alkoxy, $C_{1-6}$ haloalkoxy, 6-10 membered monocyclic or bicyclic aryl; a 5-10 membered heteroaryl comprising 1-4 heteroatoms selected from N, O and S; or a 4-12 membered monocyclic or bicyclic heterocyclyl comprising 1-4 heteroatoms selected from N, O and S, and optionally substituted with oxo;

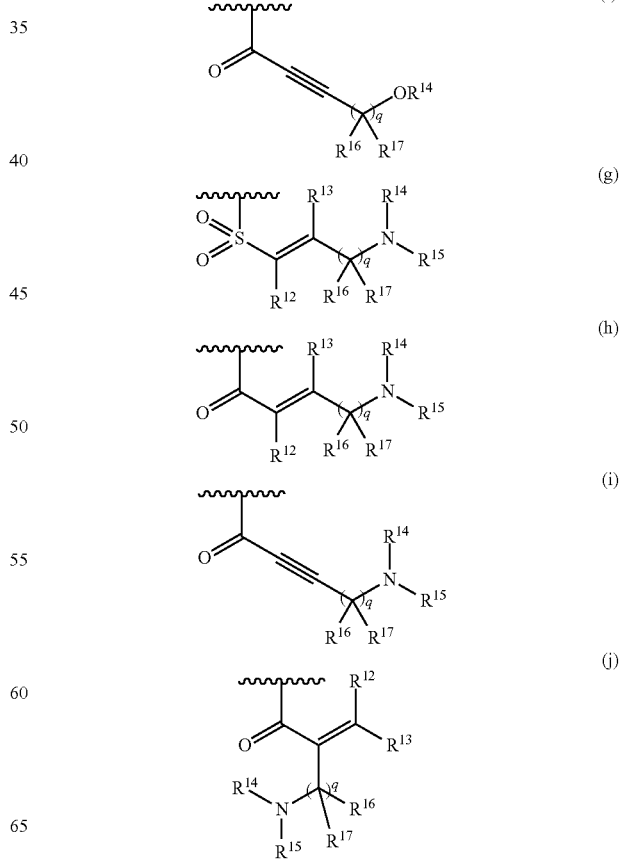

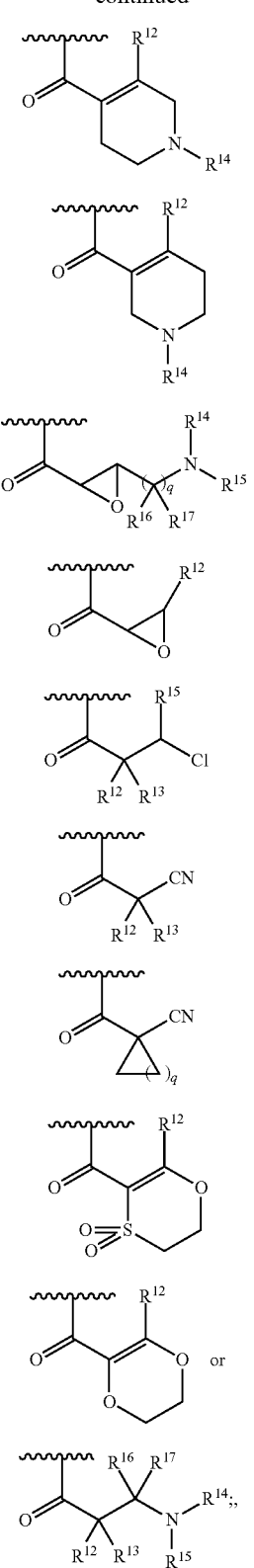

$X^1$ and $X^2$ are independently a bond or $C_{1-6}$ alkyl;
$X^3$ is $C_{1-6}$ alkyl;
$X^4$ is $C_{2-6}$ alkyl;
$R^{12}$, $R^{13}$, $R^{16}$ and $R^{17}$ are independently hydrogen or $C_{1-6}$ alkyl;

$R^{14}$ and $R^{15}$ are independently hydrogen; $C_{1-6}$ alkyl; —C(O)O—($C_{1-6}$ alkyl); $C_{3-7}$ cycloalkyl unsubstituted or substituted with $C_{1-6}$ alkyl; or $R^{14}$ and $R^{15}$ together with N in $NR^{14}R^{15}$ may form a 4-7 membered ring containing 1-2 heteroatoms selected from N, O, S, and P, and optionally substituted with 1-4 $R^{18}$ groups;

$R^7$ and $R^{18}$ are independently oxo, halo, hydroxyl, $C_{1-6}$ alkyl or $C_{1-6}$ alkoxy; and m and q are independently 1-2;

or a pharmaceutically acceptable salt thereof.

In one embodiment, $R^1$ and $R^{1'}$ are independently hydrogen; methyl; t-butyl; trifluoromethyl; methoxy; ethoxy; trifluoromethoxy; difluoromethoxy; fluoro; chloro; cyano; dimethylamino; methylsulfonyl; dimethylphosphoryl; tetrazolyl; pyrrolyl; phenyl unsubstituted or substituted by methyl; or piperidinyl.

In one embodiment, $R^2$ is hydrogen; chloro; methyl; trifluoromethyl; methoxy; isoproproxy; cyano; hydroxy methyl; methoxy methyl; ethoxymethyl; methylsulfonyl; methylcarbonyl; carboxy; methoxycarbonyl; carbamoyl; dimethylaminomethyl; pyrrolidinylmethyl unsubstituted or substituted by 1-2 hydroxy, halo or methoxy; morpholinomethyl; azeditinylmethyl unsubstituted or substituted by 1-2 halo or methoxy; piperidinylmethyl; ((4-methyl-3-oxo-piperazin-1yl)methyl); ((4-acetylpiperazin-1-yl)methyl); (1,1-dioxidothiomorpholine-4-carbonyl); pyrrolidinyl carbonyl unsubstituted or substituted by 1-2 hydroxy; pyrrolidinylethoxy; (1,1-dioxidothiomorpholino)methyl; or 1,2,4-oxadiazolyl unsubstituted or substituted by $C_{1-6}$ alkyl;

alternatively, $R^2$ is —CH$_2$—N(CH$_3$)—C(O)—CH$_3$; —CH$_2$—O—(CH$_2$)$_2$—OCH$_3$; —CH$_2$—N(CH$_3$)—(CH$_2$)$_2$—SO$_2$(CH$_3$); —C(O)NH—(CH$_2$)$_{1-2}$—C(O)—OCH$_3$; —C(O)NH—(CH$_2$)$_{1-2}$—C(O)OH; or —C(O)NH—(CH$_2$)$_2$—SO$_2$(CH$_3$).

In one embodiment, $R^8$ is

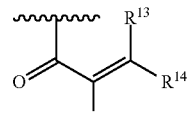 (b)

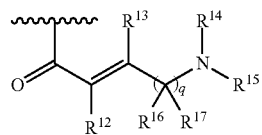 (d)

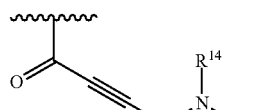 (e)

or

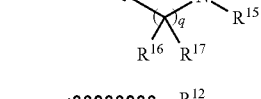 (f)

wherein $R^{14}$ and $R^{15}$ are independently hydrogen, $C_{1-6}$ alkyl or $C_{3-7}$ cycloalkyl; or $R^{14}$ and $R^{15}$ together with N in $NR^{14}R^{15}$ may form an azetidinyl, piperidyl, pyrrolidinyl or morpholinyl; where said azetidinyl or pyrrolidinyl can be optionally substituted with 1-2 halo, methoxy or hydroxyl; and $R^{12}$ and $R^{13}$ are independently hydrogen, halo, cyano, $C_{1-6}$ alkyl or $C_{1-6}$ haloalkyl;

$R_{16}$ and $R^{17}$ are independently hydrogen or $C_{1-6}$ alkyl; or $R^{16}$ and $R^{17}$ together with the carbon to which they are attached may form a $C_{3-6}$ cycloalkyl.

In one embodiment, $W^1$ is $CR^1$; $W^2$ is N; $R^1$ is methyl and $R^{1'}$ is hydrogen; $R^2$ is chloro; m=1; $R^8$ is substructure (h), q=1; $R^{12}$, $R^{13}$, $R^{16}$ and $R^{17}$ are hydrogen; $R^{14}$ and $R^{15}$ are methyl.

In one embodiment, the EGF receptor inhibitor has the following structure:

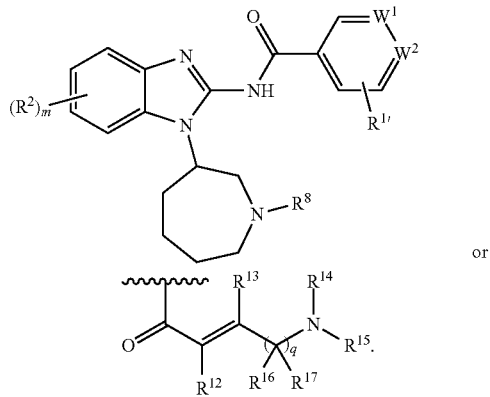

or

In one embodiment, EGF816 has the following structure:

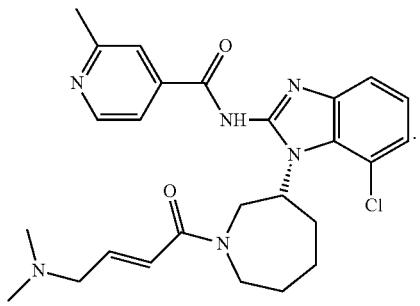

In one embodiment, EGF816 is (R,E)-N-(7-chloro-1-(1-(4-(dimethylamino)but-2-enoyl)azepan-3-yl)-1H-benzo[d]imidazol-2-yl)-2-methylisonicotinamide.

In another embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a c-MET inhibitor to treat a cancer, e.g., a cancer described herein (e.g., a cancer disclosed in Table 1). In one embodiment, the c-MET inhibitor is disclosed in Table 1, e.g., INC280, or in a publication recited in Table 1, e.g., in EP 2099447 (e.g., in claim 1 or 53) or U.S. Pat. No. 7,767,675 (e.g., in claim 4). In one embodiment, the c-MET inhibitor, e.g., INC280, has the structure (compound or generic structure) provided in Table 1, or as disclosed in the publication recited in Table 1. In one embodiment, one of Nivolumab, Pembrolizumab or MSB0010718C is used in combination with INC280 to treat a cancer described in Table 1, e.g., a solid tumor, e.g., a lung cancer (e.g., non-small cell lung cancer (NSCLC)), glioblastoma multiforme (GBM), a renal cancer, a liver cancer or a gastric cancer. In some embodiments, the cancer has, or is identified as having, a c-MET mutation (e.g., a c-MET mutation or a c-MET amplification).

In certain embodiments, INC280 is administered at an oral dose of about 100 to 1000 mg, e.g., about 200 mg to 900 mg, about 300 mg to 800 mg, or about 400 mg to 700 mg, e.g., about 400 mg, 500 mg or 600 mg. The dosing schedule can vary from e.g., every other day to daily, twice or three times a day. In one embodiment, INC280 is administered at an oral dose from about 400 to 600 mg twice a day.

In one embodiment, the c-MET inhibitor has the following structure:

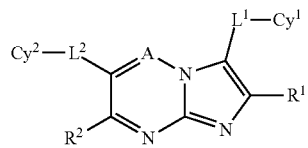

or pharmaceutically acceptable salt thereof or prodrug thereof, wherein:

A is N or $CR^3$; and $Cy^1$ is aryl, heteroaryl, cycloalkyl, or heterocycloalkyl, each optionally substituted by 1, 2, 3, 4, or 5 —W—X—Y—Z;

$Cy^2$ is aryl, heteroaryl, cycloalkyl, or heterocycloalkyl, each optionally substituted by 1, 2, 3, 4, or 5 —W'—X'—Y'—Z';

$L^1$ is $(CR^4R^5)_m$, $(CR^4R^5)_p$-(cycloalkylene)-$(CR^4R^5)_q$, $(CR^4R^5)_p$-(arylene)-$(CR^4R^5)_q$, $(CR^4R^5)_p$-(heterocycloalkylene)-$(CR^4R^5)_q$, $(CR^4R^5)_p$-(heteroarylene)-$(CR^4R^5)_q$, $(CR^4R^5)_pO(CR^4R^5)_q$, $(CR^4R^5)_pS(CR^4R^5)_q$, $(CR^4R^5)_pC(O)(CR^4R^5)_q$, $(CR^4R^5)_sC(O)NR^6(CR^4R^5)_q$, $(CR^4R^5)_pC(O)O(CR^4R^5)_q$, $(CR^4R^5)_pOC(O)(CR^4R^5)_q$, $(CR^4R^5)_pOC(O)NR^6(CR^4R^5)_q$, $(CR^4R^5)_p$, $NR^6(CR^4R^5)_q$, $(CR^4R^5)_pNR^6C(O)NR^6(CR^4R^5)_q$, $(CR^4R^5)_pS(O)(CR^4R^5)_q$, $(CR^4R^5)_pS(O)NR^4(CR^5R^6)_q$, $(CR^4R^5)_pS(O)_2(CR^4R^5)_q$, or $(CR^4R^5)_pS(O)_2NR^6(CR^4R^5)_q$, wherein said cycloalkylene, arylene, heterocycloalkylene, or heteroarylene is optionally substituted with 1, 2, or 3 substituents independently selected from $Cy^3$, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $P(R^f)_2$, $P(OR^c)_2$, $P(O)R^eR^f$, $P(O)OR^{-c}OR^f$, $S(O)R^b$, $S(O)NR^cR^d$, $S(O)_2R^b$, $NR^cS(O)_2R^b$, and $S(O)_2NR^cR^d$;

$L^2$ is $(CR^7R^8)_r$, $(CR^7R^8)_s$-(cycloalkylene)-$(CR^7R^8)_t$, $(CR^7R^8)_s$-(arylene)-$(CR^7R^8)_t$, $(CR^7R^8)_s$-(heterocycloalkylene)-$(CR^7R^8)_t$, $(CR^7R^8)_s$-(heteroarylene)-$(CR^7R^8)_t$, $(CR^7R^8)_sO(CR^7R^8)_t$, $(CR^7R^8)_sS(CR^7R^8)_t$, $(CR^7R^8)_sC(O)(CR^7R^8)_t$, $(CR^7R^8)_sC(O)NR^9(CR^7R^8)_t$, $(CR^7R^8)_sC(O)O(CR^7R^8)_t$, $(CR^7R^8)_sOC(O)(CR^7R^8)_t$, $(CR^7R^8)_sOC(O)NR^9(CR^7R^8)_t$, $(CR^7R^8)$, $NR^9(CR^7R^8)_t$, $(CR^7R^8)_sNR^9C(O)NR^9(CR^7R^8)_t$, $(CR^7R^8)_sS(O)(CR^7R^8)_t$, $(CR^7R^8)_sS(O)NR^7(CR^8R^9)_t$, $(CR^7R^8)_sS(O)_2(CR^7R^8)_t$, or $(CR^7R^8)_sS(O)_2NR^9(CR^7R^8)_t$, wherein said cycloalkylene, arylene, heterocycloalkylene, or heteroarylene is optionally substituted with 1, 2, or 3 substituents independently selected from $Cy^4$, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^1$ is H or —W''—X''—Y''—Z'';

$R^2$ is H, halo, $C_{1-6}$ alkyl, $C_{2-6}$ alkenyl, $C_{2-6}$ alkynyl, $C_{1-6}$ haloalkyl, CN, $NO_2$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^B$, $NR^CC(O)NR^CR^D$, $NR^CC(O)OR^A$, $S(O)R^B$, $S(O)NR^CR^D$, $S(O)_2R^B$, $NR^CS(O)_2R^B$, or $S(O)_2NR^CR^D$;

$R^3$ is H, cycloalkyl, aryl, heterocycloalkyl, heteroaryl, halo, $C_{1-6}$ alkyl, $C_{2-6}$ alkenyl, $C_{2-6}$ alkynyl, $C_{1-6}$ haloalkyl, CN, $NO_2$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^B$, $NR^CC(O)NR^CR^D$, $NR^CC(O)OR^A$, $S(O)R^B$, $S(O)NR^CR^D$, $S(O)_2R^B$, $NR^CS(O)_2R^B$, and $S(O)_2NR^CR^D$; wherein said cycloalkyl, aryl, heterocycloalkyl, heteroaryl, or $C_{1-6}$ alkyl is optionally substituted with 1, 2, or 3 substituents independently selected from $Cy^5$, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

or $R^2$ and $-L^2-Cy^2$ are linked together to form a group of formula:

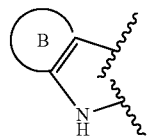

wherein ring B is a fused aryl or fused heteroaryl ring, each optionally substituted with 1, 2, or 3 —W'—X'—Y'—Z';

$R^4$ and $R^5$ are independently selected from H, halo, OH, $C_{1-6}$ alkyl, $C_{2-6}$ alkenyl, $C_{2-6}$ alkynyl, $C_{1-6}$ alkoxy, alkoxyalkyl, cyanoalkyl, heterocycloalkyl, cycloalkyl, $C_{1-6}$ haloalkyl, CN, and $NO_2$;

$R^7$ and $R^8$ are independently selected from H, halo, OH, $C_{1-6}$ alkyl, $C_{2-6}$ alkenyl, $C_{2-6}$ alkynyl, $C_{1-6}$ alkoxy, $C_{1-6}$ haloalkyl, CN, and $NO_2$;

or $R^7$ and $R^8$ together with the C atom to which they are attached form a 3, 4, 5, 6, or 7-membered cycloalkyl or heterocycloalkyl ring, each optionally substituted by 1, 2, or 3 substituent independently selected from halo, OH, $C_{1-6}$ alkyl, $C_{2-6}$ alkenyl, $C_{2-6}$ alkynyl, $C_{1-6}$ alkoxy, $C_{1-6}$ haloalkyl, CN, and $NO_2$;

$R^9$ is H, $C_{1-6}$ alkyl, $C_{2-6}$ alkenyl, or $C_{2-6}$ alkynyl;

W, W', and W'' are independently absent or independently selected from $C_{1-6}$ alkylene, $C_{2-6}$ alkenylene, $C_{2-6}$ alkynylene, O, S, $NR^h$, CO, COO, $CONR^h$, SO, $SO_2$, $SONR^h$ and $NR^hCONR^i$, wherein each of the $C_{1-6}$ alkylene, $C_{2-6}$ alkenylene, and $C_{2-6}$ alkynylene is optionally substituted by 1, 2 or 3 substituents independently selected from halo, $C_{1-6}$ alkyl, $C_{1-6}$ haloalkyl, OH, $C_{1-6}$ alkoxy, $C_{1-6}$ haloalkoxy, amino, $C_{1-6}$ alkylamino, and $C_{2-8}$ dialkylamino;

X, X', and X'' are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^j$, $C(O)NR^hR^i$, amino, $C_{1-6}$ alkylamino, and $C_{2-8}$ dialkylamino;

Y, Y', and Y'' are independently absent or independently selected from $C_{1-6}$ alkylene, $C_{2-6}$ alkenylene, $C_{2-6}$ alkynylene, O, S, $NR^h$, CO, COO, $CONR^h$, SO, $SO_2$, $SONR^h$, and $NR^hCONR^i$, wherein each of the $C_{1-6}$ alkylene, $C_{2-6}$ alkenylene, and $C_{2-6}$ alkynylene is optionally substituted by 1, 2 or 3 substituents independently selected from halo, $C_{1-6}$ alkyl, $C_{1-6}$ haloalkyl, OH, $C_{1-6}$ alkoxy, $C_{1-6}$ haloalkoxy, amino, $C_{1-6}$ alkylamino, and $C_{2-8}$ dialkylamino;

Z, Z', and Z'' are independently selected from H, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, $S(O)_2NR^{c2}R^{d2}$, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, and heterocycloalkyl are optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

wherein two adjacent —W—X—Y—Z, together with the atoms to which they are attached, optionally form a fused 4-20 membered cycloalkyl ring or a fused 4-20 membered heterocycloalkyl ring, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^g)NR^{c3}R^{d3}$, $NR^{c3}C(=NR^g)NR^{c3}R^{d3}$, $S(O)R^{b3}$, $S(O)NR^{c3}R^{d3}$, $S(O)_2R^{b3}$, $NR^{c3}S(O)_2R^{b3}$, $S(O)_2NR^{c3}R^{d3}$, aryl, cycloalkyl, heteroaryl, and heterocycloalkyl;

wherein two adjacent —W'—X'—Y'—Z', together with the atoms to which they are attached, optionally form a fused 4-20 membered cycloalkyl ring or a fused 4-20 membered heterocycloalkyl ring, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^g)NR^{c3}R^{d3}$, $NR^{c3}C(=NR^g)NR^{c3}R^{d3}$, $S(O)R^{b3}$, $S(O)NR^{c3}R^{d3}$, $S(O)_2R^{b3}$, $NR^{c3}S(O)_2R^{b3}$, $S(O)_2NR^{c3}R^{d3}$, aryl, cycloalkyl, heteroaryl, and heterocycloalkyl;

$Cy^4$, and $Cy^5$ are independently selected from aryl, cycloalkyl, heteroaryl, and heteorcycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}(O)NR^{c4}R^{d4}$, $NR^{c4}C(O)OR^{a4}$, $C(=NR^g)NR^{c4}R^{d4}$, $NR^{c4}C(=NR^g)$ $NR^{c4}R^{d4}$, $P(R^{f4})_2$, $P(OR^4)_2$, $P(O)R^{e4}R^{f4}$, $P(O)OR^{e4}OR^{f4}$, $S(O)^{b4}S(O)NR^{c4}R^{d4}$, $S(O)_2R^{b4}$, $NR^{c4}S(O)_2R^{b4}$, and $S(O)_2NR^{c4}R^{d4}$;

$R^A$ is H, $C_{1-4}$ alkyl, $C_{2-4}$ alkenyl, $C_{2-4}$ alkynyl, cycloalkyl, heterocycloalkyl, aryl, or heteroaryl wherein said $C_{1-4}$ alkyl, $C_{2-4}$ alkenyl, $C_{2-4}$ alkynyl, cycloalkyl, heterocycloalkyl, aryl or heteroaryl is optionally substituted with 1, 2, or 3 substituents independently selected from OH, CN, amino, halo, and $C_{1-4}$ alkyl;

$R^B$ is H, $C_{1-4}$ alkyl, $C_{2-4}$ alkenyl, $C_{2-4}$ alkynyl, cycloalkyl, heterocycloalkyl, aryl, or heteroaryl wherein said $C_{1-4}$ alkyl, $C_{2-4}$ alkenyl, or $C_{2-4}$ alkynyl, cycloalkyl, heterocycloalkyl, aryl, or heteroaryl is optionally substituted with 1, 2, or 3 substituents independently selected from OH, CN, amino, halo, and $C_{1-4}$ alkyl;

$R^C$ and $R^D$ are independently selected from H, $C_{1-4}$ alkyl, $C_{2-4}$ alkenyl, or $C_{2-4}$ alkynyl, wherein said $C_{1-4}$ alkyl, $C_{2-4}$ alkenyl, or $C_{2-4}$ alkynyl, is optionally substituted with 1, 2, or 3 substituents independently selected from OH, CN, amino, halo, and $C_{1-4}$ alkyl;

or $R^C$ and $R^D$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, and $C_{1-4}$ alkyl;

$R^a$, $R^{a1}$, $R^{a2}$, $R^{a3}$, and $R^{a4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^b$, $R^{b1}$, $R^{b2}$, $R^{b3}$, and $R^{b4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkyl;

or $R^c$ and $R^d$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c1}$ and $R^{d1}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c2}$ and $R^{d2}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl are each optionally substituted with 1, 2, or 3 substituents independently selected from OH, CN, amino, halo, $C_{1-6}$ alkyl, $C_{1-6}$ alkoxy, $C_{1-6}$ haloalkyl, $C_{1-6}$ haloalkoxy, hydroxyalkyl, cyanoalkyl, aryl, heteroaryl, $C(O)OR^{a4}$, $C(O)R^{b4}$, $S(O)_2R^{b3}$, alkoxyalkyl, and alkoxyalkoxy;

or $R^{c2}$ and $R^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ baloalkyl, $C_{1-6}$ haloalkoxy, hydroxyalkyl, cyanoalkyl, aryl, heteroaryl, $C(O)OR^{a4}$, $C(O)R^{b4}$, $S(O)_2R^{b3}$, alkoxyalkyl, and alkoxyalkoxy;

$R^{c3}$ and $R^{d3}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloatkoxy;

or $R^{c3}$ and $R^{d3}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c4}$ and $R^{d4}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c4}$ and $R^{d4}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^e$, $R^{e1}$, $R^{e2}$, and $R^{e4}$ are independently selected from H, $C_{1-6}$ alkyl, $C_{1-6}$ haloalkyl, $C_{2-6}$ alkenyl, ($C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl, and heterocycloalkylalkyl;

$R^f$, $R^{f1}$, $R^{f2}$, and $R^{f4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, and heterocycloalkyl;

$R^g$ is H, CN, and $NO_2$;

$R^h$ and $R^i$ are independently selected from H and $C_{1-6}$ alkyl;

$R^j$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl;

m is 0, 1, 2, 3, 4, 5, or 6;
p is 0, 1, 2, 3, or 4;
q is 0, 1, 2, 3, or 4;
r is 0, 1, 2, 3, 4, 5, or 6;
s is 0, 1, 2, 3, or 4; and
t is 0, 1, 2, 3, or 4;

with the proviso that when A is CH, then L1 is other than CO or $(CR^4R^5)_u$ wherein u is 1.

In one embodiment, $L^1$ is $(CR^4R^5)_m$, wherein $R^4$ and $R^5$ are independently H and m is 1; $Cy^1$ is heteroaryl; $R^1$ is H; A is N; $R^2$ is H; $L^2$ is $(CR^7R^8)_r$, wherein r is 0; and $Cy^2$ is aryl substituted with 2 W'—X'—Y'—Z'.

In one embodiment, INC280 has the following structure:

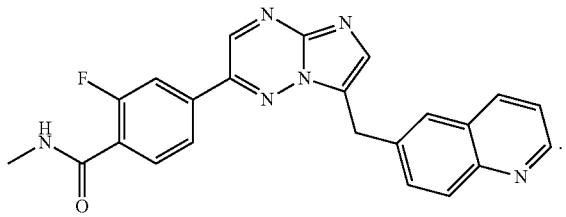 [SMILES: CNC(=O)c1ccc(-c2cnc3ncc(Cc4ccc5ncccc5c4)n3n2)cc1F]

In one embodiment, INC280 is 2-fluoro-N-methyl-4-[7-(quinolin-6-ylmethyl)imidazo[1,2-b][1,2,4]triazin-2-yl]benzamide, or a pharmaceutically acceptable salt thereof.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with an Alk inhibitor to treat a cancer, e.g., a cancer described herein (e.g., a cancer disclosed in Table 1). In one embodiment, the Alk inhibitor is disclosed in Table 1, e.g., LDK378, or in a publication recited in Table 1, e.g., in WO 2008/073687 (e.g., Example 7/Compound 66) or U.S. Pat. No. 8,039,479 (e.g., claim 1 or 5) (also known as ceritinib (Zykadia®). In one embodiment, the Alk inhibitor, e.g., LDK378, has the structure (compound or generic structure) provided in Table 1, or as disclosed in the publication recited in Table 1, e.g., in WO 2008/073687 (e.g., Example 7/Compound 66) or U.S. Pat. No. 8,039,479 (e.g., claim 1 or 5).

In one embodiment, one of Nivolumab, Pembrolizumab or MSB0010718C is used in combination with LDK378 to treat a cancer described in Table 1, e.g., a solid tumor, e.g., a lung cancer (e.g., non-small cell lung cancer (NSCLC)), a lymphoma (e.g., an anaplastic large-cell lymphoma or non-Hodgkin lymphoma), an inflammatory myofibroblastic tumor (IMT), or a neuroblastoma. In some embodiments, the NSCLC is a stage IIIB or IV NSCLC, or a relapsed locally advanced or metastic NSCLC. In some embodiments, the cancer (e.g., the lung cancer, lymphoma, inflammatory myofibroblastic tumor, or neuroblastoma) has, or is identified as having, an ALK rearrangement or translocation, e.g., an ALK fusion. In one embodiment, the ALK fusion is an EML4-ALK fusion, e.g., an EML4-ALK fusion described herein. In another embodiment, the ALK fusion is an ALK-ROS1 fusion. In certain embodiments, the cancer has progressed on, or is resistant or tolerant to, a ROS1 inhibitor, or an ALK inhibitor, e.g., an ALK inhibitor other than LDK378. In some embodiments, the cancer has progressed on, or is resistant or tolerant to, crizotinib. In one embodiment, the subject is an ALK-naïve patient, e.g., a human patient. In another embodiment, the subject is a patient, e.g., a human patient, that has been pretreated with an ALK inhibitor. In another embodiment, the subject is a patient, e.g., a human patient, that has been pretreated with LDK378.

In one embodiment, LDK378 and Nivolumab are administered to an ALK-naïve patient. In another embodiment, LDK378 and Nivolumab are administered to a patient that has been pretreated with an ALK inhibitor. In yet another embodiment, LDK378 and Nivolumab are administered to a patient that has been pretreated with LDK378.

In certain embodiments, LDK378 is administered at an oral dose of about 100 to 1000 mg, e.g., about 150 mg to 900 mg, about 200 mg to 800 mg, about 300 mg to 700 mg, or about 400 mg to 600 mg, e.g., about 150 mg, 300 mg, 450 mg, 600 mg or 750 mg. In certain embodiment, LDK378 is administered at an oral dose of about 750 mg or lower, e.g., about 600 mg or lower, e.g., about 450 mg or lower. In certain embodiments, LDK378 is administered with food. In other embodiments, the dose is under fasting condition. The dosing schedule can vary from e.g., every other day to daily, twice or three times a day. In one embodiment, LDK378 is administered daily. In one embodiment, LDK378 is administered at an oral dose from about 150 mg to 750 mg daily, either with food or in a fasting condition. In one embodiment, LDK378 is administered at an oral dose of about 750 mg daily, in a fasting condition. In one embodiment, LDK378 is administered at an oral dose of about 750 mg daily, via capsule or tablet. In another embodiment, LDK378 is administered at an oral dose of about 600 mg daily, via capsule or tablet. In one embodiment, LDK378 is administered at an oral dose of about 450 mg daily, via capsule or tablet.

In one embodiment, LDK378 is administered at a dose of about 450 mg and nivolumab is administered at a dose of about 3 mg/kg. In another embodiment, the LDK378 dose is 600 mg and the nivolumab dose is 3 mg/kg. In one embodiment, LDK378 is administered with a low fat meal.

In one embodiment, the Alk inhibitor has the following structure:

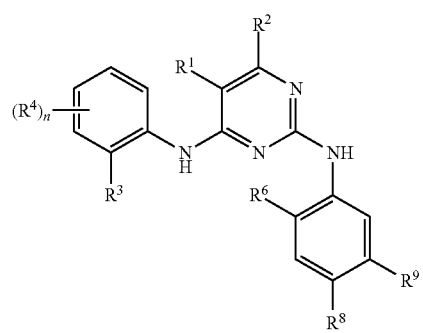

or pharmaceutically acceptable salts thereof;

wherein $R^1$ is halo or $C_{1-6}$ alkyl;
$R^2$ is H;
$R^3$ is $(CR_2)_{0-2}SO_2R^{12}$;
$R^4$ is $C_{1-6}$ alkyl, $C_{2-6}$ alkenyl or $C_{2-6}$ alkynyl; $OR^{12}$, $NR(R^{12})$, halo, nitro, $SO_2R^{12}$, $(CR_2)_pR^{13}$ or X; or $R^4$ is H;
$R^6$ is isopropoxy or methoxy;
one of $R^8$ and $R^9$ is $(CR_2)_qY$ and the other is $C_{1-6}$ alkyl, cyano, $C(O)O_{0-1}R^{12}$, $CONR(R^{12})$ or $CONR(CR_2)_pNR(R^{12})$;
X is $(CR_2)_qY$, cyano, $C(O)O_{0-1}R^{12}$, $CONR(R^{12})$, $CONR(CR_2)_pNR(R^{12})$, $CONR(CR_2)_pOR^{12}$, $CONR(CR_2)_pSR^{12}$, $CONR(CR_2)_pS(O)_{1-2}R^{12}$ or $(CR_2)_{1-6}NR(CR_2)_pOR^{12}$;
Y is pyrrolidinyl, piperidinyl or azetidinyl, each of which is attached to the phenyl ring via a carbon atom;
$R^{12}$ and $R^{13}$ are independently 3-7 membered saturated or partially unsaturated carbocyclic ring, or a 5-7 membered heterocyclic ring comprising N, O and/or S; aryl or heteroaryl; or $R^{12}$ is H or $C_{1-6}$ alkyl;
R is H or $C_{1-6}$ alkyl;
n is 0-1;
p is 0-4; and
q is 0.

In one embodiment, $R^2$ is H; $R^3$ is $SO_2R^{12}$ and $R^{12}$ is $C_{1-6}$ alkyl; $R^4$ is H (n=1); $R^6$ is isopropoxy; and one of $R^8$ and $R^9$ is $(CR^2)qY$ wherein q=0, Y is piperidinyl and the other is $C_{1-6}$ alkyl.

In one embodiment, LDK378 has the following structure:

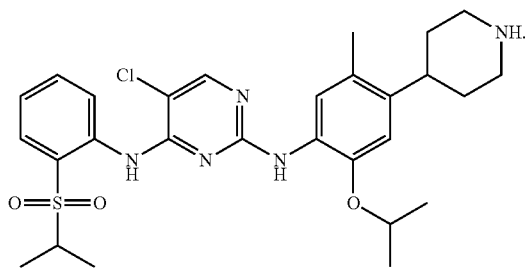 [SMILES: Cc1cc(Nc2ncc(Cl)c(Nc3ccccc3S(=O)(=O)C(C)C)n2)c(OC(C)C)cc1C1CCNCC1]

In one embodiment, LDK378 is 5-chloro-N2-(2-isopropoxy-5-methyl-4-(piperidin-4-yl)-phenyl)-N4-[2-(propane-2-sulfonyl)-phenyl]-pyrimidine-2,4-diamine, or a pharmaceutically acceptable salt thereof.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a CDK4/6 inhibitor to treat a cancer, e.g., a cancer described herein (e.g., a cancer disclosed in Table 1). In one embodiment, the CDK4/6 inhibitor is disclosed in Table 1, e.g., LEE011, or in a publication recited in Table 1, e.g., in U.S. Pat. Nos. 8,685,980 or 8,415,355 (e.g., Formula (I) in columns 3-4 or in Example 74 at column 66). In one embodiment, the CDK4/6 inhibitor, e.g., LEE011, has the structure (compound or generic structure) provided in Table 1, or as disclosed in the publication recited in Table 1, e.g., in U.S. Pat. Nos. 8,685,980 or 8,415,355 (e.g., Formula (I) in columns 3-4 or in Example 74 at column 66). In one embodiment, one of Nivolumab, Pembrolizumab or MSB0010718C is used in combination with LEE011 to treat a cancer described in Table 1, e.g., a solid tumor, e.g., a lung cancer (e.g., non-small cell lung cancer (NSCLC)), a neurologic cancer, melanoma or a breast cancer, or a hematological malignancy, e.g., lymphoma.

In one embodiment, the CDK4/6 inhibitor has the following structure:

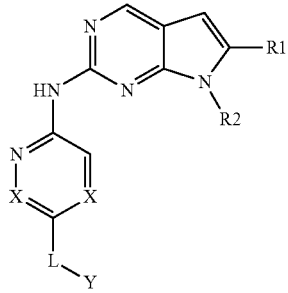

X is $CR^9$ or N;
$R^1$ is $C_{1-8}$ alkyl, CN, $C(O)OR^4$ or $CONR^5R^6$, a 5-14 membered heteroaryl group, or a 3-14 membered cycloheteroalkyl group;
$R^2$ is $C_{1-8}$alkyl, $C_{3-14}$ cycloalkyl, or a 5-14 membered heteroaryl group, and wherein $R^2$ may be substituted with one or more $C_{1-8}$alkyl, or OH;
L is a bond, $C_{1-8}$ alkylene, C(O), or $C(O)NR^{10}$, and wherein L may be substituted or unsubstituted;
Y is H, $R^{11}$, $NR^{12}R^{13}$, OH, or Y is part of the following group

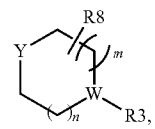

where Y is $CR^9$ or N; where 0-3 $R^8$ may be present, and $R^8$ is $C_{1-8}$ alkyl, oxo, halogen, or two or more $R^8$ may form a bridged alkyl group;
W is $CR^9$, or N, or O (where W is O, $R^3$ is absent);
$R^3$ is H, $C_{1-8}$alkyl, $C_{1-8}$ alkyl$R^{14}$, $C_{3-14}$ cycloalkyl, C(O) $C_{1-8}$ alkyl, $C_{1-8}$haloalkyl, $C_{1-8}$ alkylOH, $C(O)NR^{14}R^{15}$, $C_{1-8}$cyanoalkyl, $C(O)R^{14}$, $C_{0-8}$alkylC(O)$C_{0-8}$alkylNR$^{14}R^{15}$, $C_{0-8}$ alkylC(O)OR$^{14}$, $NR^{14}R^{15}$, $SO_2C_{1-8}$ alkyl, $C_{1-8}$ alkyl-$C_{3-14}$ cycloalkyl, $C(O)C_{1-8}$alkylC$_{3-14}$ cycloalkyl, $C_{1-8}$ alkoxy, or OH which may be substituted or unsubstituted when $R^3$ is not H.
$R^9$ is H or halogen;
$R^4$, $R^5$, $R^6$, $R^7$, $R^{10}$, $R^{11}$, $R^{12}$, $R^{13}$, $R^{14}$, and $R^{15}$ are each independently selected from H, $C_{1-8}$ alkyl, $C_{3-14}$ cycloalkyl, a 3-14 membered cycloheteroalkyl group, a $C_{6-14}$ aryl group, a 5-14 membered heteroaryl group, alkoxy, C(O)H, C(N) OH, C(N)OCH$_3$, $C(O)C_{1-3}$ alkyl, $C_{1-8}$ alkylNH$_2$, $C_{1-6}$ alkylOH, and wherein $R^4$, $R^5$, $R^6$, $R^7$, $R^{10}$, $R^{11}$, $R^{12}$, and $R^{13}$, $R^{14}$, and $R^{15}$ when not H may be substituted or unsubstituted;
m and n are independently 0-2; and
wherein L, $R^3$, $R^4$, $R^5$, $R^6$, $R^7$, $R^{10}$, $R^{11}$, $R^{12}$, and $R^{13}$, $R^{14}$, and $R^{15}$ may be substituted with one or more of $C_{1-8}$ alkyl, $C_{2-8}$ alkenyl, $C_{2-8}$ alkynyl, $C_{3-14}$ cycloalkyl, 5-14 membered heteroaryl group, $C_{6-14}$ aryl group, a 3-14 membered cycloheteroalkyl group, OH, (O), CN, alkoxy, halogen, or NH$_2$.

In one embodiment, X is CR$^9$, wherein R$^9$ is H; R$^1$ is CONR$^5$R$^6$, wherein R$^5$ and R$^6$ are both C$_{1-8}$ alkyl, specifically methyl; R$^2$ is C$_{3-14}$ cycloalkyl, specifically cyclopentyl; L is a bond; and Y is part of the group

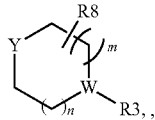

wherein Y is N, zero R$^8$ are present, W is N, m and n are both 1, and R$^3$ is H.

In one embodiment, LEE011 has the following structure:

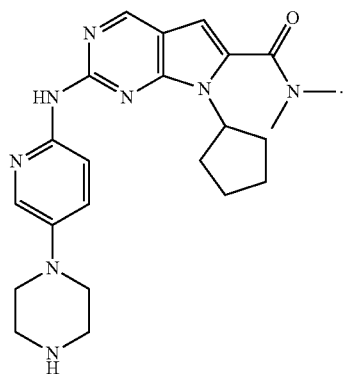 [SMILES: CN(C)C(=O)c1cc2cnc(Nc3ccc(N4CCNCC4)cn3)nc2n1C1CCCC1]

In one embodiment, LEE011 is 7-cyclopentyl-2-(5-piperazin-1-yl-pyridin-2-ylamino)-7H-pyrrolo[2,3-d]pyrimidine-6-carboxylic acid dimethylamide or a pharmaceutically acceptable salt thereof.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a PI3K-inhibitor to treat a cancer, e.g., a cancer described herein (e.g., a cancer disclosed in Table 1). In one embodiment, the PI3K-inhibitor is disclosed in Table 1, e.g., BKM120 or BYL719, or in a publications recited in Table 1, e.g., in WO2007/084786 (e.g., Example 10 in [0389] or Formula (I) in [0048]) or WO2010/029082 (e.g., Example 15 or Formula (I)). In one embodiment, the PI3K-inhibitor, e.g., BKM120 or BYL719, has the structure (compound or generic structure) provided in Table 1, or as disclosed in the publications recited in Table 1 e.g., in WO2007/084786 (e.g., Example 10 in [0389] or Formula (I) in [0048]) or WO2010/029082 (e.g., Example 15 or Formula (I)). In one embodiment, one of Nivolumab, Pembrolizumab or MSB0010718C is used in combination with BKM120 or BYL719 to treat a cancer or disorder described in Table 1, e.g., a solid tumor, e.g., a lung cancer (e.g., non-small cell lung cancer (NSCLC)), a prostate cancer, an endocrine cancer, an ovarian cancer, a melanoma, a bladder cancer, a female reproductive system cancer, a digestive/gastrointestinal cancer, a colorectal cancer, glioblastoma multiforme (GBM), a head and neck cancer, a gastric cancer, a pancreatic cancer or a breast cancer; or a hematological malignancy, e.g., leukemia, non-Hodgkin lymphoma; or a hematopoiesis disorder.

In one embodiment, the PI3K-inhibitor has the following structure:

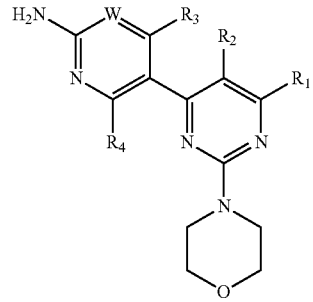

or a stereoisomer, tautomer, or pharmaceutically acceptable salt thereof, wherein, W is CRW or N, wherein Rw is selected from the group consisting of (1) hydrogen, (2) cyano, (3) halogen, (4) methyl, (5) trifluoromethyl, and (6) sulfonamido; R$_1$ is selected from the group consisting of (1) hydrogen, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —COR$_{1a}$, (13) —CO$_2$R$_{1a}$ (14) —CONR$_{1a}$R$_{1b}$, (15) —NR$_{1a}$R$_{1b}$, (16) —NR$_{1a}$COR$_{1b}$, (17) —NR$_{1a}$SO$_2$R$_{1b}$, (18) —OCOR$_{1a}$, (19) —OR$_{1a}$, (20) —SR$_{1a}$ (21) —SOR$_{1a}$, (22) —SO$_2$R$_{1a}$, and (23) —SO$_2$NR$_{1a}$R$_{1b}$, wherein R$_{1a}$, and R$_{1b}$ are independently selected from the group consisting of (a) hydrogen, (b) substituted or unsubstituted alkyl, (c) substituted and unsubstituted aryl, (d) substituted and unsubstituted heteroaryl, (e) substituted and unsubstituted heterocyclyl, and (f) substituted and unsubstituted cycloalkyl; R is selected from the group consisting (1) hydrogen, (2) cyano, (3) nitro, (4) halogen, (5) hydroxy, (6) amino, (7) substituted and unsubstituted alkyl, (8) —COR2a, and wherein R$_{2a}$— and R$_{2b}$ are independently selected from the group consisting of (a) hydrogen, and (b) substituted or unsubstituted alkyl; R$_3$ is selected from the group consisting of (1) hydrogen, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —COR$_{3a}$, (13) —NR$_{3a}$R$_{3b}$, (16) —OR$_{3a}$, (17) —SR$_{3a}$, (18) —SOR$_{3a}$, (19) —SO$_2$R$_3$, and (20) —SO$_2$NR$_{3a}$R$_{3b}$, wherein R$_{3a}$, and R$_{3b}$ are independently selected from the group consisting of (a) hydrogen, (b) substituted or unsubstituted alkyl, (c) substituted and unsubstituted aryl, (d) substituted and unsubstituted heteroaryl, (e) substituted and unsubstituted heterocyclyl, and (f) substituted and unsubstituted cycloalkyl; and R$_4$ is selected from the group consisting of (1) hydrogen, and (2) halogen.

In one embodiment, W is CRw and Rw is hydrogen, $R_1$ is unsubstituted heterocyclyl, $R_2$ is hydrogen, $R_3$ is substituted alkyl, and $R_4$ is hydrogen.

In one embodiment, BKM120 has the following structure:

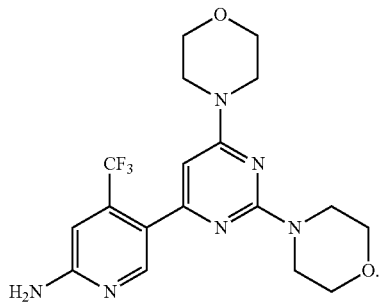 [SMILES: Nc1cc(C(F)(F)F)c(-c2cc(N3CCOCC3)nc(N3CCOCC3)n2)cn1]

In one embodiment, BKM120 is 4-(trifluoromethyl)-5-(2,6-dimorpholinopyrimidin-4-yl)pyridine-2-amine or a pharmaceutically acceptable salt thereof.

In one embodiment, the PI3K-inhibitor has the following structure:

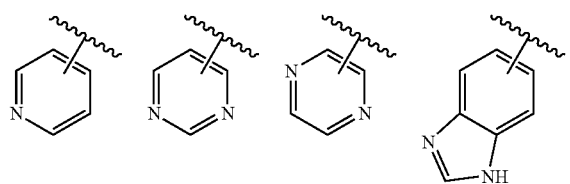

or salt thereof, wherein

A represents a heteroaryl selected from the group consisting of:

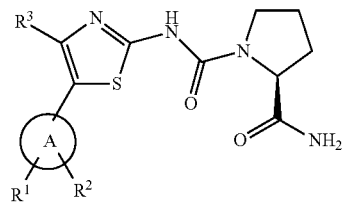

$R^1$ represents one of the following substituents: (1) unsubstituted or substituted, preferably substituted $C_1$-$C_7$ alkyl, wherein said substituents are independently selected from one or more, preferably one to nine of the following moieties: deuterium, fluoro, or one to two of the following moieties $C_3$-$C_5$ cycloalkyl; (2) optionally substituted $C_3$-$C_5$ cycloalkyl wherein said substituents are independently substituted $C_3$-$C_5$ cycloalkyl wherein said substituents are independently selected from one or more, preferably one to four of the following moieties: deuterium, $C_1$-$C_4$ alkyl (preferably methyl), fluoro, cyano, aminocarbonyl; (3) optionally substituted phenyl wherein said substituents are independently selected from one or more, preferably one to two of the following moieties: deuterium, halo, cyano, $C_1$-$C_7$ alkyl, $C_1$-$C_7$ alkylamino, di($C_1$-$C_7$ alkyl)amino, $C_1$-$C_7$ alkylaminocarbonyl, di($C_1$-$C_7$-alkyl)aminocarbonyl, $C_1$-$C_7$ alkoxy; (4) optionally mono- or di-substituted amine; wherein said substituents are independently selected from the following moieties: deuterium, $C_1$-$C_7$ alkyl (which is unsubstituted or substituted by one or more substituents selected from the group of deuterium, fluoro, chloro, hydroxyl), phenylsulfonyl (which is unsubstituted or substituted by one or more, preferably one, $C_1$-$C_7$ alkyl, $C_1$-$C_7$ alkoxy, di($C_1$-$C_7$-alkyl) amino-$C_1$-$C_7$-alkoxy); (5) substituted sulfonyl; wherein said substituent is selected from the following moieties: $C_1$-$C_7$ alkyl (which is unsubstituted or substituted by one or more substituents selected from the group of deuterium, fluoro), pyrrolidino, (which is unsubstituted or substituted by one or more substituents selected from the group of deuterium, hydroxyl, oxo; particularly one oxo); (6) fluoro, chloro; R2 represents hydrogen; R3 represents (1) hydrogen, (2) fluoro, chloro, (3) optionally substituted methyl, wherein said substituents are independently selected from one or more, preferably one to three of the following moireites: deuterium, fluoro, chloro, dimethylamino: with the exception of (S)-pyrrolidine-1,2-dicarboxylic acid 2-amide 1-({5-[2-(tert-butyl)-pyrimidin-4-yl]-4-methyl-thiazol-2-yl}-amide).

In one embodiments, A is

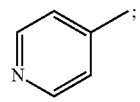

$R^1$ is substituted $C_1$-$C_7$ alkyl, wherein said substituents are independently selected from one or more, preferably one to nine of deuterium, fluoro, or $C_3$-$C_5$ cycloalkyl; $R^2$ is hydrogen, and $R^3$ is methyl.

In one embodiment, BYL719 has the following structure:

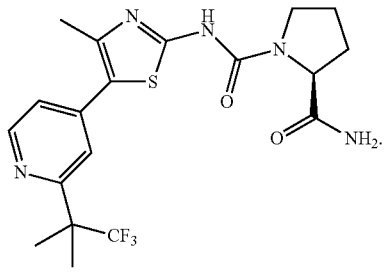 [SMILES: Cc1nc(NC(=O)N2CCC[C@H]2C(N)=O)sc1-c1ccnc(C(C)(C)C(F)(F)F)c1]

In one embodiment, BYL719 is (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a BRAF inhibitor to treat a cancer, e.g., a cancer described herein (e.g., a cancer disclosed in Table 1). In one embodiment, the BRAF inhibitor is disclosed in Table 1, e.g., LGX818, or in a publication recited in Table 1, e.g., WO2011/025927 (e.g., Example 6/Compound 6 or Formula (Ia) in [0030]) or U.S. Pat. No. 8,501,758 (e.g., Example 5 in column 45). In one embodiment, the BRAF inhibitor, e.g., LGX818, has the structure (compound or generic structure) provided in Table 1, or as disclosed in the publication recited in Table 1. In one embodiment, one of Nivolumab, Pembrolizumab or MSB0010718C is used in combination with LGX818 to treat a cancer described in Table 1, e.g., a solid tumor, e.g., a lung cancer (e.g., non-small cell lung cancer (NSCLC)), a melanoma, e.g., advanced melanoma, a thyroid cancer, e.g., papillary thyroid cancer, or a colorectal cancer. In some embodiments, the cancer has, or is identified as having, a BRAF mutation (e.g., a BRAF V600E mutation), a BRAF wildtype, a KRAS wildtype or an activating KRAS mutation. The cancer may be at an early, intermediate or late stage.

In one embodiment, the BRAF inhibitor has the following structure:

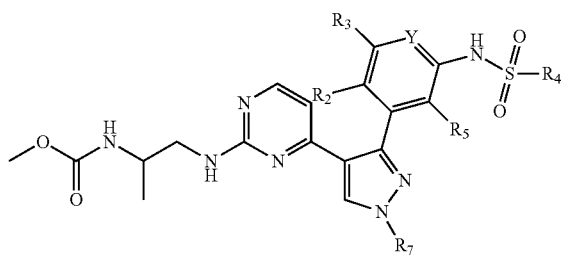

in Y is selected from N and $CR_6$; $R_2$, $R_3$, $R_5$, and $R_6$ are independently selected from hydrogen, halo, cyano, $C_{1-4}$ alkyl, halo-substituted $C_{1-4}$ alkyl, $C_{1-4}$ alkoxy and halo-substituted $C_{1-4}$ alkoxy; with the proviso that when $R_5$ is fluoro and $R_1$ is selected from hydrogen, —$X_1R_{8a}$, —$X_1C(O)NR_{8a}R_{8b}$, —$XNR_{8a}X_2R_{8b}$, —$X_1NR_{8a}C(O)X_2OR_{8b}$ and —$X_1NR_{8a}S(O)_{0-2}R_{8b}$, $R_3$ and $R_6$ are not both hydrogen; $R_4$ is selected from —$R_9$ and —$NR_{10}R_{11}$; wherein $R_9$ is selected from $C_{1-6}$ alkyl, $C_{3-8}$ cycloalkyl, $C_{3-8}$ heterocycloalkyl, aryl, and heteroaryl; wherein said aryl, cycloalkyl, heterocycloalkyl, aryl, or heteroaryl of $R_9$ is optionally substituted with 1 to 3 radicals independently selected from halo, cyano, $C_{1-4}$ alkyl, halo-substituted $C_{1-4}$ alkyl, $C_{1-4}$ alkoxy and halo-substituted $C_{1-4}$ alkoxy; and R10 and R11 are independently selected from hydrogen and R9; and R7 is selected from hydrogen, $C_{1-4}$ alkyl, C3-5 cycloalkyl and C3-5 heterocycloalkyl; wherein said alkyl, cycloalkyl, or heterocycloalkyl of R7 is optionally substituted with 1 to 3 radicals independently selected from halo, cyano, hydroxyl, $C_{1-4}$ alkyl, halo-substituted $C_{1-4}$ alkyl, $C_{1-4}$ alkoxy and halo-substituted $C_{1-4}$ alkoxy.

In one embodiment, $R_3$ is halo (e.g., chloro); $R_4$ is $R_9$; $R_9$ is $C_{1-6}$ alkyl (e.g., methyl), $R_5$ is halo (e.g., fluoro), $R_7$ is $C_{1-4}$ alkyl (e.g., isopropyl); Y is $CR_6$; and $R_6$ is H. In one embodiment, LGX818 has the following structure:

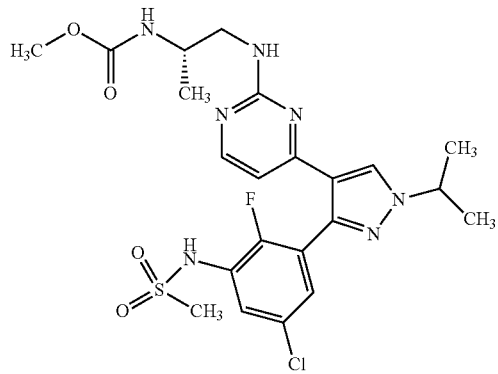 [SMILES: COC(=O)N[C@@H](C)CNc1nccc(-c2cn(C(C)C)nc2-c2cc(Cl)cc(NS(C)(=O)=O)c2F)n1]

In one embodiment, LGX818 is methyl (S)-(1-((4-(3-(5-chloro-2-fluoro-3-(methylsulfonamido)phenyl)-1-isopropyl-1H-pyrazol-4-yl)pyrimidin-2-yl)amino)propan-2-yl)carbamate or a pharmaceutically acceptable salt thereof.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a CAR T cell targeting CD19 to treat a cancer, e.g., a cancer described herein (e.g., a cancer disclosed in Table 1). In one embodiment, the CAR T cell targeting CD19 is disclosed in Table 1, e.g., CTL019, or in a publication recited in Table 1, e.g., WO2012/079000, e.g., SEQ ID NO: 12 (e.g., full-length CAR) or SEQ ID NO: 14 (e.g., CD19 scFv). In one embodiment, the CAR T cell targeting CD19, e.g., CTL019, has the structure (compound or generic structure) provided in Table 1, or as disclosed in the publication recited in Table 1. In one embodiment, one of Nivolumab, Pembrolizumab or MSB0010718C is used in combination with CTL019 to treat a cancer described in Table 1, e.g., a solid tumor, or a hematological malignancy, e.g., a lymphocytic leukemia or a non-Hodgkin lymphoma.

In one embodiment, the CAR T cell targeting CD19 has the USAN designation TISAGENLECLEUCEL-T. CTL019 is made by a gene modification of T cells is mediated by stable insertion via transduction with a self-inactivating, replicationdeficient Lentiviral (LV) vector containing the CTL019 transgene under the control of the EF-1 alpha promoter. CTL019 is a mixture of transgene positive and negative T cells that are delivered to the subject on the basis of percent transgene positive T cells.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with an FGF receptor inhibitor to treat a cancer, e.g., a cancer described herein (e.g., a cancer disclosed in Table 1). In one embodiment, the FGF receptor inhibitor is disclosed in Table 1, e.g., BGJ398, or in a publication recited in Table 1, e.g., U.S. 8,552,002 (e.g., Example 145 or Formula (I) in column 6). In one embodiment, the FGF receptor inhibitor, e.g., BGJ398, has the structure (compound or generic structure) provided in Table 1, or as disclosed in the publication recited in Table 1, e.g., U.S. 8,552,002 (e.g., Example 145 or Formula (I) in column 6). In one embodiment, one of Nivolumab, Pembrolizumab or MSB0010718C is used in combination with BGJ398 to treat a cancer described in Table 1, e.g., a solid tumor, e.g., a digestive/gastrointestinal cancer; or a hematological cancer.

In one embodiment, the FGF receptor inhibitor has the following structure:

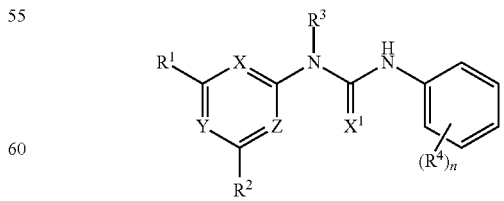

where n is 0, 1, 2, 3, 4 or 5;
X, Y and Z are each independently selected from N or C—$R^5$, wherein at least two of X, Y and Z are N; and $X^1$ is oxygen, R¹, R², R³ and R⁴ if present, are each independently selected from an organic or inorganic moiety, where the inorganic moiety is especially selected from halo, especially chloro, hydroxyl, cyano, azo (N=N=N), nitro; and where the organic moiety is substituted or unsubstituted and may be attached via a linker, -L¹-, the organic moiety being especially selected from hydrogen; lower aliphatic (especially $C_1$, $C_2$, $C_3$ or $C_4$ aliphatic) e.g. lower alkyl, lower alkenyl, lower alkynyl; amino; guanidino; hydroxyguanidino; formamidino; isothioureido; ureido; mercapto; C(O)H or other acyl; acyloxy; substituted hydroxy; carboxy; sulfo; sulfamoyl; carbamoyl; a substituted or unsubstituted cyclic group, for example the cyclic group (whether substituted or unsubstituted) may be cycloalkyl, e.g. cyclohexyl, phenyl, pyrrole, imidazole, pyrazole, isoxazole, oxazole, thiazole, pyridazine, pyrimidine, pyrazine, pyridyl, indole, isoindole, indazole, purine, indolizidine, quinoline, isoquinoline, quinazoline, pteridine, quinolizidine, piperidyl, piperazinyl, pyrollidine, morpholinyl or thiomorpholinyl and, for example, substituted lower aliphatic or substituted hydroxy may be substituted by such substituted or unsubstituted cyclic groups;

and -L¹- having 1, 2, 3, 4 or 5 in-chain atoms (e.g. selected from C, N, O and S) and optionally being selected from (i) $C_1$, $C_2$, $C_3$ or $C_4$ alkyl, such an alkyl group optionally being interrupted and/or terminated by an —O—, —C(O)— or —NR$_a$— linkage; —O—; —S—; —C(O)—; cyclopropyl (regarded as having two in-chain atoms) and chemically appropriate combinations thereof; and —NR$^a$—, wherein R$^a$ is hydrogen, hydroxy, hydrocarbyloxy or hydrocarbyl, wherein hydrocarbyl is optionally interrupted by an —O— or —NH— linkage and may be, for example, selected from an aliphatic group (e.g. having 1 to 7 carbon atoms, for example 1, 2, 3, or 4), cycloalkyl, especially cyclohexyl, cycloalkenyl, especially cyclohexenyl, or another carbocyclic group, for example phenyl; where the hydrocarbyl moiety is substituted or unsubstituted;

each R⁴ is the same or different and selected from an organic or inorganic moiety, for example, each R⁴ is the same or different and selected from halogen; hydroxy; protected hydroxy for example trialkylsilylhydroxy; amino; amidino; guanidino; hydroxyguanidino; formamidino; isothioureido; ureido; mercapto; C(O)H or other acyl; acyloxy; carboxy; sulfo; sulfamoyl; carbamoyl; cyano; azo; nitro; $C_1$-$C_7$ aliphatic optionally substituted by one or more halogens and/or one or two functional groups selected from hydroxy, protected hydroxy for example trialkylsilylhydroxy, amino, amidino, guanidino, hydroxyguanidino, formamidino, isothioureido, ureido, mercapto, C(O)H or other acyl, acyloxy, carboxy, sulfo, sulfamoyl, carbamoyl, cyano, azo, or nitro; all of the aforesaid hydroxy, amino, amidino, guanidino, hydroxyguanidino, formamidino, isothioureido, ureido, mercapto, carboxy, sulfo, sulfamoyl and carbamoyl groups in turn optionally being substituted on at least one heteroatom by one or more $C_1$-$C_7$ aliphatic groups; or salts, esters, N-oxides or prodrugs thereof.

In one embodiment, X is CR⁵, wherein R⁵ is H; X1 is oxygen; Y is N; Z is N; R¹ is a substituted organic moiety is a cyclic group (e.g., phenyl) substituted with 4-ethylpiperazinyl and -L¹- is N$^{Ra}$, wherein N$^{Ra}$ is H; R² is an organic moiety (e.g., H); R³ is an organic moiety (e.g., lower aliphatic, e.g., methyl); R⁴ is chloro or methoxy; and n is 4.

In one embodiment, BGJ398 has the following structure:

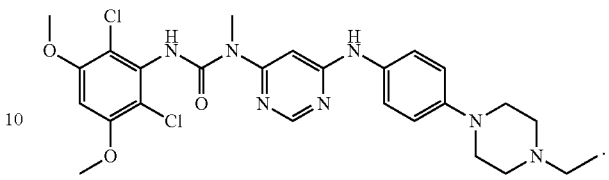

In one embodiment, BGJ398 is 3-(2,6-dichloro-3,5-dimethoxyphenyl)-1-(6-((4-(4-ethylpiperazin-1-yl)phenyl) amino)pyrimidin-4-yl)-1-methylurea.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a MEK inhibitor to treat a cancer, e.g., a cancer described herein (e.g., a cancer disclosed in Table 1). In one embodiment, the MEK inhibitor is disclosed in Table 1, e.g., MEK162, or in a publication recited in Table 1, e.g., WO2003/077914 (e.g., Example 18/Compound 29111 or Formula II). In one embodiment, the MEK inhibitor, e.g., MEK162, has the structure (compound or generic structure) provided in Table 1, or as disclosed in the publication recited in Table 1, e.g., WO2003/077914 (e.g., Example 18/Compound 29111 or Formula II). In one embodiment, one of Nivolumab, Pembrolizumab or MSB0010718C is used in combination with MEK162 to treat a cancer described in Table 1. In other embodiments, the cancer or disorder treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma, a multisystem genetic disorder, a digestive/gastrointestinal cancer, a gastric cancer, or a colorectal cancer; or rheumatoid arthritis. In some embodiments, the cancer has, or is identified as having, a KRAS mutation.

In one embodiment, the MEK inhibitor has the following structure:

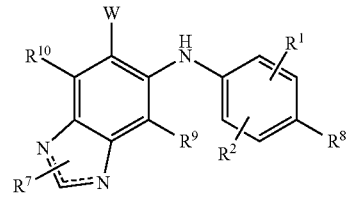

and pharmaceutically accepted salts, prodrugs, and solvates thereof, wherein:

---- is an optional bond, provided that one and only one nitrogen of the ring is double-bonded;

R¹, R², R⁹ and R¹⁰ are independently selected from hydrogen, halogen, cyano, nitro, trifluoromethyl, difluoromethoxy, trifluoromethoxy, azido, —OR³, —C(O)R³, —C(O)OR³, NR⁴C(O)OR⁶, —OC(O)R³, —NR⁴SO₂R⁶, —SO₂NR³R⁴, —NR⁴C(O)R³, —C(O)NR³R⁴, —NR⁵C(O)NR³R⁴, —NR⁵C(NCN)NR³R⁴, —NR³R⁴, and $C_1$-$C_{10}$ alkyl, $C_1$-$C_{10}$ alkenyl, $C_2$-$C_{10}$ alkynyl, $C_3$-$C_{10}$ cycloalkyl, $C_3$-$C_{10}$ cycloalkylalkyl, —S(O)$_j$($C_1$-$C_6$ alkyl), —S(O)j(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl and —NR$^4$(CR$^4$R$^5$)$_m$-heterocyclyl, where each alkyl, alkenyl, alkynyl, cycloalkyl, aryl, heteroaryl and heterocyclyl portion is optionally substituted with one to five groups independently selected from oxo, halogen, cyano, nitro, trifluoromethyl, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl;

R$^3$ is selected from hydrogen, trifluoromethyl, and

C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, and heterocyclylalkyl, where each alkyl, alkenyl, alkynyl, cycloalkyl, aryl, heteroaryl and heterocyclyl portion is optionally substituted with one to five groups independently selected from oxo, halogen, cyano, nitro, trifluoromethyl, difluoromethoxy, trifluoromethoxy, azido, —NR SO$_2$R, —SO$_2$NRR", —C(O)R, —C(O)OR, —OC(O)R, —NR'C(O)OR'", —NR'C(O)R", —C(O)NRR", —SR', —S(O)R'", —SO$_2$R"", —NRR", —NR'C(O)NR"R'", —NR'C(NCN)NR"R'", —OR, aryl, heteroaryl, arylalkyl, heteroarylalkyl, heterocyclyl, and heterocyclylalkyl;

R', R" and R'" independently are selected from hydrogen, lower alkyl, lower alkenyl, aryl and arylalkyl;

R"" is selected from lower alkyl, lower alkenyl, aryl and arylalkyl; or any two of R', R", R'" or R"" can be taken together with the atom to which they are attached to form a 4 to 10 membered carbocyclic, heteroaryl or heterocyclic ring, each of which is optionally substituted with one to three groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl; or R$^3$ and R$^4$ can be taken together with the atom to which they are attached to form a 4 to 10 membered carbocyclic, heteroaryl or heterocyclic ring, each of which is optionally substituted with one to three groups independently selected from halogen, cyano, nitro, trifluoromethyl, difluoromethoxy, trifluoromethoxy, azido, —NR SO$_2$R"", —SO$_2$NR'R", —C(O)R, —C(O)OR, —OC(O)R, —NR'C(O)OR"", —NR C(O)R", —C(O)NRR", —SO$_2$R'", —NR'R", —NR'C(O)NR"R'", —NR'C(NCN)NR"R'", —OR, aryl, heteroaryl, arylalkyl, heteroarylalkyl, heterocyclyl, and heterocyclylalkyl; or R$^4$ and R$^5$ independently represent hydrogen or C$_1$-C$_6$ alkyl; or R$^4$ and R$^5$ together with the atom to which they are attached form a 4 to 10 membered carbocyclic, heteroaryl or heterocyclic ring, each of which is optionally substituted with one to three groups independently selected from halogen, cyano, nitro, trifluoromethyl, difluoromethoxy, trifluoromethoxy, azido, —NR SO$_2$R, —SO$_2$NR'R", —C(O)R"", —C(O)OR', —OC(O)R, —NR'C(O)OR"", —NR'C(O)R",—C(O)NR'R, —SO$_2$R"", —NR'R", —NR'C(O)NR"R'", —NR'C(NCN)NR"R'"$_5$—OR, aryl, heteroaryl, arylalkyl, heteroarylalkyl, heterocyclyl, and heterocyclylalkyl;

R$^6$ is selected from trifluoromethyl, and

C$_1$-C$_6$ alkyl, C$_3$-C$_{10}$ cycloalkyl, aryl, arylalkyl, heteroaryl, heteroarylalkyl, heterocyclyl, heterocyclylalkyl, where each alkyl, cycloalkyl, aryl, heteroaryl and heterocyclyl portion is optionally substituted with one to five groups independently selected from oxo, halogen, cyano, nitro, trifluoromethyl, difluoromethoxy, trifluoromethoxy, azido, —NR SO$_2$R, —SO$_2$NR'R", —C(O)R, —C(O)OR, —OC(O)R, —NR'C(O)OR"", —NR'C(O)R", —C(O)NRR", —SO$_2$R"", —NR'R, —NR'C(O)NR"R", —NR'C(NCN)NR"R'", —OR, aryl, heteroaryl, arylalkyl, heteroarylalkyl, heterocyclyl, and heterocyclylalkyl;

R$^7$ is selected from hydrogen, and

C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, heterocyclylalkyl, where each alkyl, alkenyl, alkynyl, cycloalkyl, aryl, heteroaryl and heterocyclyl portion is optionally substituted with one to five groups independently selected from oxo, halogen, cyano, nitro, trifluoromethyl, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —SO$_2$R$^6$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl;

W is selected from heteroaryl, heterocyclyl, —C(O)OR$^3$, —C(O)NR$^3$R$^4$, —C(O)NR$^4$OR$^3$, —C(O)R$^4$OR$^3$, —C(O)(C$_3$-C$_{10}$ cycloalkyl), —C(O)(C$_1$-C$_{10}$ alkyl), —C(O)(aryl), —C(O)(heteroaryl) and —C(O)(heterocyclyl), each of which is optionally substituted with 1-5 groups independently selected from —NR$^3$R$^4$, —OR$^3$, —R$^2$, and C$_1$-C$_{10}$ alkyl, C$_2$-C$_{10}$ alkenyl, and C$_2$-C$_{10}$ alkynyl, each of which is optionally substituted with 1 or 2 groups independently selected from —NR$^3$R$^4$ and —OR$^3$;

R$^8$ is selected from hydrogen, —SCF$_3$, —Cl, —Br, —F, cyano, nitro, trifluoromethyl, difluoromethoxy, trifluoromethoxy, azido, —OR$^3$, —C(O)R$^3$, —C(O)OR$^3$, —NR$^4$C(O)OR$^6$, —OC(O)R$^3$, —NR$^4$SO$_2$R$^6$, —SO$_2$NR$^3$R$^4$, —NR$^4$C(O)R$^3$, —C(O)NR$^3$R$^4$, —NR$^5$C(O)NR$^3$R$^4$, —NR$^3$R$^4$, and C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, —S(O)$_j$(C$_1$-C$_6$ alkyl), —S(O)$_j$(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl and —NR$^4$(CR$^4$R$^5$)$_m$-heterocyclyl, where each alkyl, alkenyl, alkynyl, cycloalkyl, aryl, heteroaryl and heterocyclyl portion is optionally substituted with one to five groups independently selected from oxo, halogen, cyano, nitro, trifluoromethyl, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl;

m is 0, 1, 2, 3, 4 or 5;

and j is 1 or 2.

In one embodiment, R$^7$ is C$_1$-C$_{10}$ alkyl, C$_3$-C$_7$ cycloalkyl or C$_3$-C$_7$ cycloalkylalkyl, each of which can be optionally substituted with 1-3 groups independently selected from oxo, halogen, cyano, nitro, trifluoromethyl, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —SO$_2$R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl.

In one embodiment, R$^1$ is halogen; R$^2$ is hydrogen; R$^3$ is C$_1$-C$_{10}$ alkyl substituted with OR' and R' is hydrogen; R$^4$ is hydrogen; $R^7$ is $C_1$-$C_{10}$ alkyl; $R^8$ is bromo; $R^9$ is halogen; $R^{10}$ is hydrogen; and W is —C(O)NR$^4$OR$^3$.

In one embodiment, MEK162 has the following structure:

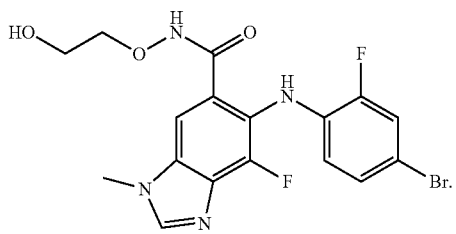 [SMILES: Cn1cnc2c(F)c(Nc3ccc(Br)cc3F)c(C(=O)NOCCO)cc21]

In one embodiment, MEK162 is 5-((4-bromo-2-fluorophenyl)amino)-4-fluoro-N-(2-hydroxyethoxy)-1-methyl-1H-benzo[d]imidazole-6-carboxamide or a pharmaceutically acceptable salt thereof.

In one embodiment, the PD-1 inhibitor, e.g., the anti-PD-1 antibody (e.g., Nivolumab or Pembrolizumab); or the PD-L1 inhibitor, e.g., the anti-PD-L1 antibody (e.g., MSB0010718C), (alone or in combination with other immunomodulators) is used in combination with a BCR-ABL inhibitor to treat a cancer, e.g., a cancer described herein (e.g., a cancer disclosed in Table 1). In one embodiment, the BCR-ABL inhibitor is disclosed in Table 1, e.g., AMN-107, or in a publication recited in Table 1, e.g., in WO 2004/005281 (e.g., in Example 92 or Formula (I) in claim 1) or U.S. Pat. No. 7,169,791 (e.g., in claim 8). In one embodiment, AMN-107 has the structure (compound or generic structure) provided in Table 1, or as disclosed in the publication recited in Table 1, e.g., in WO 2004/005281 (e.g., in Example 92 or Formula (I) in claim 1) or U.S. Pat. No. 7,169,791 (e.g., in claim 8). In one embodiment, one of Nivolumab, Pembrolizumab or MSB0010718C is used in combination with AMN-107 to treat a cancer or disorder described in Table 1, e.g., a solid tumor, e.g., a neurologic cancer, a melanoma, a digestive/gastrointestinal cancer, a colorectal cancer, a head and neck cancer; or a hematological malignancy, e.g., chronic myelogenous leukemia (CML), a lymphocytic leukemia, a myeloid leukemia; Parkinson's disease; or pulmonary hypertension.

In one embodiment, the BCR-ABL inhibitor has the following structure:

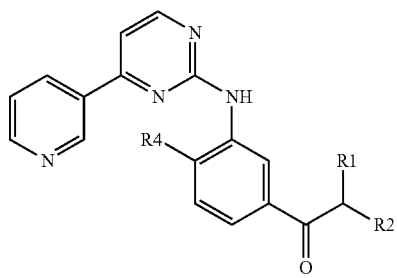

wherein $R_1$ represents hydrogen, lower alkyl, lower alkoxy-lower alkyl, acyloxy-lower alkyl, carboxy-lower alkyl, lower alkoxycarbonyl-lower alkyl, or phenyl-lower alkyl;

$R_2$ represents hydrogen, lower alkyl, optionally substituted by one or more identical or different radicals $R_3$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted; and $R_3$ represents hydroxy, lower alkoxy, acyloxy, carboxy, lower alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted; or wherein $R_1$ and $R_2$ together represent alkylene with four, five or six carbon atoms optionally mono- or disubstituted by lower alkyl, cycloalkyl, heterocyclyl, phenyl, hydroxy, lower alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, carboxy, phenyl, substituted phenyl, pyridinyl, pyrimidinyl, or pyrazinyl;

$R_4$ represents hydrogen, lower alkyl, or halogen;

and a N-oxide or a pharmaceutically acceptable salt of such a compound.

In one embodiment, $R_1$ is hydrogen, $R_2$ is phenyl substituted with $CF_3$ and

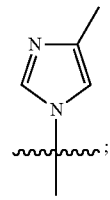

and R4 is $CH_3$.

In one embodiment, AMN-107 has the following structure:

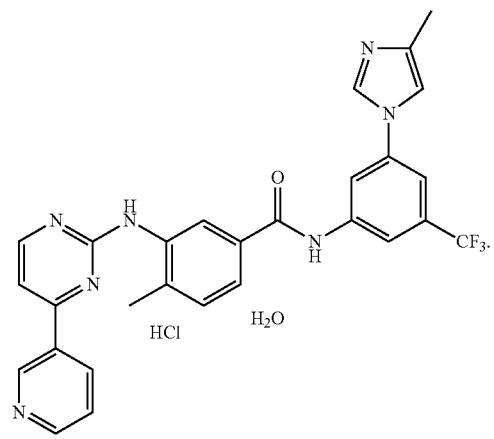

In one embodiment, AMN-107 is 4-methyl-3-[[4-(3-pyridinyl)-2-pyrimidinyl]amino]-N-[5-(4-methyl-1H- imidazol1yl)-3-(trifluoromethyl)phenyl]benzamide or an N-oxide or pharmaceutically acceptable salt thereof.

LDK378 and Nivolumab

LDK378 (ceritinib) is an Anaplastic Lymphoma Kinase (ALK) inhibitor. Its chemical formula is 5-chloro-$N^2$-(2-isopropoxy-5-methyl-4-(piperidin-4-yl)phenyl)-$N^4$-[2-(propane-2-sulfonyl)-phenyl]-pyrimidine-2,4-diamine. A process for preparing LDK378 was disclosed in WO2008/073687. The compound has been approved by the US FDA as ZYKADIA® for the treatment of patients with Anaplastic Lymphoma Kinase (ALK)-positive metastatic non-small cell lung cancer (NSCLC), who have progressed on or are intolerant to crizotinib. The currently approved daily dose for use of LDK378 (alone) in NSCLC is 750 mg orally on an empty stomach (i.e., is not to be administered within 2 hours of a meal).

In a clinical study, LDK378 demonstrated a high rate of rapid and durable responses in 246 ALK-positive NSCLC patients treated in the 750 mg dose group (RD). In these patients the overall response rate (ORR) was 58.5%. Among the 144 ALK-positive NSCLC patients with a confirmed complete response (CR) or partial response (PR), 86.1% of those patients achieved a response within 12 weeks, with a median time to response of 6.1 weeks. The estimated median duration of response (DOR) based on investigator assessment was long at 9.69 months. The median progression-free survival (PFS) was 8.21 months with 53.3% of the patients censored. Importantly, ceritinib showed this level of high anti-cancer activity regardless of prior ALK inhibitor status (i.e., whether or not the patient received previous treatment with an ALK inhibitor). A high ORR of 54.6% and 66.3% was observed in patients treated with a prior ALK inhibitor and in ALK inhibitor-naïve patients, respectively.

However, metastatic ALK-positive NSCLC remains a difficult disease to treat. Harnessing the immune system to treat patients with NSCLC represents a novel and new treatment approach, and nivolumab can be safely combined with LDK378. Combination therapy involving targeted agent LDK378 and immunotherapy (Nivolumab) can improve progression-free survival and ultimately overall survival in NSCLC patients.

In one aspect, the present disclosure relates to a pharmaceutical combination, especially a pharmaceutical combination product, comprising the combination of an immunomodulator and an agent disclosed herein.

In accordance with the present disclosure the compounds in the pharmaceutical combination, components (i) LDK378, or a pharmaceutically acceptable salt thereof, and (ii) Nivolumab, or a pharmaceutically acceptable salt thereof can be administered separately or together.

The pharmaceutical combination, according to the present disclosure, for use as a medicine, wherein LDK378 and the Nivolumab can be administered independently at the same time or separately within time intervals, wherein time intervals allow that the combination partners are jointly active.

The term "pharmaceutical combination" as used herein refers to a product obtained from mixing or combining in a non-fixed combination the active ingredients, e.g. (i) LDK378, or a pharmaceutically acceptable salt thereof, and (ii) Nivolumab or a pharmaceutically acceptable salt thereof separately or together.

The term "non-fixed combination" means that the active ingredients, e.g. LDK378 and Nivolumab, are both administered separately or together, independently at the same time or separately within time intervals, wherein such administration provides therapeutically effective levels of the active ingredient in the subject in need. The latter also applies to cocktail therapy, e.g. the administration of three or more active ingredients. This term defines especially a "kit of parts" in the sense that the combination partners (i) LDK378 and (ii) Nivolumab (and if present further one or more co-agents) as defined herein can be dosed independently of each other.

The term "jointly therapeutically effective" means that the compounds show synergistic interaction when administered separately or together, independently at the same time or separately within time intervals, to treat a subject in need, such as a warm-blooded animal in particular a human.

It was shown that the combination of the present disclosure possesses beneficial therapeutic properties, e.g. synergistic interaction, strong in-vivo and in-vitro antitumor response, which can be used as a medicine. Its characteristics render it particularly useful for the treatment of cancer.

Suitable cancers that can be treated with the combination of the present disclosure include but are not limited to anaplastic large cell lymphoma (ALCL), neuroblastoma, lung cancer, non-small cell lung cancer (NSCLC). In a preferred embodiment, the cancer is NSCLC.

The combination according to the present disclosure can besides or in addition be administered especially for cancer therapy in combination with chemotherapy, radiotherapy, immunotherapy, surgical intervention, or in combination of these. Long-term therapy is equally possible as is adjuvant therapy in the context of other treatment strategies, as described above. Other possible treatments are therapy to maintain the patient's status after tumor regression, or even chemo-preventive therapy, for example in patients at risk.

The combination of LDK378 and Nivolumab can be used to manufacture a medicament for an ALK mediated disease as described above. Likewise the combination can be used in a method for the treatment of an ALK, as described above, said method comprising administering an effective amount of a combination of (i) LDK378, or a pharmaceutically acceptable salt thereof, and (ii) Nivolumab or a pharmaceutically acceptable salt thereof separately or together, to a subject in need thereof, according to the present disclosure.

For example, the term "jointly (therapeutically) active" may mean that the compounds may be given separately or sequentially (in a chronically staggered manner, especially a sequence specific manner) in such time intervals that they preferably, in the warm-blooded animal, especially human, to be treated, and still show a (preferably synergistic) interaction (joint therapeutic effect). A joint therapeutic effect can, inter alia, be determined by following the blood levels, showing that both compounds are present in the blood of the human to be treated at least during certain time intervals, but this is not to exclude the case where the compounds are jointly active although they are not present in blood simultaneously.

The present disclosure also describes the method for the treatment of an ALK mediated disease, wherein the combination of (i) LDK378, or a pharmaceutically acceptable salt thereof, and (ii) Nivolumab or a pharmaceutically acceptable salt thereof separately or together.

The present disclosure relates to a pharmaceutical composition comprising effective amounts of (i) LDK378, or a pharmaceutically acceptable salt thereof, and (ii) Nivolumab, or a pharmaceutically acceptable salt thereof.

The present disclosure also describes the pharmaceutical combination according to the present disclosure in the form of a "kit of parts" for the combined administration. The combination can refer to either a fixed combination in one dosage unit form, or a kit of parts for the combined administration where (i) LDK378, or a pharmaceutically acceptable salt thereof, and (ii) Nivolumab, or a pharmaceutically acceptable salt thereof, may be administered independently at the same time or separately within time intervals, especially where these time intervals allow that the combination partners show a cooperative (=joint) effect. The independent formulations or the parts of the formulation, product, or composition, can then, e.g. be administered simultaneously or chronologically staggered, that is at different time points and with equal or different time intervals for any part of the kit of parts. In the combination therapies of the disclosure, the compounds useful according to the disclosure may be manufactured and/or formulated by the same or different manufacturers. Moreover, the combination partners may be brought together into a combination therapy: (i) prior to release of the combination product to physicians (e.g. in the case of a kit comprising LDK378 and the Nivolumab); (ii) by the physician themselves (or under the guidance of a physician) shortly before administration; (iii) in the patient themselves, e.g. during sequential administration of the compound of the disclosure and the other therapeutic agent. In one embodiment the effect of the combination is synergistic.

The therapeutically effective dosage of the combination of the disclosure, or pharmaceutical composition, is dependent on the species of the subject, the body weight, age and individual condition, the disorder or disease or the severity thereof being treated, and can be determined by standard clinical techniques. In addition, in vitro or in vivo assays can optionally be employed to help identify optimal dosage ranges. The precise dose to be employed can also depend on the route of administration, and the seriousness of the condition being treated and can be decided according to the judgment of the practitioner and each subject's circumstances in view of, e.g., published clinical studies. In general, satisfactory results are indicated to be obtained systemically at daily dosages of from 150 mg to 750 mg of LDK378 orally. In most cases, the daily dose for LDK378 can be between 300 mg and 750 mg.

When administered in combination with Nivolumab, LDK378 can be administered at 450 mg with 3 mg/kg nivolumab, 600 mg LDK378 with 3 mg/kg Nivolumab, or 300 mg LDK378 with 3 mg/kg nivolumab. The most preferred dose of both compounds for combination therapy is 600 mg of LDK378 with 3 mg/kg Nivolumab. Particularly 600 mg LDK378 with 3 mg/kg Nivolumab is the most preferred dosing regimen for treating ALK-positive (e.g. EML4-ALK) NSCLC. Nivolumab can be administered as the fixed dose infusion every two weeks. Ceritinib is to be taken together with a low fat meal. It is acceptable if ceritinib is administered within 30 minutes after consuming a low fat meal. A patient should refrain from eating for at least an hour after intake of ceritinib and the low fat meal. It is expected that administration of ceritinib with daily meal intake can reduce the incidence and/or severity of gastrointestinal events. It is estimated that the steady state exposure of ceritinib at 450 mg and 600 mg with daily low-fat meal intake is within 20% relative to that of ceritinib at the recommended phase II dose of 750 mg administered fasted, as predicted by model-based clinical trial simulation, using a population pharmacokinetic model established for ALK-positive cancer patients in one clinical study in conjunction with absorption parameters estimated from another clinical study.

The "low-fat meal" denotes herein a meal that contains approximately 1.5 to 15 grams of fat and approximately 100 to 500 total calories.

Without being bound by theory, ceritinib does not have a mechanism of action that would be expected to antagonize an immune response. Furthermore, immune-related adverse events have not been frequently reported in ceritinib trials. Potential overlapping toxicities between ceritinib and Nivolumab include diarrhea, nausea, AST and ALT elevations, pneumonitis, and hyperglycemia. The mechanisms of these toxicities are not expected to be similar, given the mechanisms of action of the two compounds and thus the safety profile can be managed.

Another aspect of the disclosure is LDK378 for use as a medicine, wherein LDK378, or a pharmaceutically acceptable salt thereof, is to be administered in combination with Nivolumab, or a pharmaceutically acceptable salt thereof, for the treatment of an ALK mediated disease, e.g. cancer.

The term "ALK mediated disease" refers to a disease in which activity of the kinase leads to abnormal activity of the regulatory pathways including overexpression, mutation or relative lack of activity of other regulatory pathways in the cell that result in excessive cell proliferation, e.g. cancer. In one embodiment, the ALK mediated disease can be non-small cell lung cancer (NSCLC) that is driven by the echinoderm microtubule-associated protein-like 4 (EML4)-anaplastic lymphoma kinase (ALK) translocation. ALK is a receptor tyrosine kinase of the insulin receptor superfamily that plays a role in neural development and function. ALK is translocated, mutated, and/or amplified in several tumor types, and thus ALK mediated disease include, in addition to NSCLC, neuroblastoma, and anaplastic large cell lymphoma (ALCL). Alterations in ALK play a key role in the pathogenesis of these tumors. Other fusion partners of ALK besides EML4 that can be relevant in an ALK mediated disease are KIFSB, TFG, KLC1 and PTPN3, but are expected to be less common than EML4. Preclinical experiments have shown that the various ALK fusion partners mediate ligand-independent dimerization/oligomerization of ALK resulting in constitutive kinase activity and potent oncogenic activity both in vitro and in vivo and thus once translocated, ALK is driving, i.e., mediating the disease.

Items that describe further preferred embodiments alone or in combination, are listed below:

1. A pharmaceutical combination comprising (i) LDK378, or a pharmaceutically acceptable salt thereof, and (ii) nivolumab, or a pharmaceutically acceptable salt thereof.

2. The pharmaceutical combination according to item 1 comprising components (i) and (ii) separately or together.

3. The pharmaceutical combination according to items 1 or 2 for use as a medicine, wherein LDK378 and the Nivolumab are administered independently at the same time or separately within time intervals.

4. The pharmaceutical combination according to item 3, wherein time intervals allow that the combination partners are jointly active.

5. The pharmaceutical combination according to any of items 1 to 4 comprising a quantity which is jointly therapeutically effective for the treatment of an ALK mediated disease.

6. The pharmaceutical combination according to item 5, wherein the ALK mediated disease is cancer.

7. The pharmaceutical combination according to item 6, wherein the ALK mediated disease is NSCLC or lymphoma, 8. The pharmaceutical combination according to item 6, wherein the ALK mediated disease is NSCLC.

9. The pharmaceutical combination according to any of the items 1 to 8, for use as a medicine.

10. The pharmaceutical combination according to any of the items 1 to 8, for use in the treatment of cancer.

11. The pharmaceutical combination according to item 10, wherein the cancer is a non-small cell lung cancer.

12. Use of LDK378 in combination with Nivolumab for the manufacture of a medicament for an ALK mediated disease.

13. The use of LDK378 in combination with Nivolumab for the manufacture of a medicament, according to item 12, wherein the disease is cancer.

14. The use of LDK378 in combination with Nivolumab for the manufacture of a medicament according to item 13, wherein the cancer is non-small cell lung cancer.

15. A pharmaceutical composition comprising LDK378 or a pharmaceutically acceptable salt thereof and Nivolumab or a pharmaceutically acceptable salt thereof for simultaneous or separate administration for the treatment of cancer.

16. The pharmaceutical composition according to item 15, wherein the cancer is a non-small cell lung cancer.

17. The pharmaceutical composition according to items 22 or 23, wherein the composition comprises effective amounts of LDK378 and nivolumab.

18. The pharmaceutical composition according to any one of items 15 to 18, wherein the composition further comprises a pharmaceutical acceptable carrier.

19. LDK378 for use as a medicine, wherein LDK378, or a pharmaceutically acceptable salt thereof, is to be administered in combination with Nivolumab, or a pharmaceutically acceptable salt thereof.

20. LDK378 for use as a medicine according to item 19, for the treatment of cancer.

21. LDK378 for use as a medicine according to item 20, wherein the cancer is a non-small cell lung cancer.

22. The pharmaceutical combination according to any one of items 1 to 11 in the form of a kit of parts for the combined administration.

23. The pharmaceutical combination according to item 22, wherein LDK378, or a pharmaceutically acceptable salt thereof, and the Nivolumab, or a pharmaceutically acceptable salt thereof, are administered jointly or independently at the same time or separately within time intervals.

24. A method for treating cancer in a subject in need thereof comprising administering to said subject a therapeutically effective amount of i) LDK378, or a pharmaceutically acceptable salt thereof, and (ii) nivolumab, or a pharmaceutically acceptable salt thereof.

25. The pharmaceutical combination according to any one of items 3 to 11, 22 or 23, use according to any one of items 12 to 14, a method for the treating cancer according to item 24, the pharmaceutical composition according to any one of items 15 to 18, or LDK378 for use as a medicine according to any one of items 19 to 21, wherein LDK378 and Nivolumab are administered to an ALK-naïve patient.

26. The pharmaceutical combination according to any one of items 3 to 11, 22 or 23, use according to any one of items 12 to 14, a method for the treating cancer according to item 24, the pharmaceutical composition according to any one of items 15 to 18, or LDK378 for use as a medicine according to any one of items 19 to 21, wherein LDK378 and Nivolumab are administered to a patient that has been pretreated with an ALK inhibitor.

27. The pharmaceutical combination according to any one of items 3 to 11, 22 or 23, use according to any one of items 12 to 14, a method for the treating cancer according to item 24, the pharmaceutical composition according to any one of items 15 to 18, or LDK378 for use as a medicine according to any one of items 19 to 21, wherein LDK378 and Nivolumab are administered to a patient that has been pretreated with LDK378.

28. The pharmaceutical combination according to any one of items 3 to 11, 22, 23 or 25 to 27, use according to any one of items 12 to 14 or 25 to 27, a method for the treating cancer according to any one of items 24 to 27, the pharmaceutical composition according to any one of items 15 to 18 or 25 to 27, or LDK378 for use as a medicine according to any one of items 19 to 21 or 25 to 27, wherein the cancer comprises ALK translocation or rearrangement.

29. The pharmaceutical combination according to any one of items 3 to 11, 22, 23 or 25 to 27, use according to any one of items 12 to 14 or 25 to 27, a method for the treating cancer according to any one of items 24 to 27, the pharmaceutical composition according to any one of items 15 to 18 or 25 to 27, or LDK378 for use as a medicine according to any one of items 19 to 21 or 25 to 27, wherein the cancer comprises EML4-ALK fusion.

30. The pharmaceutical combination according to any one of items 3 to 11, 22, 23 or 25 to 27, use according to any one of items 12 to 14 or 25 to 27, a method for the treating cancer according to any one of items 24 to 27, the pharmaceutical composition according to any one of items 15 to 18 or 25 to 27, or LDK378 for use as a medicine according to any one of items 19 to 21 or 25 to 27, wherein the cancer comprises ALK-ROS1 fusion.

31. The pharmaceutical combination according to any one of items 1 to 11, 22, 23 or 25 to 30, use according to any one of items 12 to 14 or 25 to 30, a method for the treating cancer according to any one of items 24 to 30, the pharmaceutical composition according to any one of items 15 to 18 or 25 to 30, or LDK378 for use as a medicine according to any one of items 19 to 21 or 25 to 30, wherein ceritinib dose is 450 mg and nivolumab dose is 3 mg/kg.

32. The pharmaceutical combination according to any one of items 1 to 11, 22, 23 or 25 to 30, use according to any one of items 12 to 14 or 25 to 30, a method for the treating cancer according to any one of items 24 to 30, the pharmaceutical composition according to any one of items 15 to 18 or 25 to 30, or LDK378 for use as a medicine according to any one of items 19 to 21 or 25 to 30, wherein ceritinib dose is 600 mg and nivolumab dose is 3 mg/kg.

33. The pharmaceutical combination according to any one of items 1 to 11, 22, 23 or 25 to 32, use according to any one of items 12 to 14 or 25 to 32, a method for the treating cancer according to any one of items 24 to 32, the pharmaceutical composition according to any one of items 15 to 18 or 25 to 32, or LDK378 for use as a medicine according to any one of items 19 to 21 or 25 to 32, wherein ceritinib is administered with a low fat meal.

EGF816 and Nivolumab

Lung cancer is the most common cancer worldwide and the sub-type non-small cell lung cancer (NSCLC) accounts for approximately 85% of lung cancer cases. In Western nations, 10-15% NSCLC patients develop epidermal growth factor receptor (EGFR) mutations in their tumors and the mutation rate is even higher in Asian nations where rates have been reported to be as high as 40%. L858R and exon 19 deletion (Ex19del) activating EGFR oncogenic mutations predominate in NSCLC patients and account for 38% and 46% of EGFR NSCLC mutations respectively. EGFR Exon 20 insertion mutations (Ex20ins) are also relatively frequent, accounting for 9% of all EGFR mutations in NSCLC patients.

Patients with EGFR mutations are initially treated with reversible EGFR Tyrosine Kinase Inhibitors (TKIs), such as erlotinib and gefitinib, as a first line therapy. However, approximately half of these patients will develop acquired resistance to TKI inhibitors via a secondary "gatekeeper" T790M mutation within 10 to 14 months of treatment.

Second-generation EGFR TKIs (such as afatinib and dacomitinib) have been developed to try to overcome the mechanism of acquired resistance. These agents are irreversible inhibitors that covalently bind to cysteine 797 at the EGFR ATP binding site with potent activity on both activating (L858R, ex19del) and acquired (T790M) EGFR mutations in pre-clinical models. However, their clinical efficacy has proven to be limited, possibly in part due to severe adverse effects caused by concomitant inhibition of wild-type (WT) EGFR.

To overcome the previous issues with the earlier generations of inhibitors, third-generation EGFR TKIs have been developed which are WT EGFR sparing but also have relative equal potency for activating EGFR (L858R and ex19del) and acquired (T790M) mutations. Third generation EFGR TKIs, such as AZD9291 (mereletinib) and CO-1686 (rociletinib), are beginning to enter clinical development and are showing significant initial promise (e.g., see "AZD9291 in EGFR Inhibitor-Resistant Non-Small-Cell Lung Cancer", Hanne et al, N Engl J Med, 2015; 372; 1689-99 and "Rociletinib in EGFR-Mutated Non-Small-Cell Lung Cancer", Sequist et al, J Med, 2015; 372; 1700-9). See also "ASP8273, a novel mutant-selective irreversible EGFR inhibitor, inhibits growth of non-small cell lung cancer (NSCLC) cells with EGFR activating and T790M resistance mutations", Sakagami et al, AACR; Cancer Res 2014; 74; 1728.

Treatment with EGFR inhibitors has however, not been shown to definitively translate into prolonged overall survival and it is unlikely that even third generation inhibitors alone will suffice. Hence there is still a need for additional treatment options for patients with cancer and, in particular, solid tumors. There is also a need for additional treatment options for patients with lung cancer, such as NSCLC. One such method of boosting effectiveness of EGFR inhibitors in vivo is by dually targeting other proteins implicated in disease progression of NSCLC patients The PD-1 pathway was described as contributing to immune escape in mouse models of EGFR driven lung tumors (Akbay et al, Cancer Discov. 2013). However, a non-significant trend toward increased levels of PD-L1 in EGFR-mutant patient-derived NSCLC cell lines was also reported. Thus, it is still unclear whether targeting PD-1/PD-L1 interaction as well as mutated-EGFR in cancer patients, especially NSCLC patients, would be safe or clinically important.

The present invention relates to the surprising finding that a combination treatment comprising the selective mutated-EGFR inhibitor EGF816 and the anti-PD-1 antagonist Nivolumab are safe and tolerated when administered as a combination therapy to treat patients with NSCLC that have mutated-EGFR.

EGF816 is an EGFR inhibitor. EGF816 is also known as (R,E)-N-(7-chloro-1-(1-(4-(dimethylamino)but-2-enoyl) azepan-3-yl)-1Hbenzo[d]imidazol-2-yl)-2-methylisonicotinamide (EGF816), or a pharmaceutically acceptable salt thereof. A particularly useful salt is the mesylate salt thereof. WO2013/184757, the contents of which are hereby incorporated by reference, describes EGF816, its method of preparation and pharmaceutical compositions comprising EGF816.

EGF816 has the following structure:

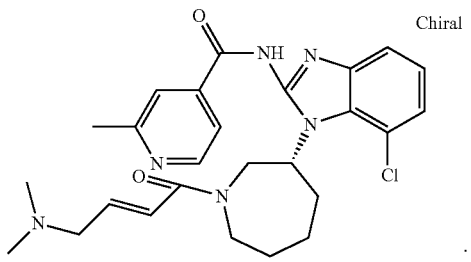 [SMILES: Cc1cc(C(=O)Nc2nc3cccc(Cl)c3n2[C@@H]2CCCCN(C(=O)/C=C/CN(C)C)C2)ccn1]

EGF816 is a targeted covalent irreversible EGFR inhibitor that selectively inhibits activating and acquired resistance mutants (L858R, ex19del and T790M), while sparing WT EGFR. (see Jia et al, Cancer Res Oct. 1, 2014 74; 1734). EGF816 has shown significant efficacy in EGFR mutant (L858R, ex19del and T790M) cancer models (in vitro and in vivo) with no indication of WT EGFR inhibition at clinically relevant efficacious concentrations.

In one aspect, the disclosure relates to a pharmaceutical combination, comprising (a) a compound of formula I:

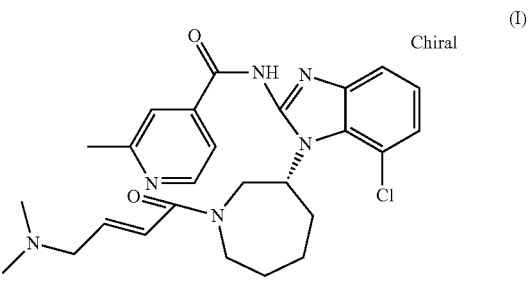 [SMILES: Cc1cc(C(=O)Nc2nc3cccc(Cl)c3n2[C@@H]2CCCCN(C(=O)/C=C/CN(C)C)C2)ccn1]

(R,E)-N-(7-chloro-1-(1-(4-(dimethylamino)but-2-enoyl) azepan-3-yl)-1H-benzo[d]imidazol-2-yl)-2-methylisonicotinamide (EGF816), or a pharmaceutically acceptable salt thereof, and (b) Nivolumab.

In one aspect, the disclosure provides a combination for use in a method of treating a cancer, especially an EGFR mutated cancer wherein:
 (i) the combined administration has clinical efficacy, e.g., as measured by determining time to disease progression;
 (ii) the combined administration shows sustained clinical benefit; or
 (iii) increases progression free survival.
 or a combination of any of the above benefits.

The progression of cancer may be monitored by methods known to those in the art. For example, the progression may be monitored by way of visual inspection of the cancer, such as, by means of X-ray, CT scan or MRI or by tumor biomarker detection. For example, an increased growth of the cancer indicates progression of the cancer. Progression of cancer such as NSCLC or tumors may be indicated by detection of new tumors or detection of metastasis or cessation of tumor shrinkage. Tumor evaluations can be made based on RECIST criteria (Therasse et al 2000), New Guidelines to Evaluate the Response to Treatment in Solid Tumors, Journal of National Cancer Institute, Vol. 92; 205-16 and revised RECIST guidelines (version 1.1) (Eisenhauer et al 2009) European Journal of Cancer; 45:228-247.

Tumor progression may be determined by comparison of tumor status between time points after treatment has commenced or by comparison of tumor status between a time point after treatment has commenced to a time point prior to initiation of the relevant treatment.

In some embodiments, the lymphoma (e.g., an anaplastic large-cell lymphoma or non-Hodgkin lymphoma) has, or is identified as having, an ALK translocation, e.g., an EML4-ALK fusion.

In some embodiments, the combination is for use in the treatment of NSCLC.

In some embodiments, the combination is for use in the treatment of NSCLC, wherein the NSCLC is characterized by one or more of: aberrant activation, or amplification, or mutations of epidermal growth factor receptor.

In some embodiments, the combination is for use in the treatment of NSCLC, wherein the NSCLC is characterized by harboring an EGFR exon 20 insertion, an EGFR exon 19 deletion, EGFR L858R mutation, EGFR T790M, or any combination thereof.

In some embodiments, the combination is for use in the treatment of NSCLC, wherein the NSCLC is characterized by harboring L858R and T790M mutations of EGFR.

In some embodiments, the combination is for use in the treatment of NSCLC, wherein the NSCLC is characterized by harboring an EGFR exon 20 insertion and T790M mutations of EGFR.

In some embodiments, the combination is for use in the treatment of NSCLC, wherein the NSCLC is characterized by harboring an EGFR exon 19 deletion and T790M mutations of EGFR.

In some embodiments, the combination is for use in the treatment of NSCLC, wherein the NSCLC is characterized by harboring EGFR mutation selected from the group consisting of an exon 20 insertion, an exon 19 deletion, L858R mutation, T790M mutation, and any combination thereof.

In another embodiment, the cancer is an inflammatory myofibroblastic tumor (IMT). In certain embodiments, the inflammatory myofibroblastic tumor has, or is identified as having, an ALK rearrangement or translocation, e.g., an ALK fusion, e.g., an EML4-ALK fusion.

In yet another embodiment, the cancer is a neuroblastoma.

In certain embodiments, the neuroblastoma has, or is identified as having, an ALK rearrangement or translocation, e.g., an ALK fusion, e.g., an EML4-ALK fusion. Methods and compositions disclosed herein are useful for treating metastatic lesions associated with the aforementioned cancers.

EGF816 may be administered at a dose of 75, 100, 150, 225, 150, 200, 225, 300 or 350 mg. These doses may be administered once daily. E.g. EGF816 may be administered at a dose of 100 or 150 mg once daily.

Nivolumab may be administered in an amount from about 1 mg/kg to 5 mg/kg, e.g., 3 mg/kg, and may be administered over a period of 60 minutes, ca. once a week to once every 2, 3 or 4 weeks.

In one embodiment, the combination of EGF816 and Nivolumab is administered as a combination therapy wherein the administration protocol is:
(i) 150 mg (R,E)-N-(7-chloro-1-(1-(4-(dimethylamino) but-2-enoyl)azepan-3-yl)-1H-benzo[d]imidazol-2-yl)-2-methylisonicotinamide, or a pharmaceutically acceptable salt thereof orally administered daily; and
(ii) 3 mg/kg Nivolumab is administered intravenously over a period of 60 minutes at least one hour after administration of (i), every 2 weeks.

In some embodiments, the administration protocol is repeated for the duration of a 28 day cycle.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula (I) and one or more combination partners, are both administered to a patient simultaneously in the form of a single entity or dosage. The term "non-fixed combination" means that the active ingredients, e.g. a compound of the present invention and one or more combination partners, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

The present disclosure provides the following aspects, advantageous features and specific embodiments, respectively alone or in combination, as listed in the following Enumerated Embodiments.

Enumerated Embodiments

1. A pharmaceutical combination comprising:
(a) a compound of formula I

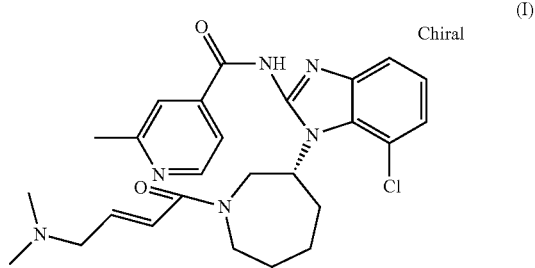 [SMILES: Cc1cc(C(=O)Nc2nc3cccc(Cl)c3n2[C@@H]2CCCCN(C(=O)/C=C/CN(C)C)C2)ccn1]

(I)

(R,E)-N-(7-chloro-1-(1-(4-(dimethylamino)but-2-enoyl) azepan-3-yl)-1H-benzo[d]imidazol-2-yl)-2-methylisonicotinamide, or a pharmaceutically acceptable salt thereof,
and (b) Nivolumab.

1. The pharmaceutical combination according to Enumerated Embodiment 1, wherein (R,E)-N-(7-chloro-1-(1-(4-(dimethylamino)but-2-enoyl)azepan-3-yl)-1H-benzo[d]imidazol-2-yl)-2-methylisonicotinamide is in mesylate form or hydrochloride salt form.

2. A pharmaceutical composition comprising a combination according to Enumerated Embodiment 1 or Enumerated Embodiment 2 and at least one pharmaceutically acceptable carrier.

3. A kit comprising the pharmaceutical combinations according to any one of Enumerated Embodiments 1 to 3 and information about using the constituents of the pharmaceutical combination simultaneously, separately or sequentially, and/or to instruct or administer the constituents of the pharmaceutical combinations according to any one of Enumerated Embodiments 1 to 3, simultaneously, separately or sequentially.

4. A method of treating or preventing cancer in a subject in need thereof, comprising sequential, simultaneous or separate administration of (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof and Nivolumab according to any one of Enumerated Embodiments 1 to 3 in a jointly therapeutically effective amount to treat or prevent said cancer.

5. The pharmaceutical combination according to any one of Enumerated Embodiments 1 to 3 in the form of a kit for combined administration comprising (a) one or more dosage units of (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof, and (b) one or more dosage units of Nivolumab.

6. The pharmaceutical combination according to any one of Enumerated Embodiments 1 to 3 or kit according to Enumerated Embodiment 4 or Enumerated Embodiment 6, for use in the treatment of cancer, wherein (R,E)-N-(7-chloro-1-(1-(4-(dimethylamino)but-2-enoyl)azepan-3-yl)-1H-benzo[d]imidazol-2-yl)-2-methylisonicotinamide and Nivolumab are administered simultaneously or sequentially or separately.

7. The pharmaceutical combination according any one of Enumerated Embodiments 1 to 3 or kit according to Enumerated Embodiment 4 or Enumerated Embodiment 6, for use according to Enumerated Embodiment 7, wherein the cancer is non-small cell lung cancer.

8. The pharmaceutical combination according to any one of Enumerated Embodiments 1 to 3 or kit according to Enumerated Embodiment 4 or Enumerated Embodiment 6, for use according to any one of Enumerated Embodiments 7 or Enumerated Embodiment 8, wherein the non-small cell lung cancer is characterized by aberrant activation, or amplification, or mutations of epidermal growth factor receptor (EGFR).

9. The pharmaceutical combination according to any one of Enumerated Embodiments 1 to 3 or kit according to Enumerated Embodiment 4 or Enumerated Embodiment 6, for use according to any one of Enumerated Embodiments 7 to 9, wherein the non-small cell lung cancer is characterized by harbouring an EGFR exon 20 insertion, an EGFR exon 19 deletion, EGFR L858R mutation, EGFR T790M, or any combination thereof.

10. The pharmaceutical combination according to any one of Enumerated Embodiments 1 to 3 or kit according to Enumerated Embodiment 4 or Enumerated Embodiment 6, for use according to any one of Enumerated Embodiments 7 to 9, wherein the non-small cell lung cancer is characterized by harbouring L858R and T790M mutations of EGFR.

11. The pharmaceutical combination according to any one of Enumerated Embodiments 1 to 3 or kit according to Enumerated Embodiment 4 or Enumerated Embodiment 6, for use according to any one of Enumerated Embodiments 7 to 9, wherein the non-small cell lung cancer is characterized by harbouring exon 20 insertion and T790M mutations of EGFR.

12. The pharmaceutical combination according to any one of Enumerated Embodiments 1 to 3 or kit according to Enumerated Embodiment 4 or Enumerated Embodiment 6, for use according to any one of Enumerated Embodiments 7 to 9, wherein the non-small cell lung cancer is characterized by harbouring exon 19 deletion and T790M mutations of EGFR.

13. The pharmaceutical combination according to any one of Enumerated Embodiments 1 to 3 or kit according to Enumerated Embodiment 4 or Enumerated Embodiment 6, for use according to any one of Enumerated Embodiments 7 to 9, wherein the non-small cell lung cancer is characterized by harbouring EGFR mutation selected from the group consisting of an exon 20 insertion, an exon 19 deletion, L858R mutation, T790M mutation, and any combination thereof.

14. A pharmaceutical combination according to any one of Enumerated Embodiments 1 to 3 or kit according to Enumerated Embodiment 4 or Enumerated Embodiment 6 for use according to any one of Enumerated Embodiments 7 to 14, wherein the combination is administered within a specified period and wherein the combination is administered for a duration of time.

15. A pharmaceutical combination according to any one of Enumerated Embodiments 1 to 3 or kit according to Enumerated Embodiment 4 or Enumerated Embodiment 6 for use according to any one of Enumerated Embodiments 7 to 14, wherein the combination is administered according to Enumerated Embodiment 15 and the amount of (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof is from about 50 to 500 mg, preferably of 75, 100, 150, 225, 150, 200, 225, 300 or 350 mg, more preferably 150 mg; every other day, daily, twice or three times a day.

16. A pharmaceutical combination according to any one of Enumerated Embodiments 1 to 3 or kit according to Enumerated Embodiment 4 or Enumerated Embodiment 6 for use according to any one of Enumerated Embodiments 7 to 14, wherein the combination is administered according to Enumerated Embodiment 15 and the amount of (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof is from about 50 to about 225 mg, preferably from about 100 to about 150 mg, more preferably 150 mg, administered daily.

17. A pharmaceutical combination according to any one of Enumerated Embodiments 1 to 3 or kit according to Enumerated Embodiment 4 or Enumerated Embodiment 6 for use according to any one of Enumerated Embodiments 7 to14, wherein the combination is administered according to Enumerated Embodiment 15 and the amount of Nivolumab is an amount from about 1 mg/kg to about 5 mg/kg, preferably 3 mg/kg and is administered parenterally over a period of 60 minutes, ca. once a week to once every 2, 3 or 4 weeks.

18. A pharmaceutical combination according to any one of Enumerated Embodiments 1 to 3 or kit according to Enumerated Embodiment 6 for use according to any one of Enumerated Embodiments 7 to 14, wherein the combination is administered according to Enumerated Embodiment 15 and (i) the amount of (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof is in an amount from about 50 to about 500 mg, preferably about 75, 100, 150, 225, 150, 200, 225, 300 or 350 mg, more preferably 150 mg, and is administered daily (ii) the amount of Nivolumab is an amount from about 1 mg/kg to about 5 mg/kg, preferably 3 mg/kg and is administered parenterally over a period of 60 minutes, no less than 12 days between each treatment and is administered every 2 weeks.

19. A pharmaceutical combination according to any one of Enumerated Embodiments 15 to 20 wherein Nivolumab is administered at least one hour after administration of (R,E)-N-(7-chloro-1-(1-(4-(dimethylamino)but-2-enoyl)azepan-3-yl)-1H-benzo[d]imidazol-2-yl)-2-methylisonicotinamide.

20. A pharmaceutical combination according to any one of Enumerated Embodiments 1 to 3 or kit according to Enumerated Embodiment 4 or Enumerated Embodiment 6 for use according to any one of Enumerated Embodiments 7 to 14, comprising (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof and Nivolumab, wherein the administration protocol comprises:

(i) 150 mg (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof orally administered daily; and (ii) 3 mg/kg Nivolumab is administered intravenously over a period of 60 minutes at least one hour after administration of (i), every 2 weeks.

21. An administration protocol according to Enumerated Embodiment 21, wherein the protocol is repeated for the duration of one or more 28-day cycle.

Pharmaceutical Compositions and Kits

In another aspect, the present invention provides compositions, e.g., pharmaceutically acceptable compositions, which include an antibody molecule described herein, formulated together with a pharmaceutically acceptable carrier. The term "pharmaceutically acceptable" refers to those compounds, materials, compositions, and/or dosage forms which are suitable for use in contact with the tissues of human beings and animals without excessive toxicity, irritation, allergic response, or other problem or complication, commensurate with a reasonable benefit/risk ratio.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g. by injection or infusion).

Pharmaceutically acceptable salts can be formed, for example, as acid addition salts, preferably with organic or inorganic acids. Suitable inorganic acids are, for example, halogen acids, such as hydrochloric acid. Suitable organic acids are, e.g., carboxylic acids or sulfonic acids, such as fumaric acid or methanesulfonic acid. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient. The salts of compounds described herein are preferably pharmaceutically acceptable salts; suitable counter-ions forming pharmaceutically acceptable salts are known in the field.

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical preferred compositions are in the form of injectable or infusible solutions. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

The pharmaceutical composition can be prepared with a pharmaceutically acceptable carrier, which can be for example any suitable pharmaceutical excipient. The carrier includes any and all binders, fillers, solvents, dispersion media, coatings, surfactants, antioxidants, preservatives (e.g., antibacterial agents, antifungal agents), isotonic agents, absorption delaying agents, salts, drug stabilizers, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329; Remington: The Science and Practice of Pharmacy, 21st Ed. Pharmaceutical Press 2011; and subsequent versions thereof). Except insofar as any conventional carrier is incompatible with the active ingredient, its use in the therapeutic or pharmaceutical compositions is contemplated. Other disclosure herein relating to the pharmaceutical composition can also be followed.

In accordance with the present disclosure, the combination partners can be administered independently at the same time or separately within time intervals in separate unit dosage forms. The two therapeutic partners may be prepared in a manner known per se and are suitable for enteral, such as oral or rectal, topical and parenteral administration to subject in need thereof, including warm-blooded animal, in particular a human being. Suitable pharmaceutical compositions contain, e.g., from about 0.1% to about 99.9% of active ingredient.

The pharmaceutical composition can be processed to prepare a final dosage form—a tablet or a capsule. This can be achieved by compressing the final blend of the combination, optionally together with one or more excipients. The compression can be achieved for example with a rotary tablet press. Tablet of different shapes can be prepared (round, ovaloid, or other suitable shape). The tablet can be coated or uncoated by known techniques to delay disintegration and absorption in the gastrointestinal tract and thereby provide a sustained action over a longer period. If not indicated otherwise, these are prepared in a manner known per se, e.g. by means of mixing, granulating, sugar-coating processes. Formulation for oral use can be presented as hard gelatin capsules wherein the active ingredient is mixed with an inert solid diluent, for example, calcium carbonate, calcium phosphate or cellulose-based excipient, or as soft gelatin capsules wherein the active ingredient is mixed with water or an oil medium, for example, olive oil, liquid paraffin or peanut oil.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody molecules can be administered by a variety of methods known in the art, although for many therapeutic applications, the preferred route/mode of administration is intravenous injection or infusion. For example, the antibody molecules can be administered by intravenous infusion at a rate of less than 10 mg/min; preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody molecule can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation. Therapeutic compositions can also be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The term "effective amount" refers to the amount of the subject compound that can engender a biological or medical response in a cell, tissue, organ, system, animal or human that is being sought by the researcher, veterinarian, medical doctor or other clinician. The effective dosage of each combination partner agents employed in the combinations disclosed herein may vary depending on the particular compound or pharmaceutical composition employed, the mode of administration, the condition being treated, the severity the condition being treated. A physician, clinician or veterinarian of ordinary skill can readily determine and prescribe the effective amount of the drug required to prevent, counter or arrest the progress of the condition. Optimal precision in achieving concentration of drug within the range that yields efficacy requires a regimen based on the kinetics of the combination's drugs availability to target sites. This involves a consideration of the distribution, equilibrium and elimination of a drug.

A "therapeutically effective amount" refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the modified antibody or antibody fragment is outweighed by the therapeutically beneficial effects. A "therapeutically effective dosage" preferably inhibits a measurable parameter, e.g., tumor growth rate by at least about 20%, more preferably by at least about 40%, even more preferably by at least about 60%, and still more preferably by at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Methods of administering the antibody molecules are known in the art and are described below. Suitable dosages of the molecules used will depend on the age and weight of the subject and the particular drug used. Dosages and therapeutic regimens of the anti-PD-1 antibody molecule can be determined by a skilled artisan. In certain embodiments, the anti-PD-1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks. In one embodiment, the anti-PD-1 antibody molecule is administered at a dose from about 10 to 20 mg/kg every other week.

An exemplary, non-limiting range for a therapeutically or prophylactically effective amount of an antibody molecule is 0.1-30 mg/kg, more preferably 1-25 mg/kg. Dosages and therapeutic regimens of the anti-PD-1 antibody molecule can be determined by a skilled artisan. In certain embodiments, the anti-PD-1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg, 15 to 25 mg/kg, or about 3 mg/kg. The dosing schedule can vary from e.g., once a week to once every 2, 3, or 4 weeks. In one embodiment, the anti-PD-1 antibody molecule is administered at a dose from about 10 to 20 mg/kg every other week. The antibody molecule can be administered by intravenous infusion at a rate of less than 10 mg/min, preferably less than or equal to 5 mg/min to reach a dose of about 1 to 100 mg/m$^2$, preferably about 5 to 50 mg/m$^2$, about 7 to 25 mg/m$^2$, and more preferably, about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The antibody molecules can be used by themselves or conjugated to a second agent, e.g., a cytotoxic drug, radioisotope, or a protein, e.g., a protein toxin or a viral protein. This method includes: administering the antibody molecule, alone or conjugated to a cytotoxic drug, to a subject requiring such treatment. The antibody molecules can be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g.; via a viral coat protein), or mixtures thereof.

Also within the scope of the invention is a kit that includes a combination therapy described herein. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

Uses of Combination Therapies

The combination therapies disclosed herein have in vitro and in vivo therapeutic and prophylactic utilities. For example, these molecules can be administered to cells in culture, in vitro or ex vivo, or to a subject, e.g., a human subject, to treat, prevent, and/or diagnose a variety of disorders, such as cancers.

As used herein, the terms "treat", "treatment" and "treating" refer to the reduction or amelioration of the progression, severity and/or duration of a disorder, e.g., a proliferative disorder (e.g., a cancer), or the amelioration of one or more symptoms (preferably, one or more discernible symptoms) of a disorder, e.g., a proliferative disorder, resulting from the administration of one or more therapies (e.g., one or more therapeutic agents such as the combination therapies disclosed herein). In specific embodiments, the terms "treat", "treatment" and "treating" refer to the amelioration of at least one measurable physical parameter of a proliferative disorder (e.g., a cancer), such as growth of a tumor, not necessarily discernible by the subject, e.g., a patient. In other embodiments the terms "treat", "treatment" and "treating" refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

In some embodiments, ameliorating the disorder includes one or more of: slowing or arresting or reducing the development of the disease or at least one of the clinical symptoms thereof), to preventing or delaying the onset or development or progression of the disease or disorder. In addition those terms refers to alleviating or ameliorating at least one physical parameter including those which may not be discernible by the patient and also to modulating the disease or disorder, either physically (e.g. stabilization of a discernible symptom), physiologically (e.g. stabilization of a physical parameter), or both.

The term "treatment" comprises, for example, the therapeutic administration of one or more combination therapies disclosed herein to a subject, e.g., warm-blooded animal, in particular a human being, in need of such treatment. In embodiment, the treatment aims to cure the disease or to have an effect on disease regression or on the delay of progression of a disease.

As used herein, the term "subject" is intended to include human and non-human animals. In one embodiment, the subject is a human subject, e.g., a human patient having a disorder or condition characterized by abnormal cell proliferation and/or immune functioning. The term "non-human animals" includes mammals and non-mammals, such as non-human primates. In one embodiment, the subject is a human. In one embodiment, the subject is a human patient in need of enhancement of an immune response. The term "subject in need" refers to a warm-blooded animal, in particular a human being that would benefit biologically, medically or in quality of life from the treatment. In one embodiment, the subject is immunocompromised, e.g., the subject is undergoing, or has undergone a chemotherapeutic or radiation therapy. Alternatively, or in combination, the subject is, or is at risk of being, immunocompromised as a result of an infection. The methods and compositions described herein are suitable for treating human patients having a disorder that can be treated by augmenting the T-cell mediated immune response. For example, the methods and compositions described herein can enhance a number of immune activities. In one embodiment, the subject has increased number or activity of tumour-infiltrating T lymphocytes (TILs). In another embodiment, the subject has increased expression or activity of interferon-gamma (IFN-γ). In yet another embodiment, the subject has decreased PD-L1 expression or activity.

Accordingly, in one aspect, the invention provides a method of modifying an immune response in a subject comprising administering to the subject the antibody molecule described herein, such that the immune response in the subject is modified. In one embodiment, the immune response is enhanced, stimulated or up-regulated. In one embodiment, the antibody molecules enhance an immune response in a subject by blockade of a checkpoint inhibitor (e.g., PD-1, PD-L1, LAG-3 or TIM-3).

Cancer

Blockade of checkpoint inhibitors, e.g., PD-1, can enhance an immune response to cancerous cells in a subject. The ligand for PD-1, PD-L1, is not expressed in normal human cells, but is abundant in a variety of human cancers (Dong et al. (2002) *Nat Med* 8:787-9). The interaction between PD-1 and PD-L1 can result in a decrease in tumor infiltrating lymphocytes, a decrease in T-cell receptor mediated proliferation, and/or immune evasion by the cancerous cells (Dong et al. (2003) *J Mol Med* 81:281-7; Blank et al. (2005) *Cancer Immunol. Immunother.* 54:307-314; Konishi et al. (2004) *Clin. Cancer Res.* 10:5094-100).

In one aspect, the invention relates to treatment of a subject in vivo using an immunomodulator, e.g., anti-PD-1 or anti-PD-L1 antibody molecule, alone or in combination with a second agent described herein, such that growth of cancerous tumors is inhibited or reduced. An immunomodulator may be used alone to inhibit the growth of cancerous tumors. Alternatively, an anti-PD-1 or anti-PD-L1 antibody may be used in combination with one or more of: an agent disclosed in Table 1, a standard of care treatment (e.g., for cancers), another antibody or antigen-binding fragment thereof, another immunomodulator (e.g., an activator of a costimulatory molecule or an inhibitor of an inhibitory molecule); a vaccine, e.g., a therapeutic cancer vaccine; or other forms of cellular immunotherapy, as described below.

Accordingly, in one embodiment, the invention provides a method of inhibiting growth of tumor cells in a subject, comprising administering to the subject a therapeutically effective amount of a combination therapy disclosed herein. In one embodiment, the methods are suitable for the treatment of cancer in vivo. When antibodies to PD-1 are administered in combination with one or more agents, the combination can be administered in either order or simultaneously.

In another aspect, a method of treating a subject, e.g., reducing or ameliorating, a proliferative condition or disorder (e.g., a cancer), e.g., solid tumor, a soft tissue tumor, or a metastatic lesion, in a subject is provided. The method includes administering to the subject one or more immunomodulators, e.g., anti-PD-1 or PD-L1 antibody molecules described herein, alone or in combination with other agents or therapeutic modalities (e.g., one or more agents from Table 1).

As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma. Metastatic lesions of the aforementioned cancers can also be treated or prevented using the methods and compositions of the invention.

Exemplary cancers whose growth can be inhibited using the antibodies molecules disclosed herein include cancers typically responsive to immunotherapy. Non-limiting examples of preferred cancers for treatment include melanoma (e.g., metastatic malignant melanoma), renal cancer (e.g., clear cell carcinoma), prostate cancer (e.g., hormone refractory prostate adenocarcinoma), breast cancer, colon cancer and lung cancer (e.g., non-small cell lung cancer). Additionally, refractory or recurrent malignancies can be treated using the antibody molecules described herein.

Examples of other cancers that can be treated include bone cancer, pancreatic cancer, skin cancer, cancer of the head or neck, cutaneous or intraocular malignant melanoma, uterine cancer, ovarian cancer, rectal cancer, anal cancer, gastro-esophageal, stomach cancer, testicular cancer, uterine cancer, carcinoma of the fallopian tubes, carcinoma of the endometrium, carcinoma of the cervix, carcinoma of the vagina, carcinoma of the vulva, Hodgkin Disease, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

Treatment of metastatic cancers, e.g., metastatic cancers that express PD-L1 (Iwai et al. (2005) *Int. Immunol.* 17:133-144) can be effected using the antibody molecules described herein. In one embodiment, the cancer expresses an elevated level of PD-L1, IFN$\gamma$ and/or CD8.

Hematological cancer conditions are the types of cancer such as leukemia and malignant lymphoproliferative conditions that affect blood, bone marrow and the lymphatic system. Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

In other embodiments, the cancer is a hematological malignancy or cancer including but is not limited to a leukemia or a lymphoma. For example, the combination therapy can be used to treat cancers and malignancies including, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. In some embodiments, the lymphoma (e.g., an anaplastic large-cell lymphoma or non- Hodgkin lymphoma) has, or is identified as having, an ALK translocation, e.g., an EML4-ALK fusion.

In one embodiment, the cancer is chosen from a lung cancer (e.g., a non-small cell lung cancer (NSCLC) (e.g., a NSCLC with squamous and/or non-squamous histology)), a melanoma (e.g., an advanced melanoma), a renal cancer (e.g., a renal cell carcinoma, e.g., clear cell renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastro-esophageal cancer, thyroid cancer, cervical cancer, a lymphoproliferative disease (e.g., a post-transplant lymphoproliferative disease) or a hematological cancer, T-cell lymphoma, a non-Hogdkin's lymphoma, or a leukemia (e.g., a myeloid leukemia).

In another embodiment, the cancer is chosen form a carcinoma (e.g., advanced or metastatic carcinoma), melanoma or a lung carcinoma, e.g., a non-small cell lung carcinoma.

In one embodiment, the cancer is a lung cancer, e.g., a non-small cell lung cancer (NSCLC). In certain embodiments, the lung cancer, e.g., the non-small cell lung cancer, has, or is identified as having, an ALK rearrangement or translocation, e.g., an ALK fusion, e.g., an EML4-ALK fusion.

In another embodiment, the cancer is an inflammatory myofibroblastic tumor (IMT). In certain embodiments, the inflammatory myofibroblastic tumor has, or is identified as having, an ALK rearrangement or translocation, e.g., an ALK fusion, e.g., an EML4-ALK fusion.

In other embodiments, the cancer is NSCLC wherein the NSCLC is characterized by one or more of: aberrant activation, amplification, or a mutation of epidermal growth factor receptor (EGFR). In certain embodiments the cancer is NSCLC wherein the NSCLC is characterized by harbouring an EGFR exon 20 insertion, an EGFR exon 19 deletion, EGFR L858R mutation, EGFR T790M, or any combination thereof. In some embodiments, the NSCLC is characterized by harboring L858R and T790M mutations of EGFR. In some embodiments, the NSCLC is characterized by harboring an EGFR exon 20 insertion and T790M mutations of EGFR. In some embodiments, the NSCLC is characterized by harboring an EGFR exon 19 deletion and T790M mutations of EGFR. In some embodiments, the NSCLC is characterized by harboring EGFR mutation selected from the group consisting of an exon 20 insertion, an exon 19 deletion, L858R mutation, T790M mutation, and any combination thereof.

In yet another embodiment, the cancer is a neuroblastoma.

In certain embodiments, the neuroblastoma has, or is identified as having, an ALK rearrangement or translocation, e.g., an ALK fusion, e.g., an EML4-ALK fusion. Methods and compositions disclosed herein are useful for treating metastatic lesions associated with the aforementioned cancers.

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC or clear cell renal cell carcinoma).

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-PD-1 or PD-L1 antibody molecule is administered after treatment with an anti-CTLA4 antibody (e.g., ipilimumab) with or without a BRAF inhibitor (e.g., vemurafenib or dabrafenib).

In another embodiment, the cancer is an inflammatory myofibroblastic tumor (IMT). In certain embodiments, the inflammatory myofibroblastic tumor has, or is identified as having, an ALK rearrangement or translocation, e.g., an ALK fusion, e.g., an EML4-ALK fusion.

In yet another embodiment, the cancer is a neuroblastoma. In certain embodiments, the neuroblastoma has, or is identified as having, an ALK rearrangement or translocation, e.g., an ALK fusion, e.g., an EML4-ALK fusion. Methods and compositions disclosed herein are useful for treating metastatic lesions associated with the aforementioned cancers.

Additional Combination Therapies

The combination therapy disclosed herein can be further co-formulated with, and/or co-administered with, one or more additional therapeutic agents, e.g., one or more anti-cancer agents, cytotoxic or cytostatic agents, hormone treatment, vaccines, and/or other immunotherapies. In other embodiments, the antibody molecules are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

For example, the combination therapies disclosed herein can also be combined with a standard cancer treatment. For example, PD-1 blockade may be effectively combined with chemotherapeutic regimes. In these instances, it may be possible to reduce the dose of chemotherapeutic reagent administered (Mokyr, M. et al. (1998) *Cancer Research* 58: 5301-5304). In certain embodiments, the methods and compositions described herein are administered in combination with one or more of other antibody molecules, chemotherapy, other anti-cancer therapy (e.g., targeted anti-cancer therapies, or oncolytic drugs), cytotoxic agents, immune-based therapies (e.g., cytokines), surgical and/or radiation procedures. Exemplary cytotoxic agents that can be administered in combination with include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation).

Exemplary combinations of with the standard of care for cancer, include at least the following.

In certain embodiments, the combination therapy, is used in combination with a standard of cancer care chemotherapeutic agent including, but not limited to, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids that can be used in combination with a combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors that can be used in combination with combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), include, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912); danoprevir (RG7227, CAS 850876-88-9); ixazomib (MLN2238, CAS 1072833-77-2); and (S)—N-[(phenylmethoxy)carbonyl]-L-leucyl-N-(1-formyl-3-methylbutyl)-L-Leucinamide (MG-132, CAS 133407-82-6).

In some embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor, a KIT inhibitor and a RET inhibitor. In some embodiments, the anti-cancer agent used in combination with the hedgehog inhibitor is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120

(VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951(tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, Sorafenib Tosylate (Bay 43-9006), SU 5402, TSU-68(SU6668), vatalanib, XL880 (GSK1363089, EXEL-2880). Further examples of hedgehog inhibitors include, but are not limited to, vismodegib (2-chloro-N-[4-chloro-3-(2-pyridinyl)phenyl]-4-(methylsulfonyl)-benzamide, GDC-0449, described in PCT Publication No. WO 06/028958); 1-(4-Chloro-3-(trifluoromethyl)phenyl)-3-((3-(4-fluorophenyl)-3,4-dihydro-4-oxo-2-quinazolinyl)methyl)-urea (CAS 330796-24-2); N-[(2S,3R,3'R,3aS,4'aR,6S,6'aR,6'bS,7aR, 12'aS,12'bS)-2',3',3a,4,4',4'a,5,5',6,6',6'a,6'b,7,7',7a,8',10', 12',12'a,12'b-Eicosahydro-3,6,11',12'b-tetramethylspiro [furo[3,2-b]pyridine-2(3H),9'(1'H)-naphth[2,1-a]azulen]-3'-yl]-methanesulfonamide (IPI926, CAS 1037210-93-7); and 4-Fluoro-N-methyl-N-[1-[4-(1-methyl-1H-pyrazol-5-yl)-1-phthalazinyl]-4-piperidinyl]-2-(trifluoromethyl)-benzamide (LY2940680, CAS 1258861-20-9); and Erismodegib (LDE225). Selected tyrosine kinase inhibitors are chosen from gefitinib; erlotinib hydrochloride (Tarceva®); linifanib (N-[4-(3-amino-1H-indazol-4-yl)phenyl]-N'-(2-fluoro-5-methylphenyl)urea, also known as ABT 869, available from Genentech); sunitinib malate (Sutent®); bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, described in U.S. Pat. No. 6,780, 996); dasatinib (Sprycel®); pazopanib (Votrient®); sorafenib (Nexavar®); zactima (ZD6474); and imatinib or imatinib mesylate (Gilvec® and Gleevec®).

In certain embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a Vascular Endothelial Growth Factor (VEGF) receptor inhibitors, including but not limited to, Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1((4-((3-methoxyphenyl)amino)pyrrolo [2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta [c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

Exemplary anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599. In one embodiment, the anti-VEGF antibody is Bevacizumab (BV), also known as rhuMAb VEGF or AVASTIN®. It comprises mutated human IgG1 framework regions and antigen-binding complementarity-determining regions from the murine anti-hVEGF monoclonal antibody A.4.6.1 that blocks binding of human VEGF to its receptors. Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, the contents of these patent applications are expressly incorporated herein by reference. For additional antibodies see U.S. Pat. Nos. 7,060,269, 6,582,959, 6,703,020, 6,054,297, WO98/45332, WO 96/30046, WO94/10202, EP 0666868B1, U.S. Patent Application Publication Nos. 2006009360, 20050186208, 20030206899, 20030190317, 20030203409, and 20050112126; and Popkov et al, *Journal of Immunological Methods* 288: 149-164 (2004). Other antibodies include those that bind to a functional epitope on human VEGF comprising of residues F17, M18, D19, Y21, Y25, Q89, 191, K101, E103, and C104 or, alternatively, comprising residues F17, Y21, Q22, Y25, D63, 183 and Q89.

In some embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a PI3K inhibitor. In one embodiment, the PI3K inhibitor is an inhibitor of delta and gamma isoforms of PI3K. Exemplary PI3K inhibitors that can be used in combination are described in, e.g., WO 2010/036380, WO 2010/006086, WO 09/114870, WO 05/113556, GSK 2126458, GDC-0980, GDC-0941, Sanofi XL147, XL756, XL147, PF-46915032, BKM 120, CAL-101, CAL 263, SF1126, PX-886, and a dual PI3K inhibitor (e.g., Novartis BEZ235). Further examples of PI3K inhibitors include, but are not limited to, 4-[2-(1H-Indazol-4-yl)-6-[[4-(methylsulfonyl)piperazin-1-yl]methyl] thieno[3,2-d]pyrimidin-4-yl]morpholine (also known as GDC 0941, described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ235 or NVP-BEZ 235, described in PCT Publication No. WO 06/122806); 4-(trifluoromethyl)-5-(2,6-dimorpholinopyrimidin-4-yl)pyridin-2-amine (also known as BKM120 or NVP-BKM120, described in PCT Publication No. WO2007/ 084786); Tozasertib (VX680 or MK-0457, CAS 639089-54-6); (5Z)-5-[[4-(4-Pyridinyl)-6-quinolinyl]methylene]-2, 4-thiazolidinedione (GSK1059615, CAS 958852-01-2);

(1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione (PX866, CAS 502632-66-8); 8-Phenyl-2-(morpholin-4-yl)-chromen-4-one (LY294002, CAS 154447-36-6); 2-Amino-8-ethyl-4-methyl-6-(1H-pyrazol-5-yl)pyrido[2,3-d]pyrimidin-7(8H)-one (SAR 245409 or XL 765); 1,3-Dihydro-8-(6-methoxy-3-pyridinyl)-3-methyl-1-[4-(1-piperazinyl)-3-(trifluoromethyl)phenyl]-2H-imidazo[4,5-c]quinolin-2-one, (2Z)-2-butenedioate (1:1) (BGT 226); 5-Fluoro-3-phenyl-2-[(1S)-1-(9H-purin-6-ylamino)ethyl]-4(3H)-quinazolinone (CAL101); 2-Amino-N-[3-[N-[3-[(2-chloro-5-methoxyphenyl)amino]quinoxalin-2-yl]sulfamoyl]phenyl]-2-methylpropanamide (SAR 245408 or XL 147); and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (BYL719).

In some embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a mTOR inhibitor, e.g., one or more mTOR inhibitors chosen from one or more of rapamycin, temsirolimus (TORISEL®), AZD8055, BEZ235, BGT226, XL765, PF-4691502, GDC0980, SF1126, OSI-027, GSK1059615, KU-0063794, WYE-354, Palomid 529 (P529), PF-04691502, or PKI-587. ridaforolimus (formally known as deferolimus, (1R,2R,4S)-4-[(2R)-2[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126, CAS 936487-67-1), (1r,4r)-4-(4-amino-5-(7-methoxy-1H-indol-2-yl)imidazo[1,5-f][1,2,4]triazin-7-yl)cyclohexanecarboxylic acid (OSI-027); and XL765.

In some embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a BRAF inhibitor, e.g., GSK2118436, RG7204, PLX4032, GDC-0879, PLX4720, and sorafenib tosylate (Bay 43-9006). In further embodiments, a BRAF inhibitor includes, but is not limited to, regorafenib (BAY73-4506, CAS 755037-03-7); tuvizanib (AV951, CAS 475108-18-0); vemurafenib (Zelboraf®, PLX-4032, CAS 918504-65-1); encorafenib (also known as LGX818); 1-Methyl-5-[[2-[5-(trifluoromethyl)-1H-imidazol-2-yl]-4-pyridinyl]oxy]-N-[4-(trifluoromethyl) phenyl-1H-benzimidazol-2-amine (RAF265, CAS 927880-90-8); 5-[1-(2-Hydroxyethyl)-3-(pyridin-4-yl)-1H-pyrazol-4-yl]-2,3-dihydroinden-1-one oxime (GDC-0879, CAS 905281-76-7); 5-[2-[4-[2-(Dimethylamino)ethoxy]phenyl]-5-(4-pyridinyl)-1H-imidazol-4-yl]-2,3-dihydro-1H-Inden-1-one oxime (GSK2118436 or SB590885); (+/−)-Methyl (5-(2-(5-chloro-2-methylphenyl)-1-hydroxy-3-oxo-2,3-dihydro-1H-isoindol-1-yl)-1H-benzimidazol-2-yl)carbamate (also known as XL-281 and BMS908662) and N-(3-(5-chloro-1H-pyrrolo[2,3-b]pyridine-3-carbonyl)-2,4-difluorophenyl)propane-1-sulfonamide (also known as PLX4720).

In some embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a MEK inhibitor. In some embodiments, the combination of the anti-PD-1 antibody and the MEK inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. In certain embodiments, the cancer includes a BRAF mutation (e.g., a BRAF V600E mutation), a BRAF wildtype, a KRAS wildtype or an activating KRAS mutation. The cancer may be at an early, intermediate or late stage. Any MEK inhibitor can be used in combination including, but not limited to, selumetinib (5-[(4-bromo-2-chlorophenyl)amino]-4-fluoro-N-(2-hydroxyethoxy)-1-methyl-1H-benzimidazole-6-carboxamide, also known as AZD6244 or ARRY 142886, described in PCT Publication No. WO2003077914); trametinib dimethyl sulfoxide (GSK-1120212, CAS 1204531-25-80); RDEA436; N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766, described in PCT Publication No. WO2007014011); AS703026; BIX 02188; BIX 02189; 2-[(2-Chloro-4-iodophenyl)amino]-N-(cyclopropylmethoxy)-3,4-difluoro-benzamide (also known as CI-1040 or PD184352, described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2'-amino-3'-methoxyflavone (also known as PD98059 available from Biaffin GmbH & Co., KG, Germany); 2,3-bis[amino[(2-aminophenyl)thio]methylene]-butanedinitrile (also known as U0126 and described in U.S. Pat. No. 2,779,780); XL-518 (also known as GDC-0973, Cas No. 1029872-29-4, available from ACC Corp.); G-38963; and G02443714 (also known as AS703206), or a pharmaceutically acceptable salt or solvate thereof. Additional examples of MEK inhibitors are disclosed in WO 2013/019906, WO 03/077914, WO 2005/121142, WO 2007/04415, WO 2008/024725 and WO 2009/085983, the contents of which are incorporated herein by reference. Further examples of MEK inhibitors include, but are not limited to, benimetinib (6-(4-bromo-2-fluorophenylamino)-7-fluoro-3-methyl-3H-benzoimidazole-5-carboxylic acid (2-hydroxyethyoxy)-amide, also known as MEK162, CAS 1073666-70-2, described in PCT Publication No. WO2003077914); 2,3-Bis[amino[(2-aminophenyl)thio]methylene]-butanedinitrile (also known as U0126 and described in U.S. Pat. No. 2,779,780); (3S,4R,5Z,8S,9S,11E)-14-(Ethylamino)-8,9,16-trihydroxy-3,4-dimethyl-3,4,9,19-tetrahydro-1H-2-benzoxacyclotetradecine-1,7(8H)-dione] (also known as E6201, described in PCT Publication No. WO2003076424); vemurafenib (PLX-4032, CAS 918504-65-1); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); pimasertib (AS-703026, CAS 1204531-26-9); 2-(2-Fluoro-4-iodophenylamino)-N-(2-hydroxyethoxy)-1,5-dimethyl-6-oxo-1,6-dihydropyridine-3-carboxamide (AZD 8330); and 3,4-Difluoro-2-[(2-fluoro-4-iodophenyl)amino]-N-(2-hydroxyethoxy)-5-[(3-oxo-[1,2]oxazinan-2-yl)methyl]benzamide (CH 4987655 or Ro 4987655).

In some embodiments, the combination therapy disclosed herein (e.g., an anti-PD-1 or PD-L1 antibody molecule, alone or in combination with another immunomodulator (e.g., an anti-LAG-3, or anti-TIM-3 antibody molecule) and a compound of Table 1), in combination with a JAK2 inhibitor, e.g., CEP-701, INCB18424, CP-690550 (tasocitinib). Exemplary JAK inhibitors include, but are not limited to, ruxolitinib (Jakafi®); tofacitinib (CP690550); axitinib (AG013736, CAS 319460-85-0); 5-Chloro-N2-[(1S)-1-(5-fluoro-2-pyrimidinyl)ethyl]-N4-(5-methyl-1H-pyrazol-3-y)-12,4-pyrimidinediamine (AZD1480, CAS 935666-88-9); (9E)-15-[2-(1-Pyrrolidinyl)ethoxy]-7,12,26-trioxa-19,21,24-triazatetracyclo[18.3.1.12,5.114,18]-hexacosa-1(24),2,4,9,14,16,18(25),20,22-nonaene (SB-1578, CAS 937273-04-6); momelotinib (CYT 387); baricitinib (INCB-028050 or LY-3009104); pacritinib (SB1518); (16E)-14-Methyl-20-oxa-5,7,14,27-tetraazatetracyclo[19.3.1.12,6.18,12]heptacosa-1(25),2,4,6(27),8,10,12(26),16,21,23-decaene (SB 1317); gandotinib (LY 2784544); and N,N-cicyclopropyl-4-[(1,5-dimethyl-1H-pyrazol-3-yl)amino]-6-ethyl-1,6-dihydro-1-methyl-imidazo[4,5-d]pyrrolo[2,3-b]pyridine-7-carboxamide (BMS 911543).

In some embodiments, the combination therapies disclosed herein include paclitaxel or a paclitaxel agent, e.g., TAXOL®, protein-bound paclitaxel (e.g., ABRAXANE®). Exemplary paclitaxel agents include, but are not limited to, nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., *Biopolymers* (2007) 87:225-230), and glucose-conjugated paclitaxel (e.g., 2'-paclitaxel methyl 2-glucopyranosyl succinate, see Liu et al., *Bioorganic & Medicinal Chemistry Letters* (2007) 17:617-620).

In certain embodiments, the anti-PD-1 or PD-L1 antibody molecule, alone or in combination with another immunomodulator (e.g., an anti-LAG-3 or anti-TIM-3 antibody molecule), is administered in combination with an antibody against a Killer-cell Immunoglobulin-like Receptors (also referred to herein as an "anti-KIR antibody"). In certain embodiments, the combination of anti-PD-1 antibody molecule and anti-KIR antibody described herein is used to treat a cancer, e.g., a cancer as described herein (e.g., a solid tumor, e.g., an advanced solid tumor).

In one embodiment, the anti-PD-1 or PD-L1 antibody molecule, alone or in combination with another immunomodulator (e.g., an anti-LAG-3 or anti-TIM-3 antibody molecule), is administered in combination with a cellular immunotherapy (e.g., Provenge (e.g., Sipuleucel)), and optionally in combination with cyclophosphamide. In certain embodiments, the combination of anti-PD-1 antibody molecule, Provenge and/or cyclophosphamide is used to treat a cancer, e.g., a cancer as described herein (e.g., a prostate cancer, e.g., an advanced prostate cancer).

In another embodiment, the anti-PD-1 or PD-L1 antibody molecule, alone or in combination with another immunomodulator (e.g., an anti-LAG-3 or anti-TIM-3 antibody molecule), is administered in combination with a vaccine, e.g., a dendritic cell renal carcinoma (DC-RCC) vaccine. In certain embodiments, the combination of anti-PD-1 antibody molecule and the DC-RCC vaccine is used to treat a cancer, e.g., a cancer as described herein (e.g., a renal carcinoma, e.g., metastatic renal cell carcinoma (RCC) or clear cell renal cell carcinoma (CCRCC)).

In yet another embodiment, the anti-PD-1 or PD-L1 antibody molecule, alone or in combination with another immunomodulator (e.g., an anti-LAG-3 or anti-TIM-3 antibody molecule), is administered in combination with chemotherapy, and/or immunotherapy. For example, the anti-PD-1 or PD-L1 antibody molecule can be used to treat a myeloma, alone or in combination with one or more of: chemotherapy or other anti-cancer agents (e.g., thalidomide analogs, e.g., lenalidomide), an anti-TIM3 antibody, tumor antigen-pulsed dendritic cells, fusions (e.g., electrofusions) of tumor cells and dendritic cells, or vaccination with immunoglobulin idiotype produced by malignant plasma cells. In one embodiment, the anti-PD-1 or PD-L1 antibody molecule is used in combination with an anti-TIM-3 antibody to treat a myeloma, e.g., a multiple myeloma.

In one embodiment, the anti-PD-1 or PD-L1 antibody molecule, alone or in combination with another immunomodulator (e.g., an anti-LAG-3 or anti-TIM-3 antibody molecule), is used in combination with chemotherapy to treat a lung cancer, e.g., non-small cell lung cancer. In one embodiment, the anti-PD-1 or PD-L1 antibody molecule is used with platinum doublet therapy to treat lung cancer.

In yet another embodiment, the anti-PD-1 or PD-L1 antibody molecule, alone or in combination with another immunomodulator (e.g., an anti-LAG-3 or anti-TIM-3 antibody molecule), is used to treat a renal cancer, e.g., renal cell carcinoma (RCC) (e.g., clear cell renal cell carcinoma (CCRCC) or metastatic RCC. The anti-PD-1 or PD-L1 antibody molecule can be administered in combination with one or more of: an immune-based strategy (e.g., interleukin-2 or interferon-α), a targeted agent (e.g., a VEGF inhibitor such as a monoclonal antibody to VEGF); a VEGF tyrosine kinase inhibitor such as sunitinib, sorafenib, axitinib and pazopanib; an RNAi inhibitor), or an inhibitor of a downstream mediator of VEGF signaling, e.g., an inhibitor of the mammalian target of rapamycin (mTOR), e.g., everolimus and temsirolimus.

An example of suitable therapeutics for use in combination for treatment of pancreatic cancer includes, but is not limited to, a chemotherapeutic agent, e.g., paclitaxel or a paclitaxel agent (e.g., a paclitaxel formulation such as TAXOL, an albumin-stabilized nanoparticle paclitaxel formulation (e.g., ABRAXANE) or a liposomal paclitaxel formulation); gemcitabine (e.g., gemcitabine alone or in combination with AXP107-11); other chemotherapeutic agents such as oxaliplatin, 5-fluorouracil, capecitabine, rubitecan, epirubicin hydrochloride, NC-6004, cisplatin, docetaxel (e.g., TAXOTERE), mitomycin C, ifosfamide; interferon; tyrosine kinase inhibitor (e.g., EGFR inhibitor (e.g., erlotinib, panitumumab, cetuximab, nimotuzumab); HER2/neu receptor inhibitor (e.g., trastuzumab); dual kinase inhibitor (e.g., bosutinib, saracatinib, lapatinib, vandetanib); multikinase inhibitor (e.g., sorafenib, sunitinib, XL184, pazopanib); VEGF inhibitor (e.g., bevacizumab, AV-951, brivanib); radioimmunotherapy (e.g., XR303); cancer vaccine (e.g., GVAX, survivin peptide); COX-2 inhibitor (e.g., celecoxib); IGF-1 receptor inhibitor (e.g., AMG 479, MK-0646); mTOR inhibitor (e.g., everolimus, temsirolimus); IL-6 inhibitor (e.g., CNTO 328); cyclin-dependent kinase inhibitor (e.g., P276-00, UCN-01); Altered Energy Metabolism-Directed (AEMD) compound (e.g., CPI-613); HDAC inhibitor (e.g., vorinostat); TRAIL receptor 2 (TR-2) agonist (e.g., conatumumab); MEK inhibitor (e.g., AS703026, selumetinib, GSK1120212); Raf/MEK dual kinase inhibitor (e.g., RO5126766); Notch signaling inhibitor (e.g., MK0752); monoclonal antibody-antibody fusion protein (e.g., L19IL2); curcumin; HSP90 inhibitor (e.g., tanespimycin, STA-9090); rIL-2; denileukin diftitox; topoisomerase 1 inhibitor (e.g., irinotecan, PEP02); statin (e.g., simvastatin); Factor VIIa inhibitor (e.g., PCI-27483); AKT inhibitor (e.g., RX-0201); hypoxia-activated prodrug (e.g., TH-302); metformin hydrochloride, gamma-secretase inhibitor (e.g., RO4929097); ribonucleotide reductase inhibitor (e.g., 3-AP); immunotoxin (e.g., HuC242-DM4); PARP inhibitor (e.g., KU-0059436, veliparib); CTLA-4 inhbtor (e.g., CP-675,206, ipilimumab); AdV-tk therapy; proteasome inhibitor (e.g., bortezomib (Velcade), NPI-0052); thiazolidinedione (e.g., pioglitazone); NPC-1C; Aurora kinase inhibitor (e.g., R763/AS703569), CTGF inhibitor (e.g., FG-3019); siG12D LODER; and radiation therapy (e.g., tomotherapy, stereotactic radiation, proton therapy), surgery, and a combination thereof. In certain embodiments, a combination of paclitaxel or a paclitaxel agent, and gemcitabine can be used with the anti-PD-1 antibody molecules described herein.

An example of suitable therapeutics for use in combination for treatment of small cell lung cancer includes, but is not limited to, a chemotherapeutic agent, e.g., etoposide, carboplatin, cisplatin, irinotecan, topotecan, gemcitabine, liposomal SN-38, bendamustine, temozolomide, belotecan, NK012, FR901228, flavopiridol); tyrosine kinase inhibitor (e.g., EGFR inhibitor (e.g., erlotinib, gefitinib, cetuximab, panitumumab); multikinase inhibitor (e.g., sorafenib, sunitinib); VEGF inhibitor (e.g., bevacizumab, vandetanib); cancer vaccine (e.g., GVAX); Bcl-2 inhibitor (e.g., oblimersen sodium, ABT-263); proteasome inhibitor (e.g., bortezomib (Velcade), NPI-0052), paclitaxel or a paclitaxel agent; docetaxel; IGF-1 receptor inhibitor (e.g., AMG 479); HGF/SF inhibitor (e.g., AMG 102, MK-0646); chloroquine; Aurora kinase inhibitor (e.g., MLN8237); radioimmunotherapy (e.g., TF2); HSP90 inhibitor (e.g., tanespimycin, STA-9090); mTOR inhibitor (e.g., everolimus); Ep-CAM-/CD3-bispecific antibody (e.g., MT110); CK-2 inhibitor (e.g., CX-4945); HDAC inhibitor (e.g., belinostat); SMO antagonist (e.g., BMS 833923); peptide cancer vaccine, and radiation therapy (e.g., intensity-modulated radiation therapy (IMRT), hypofractionated radiotherapy, hypoxia-guided radiotherapy), surgery, and combinations thereof.

An example of suitable therapeutics for use in combination for treatment of non-small cell lung cancer includes, but is not limited to, a chemotherapeutic agent, e.g., vinorelbine, cisplatin, docetaxel, pemetrexed disodium, etoposide, gemcitabine, carboplatin, liposomal SN-38, TLK286, temozolomide, topotecan, pemetrexed disodium, azacitidine, irinotecan, tegafur-gimeracil-oteracil potassium, sapacitabine); tyrosine kinase inhibitor (e.g., EGFR inhibitor (e.g., erlotinib, gefitinib, cetuximab, panitumumab, necitumumab, PF-00299804, nimotuzumab, RO5083945), MET inhibitor (e.g., PF-02341066, ARQ 197), PI3K kinase inhibitor (e.g., XL147, GDC-0941), Raf/MEK dual kinase inhibitor (e.g., RO5126766), PI3K/mTOR dual kinase inhibitor (e.g., XL765), SRC inhibitor (e.g., dasatinib), dual inhibitor (e.g., BIBW 2992, GSK1363089, ZD6474, AZD0530, AG-013736, lapatinib, MEHD7945A, linifanib), multikinase inhibitor (e.g., sorafenib, sunitinib, pazopanib, AMG 706, XL184, MGCD265, BMS-690514, R935788), VEGF inhibitor (e.g., endostar, endostatin, bevacizumab, cediranib, BIBF 1120, axitinib, tivozanib, AZD2171), cancer vaccine (e.g., BLP25 liposome vaccine, GVAX, recombinant DNA and adenovirus expressing L523S protein), Bcl-2 inhibitor (e.g., oblimersen sodium), proteasome inhibitor (e.g., bortezomib, carfilzomib, NPI-0052, MLN9708), paclitaxel or a paclitaxel agent, docetaxel, IGF-1 receptor inhibitor (e.g., cixutumumab, MK-0646, OSI 906, CP-751,871, BIIB022), hydroxychloroquine, HSP90 inhibitor (e.g., tanespimycin, STA-9090, AUY922, XL888), mTOR inhibitor (e.g., everolimus, temsirolimus, ridaforolimus), Ep-CAM-/CD3-bispecific antibody (e.g., MT110), CK-2 inhibitor (e.g., CX-4945), HDAC inhibitor (e.g., MS 275, LBH589, vorinostat, valproic acid, FR901228), DHFR inhibitor (e.g., pralatrexate), retinoid (e.g., bexarotene, tretinoin), antibody-drug conjugate (e.g., SGN-15), bisphosphonate (e.g., zoledronic acid), cancer vaccine (e.g., belagenpumatucel-L), low molecular weight heparin (LMWH) (e.g., tinzaparin, enoxaparin), GSK1572932A, melatonin, talactoferrin, dimesna, topoisomerase inhibitor (e.g., amrubicin, etoposide, karenitecin), nelfinavir, cilengitide, ErbB3 inhibitor (e.g., MM-121, U3-1287), survivin inhibitor (e.g., YM155, LY2181308), eribulin mesylate, COX-2 inhibitor (e.g., celecoxib), pegfilgrastim, Polo-like kinase 1 inhibitor (e.g., BI 6727), TRAIL receptor 2 (TR-2) agonist (e.g., CS-1008), CNGRC peptide-TNF alpha conjugate, dichloroacetate (DCA), HGF inhibitor (e.g., SCH 900105), SAR240550, PPAR-gamma agonist (e.g., CS-7017), gamma-secretase inhibitor (e.g., RO4929097), epigenetic therapy (e.g., 5-azacitidine), nitroglycerin, MEK inhibitor (e.g., AZD6244), cyclin-dependent kinase inhibitor (e.g., UCN-01), cholesterol-Fust, antitubulin agent (e.g., E7389), farnesyl-OH-transferase inhibitor (e.g., lonafarnib), immunotoxin (e.g., BB-10901, SS1 (dsFv) PE38), fondaparinux, vascular-disrupting agent (e.g., AVE8062), PD-L1 inhibitor (e.g., MDX-1105, MDX-1106), beta-glucan, NGR-hTNF, EMD 521873, MEK inhibitor (e.g., GSK1120212), epothilone analog (e.g., ixabepilone), kinesin-spindle inhibitor (e.g., 4SC-205), telomere targeting agent (e.g., KML-001), P70 pathway inhibitor (e.g., LY2584702), AKT inhibitor (e.g., MK-2206), angiogenesis inhibitor (e.g., lenalidomide), Notch signaling inhibitor (e.g., OMP-21M18), radiation therapy, surgery, and combinations thereof.

An example of suitable therapeutics for use in combination for treatment of ovarian cancer includes, but is not limited to, a chemotherapeutic agent (e.g., paclitaxel or a paclitaxel agent; docetaxel; carboplatin; gemcitabine; doxorubicin; topotecan; cisplatin; irinotecan, TLK286, ifosfamide, olaparib, oxaliplatin, melphalan, pemetrexed disodium, SJG-136, cyclophosphamide, etoposide, decitabine); ghrelin antagonist (e.g., AEZS-130), immunotherapy (e.g., APC8024, oregovomab, OPT-821), tyrosine kinase inhibitor (e.g., EGFR inhibitor (e.g., erlotinib), dual inhibitor (e.g., E7080), multikinase inhibitor (e.g., AZD0530, JI-101, sorafenib, sunitinib, pazopanib), ON 01910.Na), VEGF inhibitor (e.g., bevacizumab, BIBF 1120, cediranib, AZD2171), PDGFR inhibitor (e.g., IMC-3G3), paclitaxel, topoisomerase inhibitor (e.g., karenitecin, Irinotecan), HDAC inhibitor (e.g., valproate, vorinostat), folate receptor inhibitor (e.g., farletuzumab), angiopoietin inhibitor (e.g., AMG 386), epothilone analog (e.g., ixabepilone), proteasome inhibitor (e.g., carfilzomib), IGF-1 receptor inhibitor (e.g., OSI 906, AMG 479), PARP inhibitor (e.g., veliparib, AG014699, iniparib, MK-4827), Aurora kinase inhibitor (e.g., MLN8237, ENMD-2076), angiogenesis inhibitor (e.g., lenalidomide), DHFR inhibitor (e.g., pralatrexate), radioimmunotherapeutic agnet (e.g., Hu3S193), statin (e.g., lovastatin), topoisomerase 1 inhibitor (e.g., NKTR-102), cancer vaccine (e.g., p53 synthetic long peptides vaccine, autologous OC-DC vaccine), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 6727), gamma-secretase inhibitor (e.g., RO4929097), Wee-1 inhibitor (e.g., MK-1775), antitubulin agent (e.g., vinorelbine, E7389), immunotoxin (e.g., denileukin diftitox), SB-485232, vascular-disrupting agent (e.g., AVE8062), integrin inhibitor (e.g., EMD 525797), kinesin-spindle inhibitor (e.g., 4SC-205), revlimid, HER2 inhibitor (e.g., MGAH22), ErrB3 inhibitor (e.g., MM-121), radiation therapy; and combinations thereof.

An example of suitable therapeutics for use in combination to treat a myeloma, alone or in combination with one or more of: chemotherapy or other anti-cancer agents (e.g., thalidomide analogs, e.g., lenalidomide), HSCT (Cook, R. (2008) *J Manag Care Pharm.* 14(7 Suppl):19-25), an anti-TIM3 antibody (Hallett, W H D et al. (2011) *J of American Society for Blood and Marrow Transplantation* 17(8):1133-145), tumor antigen-pulsed dendritic cells, fusions (e.g., electrofusions) of tumor cells and dendritic cells, or vaccination with immunoglobulin idiotype produced by malignant plasma cells (reviewed in Yi, Q. (2009) *Cancer J.* 15(6):502-10).

An example of suitable therapeutics for use in combination to treat a renal cancer, e.g., renal cell carcinoma (RCC) or metastatic RCC. The anti-PD-1 antibody molecule can be administered in combination with one or more of: an immune-based strategy (e.g., interleukin-2 or interferon-α), a targeted agent (e.g., a VEGF inhibitor such as a monoclonal antibody to VEGF, e.g., bevacizumab (Rini, B. I. et al. (2010) *J. Clin. Oncol.* 28(13):2137-2143)); a VEGF tyrosine kinase inhibitor such as sunitinib, sorafenib, axitinib and pazopanib (reviewed in Pal. S. K. et al. (2014) *Clin. Advances in Hematology & Oncology* 12(2):90-99)); an RNAi inhibitor), or an inhibitor of a downstream mediator of VEGF signaling, e.g., an inhibitor of the mammalian target of rapamycin (mTOR), e.g., everolimus and temsirolimus (Hudes, G. et al. (2007) *N. Engl. J. Med.* 356(22): 2271-2281, Motzer, R. J. et al. (2008) *Lancet* 372: 449-456).

An example of suitable therapeutics for use in combination for treatment of chronic myelogenous leukemia (AML) according to the invention includes, but is not limited to, a chemotherapeutic (e.g., cytarabine, hydroxyurea, clofarabine, melphalan, thiotepa, fludarabine, busulfan, etoposide, cordycepin, pentostatin, capecitabine, azacitidine, cyclophosphamide, cladribine, topotecan), tyrosine kinase inhibitor (e.g., BCR/ABL inhibitor (e.g., imatinib, nilotinib), ON 01910.Na, dual inhibitor (e.g., dasatinib, bosutinib), multikinase inhibitor (e.g., DCC-2036, ponatinib, sorafenib, sunitinib, RGB-286638)), interferon alfa, steroids, apoptotic agent (e.g., omacetaxine mepesuccinat), immunotherapy (e.g., allogeneic CD4+ memory Th1-like T cells/microparticle-bound anti-CD3/anti-CD28, autologous cytokine induced killer cells (CIK), AHN-12), CD52 targeting agent (e.g., alemtuzumab), HSP90 inhibitor (e.g., tanespimycin, STA-9090, AUY922, XL888), mTOR inhibitor (e.g., everolimus), SMO antagonist (e.g., BMS 833923), ribonucleotide reductase inhibitor (e.g., 3-AP), JAK-2 inhibitor (e.g., INCB018424), Hydroxychloroquine, retinoid (e.g., fenretinide), cyclin-dependent kinase inhibitor (e.g., UCN-01), HDAC inhibitor (e.g., belinostat, vorinostat, JNJ-26481585), PARP inhibitor (e.g., veliparib), MDM2 antagonist (e.g., RO05045337), Aurora B kinase inhibitor (e.g., TAK-901), radioimmunotherapy (e.g., actinium-225-labeled anti-CD33 antibody HuM195), Hedgehog inhibitor (e.g., PF-04449913), STAT3 inhibitor (e.g., OPB-31121), KB004, cancer vaccine (e.g., AG858), bone marrow transplantation, stem cell transplantation, radiation therapy, and combinations thereof.

An example of suitable therapeutics for use in combination for treatment of chronic lymphocytic leukemia (CLL) includes, but is not limited to, a chemotherapeutic agent (e.g., fludarabine, cyclophosphamide, doxorubicin, vincristine, chlorambucil, bendamustine, chlorambucil, busulfan, gemcitabine, melphalan, pentostatin, mitoxantrone, 5-azacytidine, pemetrexed disodium), tyrosine kinase inhibitor (e.g., EGFR inhibitor (e.g., erlotinib), BTK inhibitor (e.g., PCI-32765), multikinase inhibitor (e.g., MGCD265, RGB-286638), CD-20 targeting agent (e.g., rituximab, ofatumumab, RO5072759, LFB-R603), CD52 targeting agent (e.g., alemtuzumab), prednisolone, darbepoetin alfa, lenalidomide, Bcl-2 inhibitor (e.g., ABT-263), immunotherapy (e.g., allogeneic CD4+ memory Th1-like T cells/microparticle-bound anti-CD3/anti-CD28, autologous cytokine induced killer cells (CIK)), HDAC inhibitor (e.g., vorinostat, valproic acid, LBH589, JNJ-26481585, AR-42), XIAP inhibitor (e.g., AEG35156), CD-74 targeting agent (e.g., milatuzumab), mTOR inhibitor (e.g., everolimus), AT-101, immunotoxin (e.g., CAT-8015, anti-Tac(Fv)-PE38 (LMB-2)), CD37 targeting agent (e.g., TRU-016), radioimmunotherapy (e.g., 131-tositumomab), hydroxychloroquine, perifosine, SRC inhibitor (e.g., dasatinib), thalidomide, PI3K delta inhibitor (e.g., CAL-101), retinoid (e.g., fenretinide), MDM2 antagonist (e.g., RO5045337), plerixafor, Aurora kinase inhibitor (e.g., MLN8237, TAK-901), proteasome inhibitor (e.g., bortezomib), CD-19 targeting agent (e.g., MEDI-551, MOR208), MEK inhibitor (e.g., ABT-348), JAK-2 inhibitor (e.g., INCB018424), hypoxia-activated prodrug (e.g., TH-302), paclitaxel or a paclitaxel agent, HSP90 inhibitor, AKT inhibitor (e.g., MK2206), HMG-CoA inhibitor (e.g., simvastatin), GNKG186, radiation therapy, bone marrow transplantation, stem cell transplantation, and a combination thereof.

An example of suitable therapeutics for use in combination for treatment of acute lymphocytic leukemia (ALL) includes, but is not limited to, a chemotherapeutic agent (e.g., prednisolone, dexamethasone, vincristine, asparaginase, daunorubicin, cyclophosphamide, cytarabine, etoposide, thioguanine, mercaptopurine, clofarabine, liposomal annamycin, busulfan, etoposide, capecitabine, decitabine, azacitidine, topotecan, temozolomide), tyrosine kinase inhibitor (e.g., BCR/ABL inhibitor (e.g., imatinib, nilotinib), ON 01910.Na, multikinase inhibitor (e.g., sorafenib)), CD-20 targeting agent (e.g., rituximab), CD52 targeting agent (e.g., alemtuzumab), HSP90 inhibitor (e.g., STA-9090), mTOR inhibitor (e.g., everolimus, rapamycin), JAK-2 inhibitor (e.g., INCB018424), HER2/neu receptor inhibitor (e.g., trastuzumab), proteasome inhibitor (e.g., bortezomib), methotrexate, asparaginase, CD-22 targeting agent (e.g., epratuzumab, inotuzumab), immunotherapy (e.g., autologous cytokine induced killer cells (CIK), AHN-12), blinatumomab, cyclin-dependent kinase inhibitor (e.g., UCN-01), CD45 targeting agent (e.g., BC8), MDM2 antagonist (e.g., RO5045337), immunotoxin (e.g., CAT-8015, DT2219ARL), HDAC inhibitor (e.g., JNJ-26481585), JVRS-100, paclitaxel or a paclitaxel agent, STAT3 inhibitor (e.g., OPB-31121), PARP inhibitor (e.g., veliparib), EZN-2285, radiation therapy, steroid, bone marrow transplantation, stem cell transplantation, or a combination thereof.

An example of suitable therapeutics for use in combination for treatment of acute myeloid leukemia (AML) includes, but is not limited to, a chemotherapeutic agent (e.g., cytarabine, daunorubicin, idarubicin, clofarabine, decitabine, vosaroxin, azacitidine, clofarabine, ribavirin, CPX-351, treosulfan, elacytarabine, azacitidine), tyrosine kinase inhibitor (e.g., BCR/ABL inhibitor (e.g., imatinib, nilotinib), ON 01910.Na, multikinase inhibitor (e.g., midostaurin, SU 11248, quizartinib, sorafinib)), immunotoxin (e.g., gemtuzumab ozogamicin), DT388IL3 fusion protein, HDAC inhibitor (e.g., vorinostat, LBH589), plerixafor, mTOR inhibitor (e.g., everolimus), SRC inhibitor (e.g., dasatinib), HSP90 inhbitor (e.g., STA-9090), retinoid (e.g., bexarotene, Aurora kinase inhibitor (e.g., BI 811283), JAK-2 inhibitor (e.g., INCB018424), Polo-like kinase inhibitor (e.g., BI 6727), cenersen, CD45 targeting agent (e.g., BC8), cyclin-dependent kinase inhibitor (e.g., UCN-01), MDM2 antagonist (e.g., RO5045337), mTOR inhibitor (e.g., everolimus), LY573636-sodium, ZRx-101, MLN4924, lenalidomide, immunotherapy (e.g., AHN-12), histamine dihydrochloride, radiation therapy, bone marrow transplantation, stem cell transplantation, and a combination thereof.

An example of suitable therapeutics for use in combination for treatment of multiple myeloma (MM) includes, but is not limited to, a chemotherapeutic agent (e.g., melphalan, amifostine, cyclophosphamide, doxorubicin, clofarabine, bendamustine, fludarabine, adriamycin, SyB L-0501), thalidomide, lenalidomide, dexamethasone, prednisone, pomalidomide, proteasome inhibitor (e.g., bortezomib, carfilzomib, MLN9708), cancer vaccine (e.g., GVAX), CD-40 targeting agent (e.g., SGN-40, CHIR-12.12), perifosine, zoledronic acid, Immunotherapy (e.g., MAGE-A3, NY-ESO-1, HuMax-CD38), HDAC inhibitor (e.g., vorinostat, LBH589, AR-42), aplidin, cycline-dependent kinase inhibitor (e.g., PD-0332991, dinaciclib), arsenic trioxide, CB3304, HSP90 inhibitor (e.g., KW-2478), tyrosine kinase inhibitor (e.g., EGFR inhibitor (e.g., cetuximab), multikinase inhibitor (e.g., AT9283)), VEGF inhibitor (e.g., bevacizumab), plerixafor, MEK inhibitor (e.g., AZD6244), IPH2101, atorvastatin, immunotoxin (e.g., BB-10901), NPI-0052, radioimmunotherapeutic (e.g., yttrium Y 90 ibritumomab tiuxetan), STAT3 inhibitor (e.g., OPB-31121), MLN4924, Aurora kinase inhibitor (e.g., ENMD-2076), IMGN901, ACE-041, CK-2 inhibitor (e.g., CX-4945), radiation therapy, bone marrow transplantation, stem cell transplantation, and a combination thereof.

An example of suitable therapeutics for use in combination for treatment of prostate cancer includes, but is not limited to, a chemotherapeutic agent (e.g., docetaxel, carboplatin, fludarabine), abiraterone, hormonal therapy (e.g., flutamide, bicalutamide, nilutamide, cyproterone acetate, ketoconazole, aminoglutethimide, abarelix, degarelix, leuprolide, goserelin, triptorelin, buserelin), tyrosine kinase inhibitor (e.g., dual kinase inhibitor (e.g., lapatanib), multikinase inhibitor (e.g., sorafenib, sunitinib)), VEGF inhibitor (e.g., bevacizumab), TAK-700, cancer vaccine (e.g., BPX-101, PEP223), lenalidomide, TOK-001, IGF-1 receptor inhibitor (e.g., cixutumumab), TRC105, Aurora A kinase inhibitor (e.g., MLN8237), proteasome inhibitor (e.g., bortezomib), OGX-011, radioimmunotherapy (e.g., HuJ591-GS), HDAC inhibitor (e.g., valproic acid, SB939, LBH589), hydroxychloroquine, mTOR inhibitor (e.g., everolimus), dovitinib lactate, diindolylmethane, efavirenz, OGX-427, genistein, IMC-3G3, bafetinib, CP-675,206, radiation therapy, surgery, or a combination thereof.

The combination therapies can be administered in combination with one or more of the existing modalities for treating cancers, including, but not limited to: surgery; radiation therapy (e.g., external-beam therapy which involves three dimensional, conformal radiation therapy where the field of radiation is designed, local radiation (e.g., radiation directed to a preselected target or organ), or focused radiation). Focused radiation can be selected from the group consisting of stereotactic radiosurgery, fractionated stereotactic radiosurgery, and intensity-modulated radiation therapy. The focused radiation can have a radiation source selected from the group consisting of a particle beam (proton), cobalt-60 (photon), and a linear accelerator (x-ray), e.g., as described in WO 2012/177624.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Nucleic Acids

The invention also features nucleic acids comprising nucleotide sequences that encode heavy and light chain variable regions and CDRs or hypervariable loops of the antibody molecules, as described herein. The nucleic acid can comprise a nucleotide sequence as set forth herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

Vectors

Further provided herein are vectors comprising nucleotide sequences encoding an antibody molecule described herein. In one embodiment, the vectors comprise nucleotides encoding an antibody molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

The following Examples illustrate the disclosure and provide specific embodiments, however without limiting the scope of the disclosure,

EXAMPLES

Example 1: Effects of Targeted Agents on PD-L1 Modulation

This example evaluates the effects of selected therapeutic agents (e.g., INC280, MEK162, LGX818 and LDK378) on PD-L1 (CD274) modulation. Selected therapeutic agents were examined by real time PCR and flow cytometry on PD-L1 levels. Significant inhibition of PD-L1 by INC280, MEK162, LGX818 and LDK378 on tumor cells was observed.

INC280 Downregulation of PD-L1 Protein

PD-L1 (CD274) expression was analyzed in cancer cell lines treated with INC280. Cells were obtained from ATCC and cultured in vitro following ATCC directions. The cell lines used were previously characterized by the Cancer Cell Line Encyclopedia Project (http://www.broadinstitute.org/ccle/home).

Cells plated in six-well culture plates were treated with the INC280 at different concentrations (10 nM, 100 nM, and 1000 nM) for 24, 48 and 72 hours. Equal amount of vehicle (DMSO) was used as a control. Cells were washed with PBS and then harvested using a cell scraper.

For each reaction, $0.5\text{-}1\times10^6$ cells were stained with 20 µL of anti-human monoclonal PD-L1-PE antibody, clone M1H1 (BD) for 30-60 minutes at 4° C. Cells were washed twice and data was acquired using a Canto II with FACSDiva software (BD Bioscience). Data analysis was performed using FlowJo software (Tree Star). Mean fluorescence intensity (MFI) was determined by gating on single cells. Unstained cells were used as a gating control.

In vitro treatment of EBC-1 cells (Non-Small Cell Lung Cancer (NSCLC) with cMET amplification) with INC280 led to significant downregulation of surface expression of PD-L1 as observed by flow cytometry (FIG. 1). The results presented herein suggest that INC280 functions as a PD-L1/PD1 inhibitor.

INC280, MEK162, LGX818 and LDK378 Downregulate PD-L1 mRNA

TaqMan RT PCR assays were developed to detect changes of expression levels of PD-L1 (CD274) in cell lines and xenograft tumors. mRNA was isolated from frozen cell pellets or tumor fragments using the Qiagen RNeasy Mini kit. Isolated RNA was frozen at −80° C. RNA quality was checked and RNA was quantified using a 2100 Agilent Bioanalyzer following the protocol for the Agilent RNA 6000 Nano Kit. cDNA was prepared using a High Capacity RNA- to cDNA Kit (Applied Biosystems).

Real-time PCR reactions were carried out in 20 µl total volume, including 10 µl of Universal PCR master mix (Applied Biosystems), 1 µl of human PD-L1 (CD274) probe/primer set (Applied Biosystems), and 8 µl of cDNA. Each sample was run in triplicate. The amount of cDNA produced from 25-50 ng of RNA in the reverse transcription reaction was used in each PCR reaction. Due to difference in mRNA levels between PD-L1 and GAPDH, the two real-time PCR reactions were done in separate tubes using same amount of cDNA. The real-time PCR reaction was run on the C1000 Thermal Cycle (BioRad) with the cycle program as follows: a 10 minute incubation at 95° C. followed by 40 cycles of 95° C. for 15 seconds and 60° C. for 1 minute. After the reaction was complete, the PD-L1 average Ct was normalized relative to each Ct value from the GAPDH reference reaction. Each normalized logarithmic value was then converted into a linear value.

Figure 2:
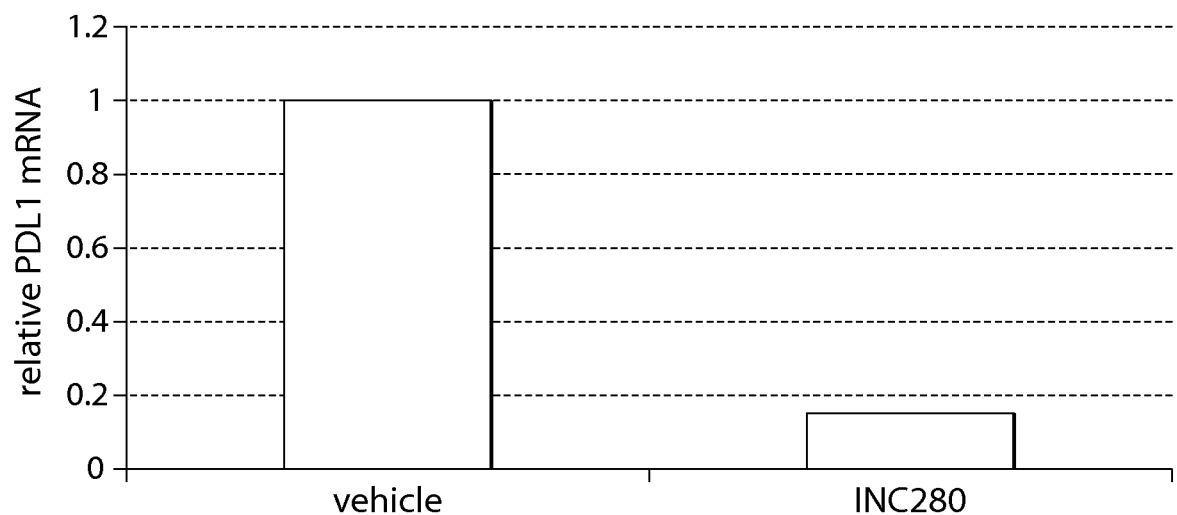
FIG. 2 shows a graphical representation of PD-L1 mRNA expression in Hs.746.T cells in a tumor xenograft model with or without INC280 treatment. Hs.746.T cells are gastric cancer cells with a c-MET amplification and a c-MET mutation.
Figure 3:
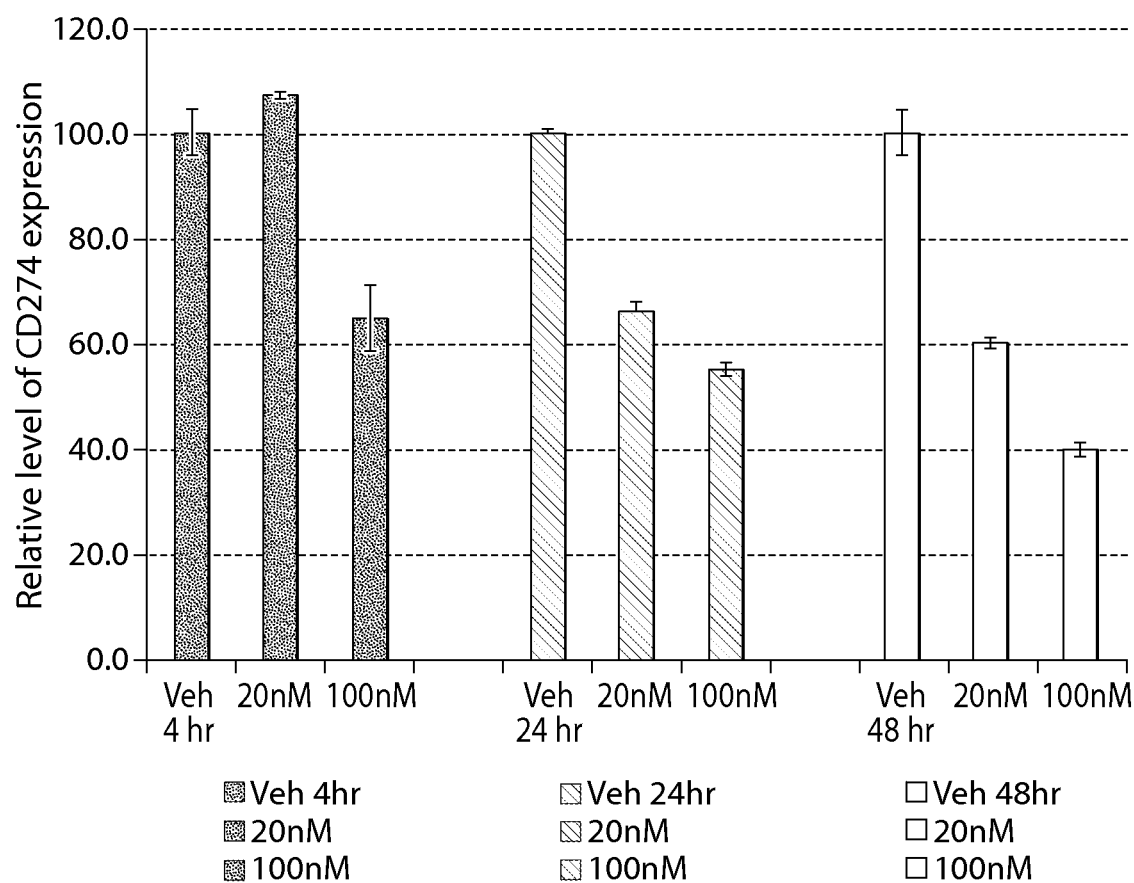
FIG. 3 shows a graphical representation of PD-L1 mRNA expression in H3122 cells in vitro with or without LDK378. H3122 cells are non-small cell lung cancer (NSCLC) cells with an ALK translocation.
Figure 4:
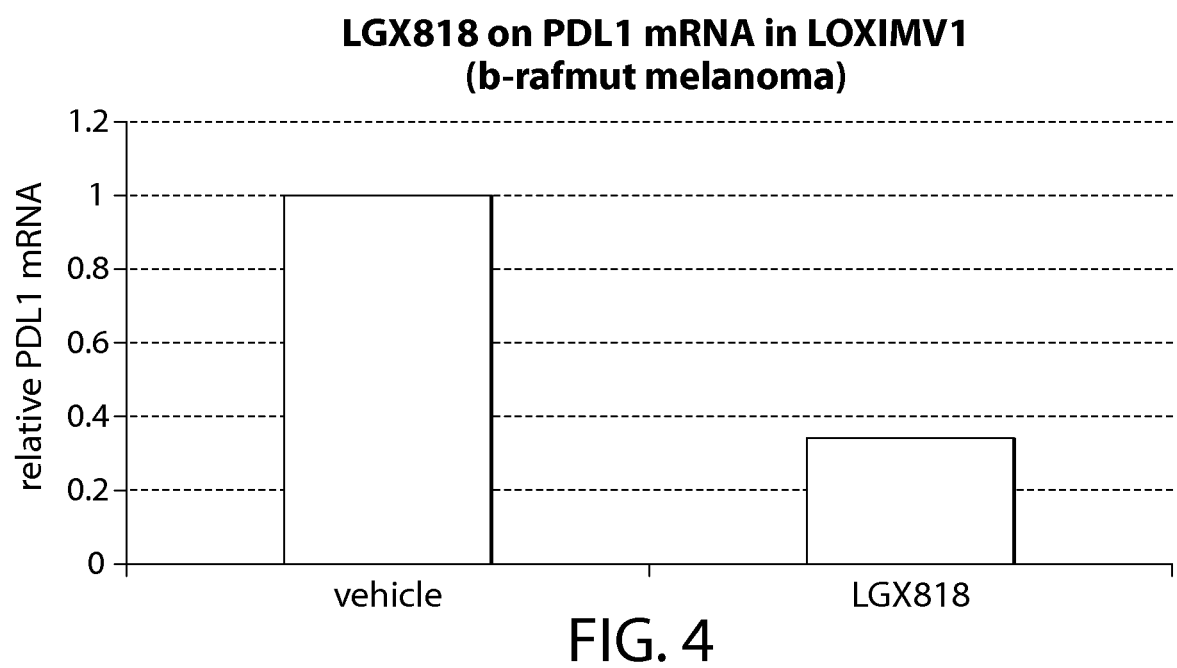
FIG. 4 shows a graphical representation of PD-L1 mRNA expression in LOXIMV1 cells (BRAF mutant melanoma cells) in a tumor xenograft model with or without LGX818 treatment.
Figure 5:
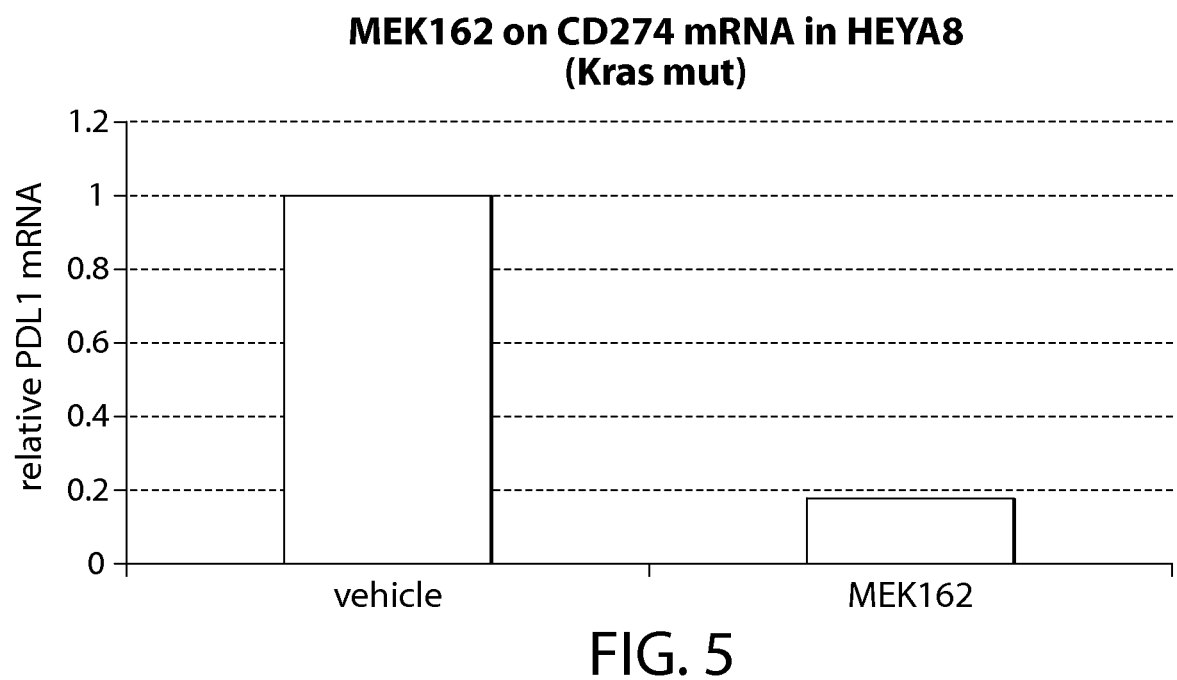
FIG. 5 shows a graphical representation of PD-L1 mRNA expression in HEYA8 cells (KRAS mutant ovarian cancer cells) in a tumor xenograft model with or without MEK162 treatment.
Figure 6:
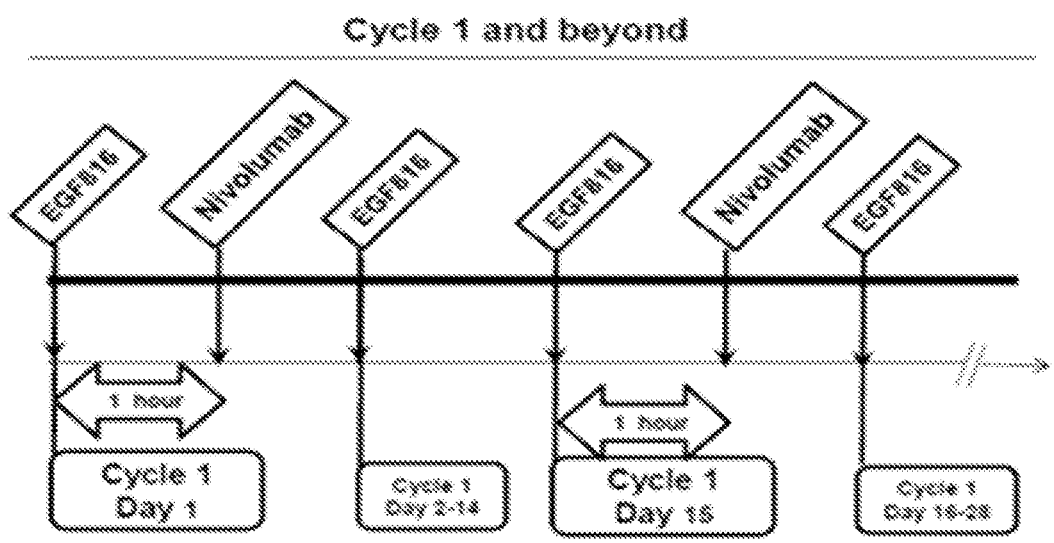
FIG. 6 is a representation of the sequence of drug administration for patients enrolled in the Phase II trial that will be treated with EGF816 and Nivolumab.

Inhibition of PD-L1 expression (mRNA) by INC280 was observed in a Hs.746.T tumor (gastric cancer cell with cMET amplification & mutation) xenograft (FIG. 2). Inhibition of PD-L1 mRNA by LDK378 was observed in H3122 (Non-Small Cell Lung Cancer (NSCLC) with ALK translocation) in vitro (FIG. 3). Downregulation of PD-L1 mRNA by LGX818, and MEK162 was observed in tumor xenograft models bearing LOXIMV1 (BRAF mutant melanoma, FIG. 4) and HEYA8 (KRAF mutant ovarian cancer, FIG. 5) tumors, respectively.

The results presented herein demonstrate a role of INC280, MEK162, LGX818 and LDK 378 in the regulation of immunecheckpoint molecules on cancer. The observed inhibition of PD-L1 expression by these agents suggests that these targeted agents may have immune-modulatory activities, in addition to their effects on cancer signaling. Thus, the results presented herein suggest that administration of targeted agents with inhibitors of immunecheckpoint inhibitors such as PD1, PD-L1, LAG3 and/or TIM3 will achieve a more potent reversal of the immunecheckpoint-mediated immune suppression.

Example 2: Dose Escalation and Expansion Study of the LDK (Certinib) and Nivolumab Combination Efficacy and safety of the ceritinib (LDK378) and nivolumab combination can be assessed in an open-label, multi-center dose escalation and expansion study. In addition to the safety and efficacy, the tolerability and PK/PD of combination of ceritinib and nivolumab for the treatment of patients with metastatic, ALK-positive non-small cell lung cancer (NSCLC) can also be evaluated. The study can begin with a screening period of up to and including 28 days prior to the first dose of the study drugs to assess eligibility. The treatment period can begin on the first day of the first cycle. The cycles are 28 days long.

Treatment with ceritinib and nivolumab may for example continue until the patient experiences unacceptable toxicity that precludes further treatment and/or disease progression.

In cases of isolated brain progression or other local progression, patients may in addition receive palliative radiotherapy.

The study can include a dose-escalation phase and a dose-expansion phase.

1. Dose-Escalation Phase

The dose-escalation phase of the study can evaluate the maximum tolerated dose (MTD)/recommended dose for expansion (RDE) of the combination of oral daily ceritinib with a low-fat meal and intravenous nivolumab every 2 weeks (Q2W) based on dose limiting toxicities (DLTs) using a Bayesian Logistic Regression Model (BLRM). For example, 12 patients are enrolled in this phase of the study. The initial dose level of ceritinib can be 450 mg daily and nivolumab is administered at the dose of 3 mg/kg Q2W. The provisional dose levels are as follows:

[−1 dose cohort] ceritinib 300 mg+nivolumab (3 mg/kg)
[1st dose cohort] ceritinib 450 mg+nivolumab (3 mg/kg)
[2nd dose cohort] ceritinib 600 mg+nivolumab (3 mg/kg)

The MTD is the highest drug dosage of both agents not expected to cause DLT in more than 35% of the treated patients in the first 6 weeks of treatment. The final recommended MTD/RDE for combination ceritinib and nivolumab is based on the recommendation from the BLRM, and on an overall assessment of safety taking into consideration tolerability and pharmacokinetic data from subsequent cycles at the tested doses. If the MTD for combination ceritinib and nivolumab is not established after the evaluation of all planned dose levels including the target doses of ceritinib (600 mg with low-fat meal) and nivolumab (3 mg/kg), the RDE is determined after the evaluation of all available safety, PK, and efficacy data.

2. Dose-Expansion Phase

Once the MTD of the combination has been declared and/or the RDE is determined, additional patients are evaluated in the expansion phase of the study at the RDE combination dose. For example, 60 patients are enrolled into the expansion phase of the study. The expansion phase evaluates the safety and preliminary efficacy of the ceritinib and nivolumab combination at the RDE and consists of 2 arms (approximately 30 patients in each arm):

Arm 1: ALK inhibitor-treated (Prior treatment with any ALK inhibitor except ceritinib is allowed.)
Arm 2: ALK inhibitor-naïve The data cut-off for the primary clinical study report can occur once all patients in the expansion phase have completed at least 6 cycles (24 weeks) of treatment or have discontinued earlier.

Example 3: Effects of the LDK378 and Nivolumab Combination in Humans

Eight patients were enrolled to the first dose cohort in the study just as outlined in the Example 2 and below is the data of the only patient with a valid tumor assessment. A partial response was observed with this patient. A second assessment is required to fully confirm the response.

Patient assessed was a 64 year old Caucasian male with diagnosed stage IV NSCLC. Sites of disease included lung, adrenal and abdominal lymph nodes. The patient received one prior chemotherapy regimen of cisplatin and pemetrexed and achieved a partial response. Additional medical conditions include adrenal insufficiency, mitral valve prolapse, hypercholesterolemia, and urolithiasis.

The patient started study treatment with LDK378 450 mg QD (oral), administered with a low fat meal, in combination with Nivolumab 3 mg/kg every 2 weeks (intravenous). 29 days after the first dose of the study medications (combination of LDK378+Nivolumab) the patient presented with fever, abdominal pain, nausea, and vomiting. Abdominal ultrasound was negative but computerized tomogram (CT) of the abdomen demonstrated acute pancreatitis. In addition, there were elevations in lipase, amylase, ALT, AST, bilirubin, ALP, and GGT. The patient was hospitalized and treatment with study medication LDK378 was temporarily interrupted. Treatment with intravenous fluids, paracetamol, Contramal (tramadol hydrochloride) and Litican (alizapride) was administered. In the following days the patient's laboratory results improved and the patient's condition improved; there were no more complaints of pain, fever, nausea and vomiting. All supporting medications were stopped and the patient was discharged from the hospital.

At a later evaluation at the clinic there were no complaints (no fever, vomiting, nausea or abdominal pain). After the patient had been discharged from the hospital, the patient did not receive pain medication or anti-emetics. Blood chemistry showed:

Lipase and amylase within normal limits, Gr1: bilirubin, AST, and ALT Gr2: Alkaline Phosphatase Grade 3: GGT 1 day after the evaluation at the clinic LDK378 was restarted at a reduced dose of 300 mg daily. Nivolumab treatment was restarted about a week later.

Patient had vomited once without nausea or abdominal pain. He was afebrile although once had a fever of 38 degrees. Patient had no physical complaints.

Lab values when Nivolumab was restarted: AST: 120 U/L, ALT: 139 U/L, Bilirubin total 33 Umol/L, Alkaline Phosphatase 551 U/L. Amylase and Lipase were normal.

LDK378 was discontinued and restarted again at 300 mg dose.

Tumor Assessment:

CT scan at the first tumor assessment demonstrated a 62.9% decrease in overall target lesions in the right adrenal gland and abdominal lymph nodes from the baseline CT scan. There is also a non-target lesion in the Left lower lobe of the lung which was assessed as present.

| RECIST Target lesion | |
| --- | --- |
| Location | Adrenal, lesion #1 |
| | Lesion diameter |
| Baseline | 17 mm |
| Tumor Assessment | 0 mm |
| Location | Other lymph nodes (abdominal), lesion #2 |
| | Lesion diameter |

-continued

| RECIST Target lesion | |
|---|---|
| Baseline | 22 mm |
| Tumor Assessment | 7 mm |
| Location | Other lymph nodes (abdominal), lesion #3 |
| | Lesion diameter |
| Baseline | 23 mm |
| Tumor Assessment | 16 mm |

| RECIST Non-Target lesion | |
|---|---|
| Location | Lung, lower lobe |
| | Lesion status |
| Baseline | Present |
| Tumor Assessment | Present |
| Location | Other lymph nodes (abdominal) |
| | Lesion diameter |
| Evaluation | 22 mm |
| Baseline | 7 mm |

Example 4: A Phase II, Multicenter, Open-Label Study of EGF816 in Combination with Nivolumab in Adult Patients with EGFR Mutated Non-Small Cell Lung Cancer Currently approved EGFR TKIs are effective in activated EGFR mutant NSCLC, however nearly all patients develop resistance. Harnessing the immune system to treat patients with non-small cell lung cancer (NSCLC) is a novel and exciting new treatment approach.

Concurrent treatment with an immune checkpoint inhibitor along with a targeted therapy is considered to be safe and is expected to result in durable and sustained responses. Nivolumab is combined with the third generation EGFR TKI, EGF816, in EGFR T790M NSCLC patients who have developed resistance to EGFR TKI treatment. It is expected that the combination of Nivolumab with the EGFR inhibitor, EGF816, provides sustained clinical benefit to NSCLC patients whose tumors have become resistant to EGFR TKI treatment through acquiring T790M mutation by stimulating the host immune system and inhibiting EGFR T790M.

This study is a phase II, multicenter, open-label study of EGF816 in combination with Nivolumab in adult patients with EGFR mutated non-small cell lung cancer, e.g. patients with NSCLC progressing on standard of care (i.e.,erlotinib or gefitinib for EGFR-mutant NSCLC).

An exemplary dose of EGF816 is 150 mg qd on a continuous daily dose for EGF816 (capsule formulation). Different EGF816 doses may also be used. EGF816 is administered prior to Nivolumab. A minimum of 1 hour must pass from the time of EGF816 administration to the administration of EGF816.

The dose and schedule of Nivolumab is 3 mg/kg every 2 weeks. This dose and schedule selection is based on results of safety, efficacy, and exposure-response analyses obtained from studies. This dose and schedule of Nivolumab has been safely combined with other EGFR inhibitors (e.g., erlotinib) at registered doses as well as with other standard of care therapies.

This is a phase II, multi-center, open-label study of patients with advanced NSCLC.

Patients are allocated based on their EGFR status e.g. EGFR-T790M NSCLC.

Suitable patients may be patients with advanced, recurrent or metastatic/unresectable EGFRT790M NSCLC progressing on standard of care (i.e., erlotinib, gefitinib or other approved EGFR TKI).

EGFR mutation status may be determined by tests available in the art, e.g. QIAGEN Therascreen® EGFR test. The therascreen EGFR RGQ PCR Kit is an FDA-approved, qualitative real-time PCR assay for the detection of specific mutations in the EGFR oncogene. Evidence of EGFR mutation can be obtained from existing local data and testing of tumor samples. EGFR mutation status may be determined from any available tumor tissue.

Patients are treated as follows:

EGF816 is administered prior to nivolumab+Nivolumab

A cycle will be defined as 28 days.

At least six patients of each group constitute a safety monitoring cohort for that group.

For each cohort, patients are treated with either Nivolumab 3 mg/kg every two weeks and EGF816 at 150 mg qd (once daily).

As part of the safety monitoring cohort, steady state PK profile for EGF816 is collected on Cycle 1 day 15; and trough samples for Nivolumab is collected on Cycle 1 Day 15.

The treatment period begins on Cycle 1 Day 1. The study treatment is administered during 28-days cycles. Patients are treated until unacceptable toxicity, progressive disease, treatment discontinuation at the discretion of the investigator, or withdrawal of consent.

TABLE 2

| Trial objectives and related endpoints | |
|---|---|
| Objective | Endpoint |
| Primary | |
| To estimate the clinical activity of Nivolumab in combination with EGF816 | 6 month PFS rate using RECIST version1.1 (6 mo PFS rate = 6 cycles = 168 days) |
| Secondary | |
| To evaluate the preliminary antitumor activity of EGF816 and Nivolumab | ORR, DCR, other PFS measures, OS |
| To characterize the safety and tolerability of EGF816 and Nivolumab | Safety, incidence and severity of AEs, including changes in hematology and chemistry values, vital signs and ECGs Tolerability: Dose interruptions, reductions, and dose intensity |
| To evaluate PK of EGF816 and Nivolumab in the combination setting | PK parameters of Nivolumab and EGF816 as Cmax, AUC and Cmin |
| Exploratory | |
| Explore correlation of baseline PD-L1 & other immune checkpoint molecules levels in relation to disease progression | Baseline levels of PD-L1 & other immune checkpoint molecules in tumor |

TABLE 3

Dose and treatment schedule

| Study treatments | Pharmaceutical form and route of administration | Dose | Frequency and/or Regimen |
|---|---|---|---|
| EGF816 | Capsule for oral use | 150 mg | Daily |
| Nivolumab | Solution for injection | 3 mg/kg | Every two weeks |

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method of treating a cancer in a subject, comprising administering to the subject an antibody molecule comprising a heavy chain amino acid sequence of SEQ ID NO: 2 and a light chain amino acid sequence of SEQ ID NO: 3 and a c-Met inhibitor, wherein the c-MET inhibitor is 2-fluoro-N-methyl-4-[7-(quinolin-6-ylmethyl)imidazo[1,2-b][1,2,4]triazin-2-yl]benzamide (INC280), or a pharmaceutically acceptable salt thereof, thereby treating the cancer.

2. The method of claim 1, wherein the antibody molecule and the c-MET inhibitor are administered together in a single composition.

3. The method of claim 1, wherein the cancer is a solid tumor, a soft tissue tumor, or a metastatic lesion thereof.

4. The method of claim 1, wherein the subject is a human.

5. The method of claim 1, wherein the antibody molecule is administered by injection at a dose of about 1 to 30 mg/kg.

6. The method of claim 1, wherein the c-Met inhibitor is administered at an oral dose of about 100 mg to 1000 mg.

7. The method of claim 5, wherein the antibody molecule is administered subcutaneously or intravenously.

8. The method of claim 5, wherein the antibody molecule is administered once a week to once every 2, 3, or 4 weeks.

9. The method of claim 8, wherein the antibody molecule is administered at a dose from about 1 mg/kg to about 20 mg/kg every other week.

10. The method of claim 1, wherein the cancer is a solid tumor.

11. The method of claim 1, wherein the antibody molecule and the c-MET inhibitor are administered separately in two or more different compositions or dosage forms, wherein the antibody molecule is administered concurrently with, prior to, or subsequent to, the c-MET inhibitor.

12. The method of claim 1, wherein the cancer is a hematological cancer or a metastatic lesion thereof.

13. The method of claim 12, wherein the hematological cancer is a leukemia, a lymphoma, or a myeloma.

14. The method of claim 12, wherein the hematological cancer is chosen from a Hodgkin lymphoma, a non-Hodgkin lymphoma, a lymphocytic leukemia, or a myeloid leukemia.

15. The method of claim 3, wherein the solid tumor is a cancer of the lung, breast, lymphoid tissue, gastrointestinal tract, anal, genitourinary tract, CNS, neural, glial cells, head and neck, skin, pancreas, or liver.

16. The method of claim 3, wherein the solid tumor is a melanoma, a renal cell carcinoma, or a non-small cell lung cancer.

17. The method of claim 1, wherein the antibody molecule is administered by injection at a dose of about 5 to 25 mg/kg.

18. The method of claim 1, wherein the antibody molecule is administered by injection at a dose of about 10 to 20 mg/kg.

19. The method of claim 1, wherein the antibody molecule is administered by injection at a dose of about 1 to 5 mg/kg.

20. The method of claim 1, wherein the antibody molecule is administered by injection at a dose of about 3 mg/kg.

21. The method of claim 1, wherein the c-Met inhibitor is administered at an oral dose of about 200 mg to 900 mg.

22. The method of claim 1, wherein the c-Met inhibitor is administered at an oral dose of about 300 mg to 800 mg.

23. The method of claim 1, wherein the c-Met inhibitor is administered at an oral dose of about 400 mg to 700 mg.

24. The method of claim 1, wherein the c-Met inhibitor is administered at an oral dose of about 400 mg, 500 mg, or 600 mg.

25. The method of claim 1, wherein the c-Met inhibitor is administered every other day, daily, twice or three times a day.

26. The method of claim 1, wherein the c-Met inhibitor is administered at an oral dose from about 400 to 600 mg twice a day.

27. The method of claim 8, wherein the antibody molecule is administered intravenously at a dose from about 1 mg/kg to about 3 mg/kg every two weeks.

28. The method of claim 8, wherein the antibody molecule is administered intravenously at a dose of about 1 mg/kg, about 2 mg/kg, or about 3 mg/kg, every two weeks.

29. The method of claim 8, wherein the antibody molecule is administered intravenously at a dose of about 2 mg/kg at 3-week intervals.

30. The method of claim 1, wherein the cancer is a lung cancer, a glioblastoma multiforme, a renal cancer, or a liver cancer.

31. The method of claim 1, wherein the cancer is a non-small cell lung cancer (NSCLC).

32. The method of claim 15, wherein:
(a) the cancer of the gastrointestinal tract is a colon cancer, a rectal cancer, a cancer of the small intestines, or a cancer of the esophagus;
(b) the cancer of the genitourinary tract is a cancer of the genitals, a renal cancer, a urothelial cancer, a bladder cancer, or a prostate cancer;
(c) the cancer of the CNS is a brain cancer; or
(d) the cancer of the head and neck is a cancer of the pharynx.

33. The method of claim 8, wherein the antibody molecule is administered intravenously at a dose of about 3 mg/kg at 2-week intervals.

34. The method of claim 1, wherein the antibody molecule is administered intravenously at a dose of about 3 mg/kg at 2-week intervals and the c-Met inhibitor is administered at an oral dose of 400 mg twice a day.

35. A method of reducing one, two, or three of growth, survival, or viability of a cancer cell, comprising contacting the cell with an antibody molecule comprising a heavy chain amino acid sequence of SEQ ID NO: 2 and a light chain amino acid sequence of SEQ ID NO: 3 and a c-Met inhibitor, wherein the c-MET inhibitor is 2-fluoro-N-methyl-4-[7-(quinolin-6-ylmethyl)imidazo[1,2-b][1,2,4]triazin-2-yl]benzamide (INC280), or a pharmaceutically acceptable salt thereof, thereby reducing the growth, survival, or viability of the cancer cell.

36. A composition comprising an antibody molecule comprising a heavy chain amino acid sequence of SEQ ID NO: 2 and a light chain amino acid sequence of SEQ ID NO: 3 and a c-Met inhibitor, wherein the c-MET inhibitor is 2-fluoro-N-methyl-4-[7-(quinolin-6-ylmethyl)imidazo[1,2-b][1,2,4]triazin-2-yl]benzamide (INC280), or a pharmaceutically acceptable salt thereof.

* * * * *

SEQUENCE LISTING

```
<160> NUMBER OF SEQ ID NOS: 7

<210> SEQ ID NO 1
<211> LENGTH: 5
<212> TYPE: PRT
<213> ORGANISM: Unknown
<220> FEATURE:
<221> NAME/KEY: source
<223> OTHER INFORMATION: /note="Description of Unknown:
      PD-1 motif peptide"

<400> SEQUENCE: 1

Met Tyr Pro Pro Tyr
1               5

<210> SEQ ID NO 2
<211> LENGTH: 440
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160
```

Ser Gly Val His Thr Phe Pro Ala Val Leu Gln Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 3
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

-continued

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 5
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95
```

```
Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 6
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Ile Lys Leu Gly Thr Val Thr Thr Val Asp Tyr Trp Gly Gln Gly Thr
            100                 105                 110

Leu Val Thr Val Ser Ser
        115

<210> SEQ ID NO 7
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30
```

-continued

```
Asn Tyr Val Ser Trp Tyr Gln Gln His Pro Gly Lys Ala Pro Lys Leu
            35                  40              45

Met Ile Tyr Asp Val Ser Asn Arg Pro Ser Gly Val Ser Asn Arg Phe
        50                  55              60

Ser Gly Ser Lys Ser Gly Asn Thr Ala Ser Leu Thr Ile Ser Gly Leu
65              70                      75                  80

Gln Ala Glu Asp Glu Ala Asp Tyr Tyr Cys Ser Ser Tyr Thr Ser Ser
                85                  90              95

Ser Thr Arg Val Phe Gly Thr Gly Thr Lys Val Thr Val Leu
            100             105             110
```